US010391089B2

(12) United States Patent
Duncan et al.

(10) Patent No.: US 10,391,089 B2
(45) Date of Patent: *Aug. 27, 2019

(54) PRMT5 INHIBITORS AND USES THEROF

(71) Applicant: Epizyme, Inc., Cambridge, MA (US)

(72) Inventors: Kenneth W. Duncan, Westwood, MA (US); Richard Chesworth, Concord, MA (US); Paula Ann Boriack-Sjodin, Lexington, MA (US); Michael John Munchhof, Salem, CT (US); Lei Jin, Wellesley, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,097

(22) Filed: Dec. 15, 2017

(65) Prior Publication Data
US 2018/0303822 A1    Oct. 25, 2018

Related U.S. Application Data

(63) Continuation of application No. 15/586,775, filed on May 4, 2017, now abandoned, which is a continuation of application No. 15/054,193, filed on Feb. 26, 2016, now Pat. No. 9,675,614, which is a continuation of application No. 14/619,371, filed on Feb. 11, 2015, now Pat. No. 9,365,519, which is a continuation of application No. 14/136,569, filed on Dec. 20, 2013, now Pat. No. 8,993,555.

(60) Provisional application No. 61/790,525, filed on Mar. 15, 2013, provisional application No. 61/745,485, filed on Dec. 21, 2012.

(51) Int. Cl.
| | | |
|---|---|---|
| C07D 401/14 | (2006.01) | |
| A61K 31/4725 | (2006.01) | |
| C07D 217/12 | (2006.01) | |
| C07D 401/12 | (2006.01) | |
| C07D 405/12 | (2006.01) | |
| C07D 217/04 | (2006.01) | |
| C07D 405/14 | (2006.01) | |
| C07D 413/12 | (2006.01) | |
| A61K 31/506 | (2006.01) | |
| C12N 9/10 | (2006.01) | |
| A61P 7/06 | (2006.01) | |
| A61P 3/04 | (2006.01) | |
| A61P 3/10 | (2006.01) | |
| A61P 35/00 | (2006.01) | |
| A61K 31/496 | (2006.01) | |
| A61K 31/498 | (2006.01) | |
| A61K 31/5377 | (2006.01) | |
| A61K 31/538 | (2006.01) | |

(52) U.S. Cl.
CPC ........ *A61K 31/4725* (2013.01); *A61K 31/496* (2013.01); *A61K 31/498* (2013.01); *A61K 31/506* (2013.01); *A61K 31/538* (2013.01); *A61K 31/5377* (2013.01); *A61P 3/04* (2018.01); *A61P 3/10* (2018.01); *A61P 7/06* (2018.01); *A61P 35/00* (2018.01); *C07D 217/04* (2013.01); *C07D 217/12* (2013.01); *C07D 401/12* (2013.01); *C07D 401/14* (2013.01); *C07D 405/12* (2013.01); *C07D 405/14* (2013.01); *C07D 413/12* (2013.01); *C12N 9/1007* (2013.01); *Y02A 50/414* (2018.01)

(58) Field of Classification Search
None
See application file for complete search history.

(56) References Cited

U.S. PATENT DOCUMENTS

| | | |
|---|---|---|
| 4,022,776 A | 5/1977 | Nakagawa et al. |
| 4,059,621 A | 11/1977 | Vincent et al. |
| 4,113,463 A | 9/1978 | Oshio et al. |
| 4,365,064 A | 12/1982 | Takacs et al. |
| 4,604,400 A | 8/1986 | Collins et al. |
| 4,684,459 A | 8/1987 | Klimpel et al. |
| 4,746,655 A | 5/1988 | Cale, Jr. |
| 4,912,115 A | 3/1990 | Bomhard et al. |
| 5,204,357 A | 4/1993 | Henning et al. |
| 5,294,621 A | 3/1994 | Russell |

(Continued)

FOREIGN PATENT DOCUMENTS

| | | |
|---|---|---|
| AU | 616071 B2 | 10/1991 |
| CA | 2383340 A1 | 3/2001 |

(Continued)

OTHER PUBLICATIONS

Hawley's Condensed Chemical Dictionary online pub Mar. 2007, excerpt "aliphatic".*

(Continued)

*Primary Examiner* — Heidi Reese
(74) *Attorney, Agent, or Firm* — Wolf, Greenfield & Sacks, P.C.

(57) ABSTRACT

Described herein are compounds of Formula (I), pharmaceutically acceptable salts thereof, and pharmaceutical compositions thereof. Compounds of the present invention are useful for inhibiting PRMT5 activity. Methods of using the compounds for treating PRMT5-mediated disorders are also described.

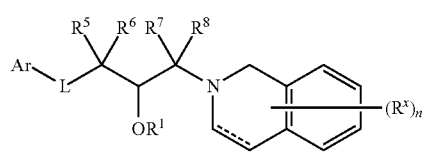

19 Claims, No Drawings

Specification includes a Sequence Listing.

(56) References Cited

U.S. PATENT DOCUMENTS

| | | |
|---|---|---|
| 5,514,694 A | 5/1996 | Powers et al. |
| 5,693,847 A | 12/1997 | Tung et al. |
| 6,034,097 A | 3/2000 | DiMaio et al. |
| 6,130,217 A | 10/2000 | Arnold et al. |
| 6,218,393 B1 | 4/2001 | Ryder et al. |
| 7,176,242 B2 | 2/2007 | John et al. |
| 7,253,165 B2 | 8/2007 | Shutske et al. |
| 7,265,122 B2 | 9/2007 | Wu et al. |
| 7,335,779 B2 | 2/2008 | Ammendola et al. |
| 7,338,969 B2 | 3/2008 | Ammendola et al. |
| 7,423,067 B2 | 9/2008 | Hagmann et al. |
| 7,727,997 B2 | 6/2010 | John et al. |
| 7,829,713 B2 | 11/2010 | Keenan et al. |
| 8,071,624 B2 | 12/2011 | Yao et al. |
| 8,076,516 B2 | 12/2011 | Scott et al. |
| 8,084,621 B2 | 12/2011 | Tang et al. |
| 8,119,633 B2 | 2/2012 | Merla et al. |
| 8,247,436 B2 | 8/2012 | Baettig et al. |
| 8,309,547 B2 | 11/2012 | Bodhuri et al. |
| 8,450,527 B2 | 5/2013 | Scott et al. |
| 8,546,579 B2 | 10/2013 | Kelly |
| 8,642,660 B2 | 2/2014 | Goldfarb |
| 8,722,851 B2 | 5/2014 | Wang et al. |
| 8,906,900 B2 | 12/2014 | Duncan et al. |
| 8,940,726 B2 | 1/2015 | Duncan et al. |
| 8,952,026 B2 | 2/2015 | Mitchell et al. |
| 8,993,555 B2 | 3/2015 | Duncan et al. |
| 9,023,883 B2 | 5/2015 | Kuntz et al. |
| 9,045,455 B2 | 6/2015 | Mitchell et al. |
| 9,120,757 B2 | 9/2015 | Chesworth et al. |
| 9,133,189 B2 | 9/2015 | Chesworth et al. |
| 9,221,794 B2 | 12/2015 | Duncan et al. |
| 9,266,836 B2 | 2/2016 | Duncan et al. |
| 9,346,761 B2 | 5/2016 | Chesworth et al. |
| 9,346,802 B2 | 5/2016 | Chesworth et al. |
| 9,354,223 B2 | 5/2016 | Wang et al. |
| 9,365,519 B2 | 6/2016 | Duncan et al. |
| 9,365,527 B2 | 6/2016 | Chesworth et al. |
| 9,365,555 B2 | 6/2016 | Duncan et al. |
| 9,388,173 B2 | 7/2016 | Duncan et al. |
| 9,394,258 B2 | 7/2016 | Chesworth et al. |
| 9,440,950 B2 | 9/2016 | Mitchell et al. |
| 9,447,079 B2 | 9/2016 | Mitchell et al. |
| 9,475,776 B2 | 10/2016 | Kuntz et al. |
| 9,598,374 B2 | 3/2017 | Chesworth et al. |
| 9,604,930 B2 | 3/2017 | Duncan et al. |
| 9,611,257 B2 | 4/2017 | Duncan et al. |
| 9,630,961 B2 | 4/2017 | Chesworth et al. |
| 9,675,614 B2 | 6/2017 | Duncan et al. |
| 9,718,816 B2 | 8/2017 | Chesworth et al. |
| 9,724,332 B2 | 8/2017 | Chesworth et al. |
| 9,732,041 B2 | 8/2017 | Chesworth et al. |
| 9,732,072 B2 | 8/2017 | Duncan et al. |
| 9,745,291 B2 | 8/2017 | Duncan et al. |
| 9,765,035 B2 | 9/2017 | Chesworth et al. |
| 9,765,068 B2 | 9/2017 | Duncan et al. |
| 9,776,972 B2 | 10/2017 | Chesworth et al. |
| 9,777,008 B2 | 10/2017 | Duncan et al. |
| 9,856,267 B2 | 1/2018 | Chesworth et al. |
| 9,868,703 B2 | 1/2018 | Kuntz et al. |
| 9,884,846 B2 | 2/2018 | Clark |
| 9,908,887 B2 | 3/2018 | Duncan et al. |
| 9,943,504 B2 | 4/2018 | Chesworth et al. |
| 9,981,948 B2 | 5/2018 | Clark |
| 10,039,748 B2 | 8/2018 | Mitchell et al. |
| 10,081,603 B2 | 9/2018 | Chesworth et al. |
| 10,118,931 B2 | 11/2018 | Chesworth et al. |
| 10,150,758 B2 | 12/2018 | Duncan et al. |
| 2002/0169101 A1 | 11/2002 | Gonzalez et al. |
| 2003/0130280 A1 | 7/2003 | O'Farrell et al. |
| 2005/0124001 A1 | 6/2005 | Coats et al. |
| 2005/0154202 A1 | 7/2005 | Hagmann et al. |
| 2005/0239790 A1 | 10/2005 | John et al. |
| 2006/0009510 A1 | 1/2006 | Havens et al. |
| 2007/0004695 A1 | 1/2007 | Fink et al. |
| 2007/0010526 A1 | 1/2007 | Haeberlein et al. |
| 2007/0185152 A1 | 8/2007 | Yamashita et al. |
| 2007/0203124 A1 | 8/2007 | Keenan et al. |
| 2009/0093493 A1 | 4/2009 | Berardi et al. |
| 2009/0176776 A1 | 7/2009 | Prevelige |
| 2010/0048590 A1 | 2/2010 | Gailunas et al. |
| 2010/0093865 A1 | 4/2010 | Scott et al. |
| 2010/0113539 A1 | 5/2010 | Scott et al. |
| 2010/0222304 A1 | 9/2010 | Chiang et al. |
| 2011/0009420 A1 | 1/2011 | Andersen |
| 2011/0178123 A1 | 7/2011 | Ghosh |
| 2012/0014968 A1 | 1/2012 | Walsh et al. |
| 2012/0277232 A1 | 11/2012 | Baettig et al. |
| 2013/0158019 A1 | 6/2013 | Bryan et al. |
| 2014/0213582 A1 | 7/2014 | Duncan et al. |
| 2014/0221345 A1 | 8/2014 | Duncan et al. |
| 2014/0228343 A1 | 8/2014 | Duncan et al. |
| 2014/0228360 A1 | 8/2014 | Duncan et al. |
| 2014/0329794 A1 | 11/2014 | Duncan et al. |
| 2015/0133427 A1 | 5/2015 | Duncan et al. |
| 2015/0191432 A1 | 7/2015 | Duncan et al. |
| 2015/0252031 A1 | 9/2015 | Duncan et al. |
| 2015/0344433 A1 | 12/2015 | Duncan et al. |
| 2015/0344434 A1 | 12/2015 | Duncan et al. |
| 2015/0344457 A1 | 12/2015 | Duncan et al. |
| 2015/0344463 A1 | 12/2015 | Duncan et al. |
| 2015/0361042 A1 | 12/2015 | Duncan et al. |
| 2016/0031839 A1 | 2/2016 | Chesworth et al. |
| 2016/0039767 A1 | 2/2016 | Mitchell et al. |
| 2016/0039834 A1 | 2/2016 | Chesworth et al. |
| 2016/0137609 A1 | 5/2016 | Chesworth et al. |
| 2016/0137631 A1 | 5/2016 | Duncan et al. |
| 2016/0214985 A1 | 7/2016 | Duncan et al. |
| 2016/0368907 A1 | 12/2016 | Duncan et al. |
| 2017/0027935 A1 | 2/2017 | Duncan et al. |
| 2017/0056409 A1 | 3/2017 | Chesworth et al. |
| 2017/0057926 A1 | 3/2017 | Chesworth et al. |
| 2017/0088529 A1 | 3/2017 | Chesworth et al. |
| 2017/0088541 A1 | 3/2017 | Duncan et al. |
| 2017/0114061 A1 | 4/2017 | Duncan et al. |
| 2017/0119735 A1 | 5/2017 | Chesworth et al. |
| 2017/0182005 A1 | 6/2017 | Mitchell et al. |
| 2017/0198006 A1 | 7/2017 | Duncan et al. |
| 2017/0210751 A1 | 7/2017 | Duncan et al. |
| 2017/0224685 A1 | 8/2017 | Duncan et al. |
| 2017/0233347 A1 | 8/2017 | Kuntz et al. |
| 2017/0240537 A1 | 8/2017 | Duncan et al. |
| 2017/0267642 A1 | 9/2017 | Chesworth et al. |
| 2017/0280720 A1 | 10/2017 | Chesworth et al. |
| 2017/0283400 A1 | 10/2017 | Mitchell et al. |
| 2017/0283440 A1 | 10/2017 | Chesworth et al. |
| 2017/0291905 A1 | 10/2017 | Chesworth et al. |
| 2017/0298073 A1 | 10/2017 | Olhava et al. |
| 2017/0334861 A1 | 11/2017 | Duncan et al. |
| 2018/0105497 A1 | 4/2018 | Chesworth et al. |
| 2018/0162847 A1 | 6/2018 | Duncan et al. |
| 2018/0186798 A1 | 7/2018 | Duncan et al. |
| 2018/0237397 A1 | 8/2018 | Chesworth et al. |
| 2018/0265478 A1 | 9/2018 | Kuntz et al. |
| 2018/0289671 A1 | 10/2018 | Chesworth et al. |
| 2018/0290982 A1 | 10/2018 | Chesworth et al. |
| 2018/0298010 A1 | 10/2018 | Duncan et al. |
| 2018/0303822 A1 | 10/2018 | Duncan et al. |

FOREIGN PATENT DOCUMENTS

| | | |
|---|---|---|
| CN | 101 012 223 A | 8/2007 |
| DE | 63776 A | 9/1968 |
| DE | 68906 A | 9/1969 |
| EP | 2409977 A1 | 1/2012 |
| WO | WO 91/13865 A1 | 9/1991 |
| WO | WO 93/01174 A1 | 1/1993 |
| WO | WO 94/01408 A1 | 1/1994 |
| WO | WO 95/11680 A1 | 5/1995 |
| WO | WO 01/19821 A1 | 3/2001 |
| WO | WO 01/19833 A1 | 3/2001 |
| WO | WO 02/14277 A1 | 2/2002 |
| WO | WO 2004/022558 A2 | 3/2004 |
| WO | WO 2004/060882 A1 | 7/2004 |

(56) References Cited

FOREIGN PATENT DOCUMENTS

| | | |
|---|---|---|
| WO | WO 2004/078114 A2 | 9/2004 |
| WO | WO 2005/118543 A1 | 12/2005 |
| WO | WO 2007/015805 A1 | 2/2007 |
| WO | WO 2007/087572 A2 | 8/2007 |
| WO | WO 2008/100621 A2 | 8/2008 |
| WO | WO 2008/104077 A1 | 9/2008 |
| WO | WO 2008/145398 A1 | 12/2008 |
| WO | WO 2010/057101 A2 | 5/2010 |
| WO | WO 2011/077133 A2 | 6/2011 |
| WO | WO 2011/079236 A1 | 6/2011 |
| WO | WO 2012/051692 A1 | 4/2012 |
| WO | WO 2013/038378 A1 | 3/2013 |
| WO | WO 2013/038381 A1 | 3/2013 |
| WO | WO 2013/071697 A1 | 5/2013 |
| WO | WO 2013/098416 A2 | 7/2013 |
| WO | WO 2014/048547 A1 | 4/2014 |
| WO | WO 2014/100695 A1 | 6/2014 |
| WO | WO 2014/100716 A1 | 6/2014 |
| WO | WO 2014/100719 A1 | 6/2014 |
| WO | WO 2014/100730 A1 | 6/2014 |
| WO | WO 2014/100734 A1 | 6/2014 |
| WO | WO 2014/100764 A1 | 6/2014 |
| WO | WO 2014/144169 A1 | 9/2014 |
| WO | WO 2014/144455 A1 | 9/2014 |
| WO | WO 2014/144659 A1 | 9/2014 |
| WO | WO 2014/153090 A1 | 9/2014 |
| WO | WO 2014/153100 A1 | 9/2014 |
| WO | WO 2014/153172 A1 | 9/2014 |
| WO | WO 2014/153208 A1 | 9/2014 |
| WO | WO 2014/153214 A1 | 9/2014 |
| WO | WO 2014/153226 A1 | 9/2014 |
| WO | WO 2014/153235 A1 | 9/2014 |
| WO | WO 2014/178954 A1 | 11/2014 |
| WO | WO 2015/200677 A1 | 12/2015 |
| WO | WO 2015/200680 A1 | 12/2015 |
| WO | WO 2016/022605 A1 | 2/2016 |
| WO | WO 2016/044556 A2 | 3/2016 |
| WO | WO 2016/044569 A1 | 3/2016 |
| WO | WO 2016/044576 A1 | 3/2016 |
| WO | WO 2016/044585 A1 | 3/2016 |
| WO | WO 2016/044604 A1 | 3/2016 |
| WO | WO 2016/044626 A1 | 3/2016 |
| WO | WO 2016/044641 A2 | 3/2016 |
| WO | WO 2016/044650 A1 | 3/2016 |
| WO | WO 2017/136699 A1 | 8/2017 |

OTHER PUBLICATIONS

Carey, F. Organic Chemistry NY McGraw-Hill 2000, p. G-2.*
Collins et al., Macrocyclizations for medicinal chemistry: synthesis of druglike macrocycles by high-concentration Ullmann coupling. J Org Chem. Dec. 21, 2012;77(24):11079-90. doi: 10.1021/jo302089f. Epub Dec. 6, 2012. PubMed PMID: 23167628.
Feki et al., Mutational spectrum of p53 mutations in primary breast and ovarian tumors. Crit Rev Oncol Hematol. Nov. 2004;52(2):103-16.
Iida et al., 1.Total synthesis of .+-.-isocyclocelabenzene. J Org Chem. 1986;51(24):4701-4703. DOI: 10.1021/jo00374a035.
Li et al., Novel peptidyl alpha-keto amide inhibitors of calpains and other cysteine proteases. J Med Chem. Sep. 27, 1996;39(20):4089-98. PubMed PMID: 8831774.
Mokrosz et al., 1,2,3,4-tetrahydroisoquinoline derivatives: a new class of 5-HT1A receptor ligands. Bioorg Med Chem. Feb. 1999;7(2):287-95. PubMed PMID: 10218820.
Rödicker et al., p73 is effective in p53-null pancreatic cancer cells resistant to wild-type TP53 gene replacement. Cancer Res. Jun. 1, 2003;63(11):2737-41.
Schultz et al., Total Synthesis of the Spermidine Alkaloid (+)-(9S,13S)-Isocyclocelabenzine. Tetrahedron. Nov. 1996;52(45):14189-14198. doi:10.1016/0040-4020(96)00872-1.
CAS Registry Nos. 1390524-87-4, 1390490-16-0, 1390364-38-1, 1390262-63-1, 1389804-10-7, 1389608-63-2, 1389477-08-0, 1389191-79-0, 1389186-88-2, 1389150-41-7, 1389143-93-4, 1389138-17-3, 1388976-86-0, 1388976-44-0, 1388908-64-2, 1388701-97-0, 1388690-94-5, 1388642-81-6, 1388576-16-6, 1388555-08-5, 1388432-00-5, 1388397-52-1, 1388369-92-3, 1388367-52-9, 1387845-06-8, 1387782-64-0, 1387456-55-4, 1387169-74-5, 1387110-73-7, 1387108-14-6, 1386827-14-0, 1386608-97-4, 1386280-12-1, 1386280-07-4, 1386148-41-9, 1386010-87-2, 1322579-97-4, 1322145-39-0, 1321571-71-4, 1320022-45-4, 1320021-13-3, 1319342-38-5, 1319121-25-9, 1319002-83-9, 1318997-32-8, 1318913-98-2, 1318883-46-3, 1318644-07-3, 1317982-41-4, 1317968-41-4, 1317886-59-1, 1317589-67-5, 1317515-43-7, 1317334-82-9, 1316369-94-4, 1316197-59-7, 1302193-68-5, 1288518-05-7, 1281089-87-9, 1280921-87-0, 1223357-53-6, 1223349-33-4, 1223239-90-4, 1223228-05-4, 1223214-63-8, 1222970-06-0, 1211677-43-8, 1208850-42-3, 1197943-03-5, 1197564-92-3, 1181543-32-7, 1147700-86-4, 1147642-86-1, 1445676-20-9, 1445676-11-8, 1445163-85-8, 1444874-40-1, 1444830-50-5, 1444828-93-6, 1444693-38-2, 1444637-79-9, 1436034-24-0, 1427932-67-9, 1385797-51-2, 1385797-47-6, and 1385614-49-2. 53 pages.
Havelek et al., The effect of Amaryllidaceae alkaloids haemanthamine and haemanthidine on cell cycle progression and apoptosis in p53-negative human leukemic Jurkat cells. Phytomedicine. Mar. 15, 2014;21(4):479-90. doi: 10.1016/j.phymed.2013.09.005. Epub Oct. 29, 2013.
International Search Report and Written Opinion for International Application No. PCT/US2013/077151 dated Jun. 2, 2014.
International Search Report and Written Opinion for International Application No. PCT/US2013/077221 dated Apr. 30, 2014.
International Search Report and Written Opinion for International Application No. PCT/US2013/077235 dated Jun. 16, 2014.
International Search Report and Written Opinion for International Application No. PCT/U52013/077250 dated May 16, 2014.
International Search Report and Written Opinion for International Application No. PCT/US2013/077308 dated Aug. 7, 2014.
International Search Report and Written Opinion for International Application No. PCT/US2013/077256 dated Apr. 14, 2014.
International Search Report and Written Opinion for International Application No. PCT/US2015/037759 dated Jan. 11, 2016.
International Search Report and Written Opinion for International Application No. PCT/US2015/037768 dated Jan. 11, 2016.
International Search Report and Written Opinion for International Application No. PCT/US2015/043679 dated Nov. 24, 2015.
Notice of Opposition for Chilean Application No. CL 01790-2015 dated Feb. 9, 2016.
[No Author Listed], Cancer [online], [retrieved on Jul. 6, 2007]. Medline Plus. Retrieved from the internet, URL www.nlm.nih.gov/medlineplus/cancer.html. 10 pages.
[No Author Listed], Cancer [online], [retrieved on Jul. 6, 2007]. Wikipedia. Retrieved from the internet, URL http://en.wikipedia.org/wiki/Cancer. 2 pages.
[No Author Listed], EnamineStore, 1 page retrieved from the Internet athttp://www.enamine.net/index.php?option=com_content&task=view&id=22. Accessed Apr. 13, 2015.
Abate et al., Arylamides hybrids of two high-affinity σ2 receptor ligands as tools for the development of PET radiotracers. Eur J Med Chem. Sep. 2011;46(9):4733-41. doi: 10.1016/j.ejmech.2011.05.057.
Aggarwal et al., Nuclear cyclin D1/CDK4 kinase regulates CUL4 expression and triggers neoplastic growth via activation of the PRMT5 methyltransferase. Cancer Cell. Oct. 19, 2010;18(4):329-40. doi: 10.1016/j.ccr.2010.08.012.
Andreu-Pérez et al., Protein arginine methyltransferase 5 regulates ERK1/2 signal transduction amplitude and cell fate through CRAF. Sci Signal. Sep, 13, 2011;4(190):ra58. doi: 10.1126/scisignal.2001936.
Ando et al., Discrimination of p53 immunohistochemistry-positive tumors by its staining pattern in gastric cancer. Cancer Med. Jan. 2015;4(1):75-83. doi: 10.1002/cam4.346. Epub Oct. 30, 2014.
Antonysamy et al., Crystal structure of the human PRMT5:MEP50 complex. Proc Natl Acad Sci U S A. Oct. 30, 2012;109(44):17960-5. doi: 10.1073/pnas.1209814109. Epub Oct. 15, 2012.

(56) References Cited

OTHER PUBLICATIONS

Bandyopadhyay et al., HOXA9 methylation by PRMT5 is essential for endothelial cell expression of leukocyte adhesion molecules. Mol Cell Biol. Apr. 2012;32(7):1202-13. doi: 10.1128/MCB.05977-11. Epub Jan. 23, 2012.
Bao et al., Overexpression of PRMT5 Promotes Tumor Growth and is Associated with Poor Disease Prognosis in Epithelial Ovarian Cancer. J Histochem Cytochem. Mar. 2013;61(3):206-17. doi: 10.1369/0022155413475452. Epub Jan. 4, 2013.
Bergmann et al., Synthesis and structure-activity relationship of some new β-blocking agents with possible α-adrenoreceptor activity. Arch Pharm. 1990;323:387-91.
Bezzi et al., Regulation of constitutive and alternative splicing by PRMT5 reveals a role for Mdm4 pre-mRNA in sensing defects in the spliceosomal machinery. Genes Dev. Sep. 1, 2013;27(17):1903-16. doi: 10.1101/gad.219899.113.
Brown et al., Receptor binding sites of hypoglycemic sulfonylureas and related [(acylamino)alkyl]benzoic acids. J Med Chem. Jan. 1984;27(1):79-81.
CA Registry No. 1301253-27-9, entered into CA Registry File on May 26, 2011, supplied by FCH Group.
Camp et al., Adipogenesis and fat-cell function in obesity and diabetes. Trends Mol Med. Sep. 2002;8(9):442-7.
CAPLUS Accesion No. 2000:487675. 4 pages.
CAPLUS Accesion No. 2009:1302026. 1 page. Korotkii et al., Synthesis and antimicrobial activity of 1-[4-(1-adamantyl)phenoxy]-3-amino-2-propanol. Pharma Chem J. 2009;43(6):301-4. Abstract.
CAPLUS Accesion No. 2010:485537. Prytula et al., Synthesis and spasmolytic activity of (di)hydrochlorides and quaternary salts of some adamantyl-containing derivatives of 1-alkoxy-3-dialkylamino-2-propanol. Zhurnal Organichnoi ta Farmatsevtichnoi Khimii. 2010;8(1):25-9. Abstract.
Carey, Organic Chemisry. NY McGraw-Hill 2000 p. G-2.
CAS Registry No. 923141-67-7. Feb. 26, 2007. 1 page.
CAS Registry No. 1008707-00-3. Mar. 18, 2008. 1 page.
CAS Registry No. 1022648-78-7. May 26, 2008. 1 page.
CAS Registry No. 1023185-95-6. May 28, 2008. 1 page.
CAS Registry No. 1119379-87-1. Mar. 12, 2009. 1 page.
CAS Registry No. 1181543-32-7. Sep. 9, 2009. 1 page.
CAS Registry No. 1208850-42-3. Mar. 11, 2010. 1 page.
CAS Registry No. 1211677-43-8. Mar. 19, 2010. 1 page.
CAS Registry No. 1222970-06-0. May 13, 2010. 1 page.
CAS Registry No. 1240952-30-0. Sep. 14, 2010. 1 page.
CAS Registry No. 1252266-42-4. Nov. 10, 2010. 1 page.
CAS Registry No. 1277113-61-7. Apr. 8, 2011. 1 page.
CAS Registry No. 1278970-87-8. Apr. 12, 2011. 1 page.
CAS Registry No. 1284717-34-5. Apr. 24, 2011. 1 page.
CAS Registry No. 1288518-05-7. May 1, 2011. 1 page.
CAS Registry No. 1299664-19-9. May 24, 2011. 1 page.
CAS Registry No. 1302193-68-5. May 29, 2011. 1 page.
CAS Registry No. 1316197-59-7. Aug. 11, 2011. 1 page.
CAS Registry No. 1316369-94-4. Aug. 12, 2011. 1 page.
CAS Registry No. 1317245-22-9. Aug. 14, 2011. 1 page.
CAS Registry No. 1318219-96-3. Aug. 15, 2011. 1 page.
CAS Registry No. 1318644-07-3. Aug. 16, 2011. 1 page.
CAS Registry No. 1319342-38-5. Aug. 18, 2011. 1 page.
CAS Registry No. 1319931-54-8. Aug. 19, 2011. 1 page.
CAS Registry No. 1321571-71-4. Aug. 22, 2011. 1 page.
CAS Registry No. 1322145-39-0. Aug. 23, 2011. 1 page.
CAS Registry No. 1322579-97-4. Aug. 24, 2011. 1 page.
CAS Registry No. 1330937-75-1. Sep. 11, 2011. 1 page.
CAS Registry No. 1347256-93-2. Dec. 2, 2011. 1 page.
CAS Registry No. 1348874-66-7. Dec. 5, 2011. 1 page.
CAS Registry No. 1349512-40-8. Dec. 6, 2011. 1 page.
CAS Registry No. 1350276-64-0. Dec. 7, 2011. 1 page.
CAS Registry No. 1355706-85-2. Feb. 7, 2012. 1 page.
CAS Registry No. 1356778-99-8. Feb. 14, 2012. 1 page.
CAS Registry No. 1372312-69-0. May 2, 2012. 1 page.
CAS Registry No. 1376006-97-1. Jun. 7, 2012. 1 page.
CAS Registry No. 1410908-63-2. Dec. 4, 2012. 1 page.
CAS Registry No. 1424333-72-1. Mar. 15, 2013. 1 page. Supplied by Enamine Chemical Library.
CAS Registry No. 1424365-18-3. Mar. 15, 2013. 1 page.
CAS Registry No. 1424444-20-1. Mar. 17, 2013. 1 page.
CAS Registry No. 1424524-36-6. Mar. 17, 2013. 1 page.
CAS Registry No. 1427932-67-9. Apr. 11, 2013. 1 page.
CAS Registry No. 1428095-08-2. Apr. 11, 2013. 1 page.
CAS Registry No. 1436034-24-0. Jun. 9, 2013. 1 page.
CAS Registry No. 1444031-91-7. Jul. 15, 2013. 1 page.
CAS Registry No. 1444637-79-9. Jul. 16, 2013. 1 page.
CAS Registry No. 1444638-11-2. Jul. 16, 2013. 1 page.
CAS Registry No. 1445155-97-4. Jul. 17, 2013. 1 page.
CAS Registry No. 1445348-70-8. Jul. 18, 2013. 1 page.
CAS Registry No. 1455081-19-2. Oct. 4, 2013. 1 page.
CAS Registry No. 1455191-29-3. Oct. 4, 2013. 1 page.
CAS Registry No. 1456315-86-8. Oct. 6, 2013. 1 page.
CAS Registry No. 1479608-80-4. Nov. 24, 2013. 1 page.
CAS Registry No. 155083-65-1. May 17, 1994. 1 page.
CAS Registry No. 2002:142672. Compound 400726-94-5. Mar. 13, 2002.
CAS Registry No. 261164-91-4. Apr. 6, 2000. 1 page.
CAS Registry No. 524721-03-7. Jun. 3, 2003. 1 page.
CAS Registry No. 717121-35-2. Jul. 27, 2004. 1 page.
CAS Registry No. 737696-45-6. Sep. 2, 2004. 1 page.
CAS Registry No. 770646-48-5. Oct. 27, 2004. 1 page.
CAS Registry No. 801197-71-7. Dec. 22, 2004. 1 page.
CAS Registry No. 802313-31-1. Dec. 25, 2004. 1 page.
CAS Registry No. 802601-62-3. Dec. 26, 2004. 1 page.
CAS Registry No. 803623-34-9. Dec. 27, 2004. 1 page.
CAS Registry No. 848051-57-0. Apr. 7, 2005. 1 page.
CAS Registry No. 886136-98-7. May 31, 2006. 1 page.
CAS Registry No. 913503-11-4. Nov. 17, 2006. 1 page.
CAS Registry Nos. 1005082-40-5; 1005067-47-9. Feb. 22, 2008. 2 pages.
CAS Registry Nos. 1049761-31-0; 1049760-28-2. Sep. 17, 2008. 2 pages.
CAS Registry Nos. 1060402-35-8; 1060400-38-5; 1060393-44-3; 1060386-32-4. Oct. 13, 2008. 3 pages.
CAS Registry Nos. 1060542-64-4; 1060516-49-5; 1060507-45-0. Oct. 13, 2008. 2 pages.
CAS Registry Nos. 1061124-54-6; 1061056-39-0; 1061053-40-4. Oct. 14, 2008. 2 pages.
CAS Registry Nos. 1065507-26-7; 1065489-20-4. Oct. 24, 2008. 1 page.
CAS Registry Nos. 1066959-19-0; 1066956-31-7; 1066945-12-7; 1066929-96-1; 1066909-51-0; 1066881-34-2. Oct. 27, 2008. 3 pages.
CAS Registry Nos. 1067029-15-5; 1067022-11-0; 1067018-55-6; 1067015-90-0. Oct. 27, 2008. 2 pages.
CAS Registry Nos. 1069781-86-7; 1069771-01-2; 1069759-22-3; 1069751-87-6; 1069743-52-7. Nov. 2, 2008. 3 pages.
CAS Registry Nos. 1069895-07-3; 1069893-60-2; 1069891-30-0; 1069888-39-6. Nov. 2, 2008. 2 pages.
CAS Registry Nos. 1069906-08-6; 1069902-26-6; 1069901-02-5; 1069900-62-4; 1069899-08-6; 1069897-82-0. Nov. 2, 2008. 3 pages.
CAS Registry Nos. 1070344-15-8; 1070324-71-8; 1070322-58-5; 1070314-79-2; 1070296-71-7; 1070290-15-1; 1070285-19-6; 1070262-09-7. Nov. 3, 2008. 5 pages.
CAS Registry Nos. 1147700-86-4; 1147642-86-1. May 20, 2009. 1 page.
CAS Registry Nos. 1185407-05-09; 1185405-44-0; 1185390-39-9; 1185381-01-4. Sep. 17, 2009. 2 pages.
CAS Registry Nos. 1197943-03-5; 1197564-92-3. Dec. 16, 2009. 1 page.
CAS Registry Nos. 1203413-85-7; 1203375-38-5; 1203348-04-2; 1203233-98-0; 1203173-19-6; 1203162-75-7; 1203144-35-7. 1203022-51-8. Jan. 24, 2010. 5 pages.
CAS Registry Nos. 1212367-31-1; 1212317-85-5; 1212316-36-3; 1212282-83-1; 1212276-27-1; 1212239-64-9. Mar. 21, 2010. 3 pages.
CAS Registry Nos. 1217840-37-3; 1217668-16-0; 1217666-80-2; 1217653-64-9; 1217620-01-3. Apr. 9, 2010. 3 pages.

(56) References Cited

OTHER PUBLICATIONS

CAS Registry Nos. 1223357-53-6; 1223349-33-4; 1223239-90-4; 1223228-05-4; 1223214-63- 8. May 14, 2010. 2 pages.
CAS Registry Nos. 1241440-76-5; 1241250-19-0; 1241247-75-5; 1241156-35-3; 1241132-96-6; 1241132-91-1; 1241070-46-1; 1241070-44-9. Sep. 15, 2010. 4 pages.
CAS Registry Nos. 1252106-10-7; 1252099-82-3. Nov. 9, 2010. 1 page.
CAS Registry Nos. 1281089-87-9; 1280921-87-0. Apr. 17, 2011. 1 page.
CAS Registry Nos. 1288640-51-6; 1288640-50-5. May 1 , 2011. 1 page.
CAS Registry Nos. 1289351-04-7; 1289351-03-6. May 3, 2011. 1 page.
CAS Registry Nos. 1317589-67-5; 1317515-43-7; 1317334-82-9. Aug. 14, 2011. 2 pages.
CAS Registry Nos. 1317982-41-4; 1317968-41-4; 1317886-59-1. Aug. 15, 2011. 2 pages.
CAS Registry Nos. 1319121-25-9; 1319002-83-9; 1318997-32-8; 1318913-98-2; 1318883-46-3. Aug. 17, 2011. 3 pages.
CAS Registry Nos. 1320022-45-4; 1320021-13-3. Aug. 19, 2011. 1 page.
CAS Registry Nos. 1347539-89-2; 1347519-58-7; 1347361-44-7. Dec. 2, 2011. 3 pages.
CAS Registry Nos. 1355607-64-5; 1355578-94-7; 1355493-36-5. Feb. 7, 2012. 2 pages.
CAS Registry Nos. 1355914-92-9; 1355898-02-0. Feb. 8, 2012. 1 page.
CAS Registry Nos. 1371104-82-3; 1370816-34-4. Apr. 29, 2012. 1 page.
CAS Registry Nos. 1371555-26-8; 1371490-72-0; 1371483-54-3; 1371446-47-7; 1371346-43-8; 1371223-53-8. Apr. 30, 2012. 3 pages.
CAS Registry Nos. 1372108-95-6; 1372054-69-7. May 1, 2012. 1 page.
CAS Registry Nos. 1385588-44-2; 1385478-31-8. Aug. 2, 2012. 1 page.
CAS Registry Nos. 1385797-51-2; 1385797-47-6; 1385614-49-2. Aug. 2, 2012. 2 pages.
CAS Registry Nos. 1386280-12-1; 1386280-07-4; 1386148-41-9; 1386010-87-2. Aug. 3, 2012. 2 pages.
CAS Registry Nos. 1386827-14-0; 1386608-97-4. Aug. 6, 2012. 1 page.
CAS Registry Nos. 1387169-01-8; 1387167-55-6. Aug. 7, 2012. 1 page.
CAS Registry Nos. 1387456-55-4; 1387169-74-5; 1387110-73-7; 1387108-14-6. Aug. 7, 2012. 2 pages.
CAS Registry Nos. 1387845-06-8; 1387782-64-0. Aug. 8, 2012. 1 page.
CAS Registry Nos. 1388292-84-9; 1388292-67-8; 1388292-58-7. Aug. 9, 2012. 1 page.
CAS Registry Nos. 1388701-97-0; 1388690-94-5; 1388642-81-6; 1388576-16-6; 1388555-08-5; 1388432-00-5; 1388397-52-1; 1388369-92-3; 1388367-52-9. Aug. 9, 2012. 4 pages.
CAS Registry Nos. 1389150-41-7; 1389143-93-4; 1389138-17-3; 1388976-86-0; 1388976-44-0; 1388908-64-2. Aug. 12, 2012. 3 pages.
CAS Registry Nos. 1389191-79-0; 1389186-88-2. Aug. 10, 2012. 1 page.
CAS Registry Nos. 1389775-53-4; 1389743-08-01; 1389743-01-04. Aug. 12, 2012. 2 pages.
CAS Registry Nos. 1390079-59-0; 1390053-83-4; 1390037-12-3. Aug. 12, 2012. 1 page.
CAS Registry Nos. 1390262-63-1; 1389804-10-7; 1389608-63-2; 1389477-08-0. Aug. 12, 2012. 2 pages.
CAS Registry Nos. 1390485-95-6; 1390470-75-3; 1390466-88-2; 1390428-89-3. Aug. 13, 2012. 1 page.
CAS Registry Nos. 1390524-87-4,; 1390490-16-0; 1390364-38-1. Aug. 13, 2012. 2 pages.
CAS Registry Nos. 1394703-31-1; 1394698-39-5. Sep. 18, 2012. 1 page.
CAS Registry Nos. 1445163-85-8; 1444874-40-1; 1444830-50-5; 1444828-93-6; 1444693-38-2. Jul. 17, 2013. 3 pages.
CAS Registry Nos. 1445676-20-9; 1445676-11-8. Jul. 19, 2013. 1 page.
CAS Registry Nos. 958982-78-0; 958964-27-7. Dec. 20, 2007. 1 page.
CAS Registry Nos. 958563-68-3. Dec. 18, 2007.
Chimenti et al., Sintesi di Isoindoline N-Sostituite. Il Farmaco, Elsevier France. Scientifiques et Medicales, IT. Jan. 1974;30:884-90. French.
Cho et al., Arginine methylation controls growth regulation by E2F-1. EMBO J. Apr. 4, 2012;31(7):1785-97. doi: 10.1038/emboj.2012.17. Epub Feb. 10, 2012.
FCH Group Product Guide, 1 page, retrieved from the Internet at http://fchgroup.net/products.php on Apr. 5, 2014.
Fontan et al., Novel symmetrical ureas as modulators of protein arginine methyl transferases. Bioorg Med Chem. Apr. 1, 2013;21(7):2056-67. doi: 10.1016/j.bmc.2013.01.017. Epub Jan. 22, 2013.
Golub et al., Molecular classification of cancer: class discovery and class prediction by gene expression monitoring. Science. Oct. 15, 1999;286(5439):531-7.
Gu et al., Protein arginine methyltransferase 5 functions in opposite ways in the cytoplasm and nucleus of prostate cancer cells. PLoS One. 2012;7(8):e44033. doi: 10.1371/journal.pone.0044033. Epub Aug. 27, 2012.
Gu et al., Protein arginine methyltransferase 5 is essential for growth of lung cancer cells. Biochem J. Sep. 1, 2012;446(2):235-41. doi: 10.1042/BJ20120768.
Gunawan et al., Synthesis of Tetrazolo-Fused Benzodiazepines and Benzodiazepinones by a Two-Step Protocol Using an Ugi-Azide Reaction for Initial Diversity Generation. Tetrahedron. Jul. 8, 2012;68(27-28):5606-11. Epub Apr. 26, 2012.
Hawley's Condensed Chemical Dictionary. Excerpt "aliphatic". Online pub Mar. 2007.
Heidenbluth et al., Document No. 70:87572, retrieved from CAPLUS; Jan. 1, 1969.
Heidenbluth et al., Document No. 72:90279, retrieved from CAPLUS; Sep. 20, 1969.
Jansson et al., Arginine methylation regulates the p53 response. Nat Cell Biol. Dec. 2008;10(12):1431-9. doi: 10.1038/ncb1802. Epub Nov. 16, 2008.
Labaff, EZH2 T416 Phosphorylation Enhances Breast Cancer Tumorigenesis. Abstract. Dec. 2013.
Labrie et al., In vitro activity of novel dual action MDR anthranilamide modulators with inhibitory activity at CYP-450. Bioorg Med Chem. Dec. 1, 2006;14(23):7972-87. Epub Aug. 10, 2006.
Lala et al., Role of nitric oxide in tumor progression: lessons from experimental tumors. Cancer Metastasis Rev. Mar. 1998;17(1):91-106.
Leblanc et al., Protein arginine methyltransferase 5 (Prmt5) promotes gene expression of peroxisome proliferator-activated receptor γ2 (PPARγ2) and its target genes during adipogenesis. Mol Endocrinol. Apr. 2012;26(4):583-97. doi: 10.1210/me.2011-1162. Epub Feb. 23, 2012.
Maeda et al., Mechanism of the chemiluminescence of biisoquinolinium salts. J Chem Soc. Perkin 2. 1996;1:121-6.
Mu et al., p53 protein expression and CA19.9 values in differential cytological diagnosis of pancreatic cancer complicated with chronic pancreatitis and chronic pancreatitis. World J Gastroenterol. Aug. 2003;9(8):1815-8.
Nigro et al., Mutations in the p53 gene occur in diverse human tumour types. Nature. Dec. 7, 1989;342(6250):705-8.
Pal et al., Low levels of miR-92b/96 induce PRMT5 translation and H3R8/H4R3 methylation in mantle cell lymphoma. EMBO J. Aug. 8, 2007;26(15):3558-69. Epub Jul. 12, 2007.
PUBCHEM Submission; NIH/NCBI, Substance Identifier 103937775. BindingDB. Jan. 19, 2011. 5 pages.
PUBCHEM Submission; NIH/NCBI, Substance Identifier 107215563. AKos Consulting & Solutions. Feb. 22, 2011. 6 pages.

(56) References Cited

OTHER PUBLICATIONS

PUBCHEM Submission; NIH/NCBI, Substance Identifier 112367837. ABI Chem. Mar. 10, 2011. 6 pages.
PUBCHEM Submission; NIH/NCBI, Substance Identifier 136894295. Tetrahedron Scientific, Inc. Jul. 18, 2012. 6 pages.
PUBCHEM Submission; NIH/NCBI, Substance Identifier 144940718. AKos Consulting & Solutions. Oct. 18, 2012. 6 pages.
Rank et al., Identification of a PRMT5-dependent repressor complex linked to silencing of human fetal globin gene expression. Blood. Sep. 2, 2010;116(9):1585-92. doi: 10.1182/blood-2009-10-251116. Epub May 21, 2010.
Rhodes et al., Medium Tumor Volume graph. Epizyme 2013 Annual Report. Feb. 28, 2014.
Scoumanne et al., PRMT5 Is Required for Cell-Cycle Progression and P53 Tumor Suppressor Function. Nucleic Acids Res. Aug. 2009;37(15):4965-76. doi: 10.1093/nar/gkp516. Epub Jun. 15, 2009.
Seshadri, Attempts to find new anti-malarials. Part II. Aminoalkylquinolinium salts and some related substances. J Chem Soc. 1929:2952-9.
Silverman, The Organic Chemistry of Drug Design and Drug Action. Elsevier. 2004;29-32.
Smith et al., Epigenomic regulation of bile acid metabolism: emerging role of transcriptional cofactors. Mol Cell Endocrinol. Apr. 10, 2013;368(1-2):59-70. doi: 10.1016/j.mce.2012.04.008. Epub May 9, 2012. Review.
Spannhoff et al., Cancer treatment of the future: inhibitors of histone methyltransferases. Int J Biochem Cell Biol. Jan. 2009;41(1):4-11. doi: 10.1016/j.biocel.2008.07.024. Epub Aug. 14, 2008.
Stopa et al., The PRMT5 arginine methyltransferase: many roles in development, cancer and beyond. Cell Mol Life Sci. Jun. 2015;72(11):2041-59. doi: 10.1007/s00018-015-1847-9. Epub Feb. 7, 2015. Review.
Sun et al., Structural insights into protein arginine symmetric dimethylation by PRMT5. Proc Natl Acad Sci U S A. Dec. 20, 2011;108(51):20538-43. doi: 10.1073/pnas.1106946108. Epub Dec. 5, 2011.
Sunko et al., On the Reaction of alpha-Phthalimidoacid Chlorides with Substituted Sodiomalonates. A Method for the Preparation of alpha-Amino Ketones and Related Compounds. Arhiv Za Kemiju. 1954;26:7-14.
Tae et al., Bromodomain protein 7 interacts with PRMT5 and PRC2, and is involved in transcriptional repression of their target genes. Nucleic Acids Res. Jul. 2011;39(13):5424-38. doi: 10.1093/nar/gkr170. Epub Mar. 29, 2011.
Tanaka et al., PRMT5, a novel TRAIL receptor-binding protein, inhibits TRAIL-induced apoptosis via nuclear factor-kappaB activation. Mol Cancer Res. Apr. 2009;7(4):557-69. doi: 10.1158/1541-7786.MCR-08-0197.
Teng et al., Mutations in the Epidermal Growth Factor Receptor (EGFR) Gene in Triple Negative Breast Cancer: Possible Implications for Targeted Therapy. Abstract. Breast Cancer Research. 2011.
Tsutsui et al., Mediator complex recruits epigenetic regulators via its two cyclin-dependent kinase subunits to repress transcription of immune response genes. J Biol Chem. Jul. 19, 2013;288(29):20955-65. doi: 10.1074/jbc.M113.486746. Epub Jun. 9, 2013.
Wang et al., Protein arginine methyltransferase 5 suppresses the transcription of the RB family of tumor suppressors in leukemia and lymphoma cells. Mol Cell Biol. Oct. 2008;28(20):6262-77. doi: 10.1128/MCB.00923-08. Epub Aug. 11, 2008.
Wei et al., PRMT5 dimethylates R30 of the p65 subunit to activate NF-κB. Proc Natl Acad Sci U S A. Aug. 13, 2013;110(33):13516-21. doi: 10.1073/pnas.1311784110. Epub Jul. 31, 2013.
Wei et al., Protein arginine methyltransferase 5 is a potential oncoprotein that upregulates G1 cyclins/cyclin-dependent kinases and the phosphoinositide 3-kinase/AKT signaling cascade. Cancer Sci. Sep. 2012;103(9):1640-50. doi: 10.1111/j.1349-7006.2012.02367.x. Epub Aug. 8, 2012.
Xu et al., The role of WDR5 in silencing human fetal globin gene expression. Haematologica. Nov. 2012;97(11):1632-40. doi: 10.3324/haematol.2012.061937. Epub Jun. 11, 2012.
Zheng et al., Arginine methylation-dependent reader-writer interplay governs growth control by E2F-1. Mol Cell. Oct. 10, 2013;52(1):37-51. doi: 10.1016/j.molcel.2013.08.039. Epub Sep. 26, 2013.

\* cited by examiner

SEQUENCE LISTING

<160> NUMBER OF SEQ ID NOS: 7

<210> SEQ ID NO 1
<211> LENGTH: 637
<212> TYPE: PRT
<213> ORGANISM: Homo sapiens

<400> SEQUENCE: 1

```
Met Ala Ala Met Ala Val Gly Gly Ala Gly Gly Ser Arg Val Ser Ser
1               5                   10                  15

Gly Arg Asp Leu Asn Cys Val Pro Glu Ile Ala Asp Thr Leu Gly Ala
            20                  25                  30

Val Ala Lys Gln Gly Phe Asp Phe Leu Cys Met Pro Val Phe His Pro
        35                  40                  45

Arg Phe Lys Arg Glu Phe Ile Gln Glu Pro Ala Lys Asn Arg Pro Gly
    50                  55                  60

Pro Gln Thr Arg Ser Asp Leu Leu Ser Gly Arg Asp Trp Asn Thr
65                  70                  75                  80

Leu Ile Val Gly Lys Leu Ser Pro Trp Ile Arg Pro Asp Ser Lys Val
                85                  90                  95

Glu Lys Ile Arg Arg Asn Ser Glu Ala Ala Met Leu Gln Glu Leu Asn
            100                 105                 110

Phe Gly Ala Tyr Leu Gly Leu Pro Ala Phe Leu Leu Pro Leu Asn Gln
        115                 120                 125

Glu Asp Asn Thr Asn Leu Ala Arg Val Leu Thr Asn His Ile His Thr
    130                 135                 140

Gly His His Ser Ser Met Phe Trp Met Arg Val Pro Leu Val Ala Pro
145                 150                 155                 160

Glu Asp Leu Arg Asp Asp Ile Ile Glu Asn Ala Pro Thr Thr His Thr
                165                 170                 175

Glu Glu Tyr Ser Gly Glu Glu Lys Thr Trp Met Trp Trp His Asn Phe
            180                 185                 190

Arg Thr Leu Cys Asp Tyr Ser Lys Arg Ile Ala Val Ala Leu Glu Ile
        195                 200                 205

Gly Ala Asp Leu Pro Ser Asn His Val Ile Asp Arg Trp Leu Gly Glu
    210                 215                 220

Pro Ile Lys Ala Ala Ile Leu Pro Thr Ser Ile Phe Leu Thr Asn Lys
225                 230                 235                 240

Lys Gly Phe Pro Val Leu Ser Lys Met His Gln Arg Leu Ile Phe Arg
                245                 250                 255

Leu Leu Lys Leu Glu Val Gln Phe Ile Ile Thr Gly Thr Asn His His
            260                 265                 270

Ser Glu Lys Glu Phe Cys Ser Tyr Leu Gln Tyr Leu Glu Tyr Leu Ser
        275                 280                 285

Gln Asn Arg Pro Pro Asn Ala Tyr Glu Leu Phe Ala Lys Gly Tyr
    290                 295                 300

Glu Asp Tyr Leu Gln Ser Pro Leu Gln Pro Leu Met Asp Asn Leu Glu
305                 310                 315                 320

Ser Gln Thr Tyr Glu Val Phe Glu Lys Asp Pro Ile Lys Tyr Ser Gln
                325                 330                 335

Tyr Gln Gln Ala Ile Tyr Lys Cys Leu Leu Asp Arg Val Pro Glu Glu
            340                 345                 350

Glu Lys Asp Thr Asn Val Gln Val Leu Met Val Leu Gly Ala Gly Arg
        355                 360                 365
```

-continued

```
Gly Pro Leu Val Asn Ala Ser Leu Arg Ala Ala Lys Gln Ala Asp Arg
            370                 375                 380

Arg Ile Lys Leu Tyr Ala Val Glu Lys Asn Pro Asn Ala Val Val Thr
385                 390                 395                 400

Leu Glu Asn Trp Gln Phe Glu Glu Trp Gly Ser Gln Val Thr Val Val
                    405                 410                 415

Ser Ser Asp Met Arg Glu Trp Val Ala Pro Glu Lys Ala Asp Ile Ile
                420                 425                 430

Val Ser Glu Leu Leu Gly Ser Phe Ala Asp Asn Glu Leu Ser Pro Glu
                435                 440                 445

Cys Leu Asp Gly Ala Gln His Phe Leu Lys Asp Gly Val Ser Ile
450                 455                 460

Pro Gly Glu Tyr Thr Ser Phe Leu Ala Pro Ile Ser Ser Lys Leu
465                 470                 475                 480

Tyr Asn Glu Val Arg Ala Cys Arg Glu Lys Asp Arg Asp Pro Glu Ala
                    485                 490                 495

Gln Phe Glu Met Pro Tyr Val Val Arg Leu His Asn Phe His Gln Leu
                500                 505                 510

Ser Ala Pro Gln Pro Cys Phe Thr Phe Ser His Pro Asn Arg Asp Pro
                515                 520                 525

Met Ile Asp Asn Asn Arg Tyr Cys Thr Leu Glu Phe Pro Val Glu Val
530                 535                 540

Asn Thr Val Leu His Gly Phe Ala Gly Tyr Phe Glu Thr Val Leu Tyr
545                 550                 555                 560

Gln Asp Ile Thr Leu Ser Ile Arg Pro Glu Thr His Ser Pro Gly Met
                565                 570                 575

Phe Ser Trp Phe Pro Ile Leu Phe Pro Ile Lys Gln Pro Ile Thr Val
                580                 585                 590

Arg Glu Gly Gln Thr Ile Cys Val Arg Phe Trp Arg Cys Ser Asn Ser
                595                 600                 605

Lys Lys Val Trp Tyr Glu Trp Ala Val Thr Ala Pro Val Cys Ser Ala
610                 615                 620

Ile His Asn Pro Thr Gly Arg Ser Tyr Thr Ile Gly Leu
625                 630                 635
```

<210> SEQ ID NO 2
<211> LENGTH: 620
<212> TYPE: PRT
<213> ORGANISM: Homo sapiens

<400> SEQUENCE: 2

```
Met Arg Gly Pro Asn Ser Gly Thr Glu Lys Gly Arg Leu Val Ile Pro
1               5                   10                  15

Glu Lys Gln Gly Phe Asp Phe Leu Cys Met Pro Val Phe His Pro Arg
                20                  25                  30

Phe Lys Arg Glu Phe Ile Gln Glu Pro Ala Lys Asn Arg Pro Gly Pro
            35                  40                  45

Gln Thr Arg Ser Asp Leu Leu Leu Ser Gly Arg Asp Trp Asn Thr Leu
        50                  55                  60

Ile Val Gly Lys Leu Ser Pro Trp Ile Arg Pro Asp Ser Lys Val Glu
65                  70                  75                  80

Lys Ile Arg Arg Asn Ser Glu Ala Ala Met Leu Gln Glu Leu Asn Phe
                85                  90                  95

Gly Ala Tyr Leu Gly Leu Pro Ala Phe Leu Leu Pro Leu Asn Gln Glu
                100                 105                 110
```

```
Asp Asn Thr Asn Leu Ala Arg Val Leu Thr Asn His Ile His Thr Gly
        115                 120                 125

His His Ser Ser Met Phe Trp Met Arg Val Pro Leu Val Ala Pro Glu
130                 135                 140

Asp Leu Arg Asp Ile Ile Glu Asn Ala Pro Thr Thr His Thr Glu
145                 150                 155                 160

Glu Tyr Ser Gly Glu Glu Lys Thr Trp Met Trp Trp His Asn Phe Arg
                165                 170                 175

Thr Leu Cys Asp Tyr Ser Lys Arg Ile Ala Val Ala Leu Glu Ile Gly
                180                 185                 190

Ala Asp Leu Pro Ser Asn His Val Ile Asp Arg Trp Leu Gly Glu Pro
                195                 200                 205

Ile Lys Ala Ala Ile Leu Pro Thr Ser Ile Phe Leu Thr Asn Lys Lys
210                 215                 220

Gly Phe Pro Val Leu Ser Lys Met His Gln Arg Leu Ile Phe Arg Leu
225                 230                 235                 240

Leu Lys Leu Glu Val Gln Phe Ile Ile Thr Gly Thr Asn His His Ser
                245                 250                 255

Glu Lys Glu Phe Cys Ser Tyr Leu Gln Tyr Leu Glu Tyr Leu Ser Gln
                260                 265                 270

Asn Arg Pro Pro Pro Asn Ala Tyr Glu Leu Phe Ala Lys Gly Tyr Glu
                275                 280                 285

Asp Tyr Leu Gln Ser Pro Leu Gln Pro Leu Met Asp Asn Leu Glu Ser
                290                 295                 300

Gln Thr Tyr Glu Val Phe Glu Lys Asp Pro Ile Lys Tyr Ser Gln Tyr
305                 310                 315                 320

Gln Gln Ala Ile Tyr Lys Cys Leu Leu Asp Arg Val Pro Glu Glu Glu
                325                 330                 335

Lys Asp Thr Asn Val Gln Val Leu Met Val Leu Gly Ala Gly Arg Gly
                340                 345                 350

Pro Leu Val Asn Ala Ser Leu Arg Ala Ala Lys Gln Ala Asp Arg Arg
                355                 360                 365

Ile Lys Leu Tyr Ala Val Glu Lys Asn Pro Asn Ala Val Val Thr Leu
                370                 375                 380

Glu Asn Trp Gln Phe Glu Glu Trp Gly Ser Gln Val Thr Val Val Ser
385                 390                 395                 400

Ser Asp Met Arg Glu Trp Val Ala Pro Glu Lys Ala Asp Ile Ile Val
                405                 410                 415

Ser Glu Leu Leu Gly Ser Phe Ala Asp Asn Glu Leu Ser Pro Glu Cys
                420                 425                 430

Leu Asp Gly Ala Gln His Phe Leu Lys Asp Asp Gly Val Ser Ile Pro
                435                 440                 445

Gly Glu Tyr Thr Ser Phe Leu Ala Pro Ile Ser Ser Ser Lys Leu Tyr
450                 455                 460

Asn Glu Val Arg Ala Cys Arg Glu Lys Asp Arg Asp Pro Glu Ala Gln
465                 470                 475                 480

Phe Glu Met Pro Tyr Val Val Arg Leu His Asn Phe His Gln Leu Ser
                485                 490                 495

Ala Pro Gln Pro Cys Phe Thr Phe Ser His Pro Asn Arg Asp Pro Met
                500                 505                 510

Ile Asp Asn Asn Arg Tyr Cys Thr Leu Glu Phe Pro Val Glu Val Asn
                515                 520                 525
```

Thr Val Leu His Gly Phe Ala Gly Tyr Phe Glu Thr Val Leu Tyr Gln
            530                 535                 540

Asp Ile Thr Leu Ser Ile Arg Pro Glu Thr His Ser Pro Gly Met Phe
545                 550                 555                 560

Ser Trp Phe Pro Ile Leu Phe Pro Ile Lys Gln Pro Ile Thr Val Arg
                565                 570                 575

Glu Gly Gln Thr Ile Cys Val Arg Phe Trp Arg Cys Ser Asn Ser Lys
            580                 585                 590

Lys Val Trp Tyr Glu Trp Ala Val Thr Ala Pro Val Cys Ser Ala Ile
        595                 600                 605

His Asn Pro Thr Gly Arg Ser Tyr Thr Ile Gly Leu
    610                 615                 620

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Ser Gly Arg Gly Lys Gly Gly Lys Gly Leu Gly Lys Gly Gly Ala Lys
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 4

Met Asp Tyr Lys Asp Asp Asp Asp Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Met His His His His His His
1               5

<210> SEQ ID NO 6
<211> LENGTH: 645
<212> TYPE: PRT
<213> ORGANISM: Artificial Sequence
<220> FEATURE:
<223> OTHER INFORMATION: Synthetic Polypeptide

<400> SEQUENCE: 6

Met Asp Tyr Lys Asp Asp Asp Lys Ala Ala Met Ala Val Gly Gly
1               5                   10                  15

Ala Gly Gly Ser Arg Val Ser Ser Gly Arg Asp Leu Asn Cys Val Pro
            20                  25                  30

Glu Ile Ala Asp Thr Leu Gly Ala Val Ala Lys Gln Gly Phe Asp Phe
        35                  40                  45

Leu Cys Met Pro Val Phe His Pro Arg Phe Lys Arg Glu Phe Ile Gln
    50                  55                  60

```
Glu Pro Ala Lys Asn Arg Pro Gly Pro Gln Thr Arg Ser Asp Leu Leu
 65                  70                  75                  80

Leu Ser Gly Arg Asp Trp Asn Thr Leu Ile Val Gly Lys Leu Ser Pro
             85                  90                  95

Trp Ile Arg Pro Asp Ser Lys Val Glu Lys Ile Arg Arg Asn Ser Glu
             100                 105                 110

Ala Ala Met Leu Gln Glu Leu Asn Phe Gly Ala Tyr Leu Gly Leu Pro
             115                 120                 125

Ala Phe Leu Leu Pro Leu Asn Gln Glu Asp Asn Thr Asn Leu Ala Arg
             130                 135                 140

Val Leu Thr Asn His Ile His Thr Gly His His Ser Ser Met Phe Trp
145                 150                 155                 160

Met Arg Val Pro Leu Val Ala Pro Glu Asp Leu Arg Asp Asp Ile Ile
             165                 170                 175

Glu Asn Ala Pro Thr Thr His Thr Glu Glu Tyr Ser Gly Glu Glu Lys
             180                 185                 190

Thr Trp Met Trp Trp His Asn Phe Arg Thr Leu Cys Asp Tyr Ser Lys
             195                 200                 205

Arg Ile Ala Val Ala Leu Glu Ile Gly Ala Asp Leu Pro Ser Asn His
210                 215                 220

Val Ile Asp Arg Trp Leu Gly Glu Pro Ile Lys Ala Ala Ile Leu Pro
225                 230                 235                 240

Thr Ser Ile Phe Leu Thr Asn Lys Lys Gly Phe Pro Val Leu Ser Lys
             245                 250                 255

Met His Gln Arg Leu Ile Phe Arg Leu Leu Lys Leu Glu Val Gln Phe
             260                 265                 270

Ile Ile Thr Gly Thr Asn His His Ser Glu Lys Glu Phe Cys Ser Tyr
             275                 280                 285

Leu Gln Tyr Leu Glu Tyr Leu Ser Gln Asn Arg Pro Pro Asn Ala
             290                 295                 300

Tyr Glu Leu Phe Ala Lys Gly Tyr Glu Asp Tyr Leu Gln Ser Pro Leu
305                 310                 315                 320

Gln Pro Leu Met Asp Asn Leu Glu Ser Gln Thr Tyr Glu Val Phe Glu
             325                 330                 335

Lys Asp Pro Ile Lys Tyr Ser Gln Tyr Gln Gln Ala Ile Tyr Lys Cys
             340                 345                 350

Leu Leu Asp Arg Val Pro Glu Glu Lys Asp Thr Asn Val Gln Val
             355                 360                 365

Leu Met Val Leu Gly Ala Gly Arg Gly Pro Leu Val Asn Ala Ser Leu
             370                 375                 380

Arg Ala Ala Lys Gln Ala Asp Arg Arg Ile Lys Leu Tyr Ala Val Glu
385                 390                 395                 400

Lys Asn Pro Asn Ala Val Val Thr Leu Glu Asn Trp Gln Phe Glu Glu
                 405                 410                 415

Trp Gly Ser Gln Val Thr Val Ser Ser Asp Met Arg Glu Trp Val
             420                 425                 430

Ala Pro Glu Lys Ala Asp Ile Ile Val Ser Glu Leu Leu Gly Ser Phe
             435                 440                 445

Ala Asp Asn Glu Leu Ser Pro Glu Cys Leu Asp Gly Ala Gln His Phe
             450                 455                 460

Leu Lys Asp Asp Gly Val Ser Ile Pro Gly Glu Tyr Thr Ser Phe Leu
465                 470                 475                 480

Ala Pro Ile Ser Ser Ser Lys Leu Tyr Asn Glu Val Arg Ala Cys Arg
```

```
                    485                 490                 495
Glu Lys Asp Arg Asp Pro Glu Ala Gln Phe Glu Met Pro Tyr Val Val
                500                 505                 510

Arg Leu His Asn Phe His Gln Leu Ser Ala Pro Gln Pro Cys Phe Thr
            515                 520                 525

Phe Ser His Pro Asn Arg Asp Pro Met Ile Asp Asn Asn Arg Tyr Cys
        530                 535                 540

Thr Leu Glu Phe Pro Val Glu Val Asn Thr Val Leu His Gly Phe Ala
545                 550                 555                 560

Gly Tyr Phe Glu Thr Val Leu Tyr Gln Asp Ile Thr Leu Ser Ile Arg
                565                 570                 575

Pro Glu Thr His Ser Pro Gly Met Phe Ser Trp Phe Pro Ile Leu Phe
            580                 585                 590

Pro Ile Lys Gln Pro Ile Thr Val Arg Glu Gly Gln Thr Ile Cys Val
        595                 600                 605

Arg Phe Trp Arg Cys Ser Asn Ser Lys Val Trp Tyr Glu Trp Ala
    610                 615                 620

Val Thr Ala Pro Val Cys Ser Ala Ile His Asn Pro Thr Gly Arg Ser
625                 630                 635                 640

Tyr Thr Ile Gly Leu
                645

<210> SEQ ID NO 7
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 7

Met His His His His His Arg Lys Glu Thr Pro Pro Leu Val
1               5                   10                  15

Pro Pro Ala Ala Arg Glu Trp Asn Leu Pro Asn Ala Pro Ala Cys
            20                  25                  30

Met Glu Arg Gln Leu Glu Ala Ala Arg Tyr Arg Ser Asp Gly Ala Leu
        35                  40                  45

Leu Leu Gly Ala Ser Ser Leu Ser Gly Arg Cys Trp Ala Gly Ser Leu
    50                  55                  60

Trp Leu Phe Lys Asp Pro Cys Ala Ala Pro Asn Glu Gly Phe Cys Ser
65                  70                  75                  80

Ala Gly Val Gln Thr Glu Ala Gly Val Ala Asp Leu Thr Trp Val Gly
                85                  90                  95

Glu Arg Gly Ile Leu Val Ala Ser Asp Ser Gly Ala Val Glu Leu Trp
            100                 105                 110

Glu Leu Asp Glu Asn Glu Thr Leu Ile Val Ser Lys Phe Cys Lys Tyr
        115                 120                 125

Glu His Asp Asp Ile Val Ser Thr Val Ser Val Leu Ser Ser Gly Thr
    130                 135                 140

Gln Ala Val Ser Gly Ser Lys Asp Ile Cys Ile Lys Val Trp Asp Leu
145                 150                 155                 160

Ala Gln Gln Val Val Leu Ser Ser Tyr Arg Ala His Ala Ala Gln Val
                165                 170                 175

Thr Cys Val Ala Ala Ser Pro His Lys Asp Ser Val Phe Leu Ser Cys
            180                 185                 190

Ser Glu Asp Asn Arg Ile Leu Leu Trp Asp Thr Arg Cys Pro Lys Pro
```

```
                 195                 200                 205
Ala Ser Gln Ile Gly Cys Ser Ala Pro Gly Tyr Leu Pro Thr Ser Leu
        210                 215                 220

Ala Trp His Pro Gln Gln Ser Glu Val Phe Val Phe Gly Asp Glu Asn
225                 230                 235                 240

Gly Thr Val Ser Leu Val Asp Thr Lys Ser Thr Ser Cys Val Leu Ser
                245                 250                 255

Ser Ala Val His Ser Gln Cys Val Thr Gly Leu Val Phe Ser Pro His
                260                 265                 270

Ser Val Pro Phe Leu Ala Ser Leu Ser Glu Asp Cys Ser Leu Ala Val
                275                 280                 285

Leu Asp Ser Ser Leu Ser Glu Leu Phe Arg Ser Gln Ala His Arg Asp
            290                 295                 300

Phe Val Arg Asp Ala Thr Trp Ser Pro Leu Asn His Ser Leu Leu Thr
305                 310                 315                 320

Thr Val Gly Trp Asp His Gln Val Val His His Val Val Pro Thr Glu
                325                 330                 335

Pro Leu Pro Ala Pro Gly Pro Ala Ser Val Thr Glu
                340                 345
```

PRMT5 INHIBITORS AND USES THEROF

RELATED APPLICATIONS

This application is a continuation and claims priority under 35 U.S.C. § 120 to U.S. patent application Ser. No. 15/586,775, filed May 4, 2017; which is a continuation of and claims priority under 35 U.S.C. § 120 to U.S. patent application Ser. No. 15/054,193, filed Feb. 26, 2016, now U.S. Pat. No. 9,675,614; which is a continuation of U.S. Ser. No. 14/619,371, filed Feb. 11, 2015, now U.S. Pat. No. 9,365,519; which is a continuation of U.S. patent application Ser. No. 14/136,569, filed Dec. 20, 2013, now U.S. Pat. No. 8,993,555, which claims priority under 35 U.S.C. § 119(e) to U.S. provisional patent application, U.S. Ser. No. 61/790,525, filed Mar. 15, 2013, and to U.S. provisional patent application, U.S. Ser. No. 61/745,485, filed Dec. 21, 2012, the entire contents of each of which are incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., PRMT5), many of which are associated with specific genetic alterations that can cause human disease.

Disease-associated chromatin-modifying enzymes (e.g., PRMT5) play a role in diseases such as proliferative disorders, metabolic disorders, and blood disorders. Thus, there is a need for the development of small molecules that are capable of inhibiting the activity of PRMT5.

DETAILED DESCRIPTION OF CERTAIN EMBODIMENTS

Protein arginine methyltransferase 5 (PRMT5) catalyzes the addition of two methyl groups to the two ω-guanidino nitrogen atoms of arginine, resulting in ω-NG, N'G symmetric dimethylation of arginine (sDMA) of the target protein. PRMT5 functions in the nucleus as well as in the cytoplasm, and its substrates include histones, spliceosomal proteins, transcription factors (See e.g., Sun et al., 2011, PNAS 108: 20538-20543). PRMT5 generally functions as part of a molecule weight protein complex. While the protein complexes of PRMT5 can have a variety of components, they generally include the protein MEP50 (methylosome protein 50). In addition, PRMT5 acts in conjunction with cofactor SAM (S-adenosyl methionine).

PRMT5 is an attractive target for modulation given its role in the regulation of diverse biological processes. It has now been found that compounds described herein, and pharmaceutically acceptable salts and compositions thereof, are effective as inhibitors of PRMT5. Such compounds have the general Formula (I):

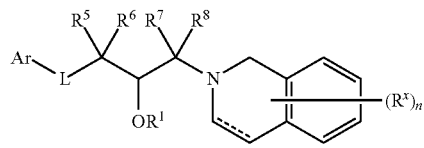

or a pharmaceutically acceptable salt thereof, wherein $R^1$, $R^5$, $R^6$, $R^7$, $R^8$, $R^x$, n, L, and Ar are as defined herein.

In some embodiments, pharmaceutical compositions are provided which comprise a compound described herein (e.g., a compound of Formula (I)), or a pharmaceutically acceptable salt thereof, and optionally a pharmaceutically acceptable excipient.

In certain embodiments, compounds described herein inhibit activity of PRMT5. In certain embodiments, methods of inhibiting PRMT5 are provided which comprise contacting PRMT5 with an effective amount of a compound of Formula (I), or a pharmaceutically acceptable salt thereof. The PRMT5 may be purified or crude, and may be present in a cell, tissue, or a subject. Thus, such methods encompass inhibition of PRMT5 activity both in vitro and in vivo. In certain embodiments, the PRMT5 is wild-type PRMT5. In certain embodiments, the PRMT5 is overexpressed. In certain embodiments, the PRMT5 is a mutant. In certain embodiments, the PRMT5 is in a cell. In certain embodiments, the PRMT5 is in an animal, e.g., a human. In some embodiments, the PRMT5 is in a subject that is susceptible to normal levels of PRMT5 activity due to one or more mutations associated with a PRMT5 substrate. In some embodiments, the PRMT5 is in a subject known or identified as having abnormal PRMT5 activity (e.g., overexpression). In some embodiments, a provided compound is selective for PRMT5 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective relative to one or more other methyltransferases.

In certain embodiments, methods of altering gene expression in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, cell is in an animal, e.g., a human.

In certain embodiments, methods of altering transcription in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, the cell is in an animal, e.g., a human.

In some embodiments, methods of treating a PRMT5-mediated disorder are provided which comprise administering to a subject suffering from a PRMT5-mediated disorder an effective amount of a compound described herein (e.g., a compound of Formula (I)), or a pharmaceutically acceptable salt thereof, or a pharmaceutical composition thereof. In certain embodiments, the PRMT5-mediated disorder is a proliferative disorder, a metabolic disorder, or a blood disorder. In certain embodiments, compounds described herein are useful for treating cancer. In certain embodiments, compounds described herein are useful for treating hematopoietic cancer, lung cancer, prostate cancer, melanoma, or pancreatic cancer. In certain embodiments, compounds described herein are useful for treating a hemoglobinopathy. In certain embodiments, compounds described herein are useful for treating sickle cell anemia. In certain embodiments, compounds described herein are useful for treating diabetes or obesity.

Compounds described herein are also useful for the study of PRMT5 in biological and pathological phenomena, the study of intracellular signal transduction pathways mediated by PRMT5, and the comparative evaluation of new PRMT5 inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

It is to be understood that the compounds of the present invention may be depicted as different tautomers. It should also be understood that when compounds have tautomeric forms, all tautomeric forms are intended to be included in the scope of the present invention, and the naming of any compound described herein does not exclude any tautomer form.

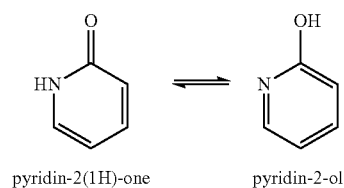 [SMILES: O=c1cccc[nH]1 ; Oc1ccccn1]

pyridin-2(1H)-one     pyridin-2-ol

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

The term "aliphatic," as used herein, includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. As will be appreciated by one of ordinary skill in the art, "aliphatic" is intended herein to include alkyl, alkenyl, alkynyl, cycloalkyl, and cycloalkenyl moieties.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —CH$_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms independently selected from nitrogen, oxygen, and sulfur. In some embodiments, the 5-6 membered heterocyclyl has 1-2 ring heteroatoms independently selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms independently selected from nitrogen, oxygen, and sulfur. In some embodiments, the 5-6 membered heteroaryl has 1-2 ring heteroatoms independently selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{1-4}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{1-4}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, —P(=O)$_2$R, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{1-4}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chlorop-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)

$SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, o-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$ and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C_alkyl)₄ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of a therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methyltransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as PRMT5 inhibitors. In some embodiments, the present disclosure provides a compound of Formula (I):

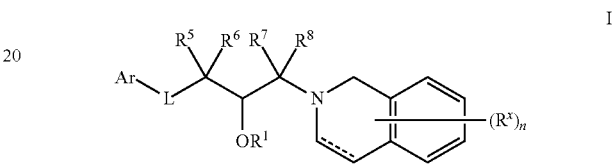

I or a pharmaceutically acceptable salt thereof, wherein

------ represents a single or double bond;

$R^1$ is hydrogen, $R^z$, or —C(O)$R^z$, wherein $R^z$ is optionally substituted $C_{1-6}$ alkyl;

L is —N(R)C(O)—, —C(O)N(R)—, —N(R)C(O)N(R)—, —N(R)C(O)O—, or —OC(O)N(R)—;

each R is independently hydrogen or optionally substituted $C_{1-6}$ aliphatic;

Ar is a monocyclic or bicyclic aromatic ring having 0-4 heteroatoms independently selected from nitrogen, oxygen, and sulfur, wherein Ar is substituted with 0, 1, 2, 3, 4, or 5 $R^y$ groups, as valency permits;

each $R^y$ is independently selected from the group consisting of halo, —CN, —NO₂, optionally substituted aliphatic, optionally substituted carbocyclyl, optionally substituted aryl, optionally substituted heterocyclyl, optionally substituted heteroaryl, —OR$^A$, —N(R$^B$)₂, —SR$^A$, C(=O)R$^A$, —C(O)OR$^A$, —C(O)SR$^A$, —C(O)N(R$^B$)₂, —C(O)N(R$^B$)N(R$^B$)₂, —OC(O)R$^A$, —OC(O)N(R$^B$)₂, —NR$^B$C(O)R$^A$, —NR$^B$C(O)N(R$^B$)₂, —NR$^B$C(O)N(R$^B$)N(R$^B$)₂, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)₂, —NR$^B$C(=NR$^B$)R$^B$, —C(=S)R$^A$, C(=S)N(R$^B$)₂, —NR$^B$C(=S)R$^A$, —S(O)R$^A$, —OS(O)₂R$^A$, —SO₂R$^A$, —NR$^B$SO₂R$^A$, or —SO₂N(R$^B$)₂;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^5$, $R^6$, $R^7$, and $R^8$ are independently hydrogen, halo, or optionally substituted aliphatic;

each $R^x$ is independently selected from the group consisting of halo, —CN, optionally substituted aliphatic, —OR', and —N(R")$_2$;

R' is hydrogen or optionally substituted aliphatic;

each R" is independently hydrogen or optionally substituted aliphatic, or two R" are taken together with their intervening atoms to form a heterocyclic ring; and n is 0, 1, 2, 3, 4, 5, 6, 7, 8, 9, or 10, as valency permits.

In certain embodiments, a provided compound is of Formula (I-a):

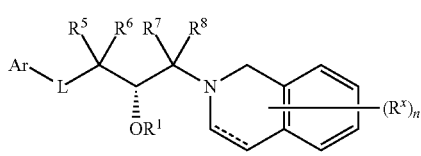
I-a or a pharmaceutically acceptable salt thereof, wherein $R^1$, $R^5$, $R^6$, $R^7$, $R^8$, $R^x$, n, L, and Ar are as described herein.

In certain embodiments, a provided compound is of Formula (I-b):

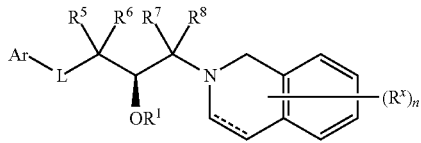
I-b or a pharmaceutically acceptable salt thereof, wherein $R^1$, $R^5$, $R^6$, $R^7$, $R^8$, $R^x$, n, L, and Ar are as described herein.

In certain embodiments, a provided compound is of Formula (I-c):

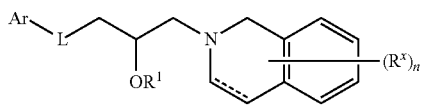
I-c or a pharmaceutically acceptable salt thereof, wherein $R^1$, $R^x$, n, L, and Ar are as described herein.

In certain embodiments, a provided compound is of Formula (I'):

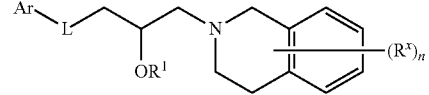
I' or a pharmaceutically acceptable salt thereof, wherein $R^1$, $R^x$, n, L, and Ar are as described herein.

In certain embodiments, a provided compound is of Formula (I'-a):

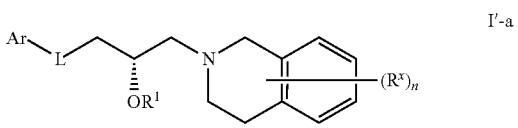
I'-a or a pharmaceutically acceptable salt thereof, wherein $R^1$, $R^x$, n, L, and Ar are as described herein.

In certain embodiments, a provided compound is of Formula (I'-b):

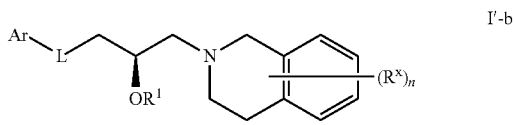
I'-b or a pharmaceutically acceptable salt thereof, wherein $R^1$, $R^x$, n, L, and Ar are as described herein.

In certain embodiments, a provided compound is of Formula (II):

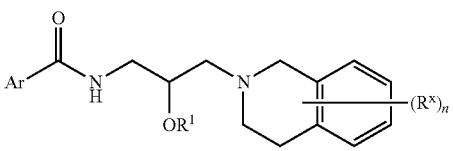
II or a pharmaceutically acceptable salt thereof, wherein $R^1$, $R^x$, n, and Ar are as described herein.

In certain embodiments, a provided compound is of Formula (II-a):

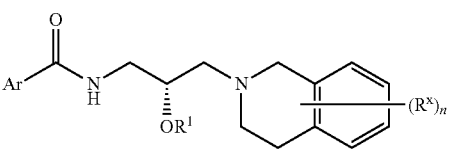
II-a or a pharmaceutically acceptable salt thereof, wherein $R^1$, $R^x$, n, and Ar are as described herein.

In certain embodiments, a provided compound is of Formula (II-b):

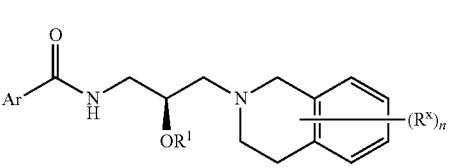
II-b or a pharmaceutically acceptable salt thereof, wherein $R^1$, $R^x$, n, and Ar are as described herein.

In certain embodiments, a provided compound is of Formula (III):

III

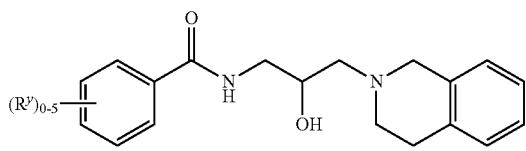

or a pharmaceutically acceptable salt thereof, wherein $R^y$ is as described herein.

In certain embodiments, a provided compound is of Formula (III-a):

III-a

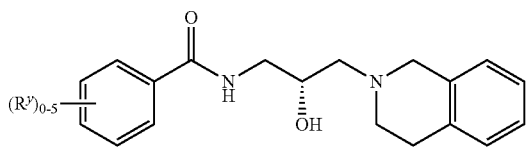

or a pharmaceutically acceptable salt thereof, wherein $R^y$ is as described herein.

In certain embodiments, a provided compound is of Formula (III-b):

III-b

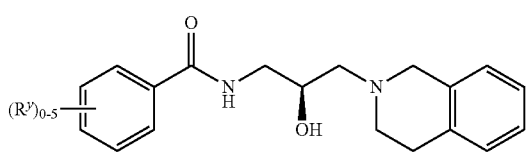

or a pharmaceutically acceptable salt thereof, wherein $R^y$ is as described herein.

In certain embodiments, a provided compound is of Formula (IV):

IV

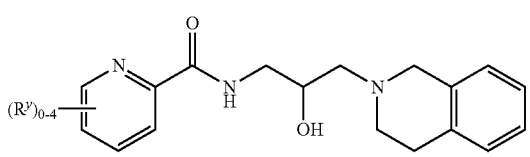

or a pharmaceutically acceptable salt thereof, wherein $R^y$ is as described herein.

In certain embodiments, a provided compound is of Formula (IV-a):

IV-a

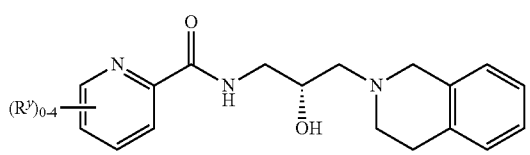

or a pharmaceutically acceptable salt thereof, wherein $R^y$ is as described herein.

In certain embodiments, a provided compound is of Formula (IV-b):

IV-b

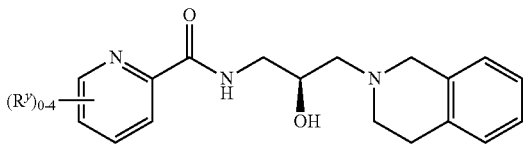

or a pharmaceutically acceptable salt thereof, wherein $R^y$ is as described herein.

In certain embodiments, a provided compound is of Formula (V):

V

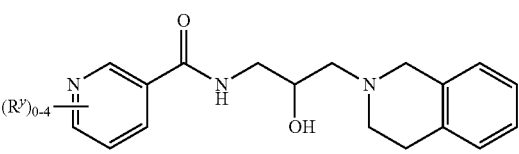

or a pharmaceutically acceptable salt thereof, wherein $R^y$ is as described herein.

In certain embodiments, a provided compound is of Formula (V-a):

V-a

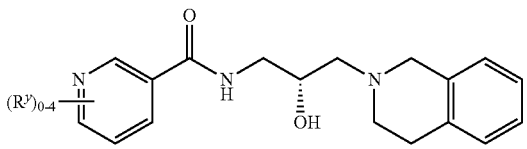

or a pharmaceutically acceptable salt thereof, wherein $R^y$ is as described herein.

In certain embodiments, a provided compound is of Formula (V-b):

V-b

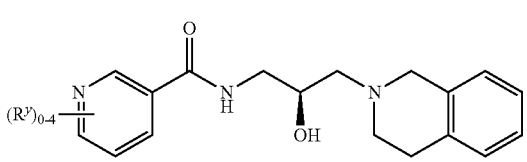

or a pharmaceutically acceptable salt thereof, wherein $R^y$ is as described herein.

In certain embodiments, a provided compound is of Formula (VI):

VI

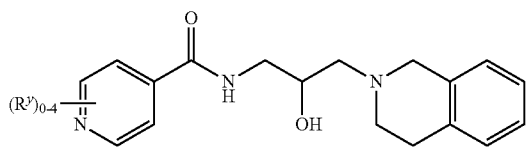

or a pharmaceutically acceptable salt thereof, wherein $R^y$ is as described herein.

In certain embodiments, a provided compound is of Formula (VI-a):

VI-a

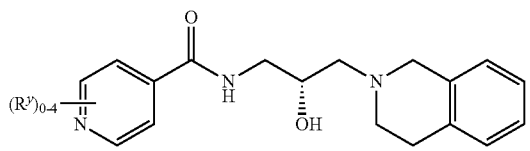

or a pharmaceutically acceptable salt thereof, wherein $R^y$ is as described herein.

In certain embodiments, a provided compound is of Formula (VI-b):

VI-b

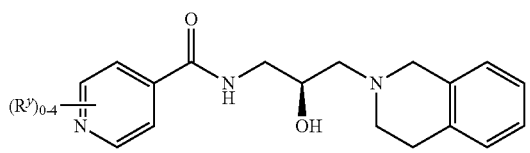

or a pharmaceutically acceptable salt thereof, wherein $R^y$ is as described herein.

In certain embodiments, a provided compound is of Formula (VII):

VII

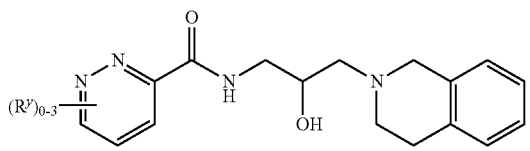

or a pharmaceutically acceptable salt thereof, wherein $R^y$ is as described herein.

In certain embodiments, a provided compound is of Formula (VII-a):

VII-a

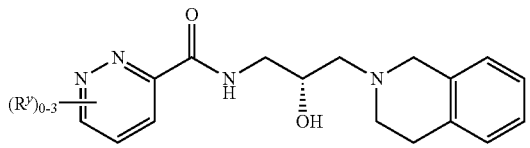

or a pharmaceutically acceptable salt thereof, wherein $R^y$ is as described herein.

In certain embodiments, a provided compound is of Formula (VII-b):

VII-b

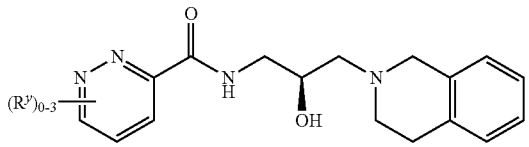

or a pharmaceutically acceptable salt thereof, wherein $R^y$ is as described herein.

In certain embodiments, a provided compound is of Formula (VIII):

VIII

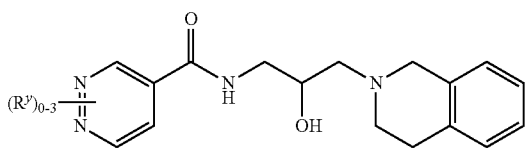

or a pharmaceutically acceptable salt thereof, wherein $R^y$ is as described herein.

In certain embodiments, a provided compound is of Formula (VIII-a):

VIII-a

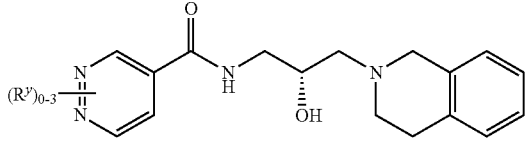

or a pharmaceutically acceptable salt thereof, wherein $R^y$ is as described herein.

In certain embodiments, a provided compound is of Formula (VIII-b):

VIII-b

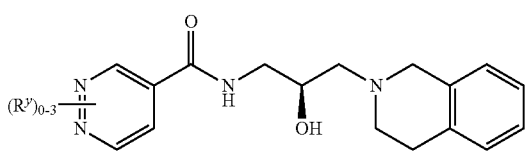

or a pharmaceutically acceptable salt thereof, wherein $R^y$ is as described herein.

In certain embodiments, a provided compound is of Formula (IX):

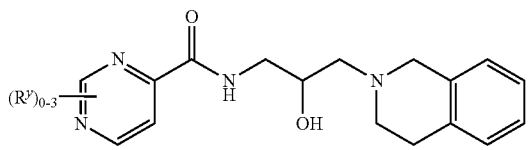

or a pharmaceutically acceptable salt thereof, wherein $R^y$ is as described herein.

In certain embodiments, a provided compound is of Formula (IX-a):

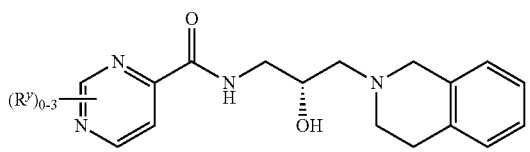

or a pharmaceutically acceptable salt thereof, wherein $R^y$ is as described herein.

In certain embodiments, a provided compound is of Formula (IX-b):

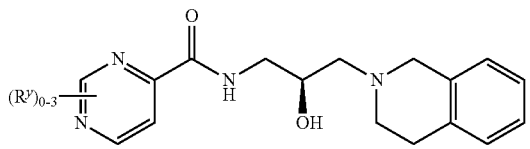

or a pharmaceutically acceptable salt thereof, wherein $R^y$ is as described herein.

In certain embodiments, a provided compound is of Formula (X):

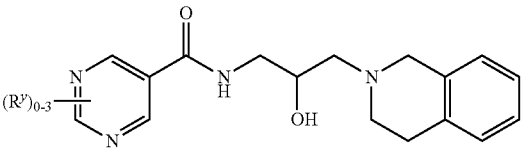

or a pharmaceutically acceptable salt thereof, wherein $R^y$ is as described herein.

In certain embodiments, a provided compound is of Formula (X-a):

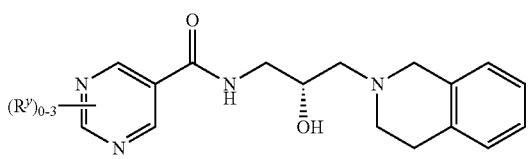

or a pharmaceutically acceptable salt thereof, wherein $R^y$ is as described herein.

In certain embodiments, a provided compound is of Formula (X-b):

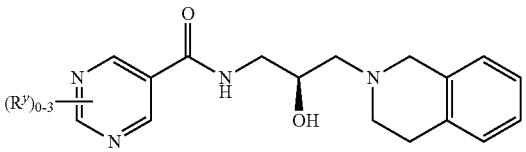

or a pharmaceutically acceptable salt thereof, wherein $R^y$ is as described herein.

In certain embodiments, a provided compound is of Formula (XI):

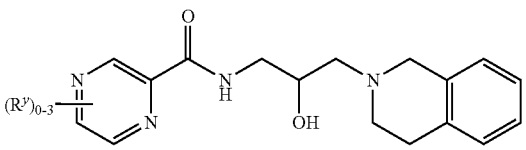

or a pharmaceutically acceptable salt thereof, wherein $R^y$ is as described herein.

In certain embodiments, a provided compound is of Formula (XI-a):

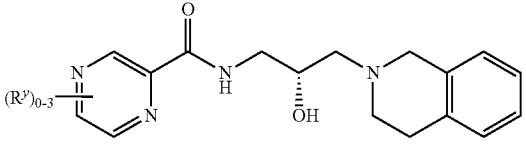

or a pharmaceutically acceptable salt thereof, wherein $R^y$ is as described herein.

In certain embodiments, a provided compound is of Formula (XI-b):

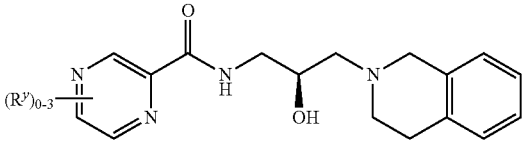

or a pharmaceutically acceptable salt thereof, wherein $R^y$ is as described herein.

In certain embodiments, a provided compound is of Formula (XII):

XII

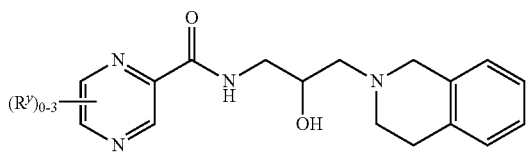

or a pharmaceutically acceptable salt thereof, wherein $R^y$ is as described herein.

In certain embodiments, a provided compound is of Formula (XII-a):

XII-a

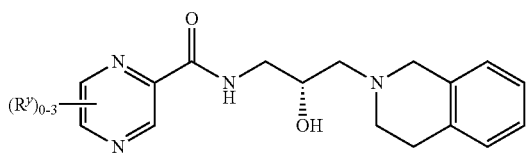

or a pharmaceutically acceptable salt thereof, wherein $R^y$ is as described herein.

In certain embodiments, a provided compound is of Formula (XII-b):

XII-b

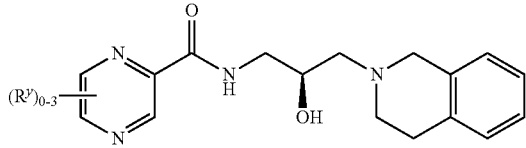

or a pharmaceutically acceptable salt thereof, wherein $R^y$ is as described herein.

In certain embodiments, a provided compound is of Formula (XIII):

XIII

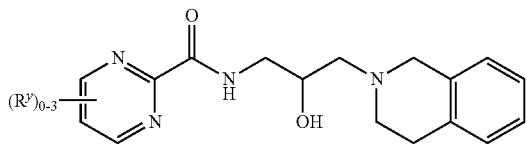

or a pharmaceutically acceptable salt thereof, wherein $R^y$ is as described herein.

In certain embodiments, a provided compound is of Formula (XIII-a):

XIII-a

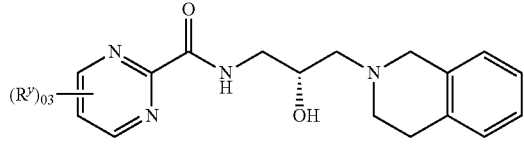

or a pharmaceutically acceptable salt thereof, wherein $R^y$ is as described herein.

In certain embodiments, a provided compound is of Formula (XIII-b):

XIII-b

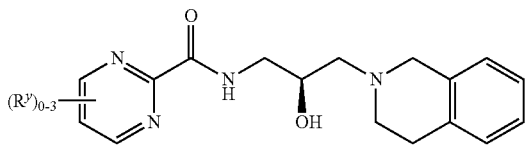

or a pharmaceutically acceptable salt thereof, wherein $R^y$ is as described herein.

As defined generally above, $R^1$ is hydrogen, $R^z$, or —C(O)$R^z$, wherein $R^z$ is optionally substituted $C_{1-6}$ alkyl. In certain embodiments, $R^1$ is hydrogen. In some embodiments, $R^1$ is optionally substituted $C_{1-6}$ alkyl. In certain embodiments, $R^1$ is unsubstituted $C_{1-6}$ alkyl. In certain embodiments, $R^1$ is methyl, ethyl, or propyl. In some embodiments, $R^1$ is —C(O)$R^z$, wherein $R^z$ is optionally substituted $C_{1-6}$ alkyl. In certain embodiments, $R^1$ is —C(O)$R^z$, wherein $R^z$ is unsubstituted $C_{1-6}$ alkyl. In certain embodiments, $R^1$ is acetyl.

As defined generally above, L is —N(R)C(O)—, —C(O)N(R)—, —N(R)C(O)N(R)—, —N(R)C(O)O—, or —OC(O)N(R)—, wherein R is as described herein. In some embodiments, L is —N(R)C(O)—. In some embodiments, L is —NHC(O)—. In some embodiments, L is —N($C_{1-6}$ alkyl)C(O)—. In some embodiments, L is —N(CH$_3$)C(O)—. In some embodiments, L is —C(O)N(R)—. In some embodiments, L is —C(O)NH—. In some embodiments, L is —C(O)N($C_{1-6}$ alkyl)-. In some embodiments, L is —C(O)N(CH$_3$)—. In some embodiments, L is —N(R)C(O)N(R)—. In some embodiments, L is —NHC(O)NH—. In some embodiments, L is —NHC(O)N(R)—. In some embodiments, L is —N(R)C(O)NH—. In some embodiments, L is —N(CH$_3$)C(O)N(R)—. In some embodiments, L is —N(R)C(O)N(CH$_3$)—. In some embodiments, L is —N(CH$_3$)C(O)N(CH$_3$)—. In some embodiments, L is —N(R)C(O)O—. In some embodiments, L is —NHC(O)O—. In some embodiments, L is —N($C_{1-6}$ alkyl)C(O)O—. In some embodiments, L is —N(CH$_3$)C(O)O—. In some embodiments, L is —OC(O)N(R)—. In some embodiments, L is —OC(O)NH—. In some embodiments, L is —OC(O)N($C_{1-6}$ alkyl)-. In some embodiments, L is —OC(O)N(CH$_3$)—.

As defined generally above, each R is independently hydrogen or optionally substituted $C_{1-6}$ aliphatic. In certain embodiments, R is hydrogen. In some embodiments, R is optionally substituted $C_{1-6}$ aliphatic. In some embodiments, R is substituted $C_{1-6}$ aliphatic. In some embodiments, R is unsubstituted $C_{1-6}$ aliphatic. In some embodiments, R is optionally substituted $C_{1-6}$ alkyl. In some embodiments, R is substituted C$_{1-6}$ alkyl. In some embodiments, R is unsubstituted C$_{1-6}$ alkyl. In some embodiments, R is methyl, ethyl, or propyl.

As defined generally above, Ar is a monocyclic or bicyclic aromatic ring having 0-4 heteroatoms independently selected from nitrogen, oxygen, and sulfur, wherein Ar is substituted with 0, 1, 2, 3, 4, or 5 R$^y$ groups, as valency permits. For avoidance of confusion, though Ar is sometimes used to denote the element argon, as used herein it denotes a monocyclic or bicyclic aromatic ring having 0-4 heteroatoms independently selected from nitrogen, oxygen, and sulfur, wherein Ar is substituted with 0, 1, 2, 3, 4, or 5 R$^y$ groups, as valency permits, and various embodiments thereof as described herein. In certain embodiments, Ar is unsubstituted. In certain embodiments, Ar is substituted with one or two R$^y$ groups. In certain embodiments, Ar is substituted with one R$^y$ group. In certain embodiments, Ar is substituted with two R$^y$ groups. In certain embodiments, Ar is substituted with three R$^y$ groups. In certain embodiments, Ar is substituted with four R$^y$ groups. In certain embodiments, Ar is substituted with five R$^y$ groups.

In certain embodiments, Ar is phenyl substituted with 0, 1, 2, 3, 4, or 5 R$^y$ groups. In certain embodiments, Ar is phenyl substituted with one or two R$^y$ groups. In certain embodiments, Ar is unsubstituted phenyl. In certain embodiments, Ar is phenyl substituted with one R$^y$ group. In certain embodiments, Ar is phenyl substituted with two R$^y$ groups. In certain embodiments, Ar is phenyl substituted with three R$^y$ groups. In certain embodiments, Ar is phenyl substituted with four R$^y$ groups. In certain embodiments, Ar is phenyl substituted with five R$^y$ groups.

In certain embodiments, Ar is heteroaryl substituted with 0, 1, 2, 3, 4, or 5 R$^y$ groups, as valency permits. In certain embodiments, Ar is a 5- to 6-membered heteroaryl having 1-3 heteroatoms independently selected from nitrogen, oxygen, and sulfur, and is substituted with 0, 1, 2, 3, or 4 R$^y$ groups. In certain embodiments, Ar is an unsubstituted 5- to 6-membered heteroaryl having 1-3 heteroatoms independently selected from nitrogen, oxygen, and sulfur. In certain embodiments, Ar is a 5- to 6-membered heteroaryl having 1-3 heteroatoms independently selected from nitrogen, oxygen, and sulfur, and is substituted with one or two R$^y$ groups. In certain embodiments, Ar is a 5- to 6-membered heteroaryl having 1-3 heteroatoms independently selected from nitrogen, oxygen, and sulfur, and is substituted with one R$^y$ group. In certain embodiments, Ar is a 5-membered heteroaryl having 1-3 heteroatoms independently selected from nitrogen, oxygen, and sulfur (e.g., furanyl, thienyl, pyrrolyl, oxazolyl, isoxazolyl, thiazolyl, imidazolyl, pyrazolyl, isothiazolyl, triazolyl, oxadiazolyl, thiadiazolyl), and is substituted with 0, 1, 2, or 3 R$^y$ groups. In certain embodiments, Ar is a 6-membered heteroaryl having 1-3 nitrogens (e.g., pyridyl, pyrimidyl, pyridazinyl, pyrazinyl, triazinyl), and is substituted with 0, 1, 2, 3, or 4 R$^y$ groups. In certain embodiments, Ar is pyridyl, and is substituted with 0, 1, 2, 3, or 4 R$^y$ groups. In certain embodiments, Ar is pyridyl, and is substituted with one R$^y$ group. In certain embodiments, Ar is pyridyl, and is substituted with two R$^y$ groups. In certain embodiments, Ar is a 6-membered heteroaryl having two nitrogens (e.g., pyrimidyl, pyridazinyl, pyrazinyl), and is substituted with 0, 1, 2, or 3 R$^y$ groups. In certain embodiments, Ar is a 6-membered heteroaryl having two nitrogens (e.g., pyrimidyl, pyridazinyl, pyrazinyl), and is substituted with one R$^y$ group. In certain embodiments, Ar is a 6-membered heteroaryl having two nitrogens (e.g., pyrimidyl, pyridazinyl, pyrazinyl), and is substituted with two R$^y$ groups.

In certain embodiments, Ar is a bicyclic aromatic ring having 0-4 heteroatoms independently selected from nitrogen, oxygen, and sulfur, wherein Ar is substituted with 0, 1, 2, 3, or 4 R$^y$ groups. In certain embodiments, Ar is an 8- to 12-membered bicyclic aromatic ring having 0-4 heteroatoms independently selected from nitrogen, oxygen, and sulfur, wherein Ar is substituted with 0, 1, 2, 3, or 4 R$^y$ groups. In certain embodiments, Ar is an unsubstituted bicyclic aromatic ring having 0-4 heteroatoms independently selected from nitrogen, oxygen, and sulfur. In certain embodiments, Ar is a bicyclic aromatic ring having 0-4 heteroatoms independently selected from nitrogen, oxygen, and sulfur, wherein Ar is substituted with one or two R$^y$ groups. In certain embodiments, Ar is a bicyclic aromatic ring having 0-4 heteroatoms independently selected from nitrogen, oxygen, and sulfur, wherein Ar is substituted with one R$^y$ group. In certain embodiments, Ar is a bicyclic aromatic ring having 0-4 heteroatoms independently selected from nitrogen, oxygen, and sulfur, wherein Ar is substituted with two R$^y$ groups. In certain embodiments, Ar is a bicyclic aromatic ring having 0-4 heteroatoms independently selected from nitrogen, oxygen, and sulfur, wherein Ar is substituted with three R$^y$ groups. In certain embodiments, Ar is a bicyclic aromatic ring having 0-4 heteroatoms independently selected from nitrogen, oxygen, and sulfur, wherein Ar is substituted with four R$^y$ groups. In certain embodiments, Ar is a bicyclic aromatic ring having 0-4 heteroatoms independently selected from nitrogen, oxygen, and sulfur, wherein Ar is substituted with five R$^y$ groups. In certain embodiments, Ar is naphthalene substituted with 0, 1, 2, 3, 4, or 5 R$^y$ groups.

In certain embodiments, Ar is an 8- to 10-membered bicyclic heteroaryl having 1-4 heteroatoms independently selected from nitrogen, oxygen, and sulfur, wherein Ar is substituted with 0, 1, 2, 3, or 4 R$^y$ groups. In certain embodiments, Ar is a 9-membered bicyclic heteroaryl having 1-3 heteroatoms independently selected from nitrogen, oxygen, and sulfur (e.g., indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl), wherein Ar is substituted with 0, 1, 2, 3, 4, or 5 R$^y$ groups. In certain embodiments, Ar is a 10-membered bicyclic heteroaryl having 1-3 heteroatoms independently selected from nitrogen, oxygen, and sulfur (e.g., naphthyridinyl, quinolinyl, isoquinolinyl, quinoxalinyl, quinazolinyl), wherein Ar is substituted with 0, 1, 2, 3, 4, or 5 R$^y$ groups. In certain embodiments, Ar is selected from the group consisting of quinoline, benzimidazole, benzopyrazole, quinoxaline, tetrahydroquinoline, tetrahydroisoquinoline, naphthalene, tetrahydronaphthalene, 2,3-dihydrobenzo[b][1,4]dioxine, isoindole, 2H-benzo[b][1,4]oxazin-3(4H)-one, 3,4-dihydro-2H-benzo[b][1,4]oxazine, and quinoxalin-2(1H)-one, wherein Ar is substituted with 0, 1, 2, 3, or 4 R$^y$ groups. In some embodiments, Ar is quinoline, wherein Ar is substituted with 0, 1, 2, 3, or 4 R$^y$ groups.

As defined generally above, each R$^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$, wherein R$^A$ and R$^B$ are described herein. In some embodiments, each R$^y$ is independently selected from the group consisting of halo, —CN, —NO$_2$, optionally substituted aliphatic, optionally substituted carbocyclyl, optionally substituted phenyl, optionally substituted heterocyclyl, optionally substituted heteroaryl, —OR$^A$, N(R$^B$)$_2$, —SR$^A$, —C(=O)R$^A$, —C(O)OR$^A$, —C(O)SR$^A$, —C(O)N(R$^B$)$_2$, —OC(O)R$^A$, —NR$^B$C(O)R$^A$, —NR$^B$C(O)N(R$^B$)$_2$, —SC(O)R$^A$, —C(=NR$^B$)R$^A$, —C(=NR$^B$)N(R$^B$)$_2$, —NR$^B$C(=NR$^B$)R$^B$, —C(=S)R$^A$, C(=S)N(R$^B$)$_2$, —NR$^B$C(=S)R$^A$, —S(O)R$^A$, —SO$_2$R$^A$, —NR$^B$SO$_2$R$^A$, and —SO$_2$N(R$^B$)$_2$, wherein R$^A$ and R$^B$ are described herein.

In some embodiments, at least one R$^y$ is halo. In certain embodiments, at least one R$^y$ is fluoro. In certain embodiments, at least one R$^y$ is chloro. In some embodiments, at least one R$^y$ is —CN. In some embodiments, at least one R$^y$ is —OR$^A$, wherein R$^A$ is optionally substituted aliphatic. In some embodiments, at least one R$^y$ is —OR$^A$, wherein R$^A$ is unsubstituted C$_{1-6}$ alkyl. In certain embodiments, at least one R$^y$ is methoxy, ethoxy, or propoxy. In certain embodiments, at least one R$^y$ is methoxy. In some embodiments, at least one R$^y$ is —OR$^A$, wherein R$^A$ is substituted C$_{1-6}$ alkyl. In certain embodiments, at least one R$^y$ is —OCH$_2$CH$_2$N(CH$_3$)$_2$. In some embodiments, at least one R$^y$ is —OR$^A$, wherein R$^A$ is optionally substituted heterocyclyl. In some embodiments, at least one R$^y$ is —OR$^A$, wherein R$^A$ is an optionally substituted 4- to 7-membered heterocyclyl having 1-2 heteroatoms independently selected from nitrogen, oxygen, and sulfur. In some embodiments, at least one R$^y$ is —OR$^A$, wherein R$^A$ is oxetanyl, tetrahydrofuranyl, or tetrahydropyranyl. In some embodiments, at least one R$^y$ is —N(R$^B$)$_2$. In some embodiments, at least one R$^y$ is —N(R$^B$)$_2$, wherein each R$^B$ is independently selected from hydrogen or C$_{1-6}$ alkyl. In some embodiments, at least one R$^y$ is —NHR$^B$. In some embodiments, at least one R$^y$ is —N(C$_{1-6}$ alkyl)$_2$, —NH(C$_{1-6}$ alkyl), or —NH$_2$. In certain embodiments, at least one R$^y$ is —NH$_2$. In certain embodiments, at least one R$^y$ is —NHCH$_3$. In certain embodiments, at least one R$^y$ is —N(CH$_3$)$_2$. In some embodiments, at least one R$^y$ is —N(R$^B$)$_2$ or —NHR$^B$, wherein at least one R$^B$ is optionally substituted heterocyclyl. In some embodiments, at least one R$^y$ is —N(R$^B$)$_2$ or —NHR$^B$, wherein at least one R$^B$ is an optionally substituted 4- to 7-membered heterocyclyl having 1-2 heteroatoms independently selected from nitrogen, oxygen, and sulfur. In some embodiments, at least one R$^y$ is —N(R$^B$)$_2$ or —NHR$^B$, wherein at least one R$^B$ is oxetanyl, tetrahydropyranyl, or tetrahydrofuranyl. In some embodiments, at least one R$^y$ is —N(R$^B$)$_2$ or —NHR$^B$, wherein at least one R$^B$ is optionally substituted piperidinyl or optionally substituted piperazinyl.

In some embodiments, at least one R$^y$ is optionally substituted aliphatic. In certain embodiments, at least one R$^y$ is substituted aliphatic. In certain embodiments, at least one R$^y$ is unsubstituted aliphatic. In some embodiments, at least one R$^y$ is optionally substituted C$_{1-6}$ alkyl. In certain embodiments, at least one R$^y$ is unsubstituted C$_{1-6}$ alkyl. In certain embodiments, at least one R$^y$ is substituted C$_{1-6}$ alkyl. In certain embodiments, at least one R$^y$ is methyl, ethyl, or propyl. In certain embodiments, at least one R$^y$ is methyl. In certain embodiments, at least one R$^y$ is —CF$_3$, CHF$_2$, or CH$_2$F. In certain embodiments, at least one R$^y$ is C$_{1-6}$ alkyl substituted with aryl, heteroaryl, or heterocyclyl. In certain embodiments, at least one R$^y$ is benzyl. In certain embodiments, at least one R$^y$ is —(C$_{1-6}$ alkyl)-aryl. In certain embodiments, at least one R$^y$ is —(C$_{1-6}$ alkyl)-heteroaryl. In certain embodiments, at least one R$^y$ is —(C$_{1-6}$ alkyl)-heterocyclyl. In certain embodiments, at least one R$^y$ is —CH$_2$-aryl. In certain embodiments, at least one R$^y$ is —CH$_2$-heteroaryl. In certain embodiments, at least one R$^y$ is —CH$_2$-heterocyclyl.

In some embodiments, at least one R$^y$ is —C(O)N(R$^B$)$_2$. In certain embodiments, at least one R$^y$ is —C(O)NHR$^B$. In certain embodiments, at least one R$^y$ is —C(O)NH$_2$. In certain embodiments, at least one R$^y$ is —C(O)N(R$^B$)$_2$, wherein the R$^B$ groups are taken together with their intervening atoms to form an optionally substituted 5- to 6-membered heterocyclyl. In certain embodiments, at least one R$^y$ is —C(O)N(R$^B$)$_2$, wherein the R$^B$ groups are taken together with their intervening atoms to form an optionally substituted morpholinyl.

In some embodiments, at least one R$^y$ is —SO$_2$N(R$^B$)$_2$. In certain embodiments, at least one R$^y$ is —SO$_2$NHR$^B$. In certain embodiments, at least one R$^y$ is —SO$_2$NH$_2$. In certain embodiments, at least one R$^y$ is —SO$_2$N(R$^B$)$_2$, wherein neither R$^B$ is hydrogen. In certain embodiments, at least one R$^y$ is —SO$_2$NH(C$_{1-6}$ alkyl) or —SO$_2$N(C$_{1-6}$ alkyl)$_2$. In certain embodiments, at least one R$^y$ is —SO$_2$N(CH$_3$)$_2$. In certain embodiments, at least one R$^y$ is —SO$_2$N(R$^B$)$_2$, wherein the R$^B$ groups are taken together with their intervening atoms to form an optionally substituted 5- to 6-membered heterocyclyl. In certain embodiments, at least one R$^y$ is —SO$_2$-morpholinyl. In certain embodiments, at least one R$^y$ is —SO$_2$-piperidinyl, —SO$_2$-piperazinyl, or —SO$_2$-piperidinyl.

In some embodiments, at least one R$^y$ is —SO$_2$R$^A$. In some embodiments, at least one R$^y$ is —SO$_2$R$^A$, wherein R$^A$ is optionally substituted aliphatic. In some embodiments, at least one R$^y$ is —SO$_2$(C$_{1-6}$ alkyl). In some embodiments, at least one R$^y$ is —SO$_2$CH$_3$. In some embodiments, at least one R$^y$ is —C(O)R$^A$. In some embodiments, at least one R$^y$ is —C(O)R$^A$, wherein R$^A$ is optionally substituted aliphatic. In some embodiments, at least one R$^y$ is —C(O)(C$_{1-6}$ alkyl). In some embodiments, at least one R$^y$ is —C(O)CH$_3$.

In some embodiments, at least one R$^y$ is —N(R$^B$)C(O)R$^A$. In certain embodiments, at least one R$^y$ is —NHC(O)R$^A$. In certain embodiments, at least one R$^y$ is —NHC(O)(C$_{1-6}$ alkyl). In certain embodiments, at least one R$^y$ is —NHC(O)CH$_3$.

In some embodiments, at least one R$^y$ is —N(R$^B$)SO$_2$R$^A$. In some embodiments, at least one R$^y$ is —NHSO$_2$R$^A$. In some embodiments, at least one R$^y$ is —N(C$_{1-6}$ alkyl)SO$_2$R$^A$. In certain embodiments, at least one R$^y$ is —NHSO$_2$(C$_{1-6}$ alkyl) or —N(C$_{1-6}$ alkyl)SO$_2$(C$_{1-6}$ alkyl). In certain embodiments, at least one R$^y$ is —NHSO$_2$CH$_3$. In certain embodiments, at least one R$^y$ is —N(CH$_3$)SO$_2$CH$_3$.

In some embodiments, at least one R$^y$ is optionally substituted heterocyclyl, optionally substituted carbocyclyl, optionally substituted aryl, or optionally substituted heteroaryl. In certain embodiments, at least one R$^y$ is an optionally substituted 5- to 6-membered heterocyclyl having 1-2 heteroatoms independently selected from nitrogen, oxygen, and sulfur. In certain embodiments, at least one R$^y$ is an optionally substituted 5-membered heterocyclyl having one heteroatom selected from nitrogen, oxygen, and sulfur. In certain embodiments, at least one R$^y$ is optionally substituted pyrrolidinyl. In certain embodiments, at least one R$^y$ is pyrroldinyl, hydroxypyrrolidinyl, or methylpyrrolidinyl. In certain embodiments, at least one R$^y$ is an optionally substituted 6-membered heterocyclyl having 1-2 heteroatoms independently selected from nitrogen, oxygen, and sulfur. In certain embodiments, at least one R$^y$ is an optionally substituted 6-membered heterocyclyl having one heteroatom selected from nitrogen, oxygen, and sulfur. In certain embodiments, at least one $R^y$ is optionally substituted piperidinyl. In certain embodiments, at least one $R^y$ is an optionally substituted 6-membered heterocyclyl having two heteroatoms independently selected from nitrogen, oxygen, and sulfur. In certain embodiments, at least one $R^y$ is optionally substituted piperdinyl, optionally substituted piperazinyl, or optionally substituted morpholinyl. In certain embodiments, at least one $R^y$ is morpholinyl, tetrahydropyranyl, piperidinyl, methylpiperidinyl, piperazinyl, methylpiperazinyl, acetylpiperazinyl, methylsulfonylpiperazinyl, aziridinyl, or methylaziridinyl. In some embodiments, at least one $R^y$ is an optionally substituted 5- to 6-membered heteroaryl having 1-3 heteroatoms independently selected from nitrogen, oxygen, and sulfur. In certain embodiments, at least one $R^y$ is an optionally substituted 5-membered heteroaryl having 1-3 heteroatoms independently selected from nitrogen, oxygen, and sulfur. In certain embodiments, at least one $R^y$ is an optionally substituted 5-membered heteroaryl having one heteroatom selected from nitrogen, oxygen, and sulfur. In certain embodiments, at least one $R^y$ is an optionally substituted 5-membered heteroaryl having two heteroatoms independently selected from nitrogen, oxygen, and sulfur. In certain embodiments, at least one $R^y$ is an optionally substituted 6-membered heteroaryl having 1-3 nitrogens. In certain embodiments, at least one $R^y$ is an optionally substituted pyrazolyl. In certain embodiments, at least one $R^y$ is an optionally substituted imidazolyl. In certain embodiments, at least one $R^y$ is an optionally substituted pyridyl. In certain embodiments, at least one $R^y$ is an optionally substituted pyrimidyl. In certain embodiments, at least one $R^y$ is pyrazolyl, methylpyrazolyl, imidazolyl, or methylimidazolyl.

In some embodiments, $R^y$ is $-OR^A$. In some embodiments, $R^y$ is $-OR^A$, wherein $R^A$ is optionally substituted heterocyclyl. In some embodiments, $R^y$ is $-OR^A$, wherein $R^A$ is optionally substituted heteroaryl. In some embodiments, $R^y$ is $-OR^A$, wherein $R^A$ is optionally substituted cycloalkyl. In some embodiments, $R^y$ is $-N(R^B)_2$. In some embodiments, $R^y$ is $-NHR^B$. In some embodiments, $R^y$ is $-NHR^B$, wherein $R^B$ is optionally substituted heterocyclyl. In some embodiments, $R^y$ is $-NHR^B$, wherein $R^B$ is optionally substituted heteroaryl. In some embodiments, $R^y$ is $-NHR^B$, wherein $R^B$ is optionally substituted cycloalkyl. In some embodiments, $R^y$ is $-N(R^B)_2$, wherein one $R^B$ is optionally substituted heterocyclyl, and the other $R^B$ is $C_{1-4}$ alkyl. In some embodiments, $R^y$ is $-N(R^B)_2$, wherein one $R^B$ is optionally substituted heteroaryl, and the other $R^B$ is $C_{1-4}$ alkyl. In some embodiments, $R^y$ is $-N(R^B)_2$, wherein one $R^B$ is optionally substituted cycloalkyl, and the other $R^B$ is $C_{1-4}$ alkyl.

In certain embodiments, Ar is selected from the group consisting of:

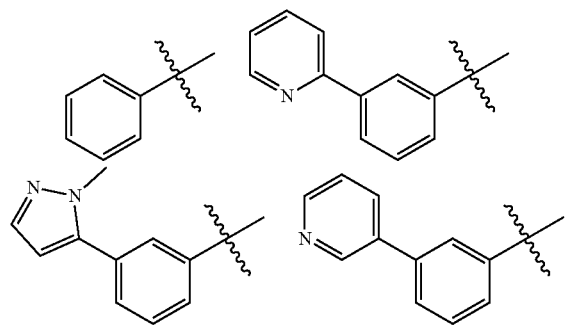

-continued

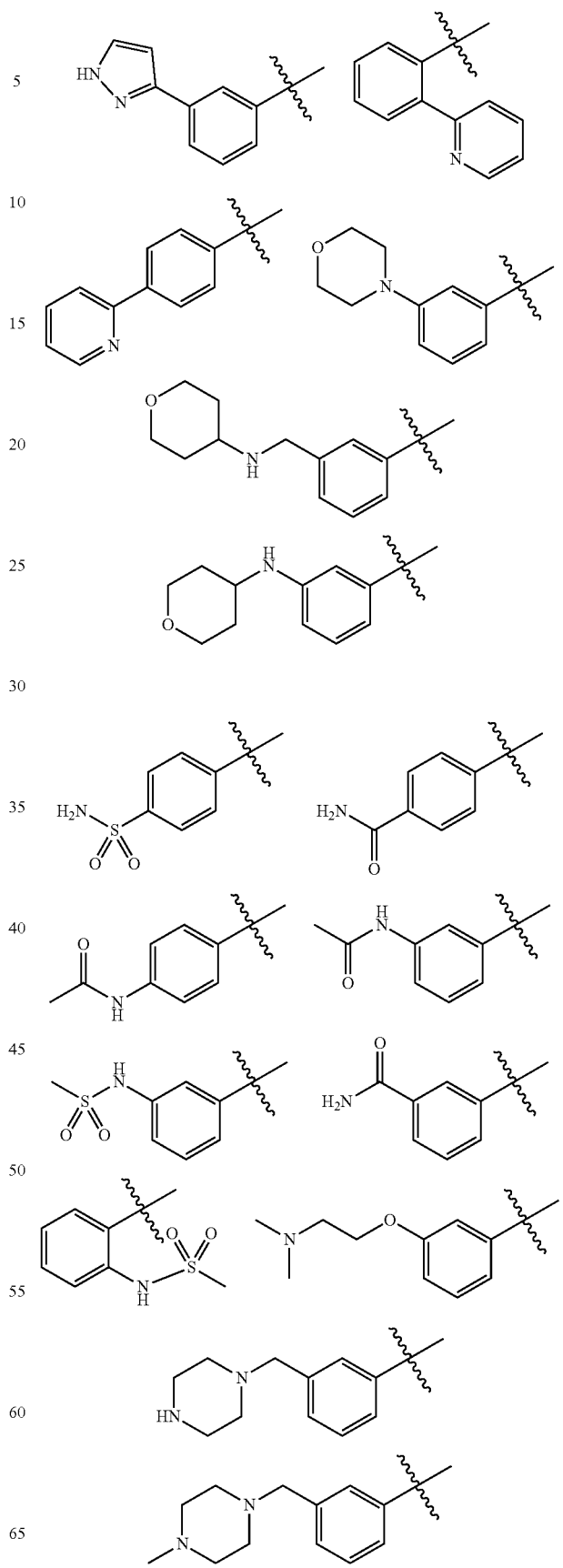

-continued
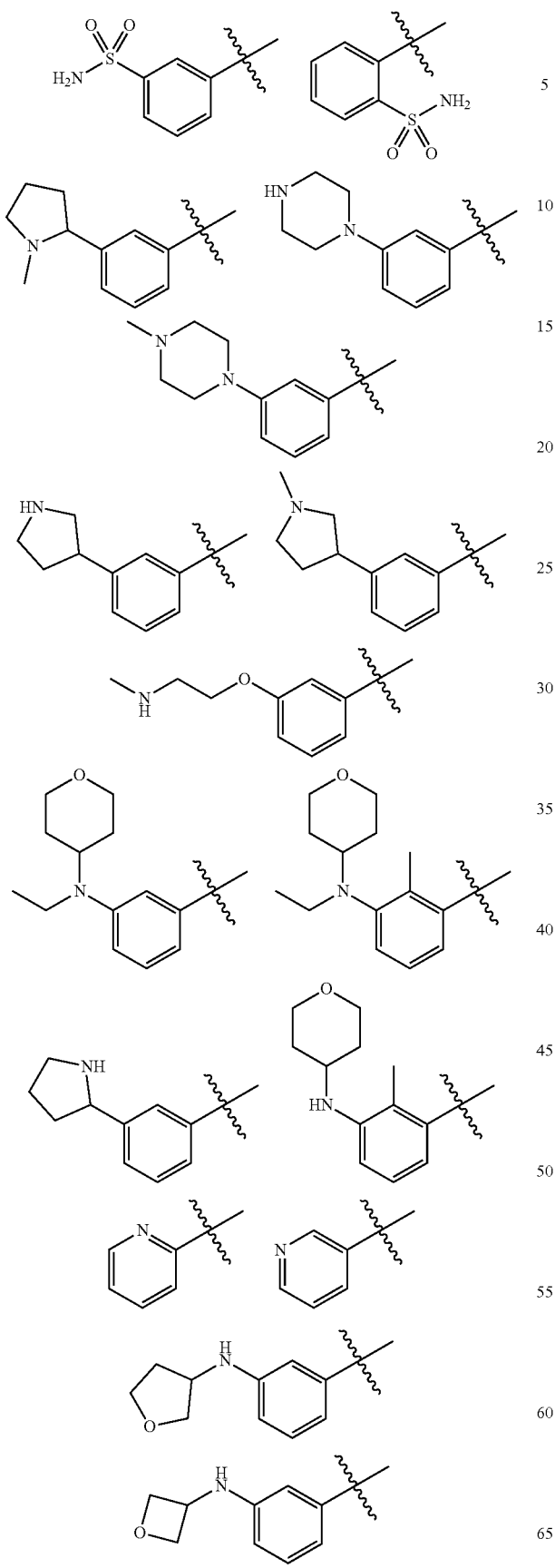
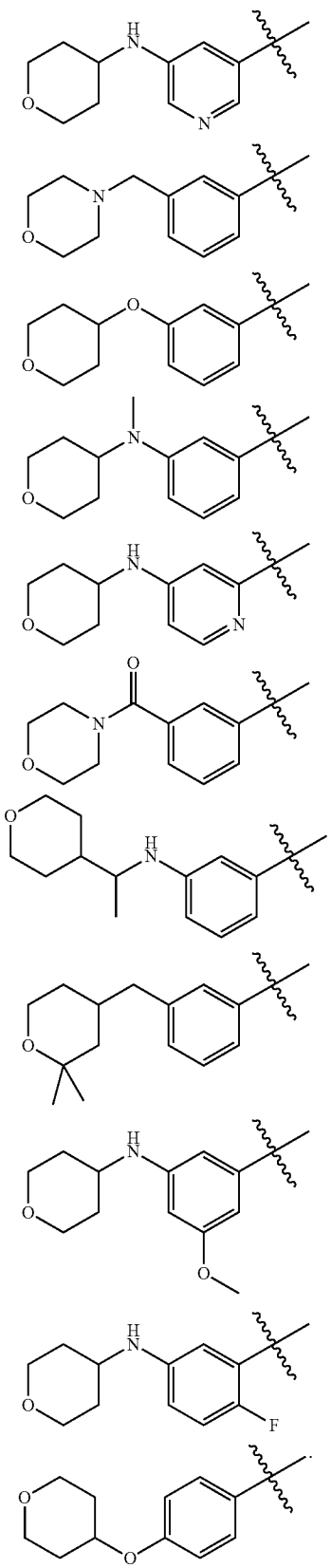
In certain embodiments, Ar is selected from the group consisting of:

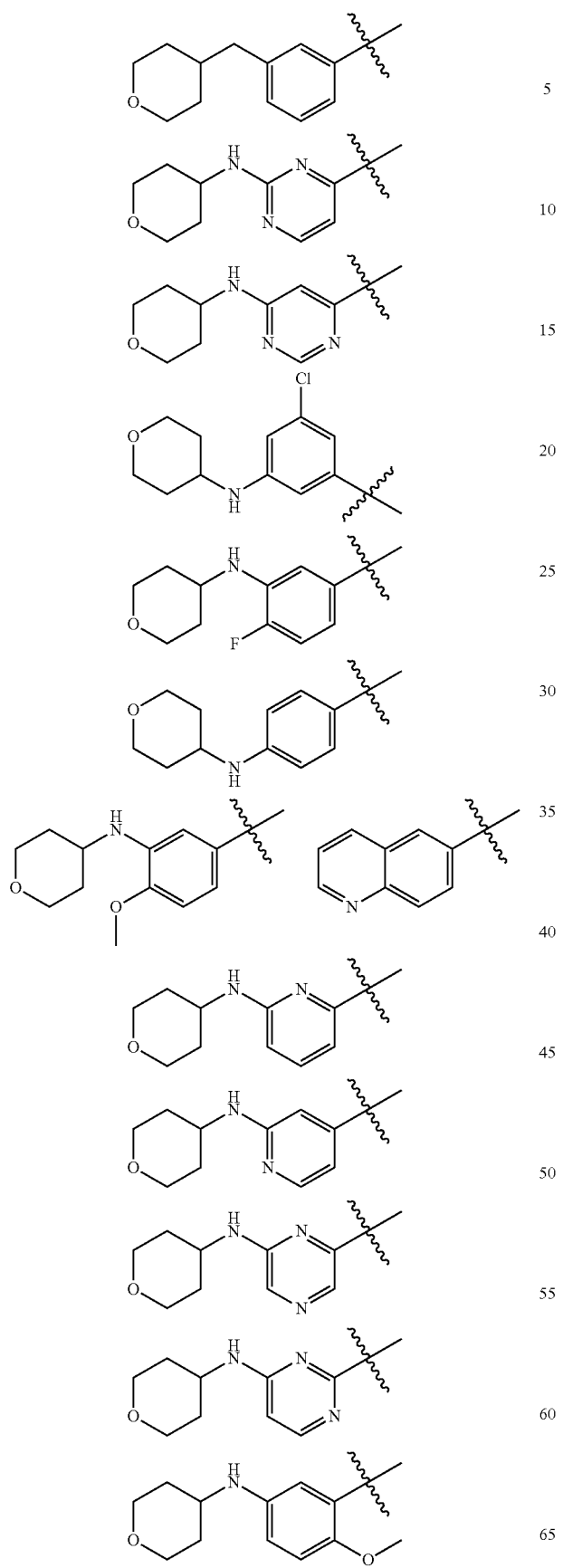
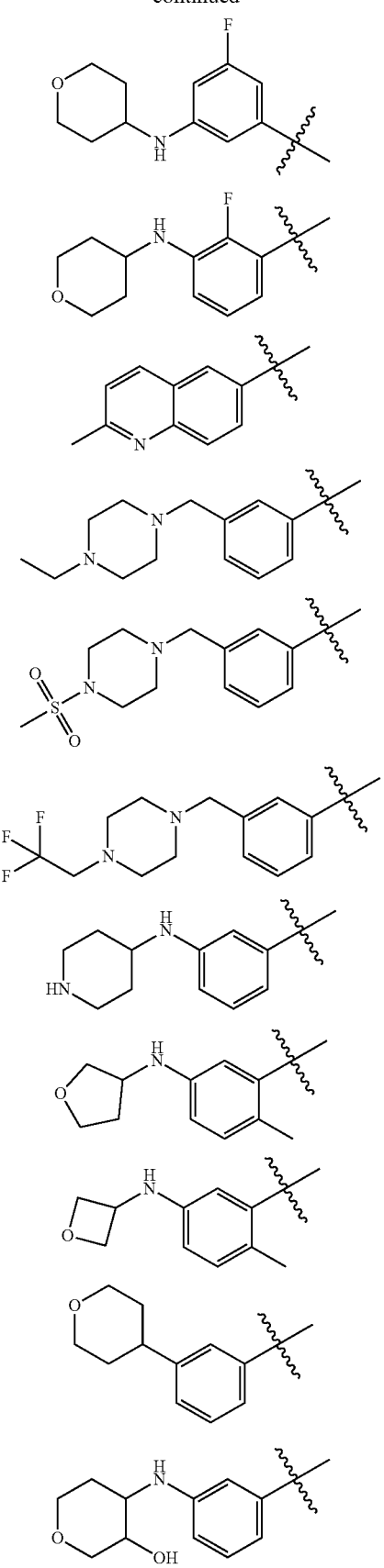

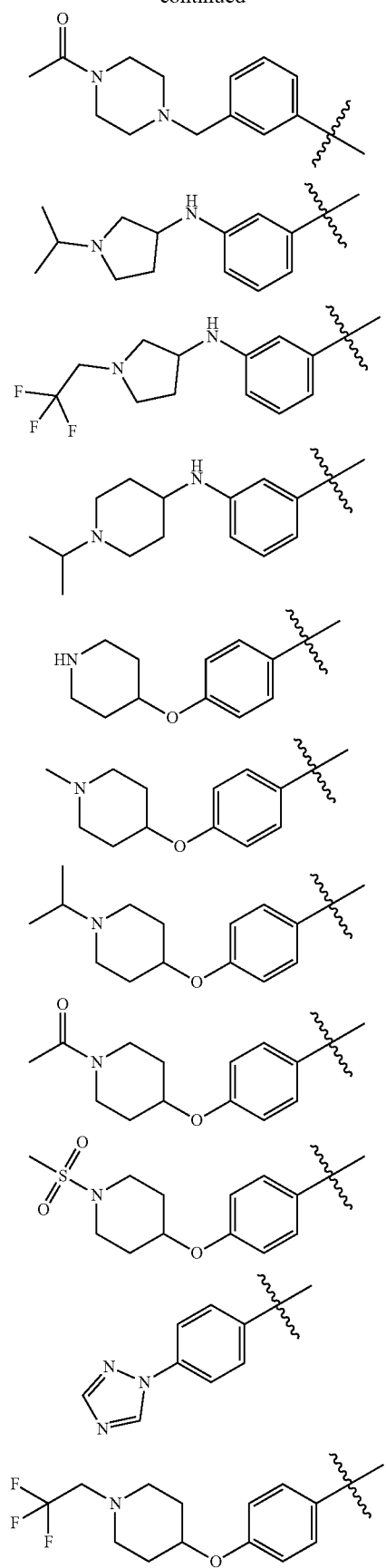
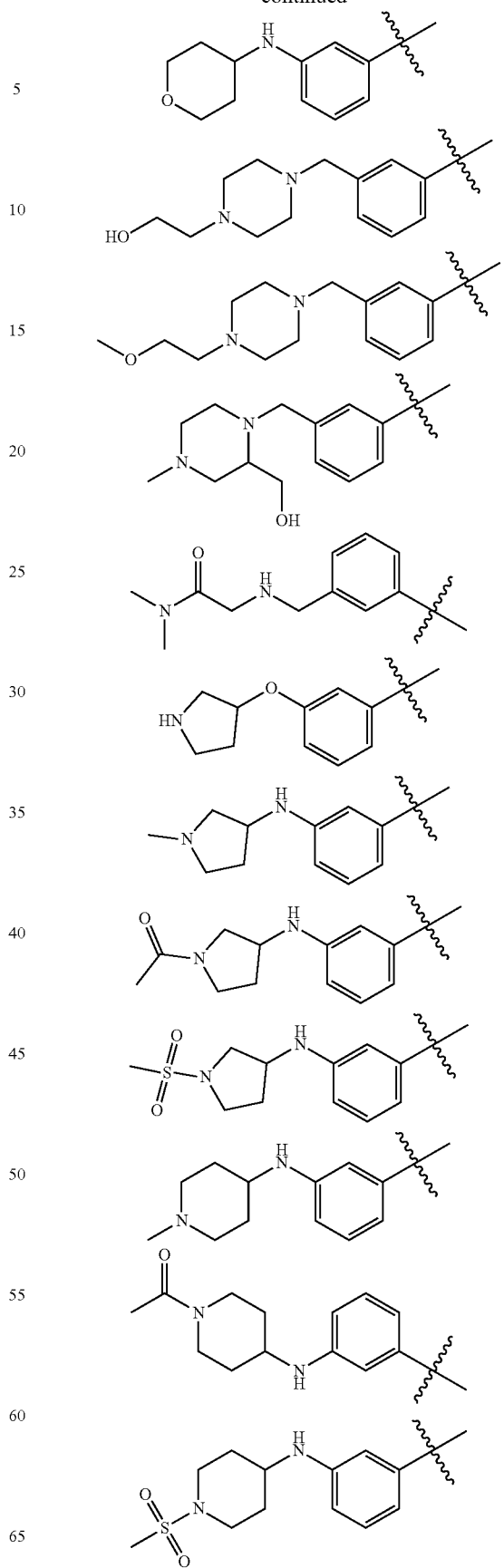

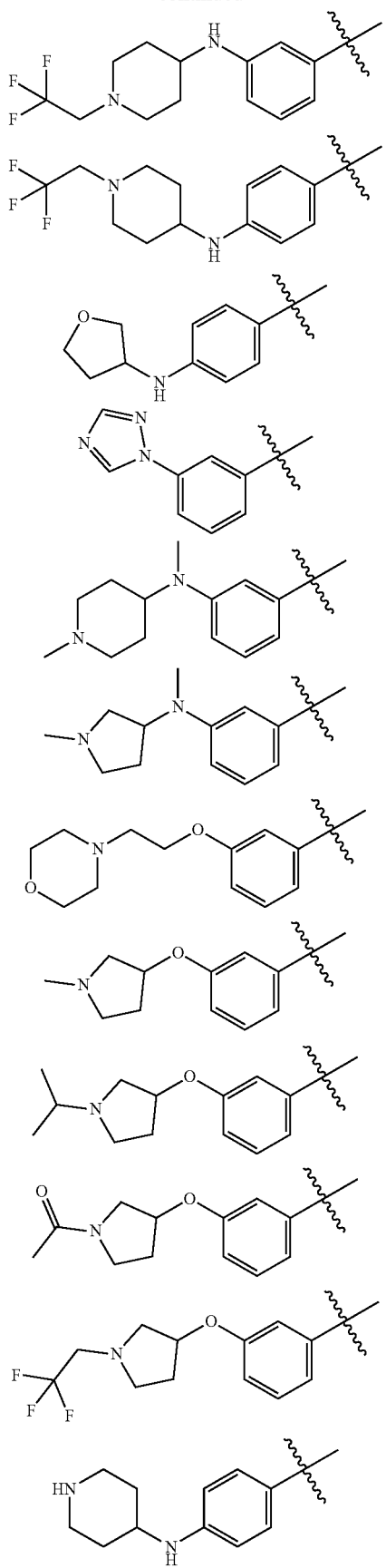
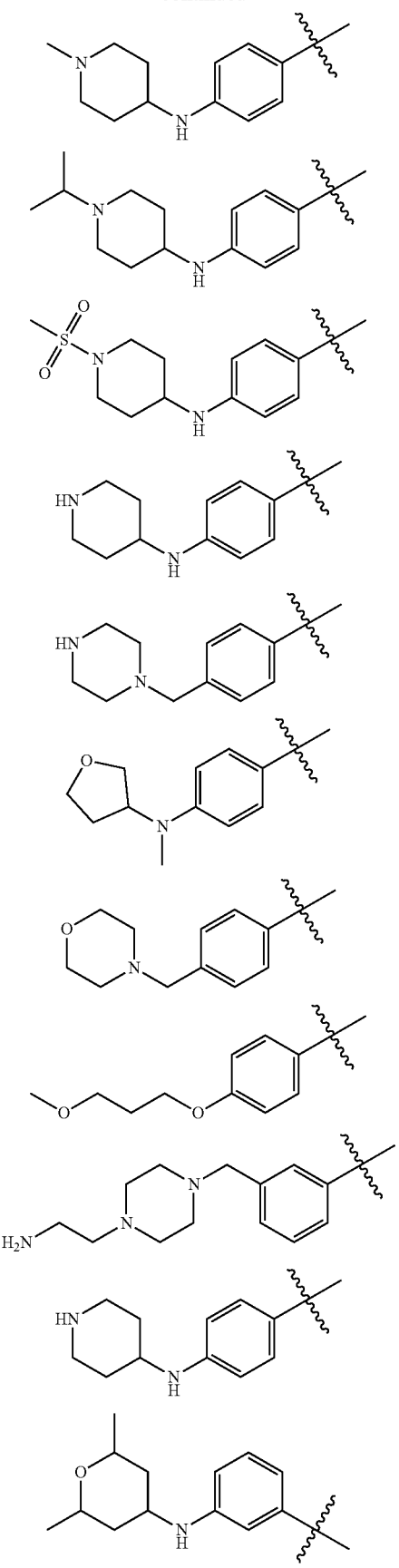

-continued

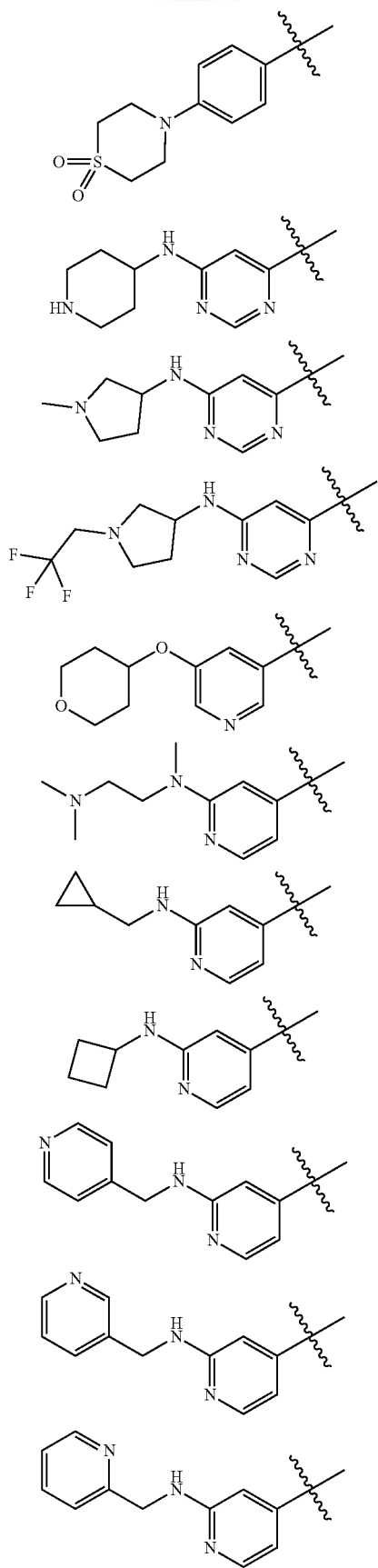
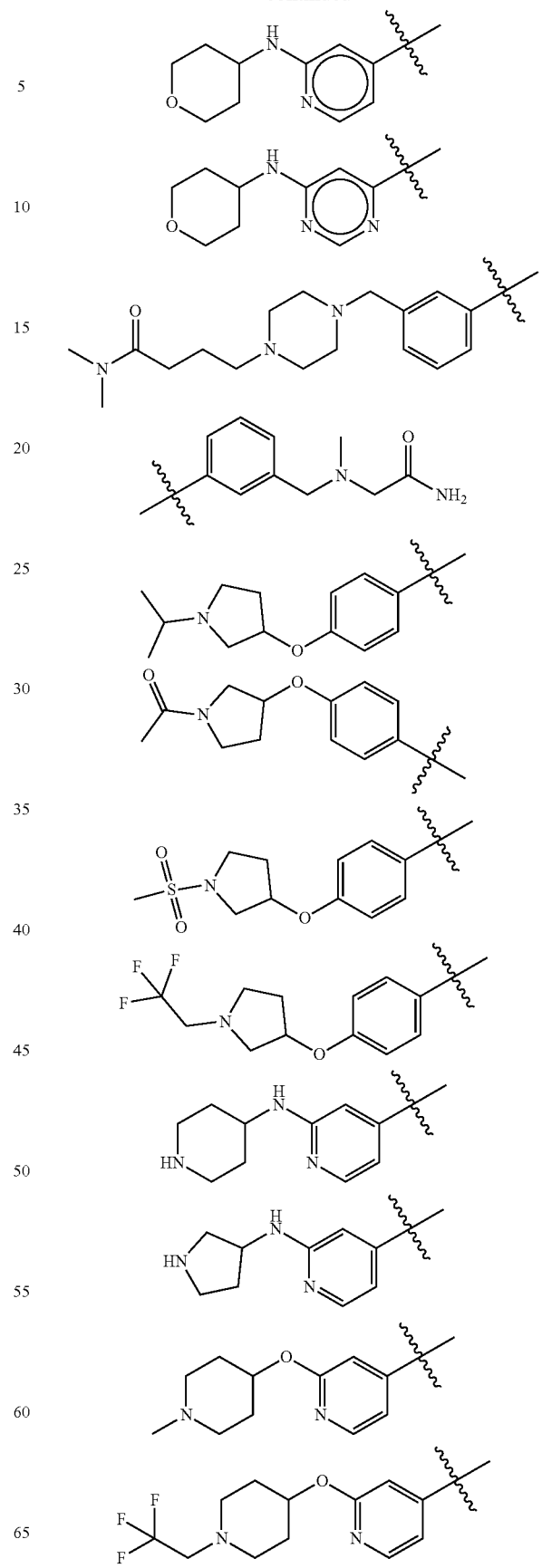

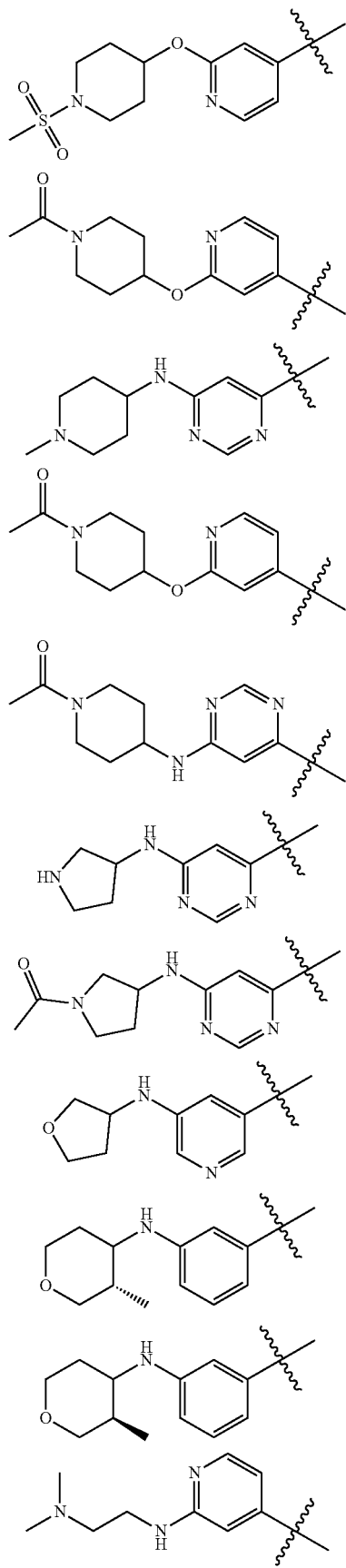
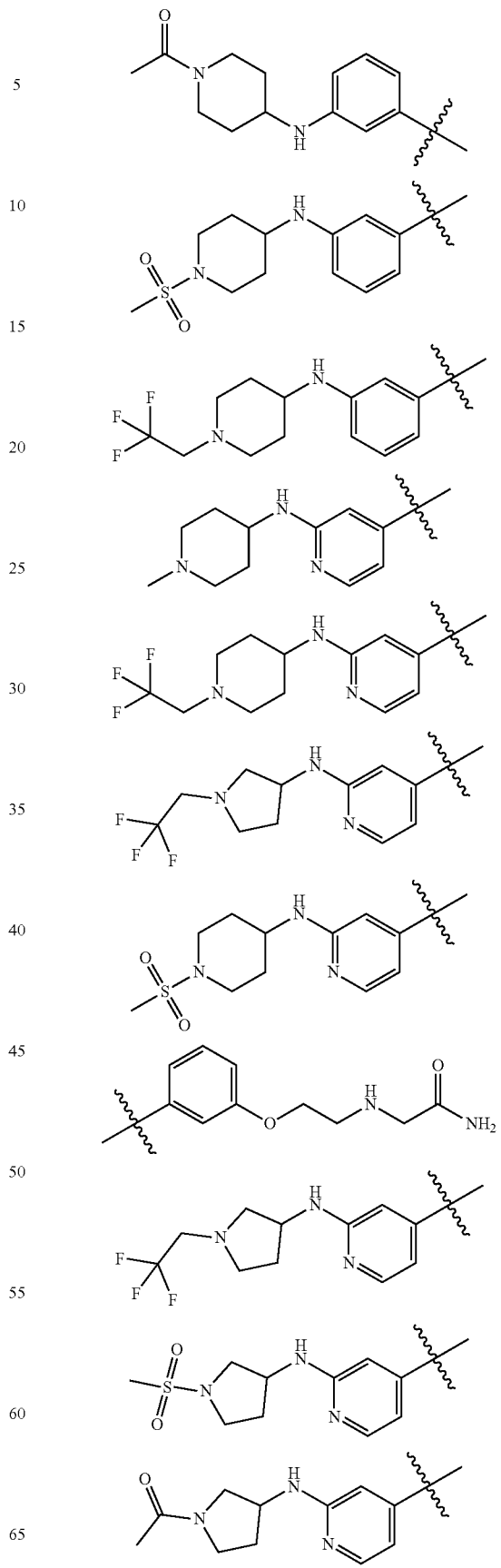

-continued
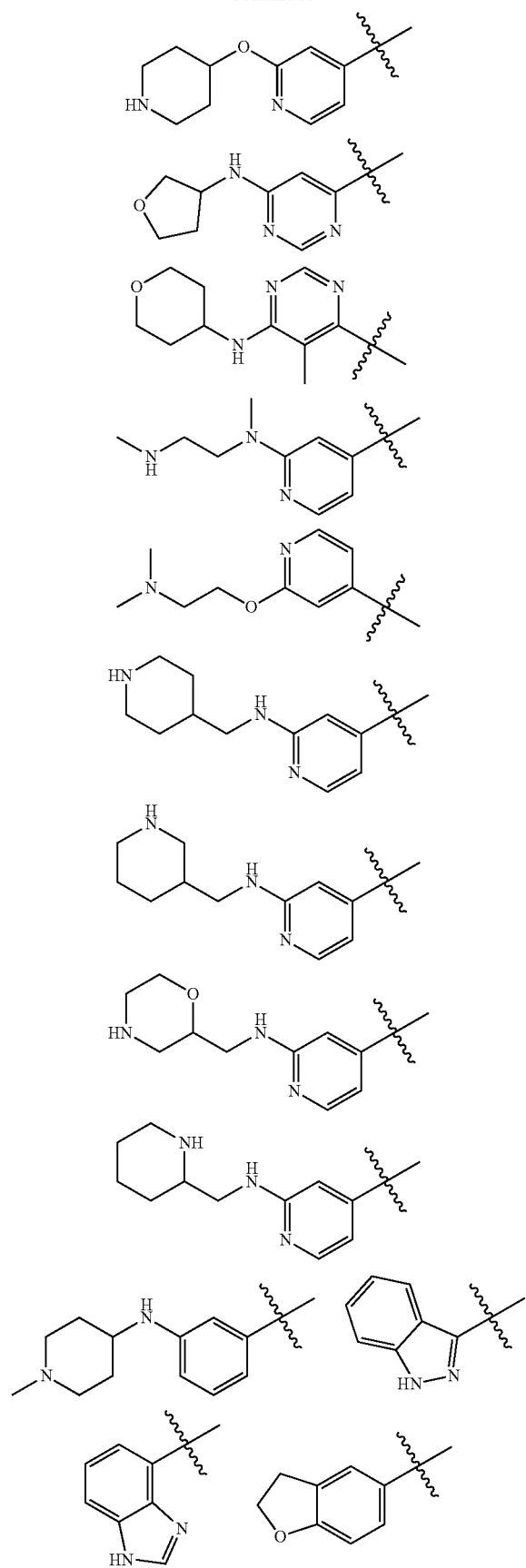
-continued
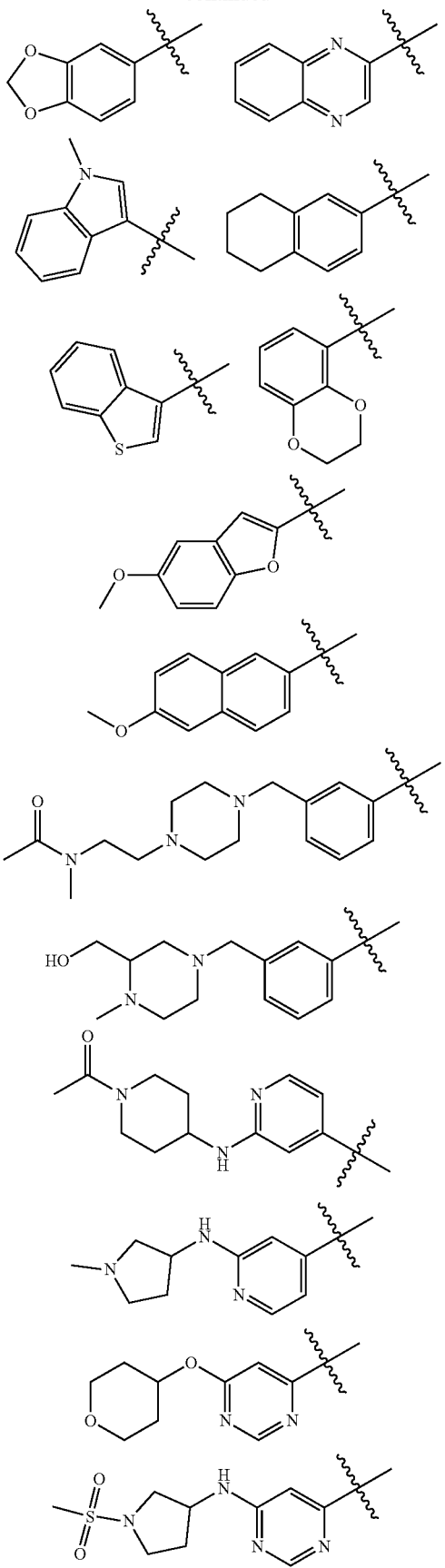

51
-continued
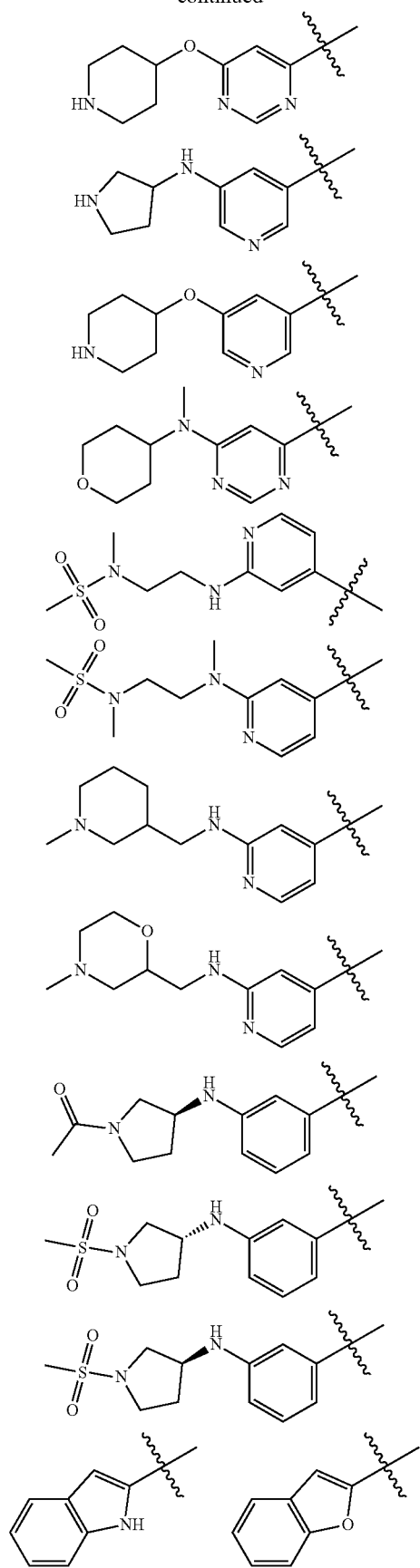
52
-continued
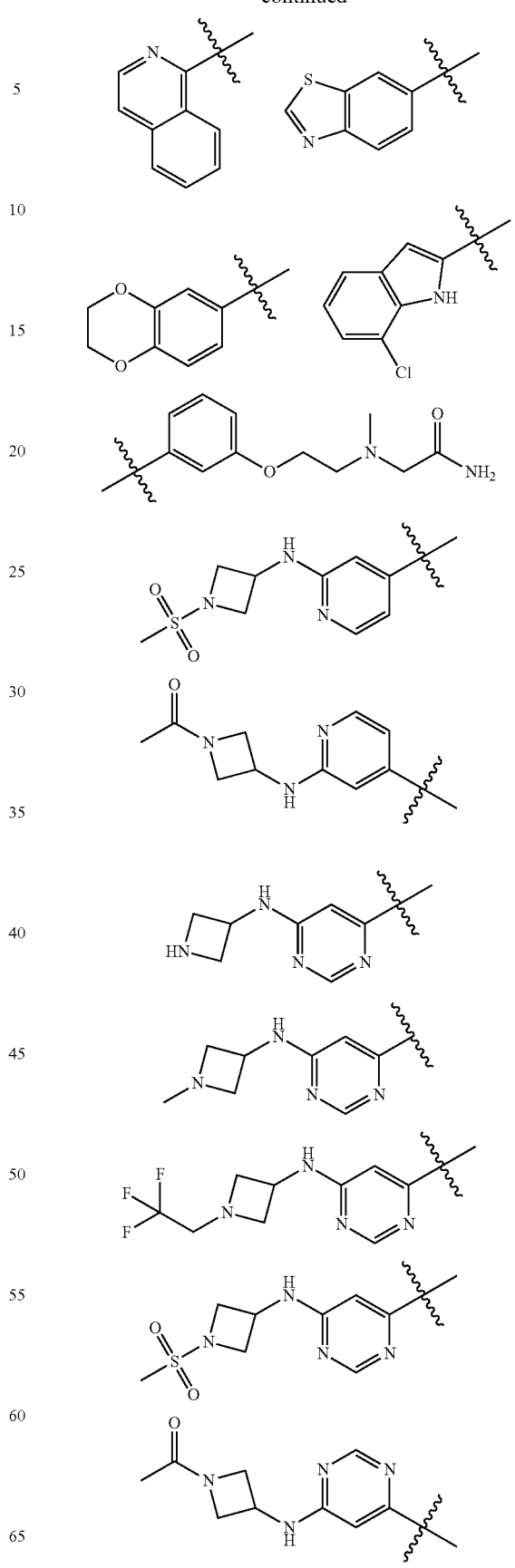

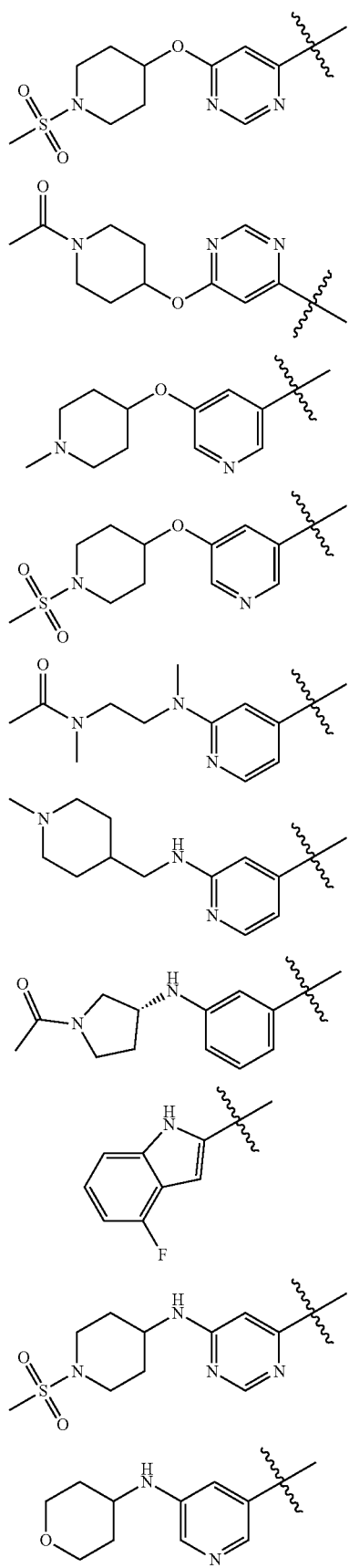
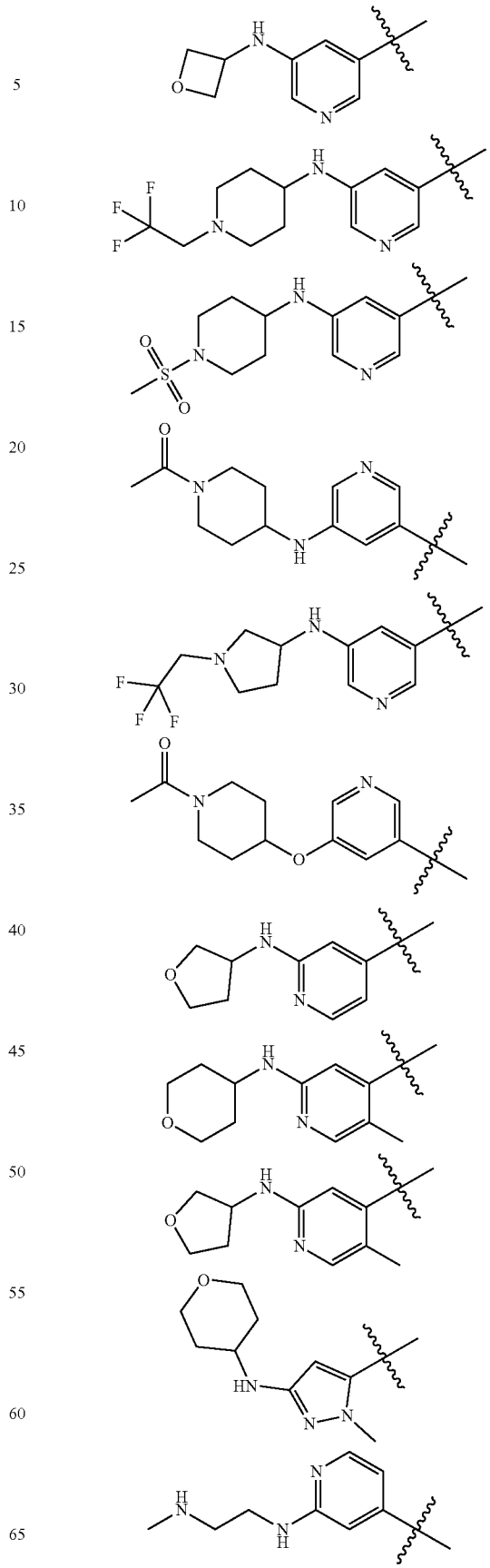

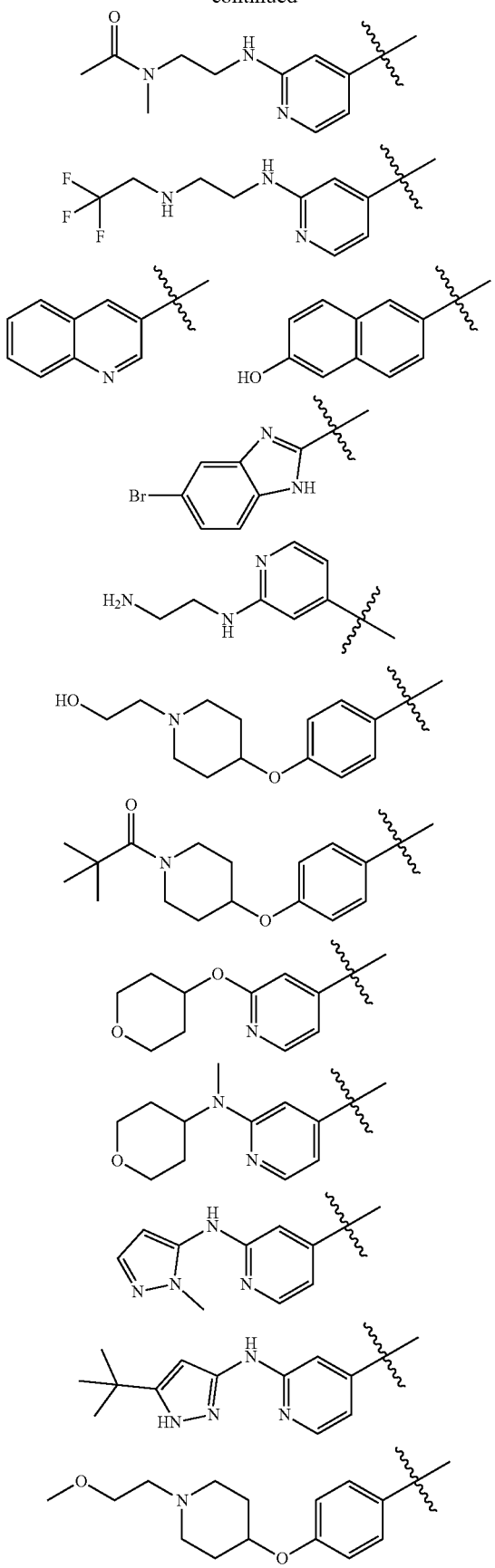

As defined generally above, each $R^x$ is independently selected from the group consisting of halo, —CN, optionally substituted aliphatic, —OR', and —N(R")$_2$. In certain embodiments, at least one $R^x$ is halo. In certain embodiments, at least one $R^x$ is fluoro. In certain embodiments, at least one $R^x$ is —CN. In certain embodiments, at least one $R^x$ is optionally substituted aliphatic. In certain embodiments, at least one $R^x$ is optionally substituted $C_{1-6}$ alkyl. In certain embodiments, at least one $R^x$ is methyl. In certain embodiments, at least one $R^x$ is —CF$_3$. In certain embodiments, at least one $R^x$ is —OR' or —N(R")$_2$. In certain embodiments, $R^x$ is not —OR' or —N(R")$_2$. In certain embodiments, at least one $R^x$ is —OCH$_3$. In certain embodiments, $R^x$ is not —OCH$_3$.

One of ordinary skill in the art will appreciate that an $R^x$ group can be attached anywhere on the tetrahydroisoquinoline or dihydroisoquinoline ring. In certain embodiments, an $R^x$ group is attached to the benzene portion of the tetrahydroisoquinoline or dihydroisoquinoline ring. In certain embodiments, an $R^x$ group is attached to the tetrahydropyridine or dihydropyridine portion of the tetrahydroisoquinoline or dihydroisoquinoline ring. In certain embodiments, $R^x$ groups are attached to both the benzene portion and the tetrahydropyridine (or dihydropyridine) portion of the tetrahydroisoquinoline (or dihydroisoquinoline) ring. See, for example, the structures shown below:

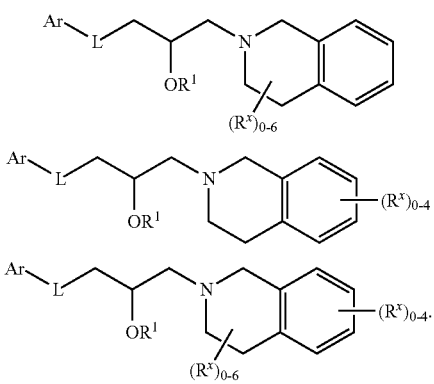

In certain embodiments, a provided compound is of Formula (XIV):

XIV

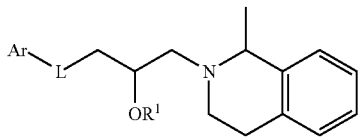

or a pharmaceutically acceptable salt thereof.

As defined generally above, n is 0, 1, 2, 3, 4, 5, 6, 7, 8, 9, or 10. In certain embodiments, n is 0. In certain embodiments, n is 1. In certain embodiments, n is 2.

In certain embodiments, a provided compound is of Formula (XV), (XVI), (XVII), or (XVIII):

XV

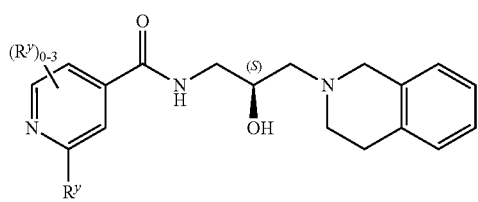

XVI

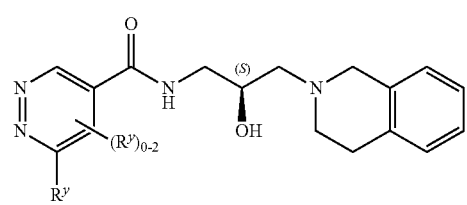

XVII

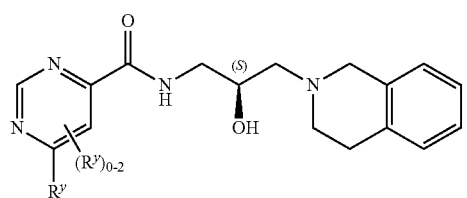

XVIII

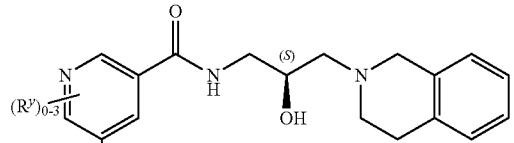

or a pharmaceutically acceptable salt thereof, wherein each $R^y$ for Formula (XV), (XVI), (XVII), or (XVIII) is independently as described herein.

In certain embodiments, a provided compound is of Formula (XV-a), (XVI-a), (XVII-a), or (XVIII-a):

XV-a

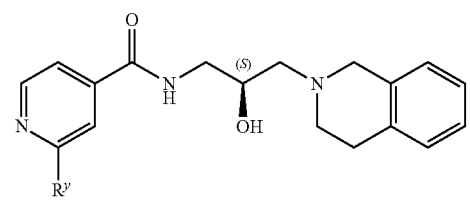

XVI-a

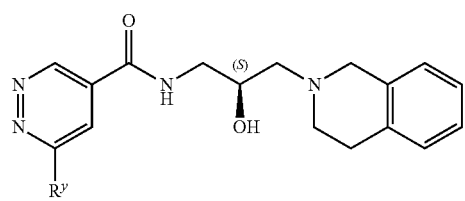

XVII-a

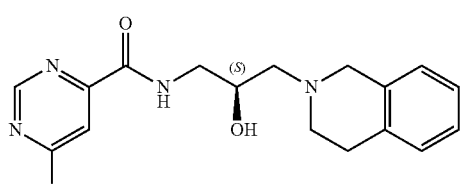

XVIII-a

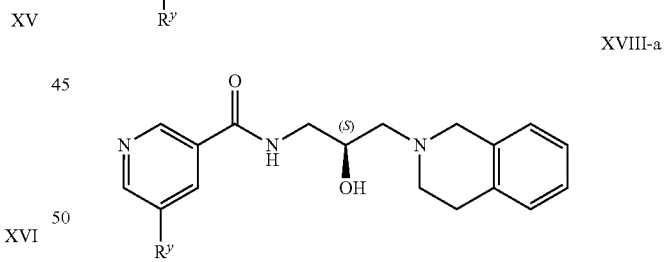

or a pharmaceutically acceptable salt thereof, wherein $R^y$ for Formula (XV-a), (XVI-a), (XVII-a), or (XVIII-a) is as described herein. In some embodiments, e.g. for Formula (XV-a), (XVI-a), (XVII-a), or (XVIII-a), $R^y$ is —$OR^A$. In some embodiments, e.g. for Formula (XV-a), (XVI-a), (XVII-a), or (XVIII-a), $R^y$ is —$OR^A$, wherein $R^A$ is optionally substituted heterocyclyl. In some embodiments, e.g. for Formula (XV-a), (XVI-a), (XVII-a), or (XVIII-a), $R^y$ is —$OR^A$, wherein $R^A$ is optionally substituted heteroaryl. In some embodiments, e.g. for Formula (XV-a), (XVI-a), (XVII-a), or (XVIII-a), $R^y$ is —$OR^A$, wherein $R^A$ is optionally substituted cycloalkyl. In some embodiments, e.g. for Formula (XV-a), (XVI-a), (XVII-a), or (XVIII-a), $R^y$ is —$N(R^B)_2$. In some embodiments, e.g. for Formula (XV-a), (XVI-a), (XVII-a), or (XVIII-a), $R^y$ is —$NHR^B$. In some embodiments, e.g. for Formula (XV-a), (XVI-a), (XVII-a), or (XVIII-a), $R^y$ is —$NHR^B$, wherein $R^B$ is optionally substituted heterocyclyl. In some embodiments, e.g. for Formula (XV-a), (XVI-a), (XVII-a), or (XVIII-a), $R^y$ is —$NHR^B$, wherein $R^B$ is optionally substituted heteroaryl. In some embodiments, e.g. for Formula (XV-a), (XVI-a), (XVII-a), or (XVIII-a), $R^y$ is —$NHR^B$, wherein $R^B$ is optionally substituted cycloalkyl. In some embodiments, e.g. for Formula (XV-a), (XVI-a), (XVII-a), or (XVIII-a), $R^y$ is —$N(R^B)_2$, wherein one $R^B$ is optionally substituted heterocyclyl, and the other $R^B$ is $C_{1-4}$ alkyl. In some embodiments, e.g. for Formula (XV-a), (XVI-a), (XVII-a), or (XVIII-a), $R^y$ is —$N(R^B)_2$, wherein one $R^B$ is optionally substituted heteroaryl, and the other $R^B$ is $C_{1-4}$ alkyl. In some embodiments, e.g. for Formula (XV-a), (XVI-a), (XVII-a), or (XVIII-a), $R^y$ is —$N(R^B)_2$, wherein one $R^B$ is optionally substituted cycloalkyl, and the other $R^B$ is $C_{1-4}$ alkyl.

In certain embodiments, a provided compound is of Formula (XV-b):

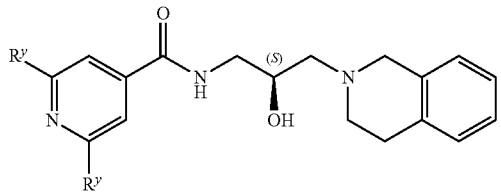

XV-b or a pharmaceutically acceptable salt thereof, wherein each $R^y$ is independently as described herein.

In some embodiments, e.g. for Formula (XV), (XVI), (XVII), (XVIII), (XV-a), (XVI-a), (XVII-a), (XVIII-a), or (XV-b), at least one $R^y$ is halo. In certain embodiments, at least one $R^y$ is fluoro. In certain embodiments, at least one $R^y$ is chloro. In some embodiments, at least one $R^y$ is —CN.

In some embodiments, e.g. for Formula (XV), (XVI), (XVII), (XVIII), (XV-a), (XVI-a), (XVII-a), (XVIII-a), or (XV-b), at least one $R^y$ is —$OR^A$, wherein $R^A$ is optionally substituted aliphatic. In some embodiments, at least one $R^y$ is —$OR^A$, wherein $R^A$ is unsubstituted $C_{1-6}$ alkyl. In certain embodiments, at least one $R^y$ is methoxy, ethoxy, or propoxy. In certain embodiments, at least one $R^y$ is methoxy. In some embodiments, at least one $R^y$ is —$OR^A$, wherein $R^A$ is substituted $C_{1-6}$ alkyl. In certain embodiments, at least one $R^y$ is —$OCH_2CH_2N(CH_3)_2$. In some embodiments, at least one $R^y$ is —$OR^A$, wherein $R^A$ is optionally substituted heterocyclyl. In some embodiments, at least one $R^y$ is —$OR^A$, wherein $R^A$ is an optionally substituted 4- to 7-membered heterocyclyl having 1-2 heteroatoms independently selected from nitrogen, oxygen, and sulfur. In some embodiments, at least one $R^y$ is —$OR^A$, wherein $R^A$ is oxetanyl, tetrahydrofuranyl, or tetrahydropyranyl. In some embodiments, at least one $R^y$ is —$OR^A$, wherein $R^A$ is optionally substituted piperidinyl or optionally substituted piperazinyl. In some embodiments, at least one $R^y$ is —$OR^A$, wherein $R^A$ is optionally substituted heterocyclyl. In some embodiments, at least one $R^y$ is —$OR^A$, wherein $R^A$ is optionally substituted heteroaryl. In some embodiments, at least one $R^y$ is —$OR^A$, wherein $R^A$ is optionally substituted cycloalkyl.

In some embodiments, e.g. for Formula (XV), (XVI), (XVII), (XVIII), (XV-a), (XVI-a), (XVII-a), (XVIII-a), or (XV-b), at least one $R^y$ is —$N(R^B)_2$. In some embodiments, at least one $R^y$ is —$N(R^B)_2$, wherein each $R^B$ is independently selected from hydrogen or $C_{1-6}$ alkyl. In some embodiments, at least one $R^y$ is —$NHR^B$. In some embodiments, at least one $R^y$ is —$N(C_{1-6}$ alkyl$)_2$, —$NH(C_{1-6}$ alkyl), or —$NH_2$. In certain embodiments, at least one $R^y$ is —$NH_2$. In certain embodiments, at least one $R^y$ is —$NHCH_3$. In certain embodiments, at least one $R^y$ is —$N(CH_3)_2$. In some embodiments, at least one $R^y$ is —$N(R^B)_2$ or —$NHR^B$, wherein at least one $R^B$ is optionally substituted heterocyclyl. In some embodiments, at least one $R^y$ is —$N(R^B)_2$ or —$NHR^B$, wherein at least one $R^B$ is an optionally substituted 4- to 7-membered heterocyclyl having 1-2 heteroatoms independently selected from nitrogen, oxygen, and sulfur. In some embodiments, at least one $R^y$ is —$N(R^B)_2$ or —$NHR^B$, wherein at least one $R^B$ is oxetanyl, tetrahydropyranyl, or tetrahydrofuranyl. In some embodiments, at least one $R^y$ is —$N(R^B)_2$ or —$NHR^B$, wherein at least one $R^B$ is optionally substituted piperidinyl or optionally substituted piperazinyl. In some embodiments, at least one $R^y$ is —$N(R^B)_2$, wherein one $R^B$ is optionally substituted heterocyclyl, and the other $R^B$ is $C_{1-4}$ alkyl. In some embodiments, at least one $R^y$ is —$N(R^B)_2$, wherein one $R^B$ is optionally substituted heteroaryl, and the other $R^B$ is $C_{1-4}$ alkyl. In some embodiments, at least one $R^y$ is —$N(R^B)_2$, wherein one $R^B$ is optionally substituted cycloalkyl, and the other $R^B$ is $C_{1-4}$ alkyl.

In some embodiments, e.g. for Formula (XV), (XVI), (XVII), (XVIII), (XV-a), (XVI-a), (XVII-a), (XVIII-a), or (XV-b), at least one $R^y$ is optionally substituted aliphatic. In certain embodiments, at least one $R^y$ is substituted aliphatic. In certain embodiments, at least one $R^y$ is unsubstituted aliphatic. In some embodiments, at least one $R^y$ is optionally substituted $C_{1-6}$ alkyl. In certain embodiments, at least one $R^y$ is unsubstituted $C_{1-6}$ alkyl. In certain embodiments, at least one $R^y$ is substituted $C_{1-6}$ alkyl. In certain embodiments, at least one $R^y$ is methyl, ethyl, or propyl. In certain embodiments, at least one $R^y$ is methyl. In certain embodiments, at least one $R^y$ is —$CF_3$, $CHF_2$, or $CH_2F$. In certain embodiments, at least one $R^y$ is $C_{1-6}$ alkyl substituted with aryl, heteroaryl, or heterocyclyl. In certain embodiments, at least one $R^y$ is benzyl. In certain embodiments, at least one $R^y$ is —($C_{1-6}$ alkyl)-aryl. In certain embodiments, at least one $R^y$ is —($C_{1-6}$ alkyl)-heteroaryl. In certain embodiments, at least one $R^y$ is —($C_{1-6}$ alkyl)-heterocyclyl. In certain embodiments, at least one $R^y$ is —$CH_2$-aryl. In certain embodiments, at least one $R^y$ is —$CH_2$-heteroaryl. In certain embodiments, at least one $R^y$ is —$CH_2$-heterocyclyl.

In some embodiments, e.g. for Formula (XV), (XVI), (XVII), (XVIII), (XV-a), (XVI-a), (XVII-a), (XVIII-a), or (XV-b), at least one $R^y$ is —$C(O)N(R^B)_2$. In certain embodiments, at least one $R^y$ is —$C(O)NHR^B$. In certain embodiments, at least one $R^y$ is —$C(O)NH_2$. In certain embodiments, at least one $R^y$ is —$C(O)N(R^B)_2$, wherein the $R^B$ groups are taken together with their intervening atoms to form an optionally substituted 5- to 6-membered heterocyclyl. In certain embodiments, at least one $R^y$ is —$C(O)N(R^B)_2$, wherein the $R^B$ groups are taken together with their intervening atoms to form an optionally substituted morpholinyl.

In some embodiments, e.g. for Formula (XV), (XVI), (XVII), (XVIII), (XV-a), (XVI-a), (XVII-a), (XVIII-a), or (XV-b), at least one $R^y$ is —$SO_2N(R^B)_2$. In certain embodiments, at least one $R^y$ is —$SO_2NHR^B$. In certain embodiments, at least one $R^y$ is —$SO_2NH_2$. In certain embodiments, at least one $R^y$ is —$SO_2N(R^B)_2$, wherein neither $R^B$ is hydrogen. In certain embodiments, at least one $R^y$ is —$SO_2NH(C_{1-6}$ alkyl) or —$SO_2N(C_{1-6}$ alkyl$)_2$. In certain embodiments, at least one $R^y$ is —$SO_2N(CH_3)_2$. In certain embodiments, at least one $R^y$ is —SO$_2$N($R^B$)$_2$, wherein the $R^B$ groups are taken together with their intervening atoms to form an optionally substituted 5- to 6-membered heterocyclyl. In certain embodiments, at least one $R^y$ is —SO$_2$-morpholinyl. In certain embodiments, at least one $R^y$ is —SO$_2$-piperidinyl, —SO$_2$-piperazinyl, or —SO$_2$-piperidinyl.

In some embodiments, e.g. for Formula (XV), (XVI), (XVII), (XVIII), (XV-a), (XVI-a), (XVII-a), (XVIII-a), or (XV-b), at least one $R^y$ is —SO$_2$$R^A$. In some embodiments, at least one $R^y$ is —SO$_2$$R^A$, wherein $R^A$ is optionally substituted aliphatic. In some embodiments, at least one $R^y$ is —SO$_2$(C$_{1-6}$ alkyl). In some embodiments, at least one $R^y$ is —SO$_2$CH$_3$. In some embodiments, at least one $R^y$ is —C(O)$R^A$. In some embodiments, at least one $R^y$ is —C(O)$R^A$, wherein $R^A$ is optionally substituted aliphatic. In some embodiments, at least one $R^y$ is —C(O)(C$_{1-6}$ alkyl). In some embodiments, at least one $R^y$ is —C(O)CH$_3$.

In some embodiments, e.g. for Formula (XV), (XVI), (XVII), (XVIII), (XV-a), (XVI-a), (XVII-a), (XVIII-a), or (XV-b), at least one $R^y$ is —N($R^B$)C(O)$R^A$. In certain embodiments, at least one $R^y$ is —NHC(O)$R^A$. In certain embodiments, at least one $R^y$ is —NHC(O)(C$_{1-6}$ alkyl). In certain embodiments, at least one $R^y$ is —NHC(O)CH$_3$.

In some embodiments, e.g. for Formula (XV), (XVI), (XVII), (XVIII), (XV-a), (XVI-a), (XVII-a), (XVIII-a), or (XV-b), at least one $R^y$ is —N($R^B$)SO$_2$$R^A$. In some embodiments, at least one $R^y$ is —NHSO$_2$$R^A$. In some embodiments, at least one $R^y$ is —N(C$_{1-6}$ alkyl)SO$_2$$R^A$. In certain embodiments, at least one $R^y$ is —NHSO$_2$(C$_{1-6}$ alkyl) or —N(C$_{1-6}$ alkyl)SO$_2$(C$_{1-6}$ alkyl). In certain embodiments, at least one $R^y$ is —NHSO$_2$CH$_3$. In certain embodiments, at least one $R^y$ is —N(CH$_3$)SO$_2$CH$_3$.

In some embodiments, e.g. for Formula (XV), (XVI), (XVII), (XVIII), (XV-a), (XVI-a), (XVII-a), (XVIII-a), or (XV-b), at least one $R^y$ is optionally substituted heterocyclyl, optionally substituted carbocyclyl, optionally substituted aryl, or optionally substituted heteroaryl. In certain embodiments, at least one $R^y$ is an optionally substituted 5- to 6-membered heterocyclyl having 1-2 heteroatoms independently selected from nitrogen, oxygen, and sulfur. In certain embodiments, at least one $R^y$ is an optionally substituted 5-membered heterocyclyl having one heteroatom selected from nitrogen, oxygen, and sulfur. In certain embodiments, at least one $R^y$ is optionally substituted pyrrolidinyl. In certain embodiments, at least one $R^y$ is pyrroldinyl, hydroxypyrrolidinyl, or methylpyrrolidinyl. In certain embodiments, at least one $R^y$ is an optionally substituted 6-membered heterocyclyl having 1-2 heteroatoms independently selected from nitrogen, oxygen, and sulfur. In certain embodiments, at least one $R^y$ is an optionally substituted 6-membered heterocyclyl having one heteroatom selected from nitrogen, oxygen, and sulfur. In certain embodiments, at least one $R^y$ is optionally substituted piperidinyl. In certain embodiments, at least one $R^y$ is an optionally substituted 6-membered heterocyclyl having two heteroatoms independently selected from nitrogen, oxygen, and sulfur. In certain embodiments, at least one $R^y$ is optionally substituted piperdinyl, optionally substituted piperazinyl, or optionally substituted morpholinyl. In certain embodiments, at least one $R^y$ is morpholinyl, tetrahydropyranyl, piperidinyl, methylpiperidinyl, piperazinyl, methylpiperazinyl, acetylpiperazinyl, methylsulfonylpiperazinyl, aziridinyl, or methylaziridinyl. In some embodiments, at least one $R^y$ is an optionally substituted 5- to 6-membered heteroaryl having 1-3 heteroatoms independently selected from nitrogen, oxygen, and sulfur. In certain embodiments, at least one $R^y$ is an optionally substituted 5-membered heteroaryl having 1-3 heteroatoms independently selected from nitrogen, oxygen, and sulfur. In certain embodiments, at least one $R^y$ is an optionally substituted 5-membered heteroaryl having one heteroatom selected from nitrogen, oxygen, and sulfur. In certain embodiments, at least one $R^y$ is an optionally substituted 5-membered heteroaryl having two heteroatoms independently selected from nitrogen, oxygen, and sulfur. In certain embodiments, at least one $R^y$ is an optionally substituted 6-membered heteroaryl having 1-3 nitrogens. In certain embodiments, at least one $R^y$ is an optionally substituted pyrazolyl. In certain embodiments, at least one $R^y$ is an optionally substituted imidazolyl. In certain embodiments, at least one $R^y$ is an optionally substituted pyridyl. In certain embodiments, at least one $R^y$ is an optionally substituted pyrimidyl. In certain embodiments, at least one $R^y$ is pyrazolyl, methylpyrazolyl, imidazolyl, or methylimidazolyl.

In certain embodiments, a provided compound is a compound listed in Table 1, or a pharmaceutically acceptable salt thereof.

TABLE 1

| Cmpd No | Structure | Exact Mass | LCMS m/z (M + H) |
|---|---|---|---|
| 1 | 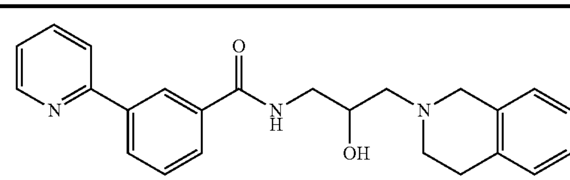 | 387.1947 | 388.2 |
| 2 | 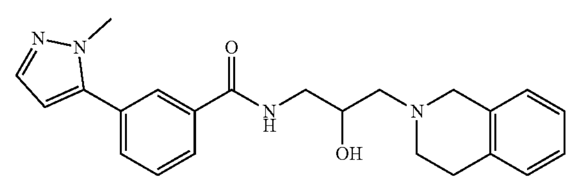 [SMILES: Cn1nccc1-c1cccc(C(=O)NCC(O)CN2CCc3ccccc3C2)c1] | 390.2056 | 391.2 |

TABLE 1-continued

Exemplary Compounds

| Cmpd No | Structure | Exact Mass | LCMS m/z (M + H) |
|---|---|---|---|
| 3 | 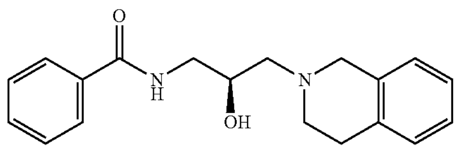 [SMILES: O=C(NC[C@H](O)CN1CCc2ccccc2C1)c1ccccc1] | 310.1681 | 311.1 |
| 4 | 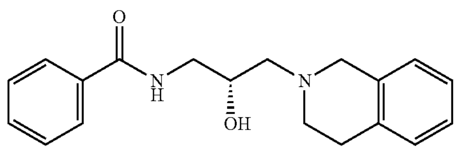 [SMILES: O=C(NC[C@@H](O)CN1CCc2ccccc2C1)c1ccccc1] | 310.1681 | 311.1 |
| 5 | 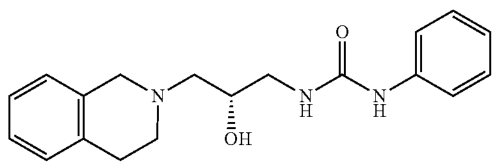 [SMILES: O=C(NC[C@H](O)CN1CCc2ccccc2C1)Nc1ccccc1] | 325.179 | 326.2 |
| 6 | 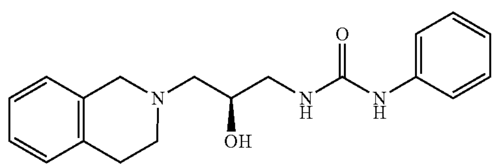 [SMILES: O=C(NC[C@@H](O)CN1CCc2ccccc2C1)Nc1ccccc1] | 325.179 | 326.2 |
| 7 | 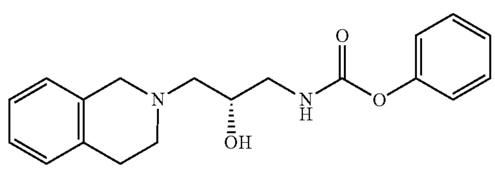 [SMILES: O=C(NC[C@H](O)CN1CCc2ccccc2C1)Oc1ccccc1] | 326.163 | 327.2 |
| 8 | 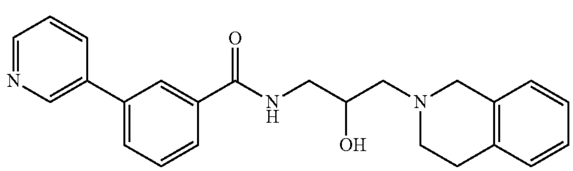 [SMILES: O=C(NCC(O)CN1CCc2ccccc2C1)c1cccc(-c2cccnc2)c1] | 387.1947 | 388.2 |
| 9 | 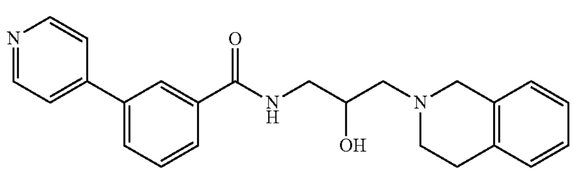 [SMILES: O=C(NCC(O)CN1CCc2ccccc2C1)c1cccc(-c2ccncc2)c1] | 387.1947 | 388.2 |
| 10 | 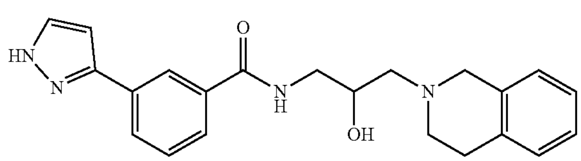 [SMILES: O=C(NCC(O)CN1CCc2ccccc2C1)c1cccc(-c2cc[nH]n2)c1] | 376.1899 | 377.2 |
| 11 | 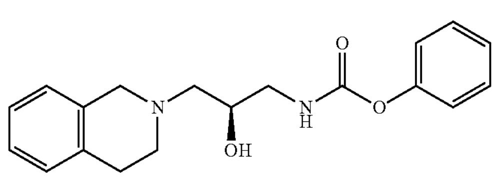 [SMILES: O=C(NC[C@@H](O)CN1CCc2ccccc2C1)Oc1ccccc1] | 326.163 | 327.2 |

TABLE 1-continued

Exemplary Compounds

| Cmpd No | Structure | Exact Mass | LCMS m/z (M + H) |
|---|---|---|---|
| 12 | 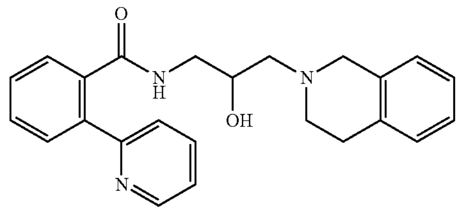 [SMILES: O=C(NCC(O)CN1CCc2ccccc2C1)c1ccccc1-c1ccccn1] | 387.1947 | 388.2 |
| 13 | 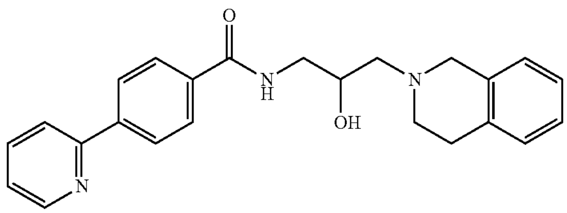 [SMILES: O=C(NCC(O)CN1CCc2ccccc2C1)c1ccc(-c2ccccn2)cc1] | 387.1947 | 388.2 |
| 14 | 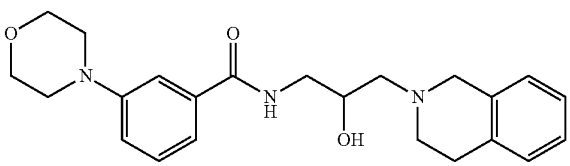 [SMILES: O=C(NCC(O)CN1CCc2ccccc2C1)c1cccc(N2CCOCC2)c1] | 395.2209 | 396.2 |
| 15 | 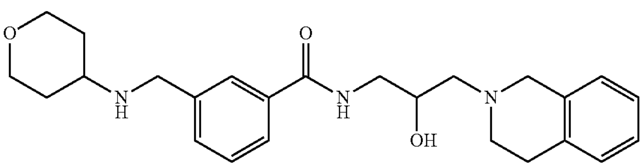 [SMILES: O=C(NCC(O)CN1CCc2ccccc2C1)c1cccc(CNC2CCOCC2)c1] | 423.2522 | 424.2 |
| 16 | 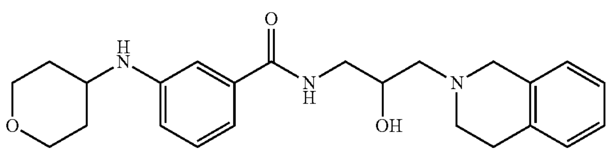 [SMILES: O=C(NCC(O)CN1CCc2ccccc2C1)c1cccc(NC2CCOCC2)c1] | 409.2365 | 410.2 |
| 17 | 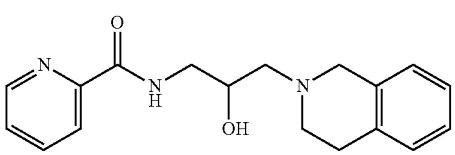 [SMILES: O=C(NCC(O)CN1CCc2ccccc2C1)c1ccccn1] | 311.1634 | 312.1 |
| 18 | 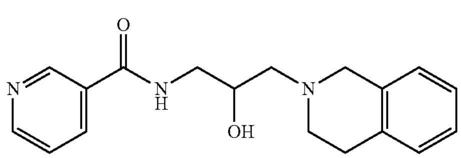 [SMILES: O=C(NCC(O)CN1CCc2ccccc2C1)c1cccnc1] | 311.1634 | 312.2 |
| 19 | 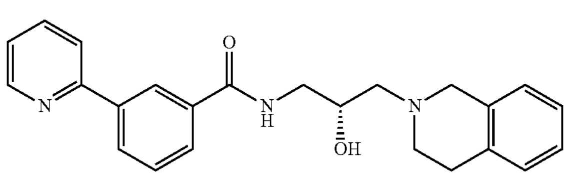 [SMILES: O=C(NC[C@@H](O)CN1CCc2ccccc2C1)c1cccc(-c2ccccn2)c1] | 387.1947 | 388.2 |

TABLE 1-continued

Exemplary Compounds

| Cmpd No | Structure | Exact Mass | LCMS m/z (M + H) |
|---|---|---|---|
| 20 | 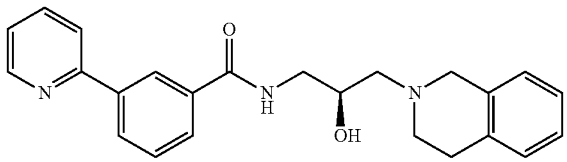 [SMILES: O=C(NC[C@H](O)CN1CCc2ccccc2C1)c1cccc(-c2ccccn2)c1] | 387.1947 | 388.2 |
| 21 | 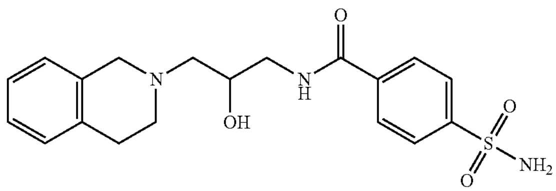 [SMILES: NS(=O)(=O)c1ccc(C(=O)NCC(O)CN2CCc3ccccc3C2)cc1] | 389.1409 | 390.1 |
| 22 | 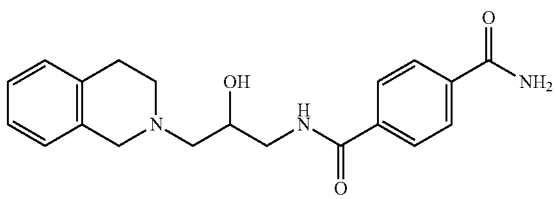 [SMILES: NC(=O)c1ccc(C(=O)NCC(O)CN2CCc3ccccc3C2)cc1] | 353.1739 | 354.1 |
| 23 | 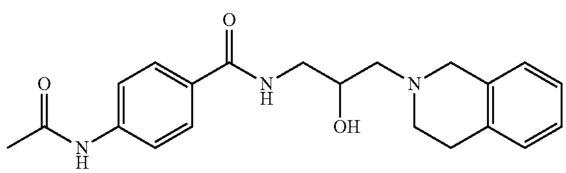 [SMILES: CC(=O)Nc1ccc(C(=O)NCC(O)CN2CCc3ccccc3C2)cc1] | 367.1896 | 368.1 |
| 24 | 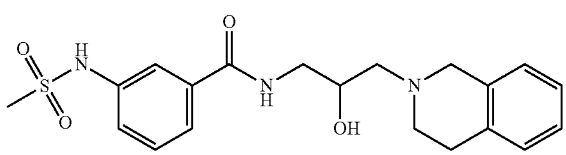 [SMILES: CS(=O)(=O)Nc1cccc(C(=O)NCC(O)CN2CCc3ccccc3C2)c1] | 403.1566 | 404.1 |
| 25 | 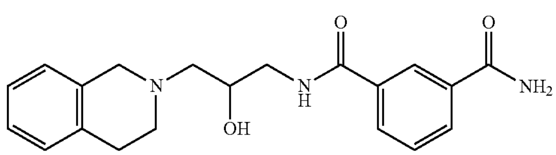 [SMILES: NC(=O)c1cccc(C(=O)NCC(O)CN2CCc3ccccc3C2)c1] | 353.1739 | 354.2 |
| 26 | 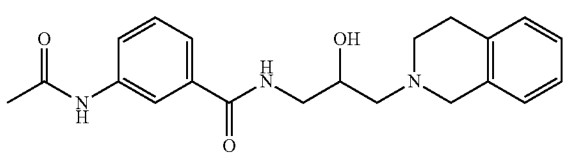 [SMILES: CC(=O)Nc1cccc(C(=O)NCC(O)CN2CCc3ccccc3C2)c1] | 367.1896 | 368.2 |
| 27 | 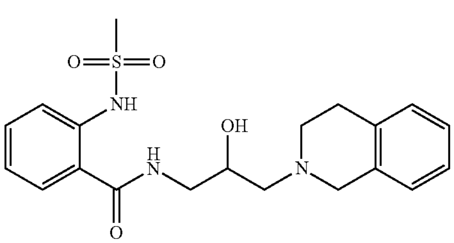 [SMILES: CS(=O)(=O)Nc1ccccc1C(=O)NCC(O)CN1CCc2ccccc2C1] | 403.1566 | 404.2 |

TABLE 1-continued

Exemplary Compounds

| Cmpd No | Structure | Exact Mass | LCMS m/z (M + H) |
|---|---|---|---|
| 28 | 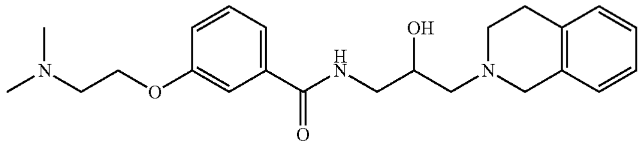 [SMILES: CN(C)CCOc1cccc(C(=O)NCC(O)CN2CCc3ccccc3C2)c1] | 397.2365 | 398.1 |
| 29 | 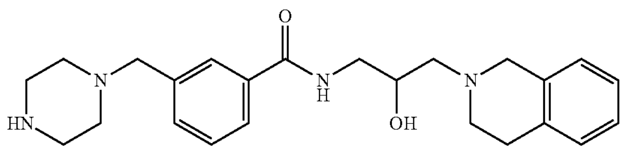 [SMILES: O=C(NCC(O)CN1CCc2ccccc2C1)c1cccc(CN2CCNCC2)c1] | 408.2525 | 409.2 |
| 30 | 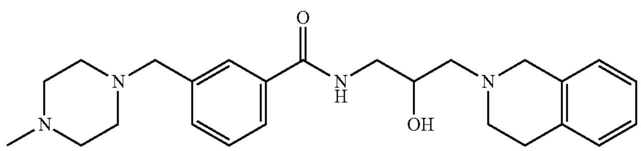 [SMILES: CN1CCN(Cc2cccc(C(=O)NCC(O)CN3CCc4ccccc4C3)c2)CC1] | 422.2682 | 423.2 |
| 31 | 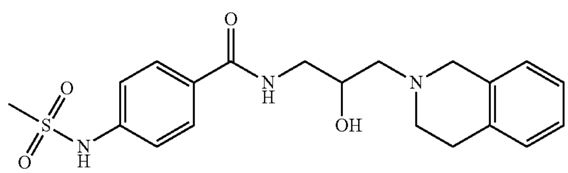 [SMILES: CS(=O)(=O)Nc1ccc(C(=O)NCC(O)CN2CCc3ccccc3C2)cc1] | 403.1566 | 404.2 |
| 32 | 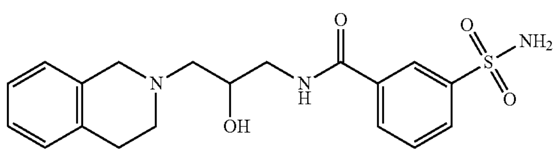 [SMILES: NS(=O)(=O)c1cccc(C(=O)NCC(O)CN2CCc3ccccc3C2)c1] | 389.1409 | 390.1 |
| 33 | 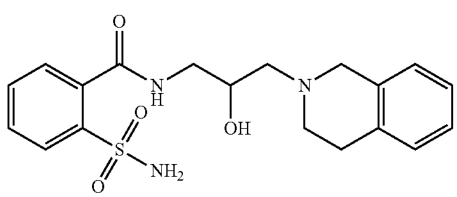 [SMILES: NS(=O)(=O)c1ccccc1C(=O)NCC(O)CN1CCc2ccccc2C1] | 389.1409 | 390 |
| 34 | 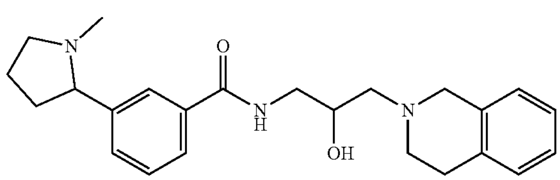 [SMILES: CN1CCCC1c1cccc(C(=O)NCC(O)CN2CCc3ccccc3C2)c1] | 393.2416 | 394.1 |
| 35 | 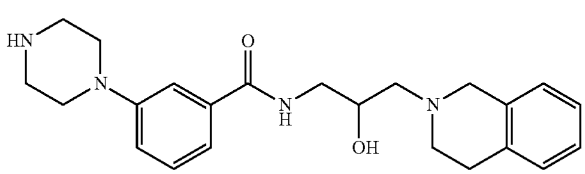 [SMILES: O=C(NCC(O)CN1CCc2ccccc2C1)c1cccc(N2CCNCC2)c1] | 394.2369 | 395.2 |
| 36 | 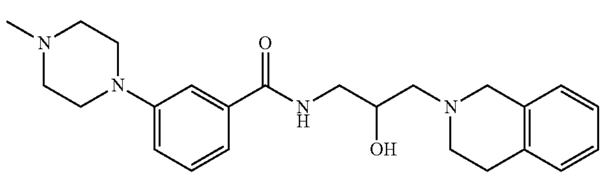 [SMILES: CN1CCN(c2cccc(C(=O)NCC(O)CN3CCc4ccccc4C3)c2)CC1] | 408.2525 | 409.2 |

TABLE 1-continued

Exemplary Compounds

| Cmpd No | Structure | Exact Mass | LCMS m/z (M + H) |
|---|---|---|---|
| 37 | 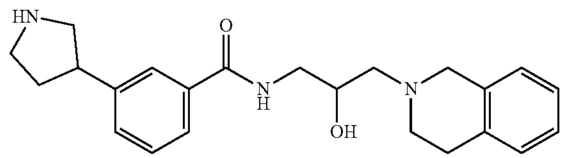 [SMILES: O=C(NCC(O)CN1CCc2ccccc2C1)c1cccc(C2CCNC2)c1] | 379.226 | 380.2 |
| 38 | 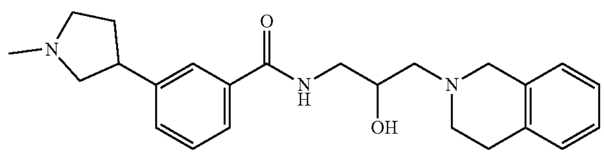 [SMILES: CN1CCC(c2cccc(C(=O)NCC(O)CN3CCc4ccccc4C3)c2)C1] | 393.2416 | 394.2 |
| 39 | 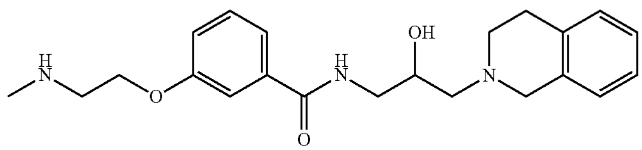 [SMILES: CNCCOc1cccc(C(=O)NCC(O)CN2CCc3ccccc3C2)c1] | 383.2209 | 384.2 |
| 40 | 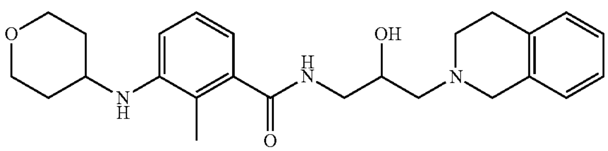 [SMILES: Cc1c(NC2CCOCC2)cccc1C(=O)NCC(O)CN1CCc2ccccc2C1] | 423.2522 | 424.2 |
| 41 | 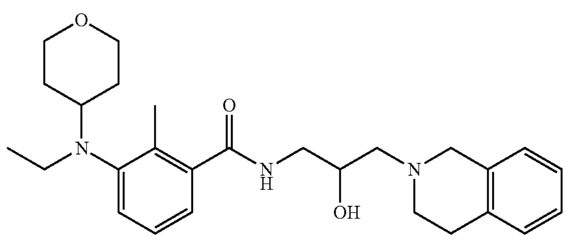 [SMILES: CCN(c1cccc(C(=O)NCC(O)CN2CCc3ccccc3C2)c1C)C1CCOCC1] | 451.2835 | 452.3 |
| 42 | 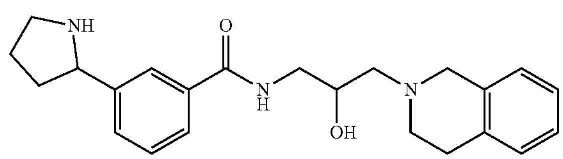 [SMILES: O=C(NCC(O)CN1CCc2ccccc2C1)c1cccc(C2CCCN2)c1] | 379.226 | 380.2 |
| 43 | 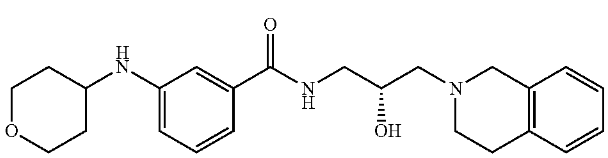 [SMILES: O=C(NC[C@@H](O)CN1CCc2ccccc2C1)c1cccc(NC2CCOCC2)c1] | 409.2365 | 410.2 |
| 44 | 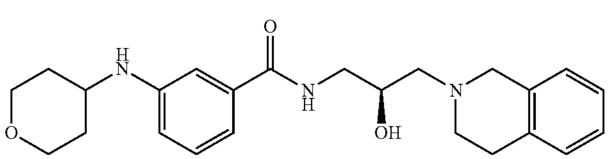 [SMILES: O=C(NC[C@H](O)CN1CCc2ccccc2C1)c1cccc(NC2CCOCC2)c1] | 409.2365 | 410.2 |
| 45 | 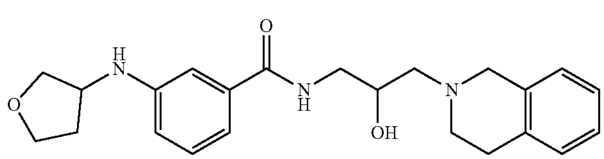 | 395.2209 | 396.2 |

TABLE 1-continued

Exemplary Compounds

| Cmpd No | Structure | Exact Mass | LCMS m/z (M + H) |
|---|---|---|---|
| 46 | 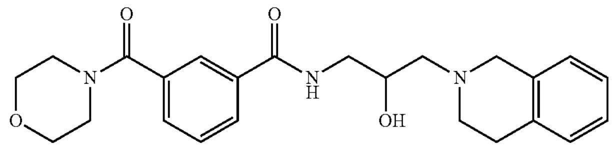 [SMILES: O=C(NCC(O)CN1CCc2ccccc2C1)c1cccc(C(=O)N2CCOCC2)c1] | 423.2158 | 424.2 |
| 47 | 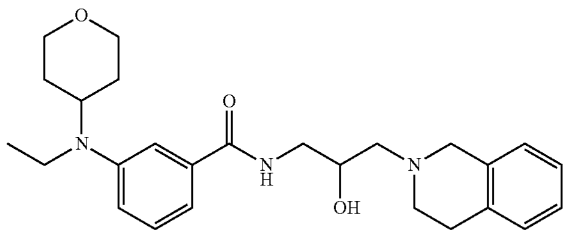 [SMILES: CCN(c1cccc(C(=O)NCC(O)CN2CCc3ccccc3C2)c1)C1CCOCC1] | 437.2678 | 438.3 |
| 48 | 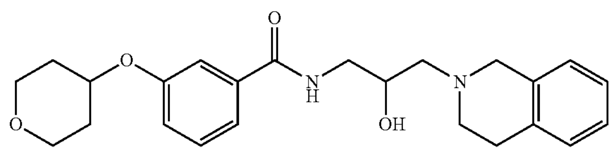 [SMILES: O=C(NCC(O)CN1CCc2ccccc2C1)c1cccc(OC2CCOCC2)c1] | 410.2206 | 411.2 |
| 49 | 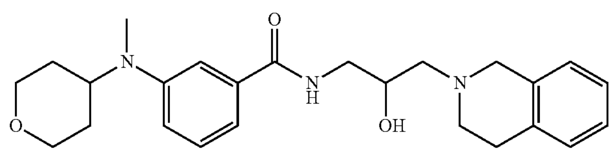 [SMILES: CN(c1cccc(C(=O)NCC(O)CN2CCc3ccccc3C2)c1)C1CCOCC1] | 423.2522 | 424.1 |
| 50 | 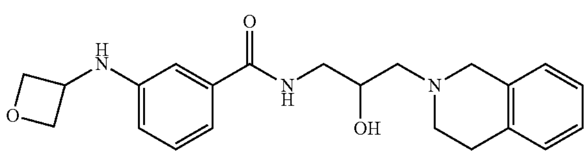 [SMILES: O=C(NCC(O)CN1CCc2ccccc2C1)c1cccc(NC2COC2)c1] | 381.2052 | 382.2 |
| 51 | 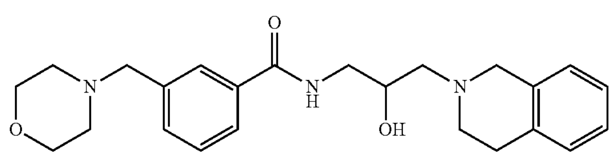 [SMILES: O=C(NCC(O)CN1CCc2ccccc2C1)c1cccc(CN2CCOCC2)c1] | 409.2365 | 410.1 |
| 52 | 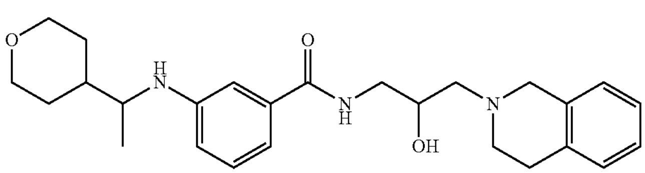 [SMILES: CC(Nc1cccc(C(=O)NCC(O)CN2CCc3ccccc3C2)c1)C1CCOCC1] | 437.2678 | 438.3 |
| 53 | 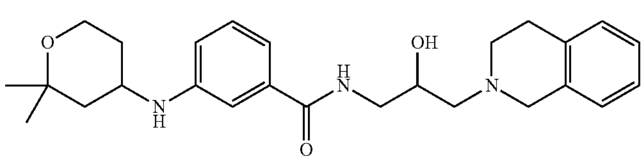 [SMILES: CC1(C)CC(Nc2cccc(C(=O)NCC(O)CN3CCc4ccccc4C3)c2)CCO1] | 437.2678 | 438.3 |
| 54 | 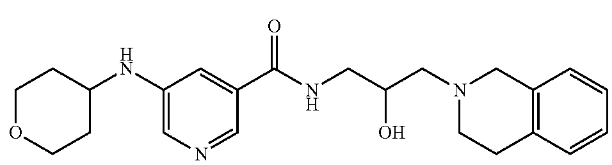 [SMILES: O=C(NCC(O)CN1CCc2ccccc2C1)c1cncc(NC2CCOCC2)c1] | 410.2318 | 411.1 |

TABLE 1-continued

Exemplary Compounds

| Cmpd No | Structure | Exact Mass | LCMS m/z (M + H) |
|---|---|---|---|
| 55 | 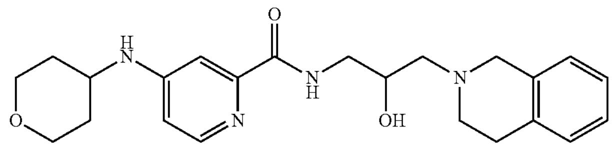 [SMILES: O=C(NCC(O)CN1CCc2ccccc2C1)c1cc(NC2CCOCC2)ccn1] | 410.2318 | 411.1 |
| 56 | 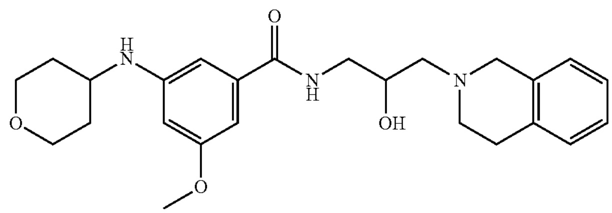 [SMILES: COc1cc(NC2CCOCC2)cc(C(=O)NCC(O)CN2CCc3ccccc3C2)c1] | 439.2471 | 440.1 |
| 57 | 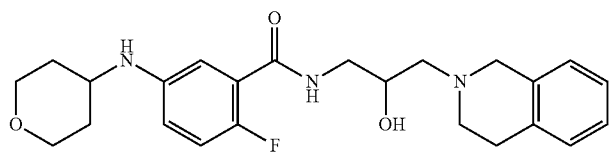 [SMILES: O=C(NCC(O)CN1CCc2ccccc2C1)c1cc(NC2CCOCC2)ccc1F] | 427.2271 | 428.2 |
| 58 | 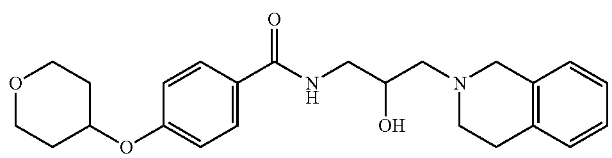 [SMILES: O=C(NCC(O)CN1CCc2ccccc2C1)c1ccc(OC2CCOCC2)cc1] | 410.2206 | 411.2 |
| 59 | 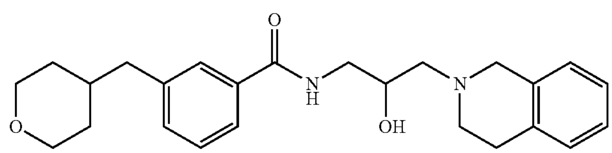 [SMILES: O=C(NCC(O)CN1CCc2ccccc2C1)c1cccc(CC2CCOCC2)c1] | 408.2413 | 409.1 |
| 60 | 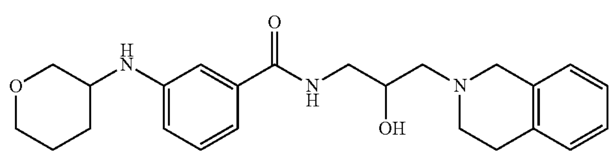 [SMILES: O=C(NCC(O)CN1CCc2ccccc2C1)c1cccc(NC2CCCOC2)c1] | 409.2365 | 410.2 |
| 61 | 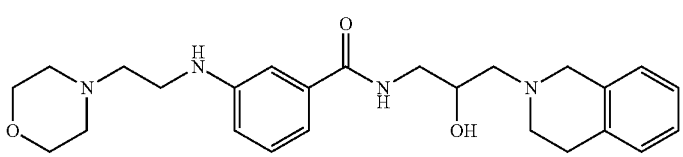 [SMILES: O=C(NCC(O)CN1CCc2ccccc2C1)c1cccc(NCCN2CCOCC2)c1] | 438.2631 | 439.2 |
| 62 | 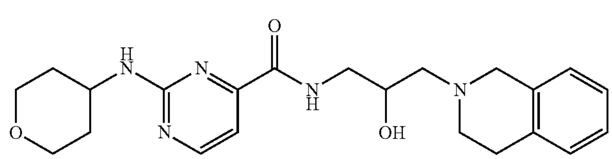 | 411.227 | 412.2 |
| 63 | 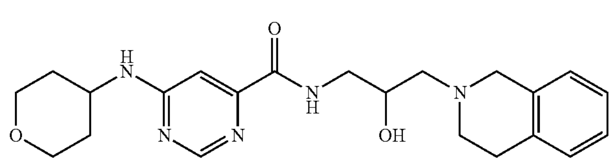 | 411.227 | 412.2 |

TABLE 1-continued
Exemplary Compounds
| Cmpd No | Structure | Exact Mass | LCMS m/z (M + H) |
|---|---|---|---|
| 64 | 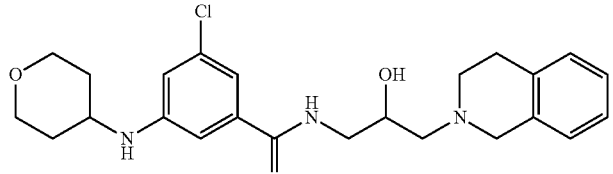 | 443.1976 | 444.1 |
| 65 | 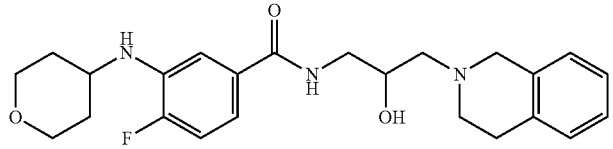 [SMILES: O=C(NCC(O)CN1CCc2ccccc2C1)c1ccc(F)c(NC2CCOCC2)c1] | 427.2271 | 428 |
| 66 | 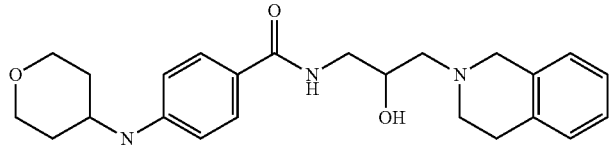 | 409.2365 | 410.1 |
| 67 | 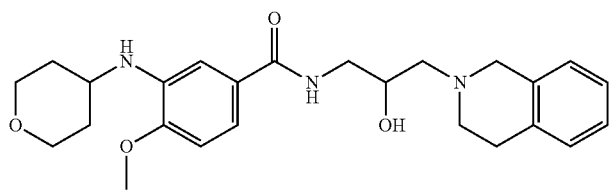 [SMILES: COc1ccc(C(=O)NCC(O)CN2CCc3ccccc3C2)cc1NC1CCOCC1] | 439.2471 | 440.2 |
| 68 | 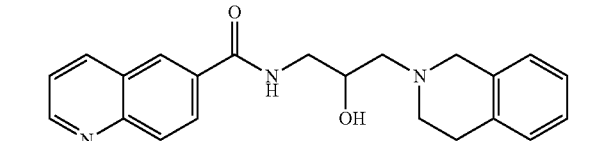 | 361.179 | 362.1 |
| 69 | 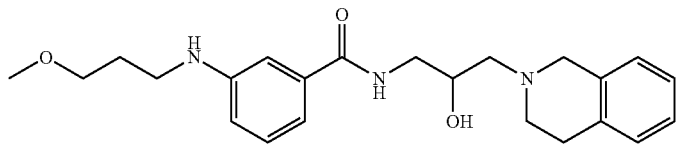 [SMILES: COCCCNc1cccc(C(=O)NCC(O)CN2CCc3ccccc3C2)c1] | 397.2365 | 398.2 |
| 70 | 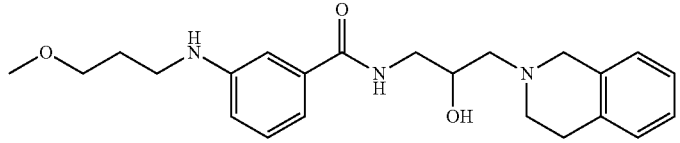 [SMILES: COCCCNc1cccc(C(=O)NCC(O)CN2CCc3ccccc3C2)c1] | 397.2365 | 398.2 |
| 71 | 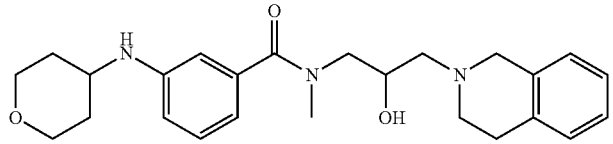 [SMILES: CN(CC(O)CN1CCc2ccccc2C1)C(=O)c1cccc(NC2CCOCC2)c1] | 423.2522 | 424.2 |
| 72 | 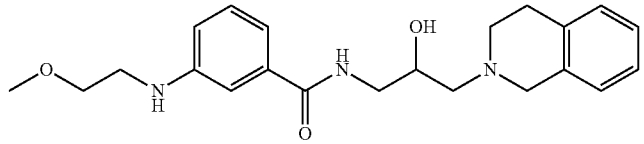 [SMILES: COCCNc1cccc(C(=O)NCC(O)CN2CCc3ccccc3C2)c1] | 383.2209 | 384.2 |

TABLE 1-continued

Exemplary Compounds

| Cmpd No | Structure | Exact Mass | LCMS m/z (M + H) |
|---|---|---|---|
| 73 | 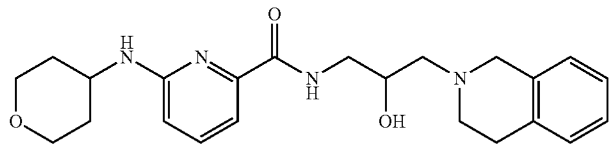 [SMILES: O=C(NCC(O)CN1CCc2ccccc2C1)c1cccc(NC2CCOCC2)n1] | 410.2318 | 411.1 |
| 74 | 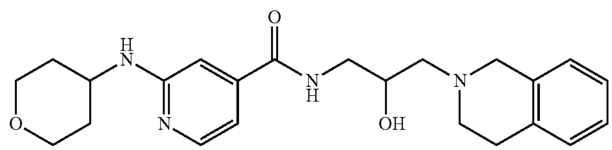 [SMILES: O=C(NCC(O)CN1CCc2ccccc2C1)c1ccnc(NC2CCOCC2)c1] | 410.2318 | 411.2 |
| 75 | 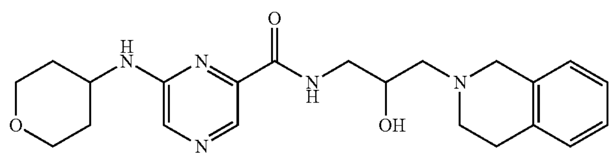 [SMILES: O=C(NCC(O)CN1CCc2ccccc2C1)c1cncc(NC2CCOCC2)n1] | 411.227 | 412.1 |
| 76 | 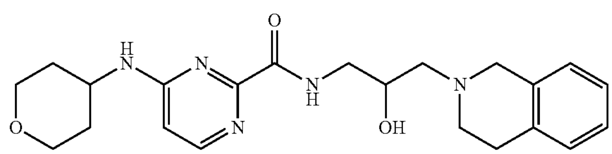 [SMILES: O=C(NCC(O)CN1CCc2ccccc2C1)c1nccc(NC2CCOCC2)n1] | 411.227 | 412.2 |
| 77 | 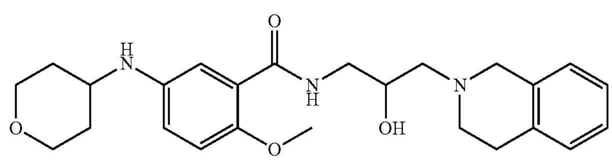 [SMILES: COc1ccc(NC2CCOCC2)cc1C(=O)NCC(O)CN1CCc2ccccc2C1] | 439.2471 | 440.2 |
| 78 | 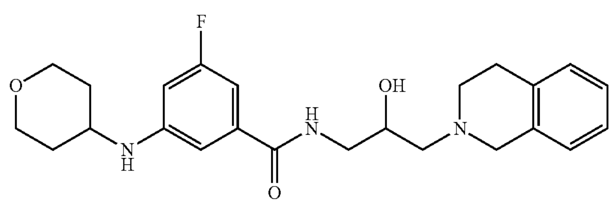 [SMILES: O=C(NCC(O)CN1CCc2ccccc2C1)c1cc(F)cc(NC2CCOCC2)c1] | 427.2271 | 428.2 |
| 79 | 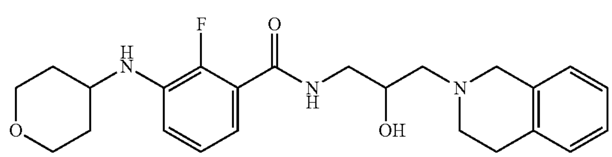 [SMILES: O=C(NCC(O)CN1CCc2ccccc2C1)c1cccc(NC2CCOCC2)c1F] | 427.2271 | 428.2 |
| 80 | 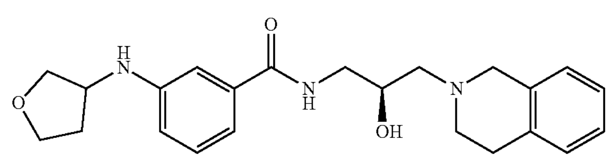 [SMILES: O=C(NC[C@H](O)CN1CCc2ccccc2C1)c1cccc(NC2CCOC2)c1] | 395.2209 | 396.2 |
| 81 | 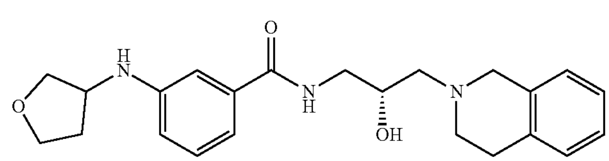 [SMILES: O=C(NC[C@@H](O)CN1CCc2ccccc2C1)c1cccc(NC2CCOC2)c1] | 395.2209 | 396.2 |

TABLE 1-continued

Exemplary Compounds

| Cmpd No | Structure | Exact Mass | LCMS m/z (M + H) |
|---|---|---|---|
| 82 | 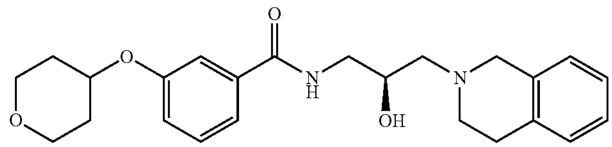 [SMILES: O=C(NC[C@H](O)CN1CCc2ccccc2C1)c1cccc(OC2CCOCC2)c1] | 410.2206 | 411.1 |
| 83 | 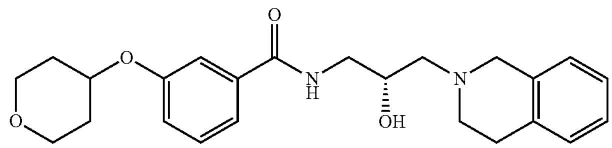 [SMILES: O=C(NC[C@@H](O)CN1CCc2ccccc2C1)c1cccc(OC2CCOCC2)c1] | 410.2206 | 411.1 |
| 84 | 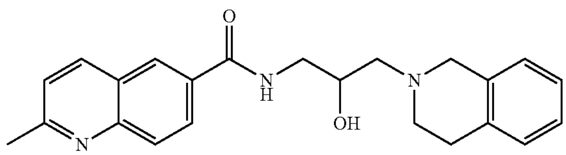 [SMILES: Cc1ccc2cc(C(=O)NCC(O)CN3CCc4ccccc4C3)ccc2n1] | 375.1947 | 376 |
| 85 | 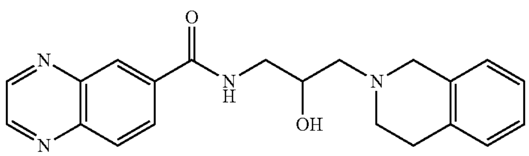 [SMILES: O=C(NCC(O)CN1CCc2ccccc2C1)c1ccc2nccnc2c1] | 362.1743 | 363.1 |
| 86 | 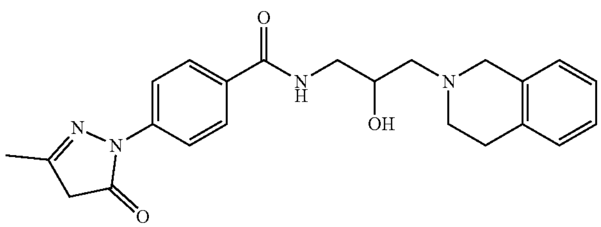 [SMILES: CC1=NN(c2ccc(C(=O)NCC(O)CN3CCc4ccccc4C3)cc2)C(=O)C1] | 406.2005 | 407.2 |
| 87 | 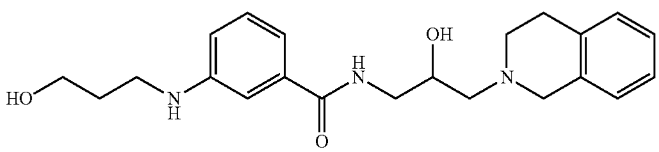 [SMILES: O=C(NCC(O)CN1CCc2ccccc2C1)c1cccc(NCCCO)c1] | 383.2209 | 384.2 |
| 88 | 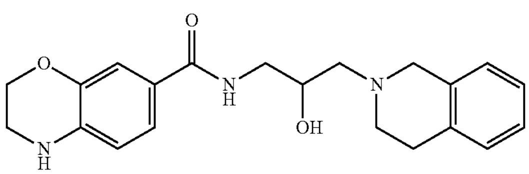 [SMILES: O=C(NCC(O)CN1CCc2ccccc2C1)c1ccc2c(c1)OCCN2] | 367.1896 | 368.1 |
| 89 | 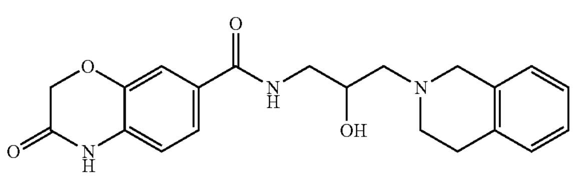 [SMILES: O=C1COc2cc(C(=O)NCC(O)CN3CCc4ccccc4C3)ccc2N1] | 381.1689 | 382.1 |
| 90 | 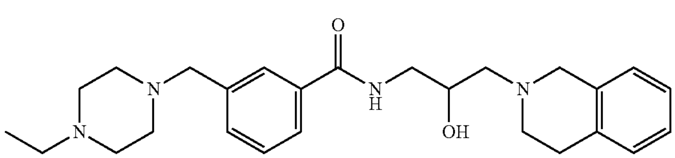 [SMILES: CCN1CCN(Cc2cccc(C(=O)NCC(O)CN3CCc4ccccc4C3)c2)CC1] | 436.2838 | 437.2 |

TABLE 1-continued
Exemplary Compounds
| Cmpd No | Structure | Exact Mass | LCMS m/z (M + H) |
|---|---|---|---|
| 91 | 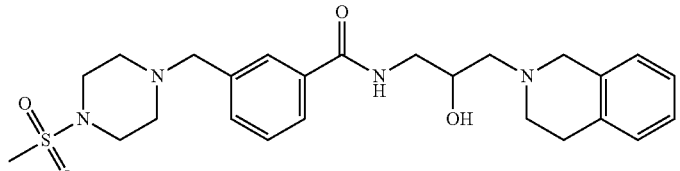 | 486.2301 | 487.2 |
| 92 | 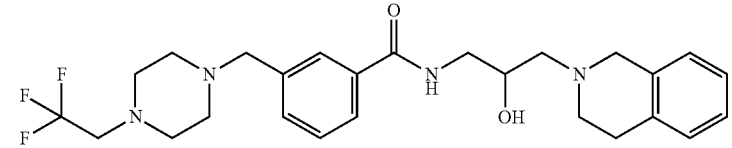 [SMILES: O=C(NCC(O)CN1CCc2ccccc2C1)c1cccc(CN2CCN(CC(F)(F)F)CC2)c1] | 490.2556 | 491.3 |
| 93 | 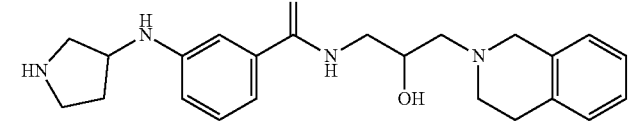 | 394.2369 | 395.2 |
| 94 | 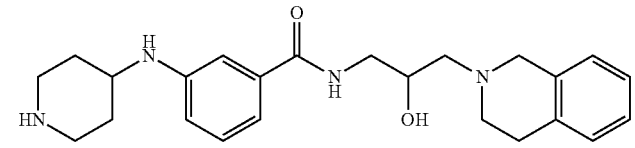 [SMILES: O=C(NCC(O)CN1CCc2ccccc2C1)c1cccc(NC2CCNCC2)c1] | 408.2525 | 409.3 |
| 95 | 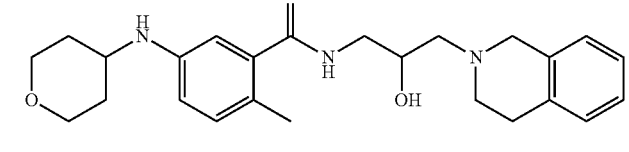 | 423.2522 | |
| 96 | 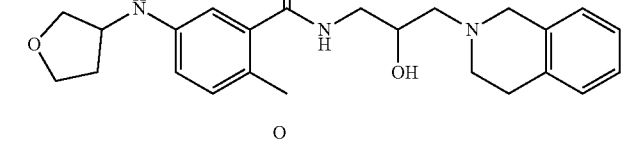 | 409.2365 | 410.3 |
| 97 | 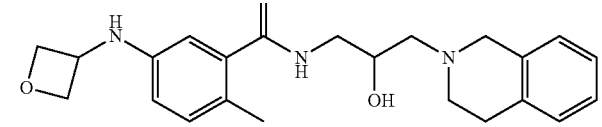 | 395.2209 | |
| 98 | 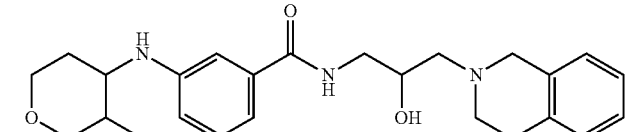 | 425.2315 | 426.2 |
| 99 | 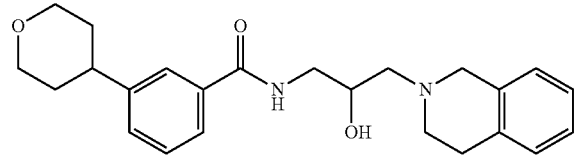 [SMILES: O=C(NCC(O)CN1CCc2ccccc2C1)c1cccc(C2CCOCC2)c1] | 394.2256 | 395.2 |

TABLE 1-continued
Exemplary Compounds
| Cmpd No | Structure | Exact Mass | LCMS m/z (M + H) |
|---|---|---|---|
| 100 | 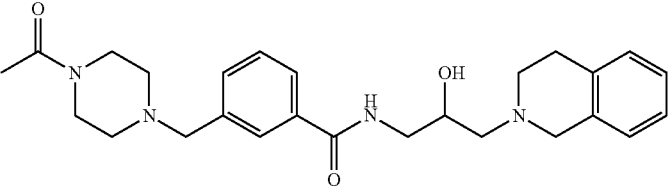 [SMILES: CC(=O)N1CCN(Cc2cccc(C(=O)NCC(O)CN3CCc4ccccc4C3)c2)CC1] | 450.2631 | 451.2 |
| 101 | 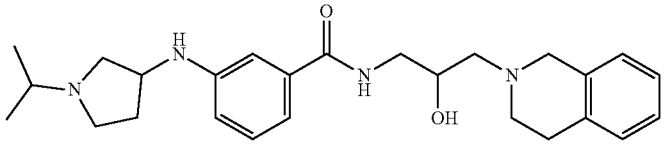 [SMILES: CC(C)N1CCC(Nc2cccc(C(=O)NCC(O)CN3CCc4ccccc4C3)c2)C1] | 436.2838 | 437.2 |
| 102 | 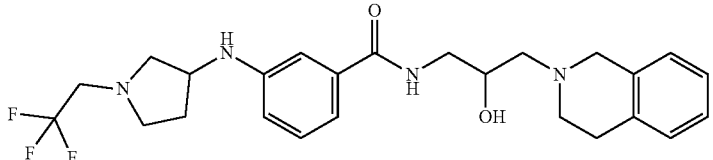 | 476.2399 | 477.2 |
| 103 | 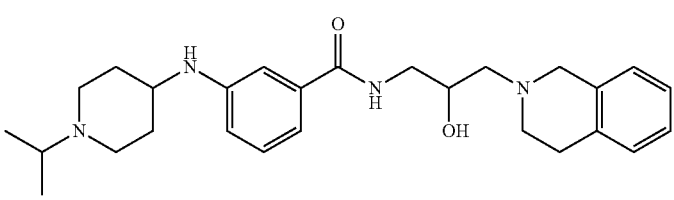 [SMILES: CC(C)N1CCC(Nc2cccc(C(=O)NCC(O)CN3CCc4ccccc4C3)c2)CC1] | 450.2995 | 451.3 |
| 104 | 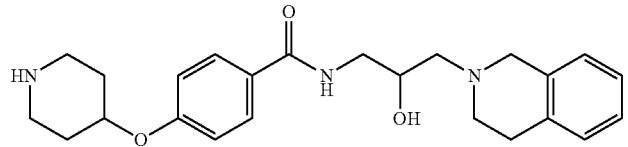 [SMILES: O=C(NCC(O)CN1CCc2ccccc2C1)c1ccc(OC2CCNCC2)cc1] | 409.2365 | 410.2 |
| 105 | 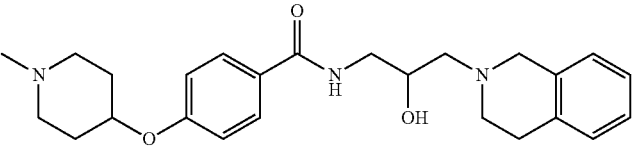 [SMILES: CN1CCC(Oc2ccc(C(=O)NCC(O)CN3CCc4ccccc4C3)cc2)CC1] | 423.2522 | 424.2 |
| 106 | 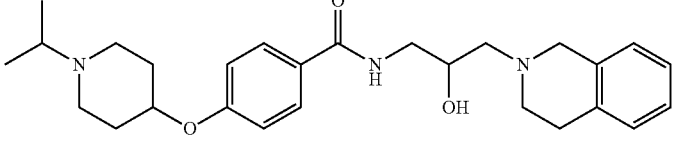 | 451.2835 | 452.2 |
| 107 | 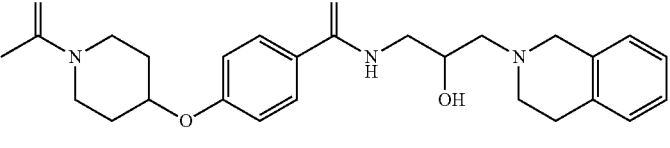 | 451.2471 | 452.2 |

TABLE 1-continued

Exemplary Compounds

| Cmpd No | Structure | Exact Mass | LCMS m/z (M + H) |
|---|---|---|---|
| 108 | 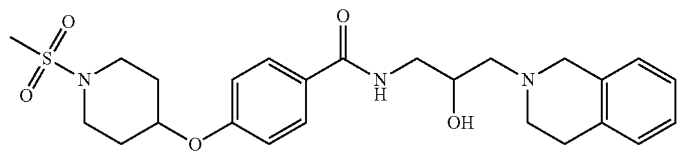 [SMILES: CS(=O)(=O)N1CCC(Oc2ccc(C(=O)NCC(O)CN3CCc4ccccc4C3)cc2)CC1] | 487.2141 | 488.2 |
| 109 | 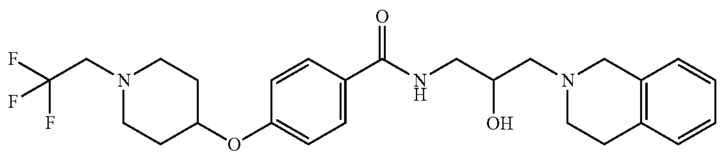 [SMILES: O=C(NCC(O)CN1CCc2ccccc2C1)c1ccc(OC2CCN(CC(F)(F)F)CC2)cc1] | 491.2396 | 492.2 |
| 110 | 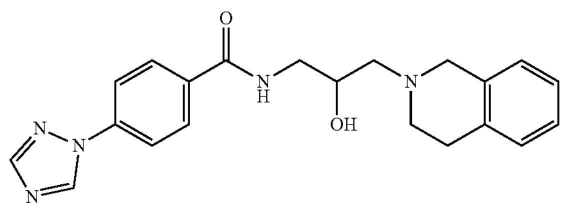 [SMILES: O=C(NCC(O)CN1CCc2ccccc2C1)c1ccc(-n2cncn2)cc1] | 377.1852 | 378.2 |
| 111 | 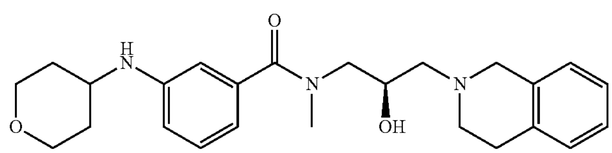 [SMILES: CN(C[C@H](O)CN1CCc2ccccc2C1)C(=O)c1cccc(NC2CCOCC2)c1] | 423.2522 | 424.2 |
| 112 | 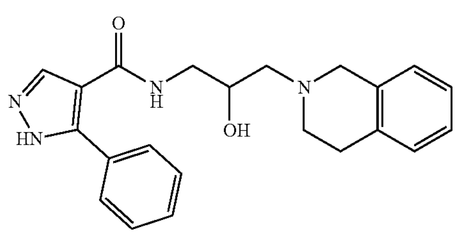 [SMILES: O=C(NCC(O)CN1CCc2ccccc2C1)c1cn[nH]c1-c1ccccc1] | 376.1899 | 377.1 |
| 113 | 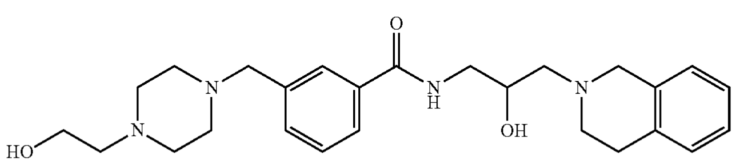 [SMILES: O=C(NCC(O)CN1CCc2ccccc2C1)c1cccc(CN2CCN(CCO)CC2)c1] | 452.2787 | 453.2 |
| 114 | 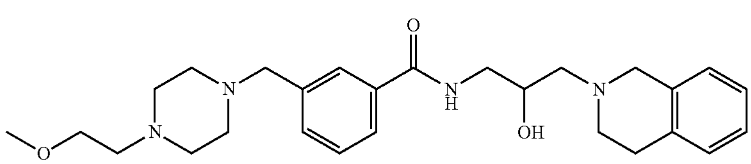 [SMILES: COCCN1CCN(Cc2cccc(C(=O)NCC(O)CN3CCc4ccccc4C3)c2)CC1] | 466.2944 | 467.2 |
| 115 | 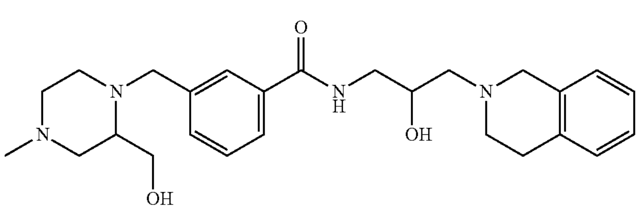 [SMILES: CN1CCN(Cc2cccc(C(=O)NCC(O)CN3CCc4ccccc4C3)c2)C(CO)C1] | 452.2787 | 453.2 |

TABLE 1-continued

Exemplary Compounds

| Cmpd No | Structure | Exact Mass | LCMS m/z (M + H) |
|---|---|---|---|
| 116 | 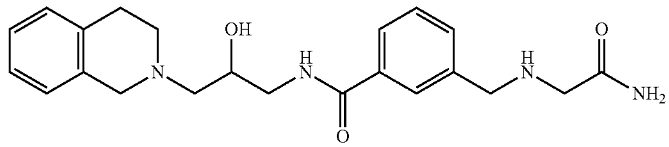 [SMILES: NC(=O)CNCc1cccc(C(=O)NCC(O)CN2CCc3ccccc3C2)c1] | 396.2161 | 397.1 |
| 117 | 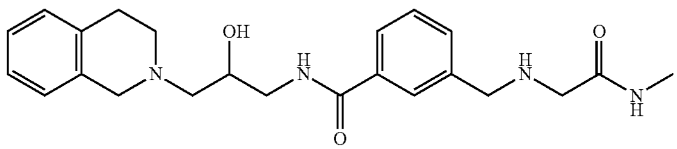 [SMILES: CNC(=O)CNCc1cccc(C(=O)NCC(O)CN2CCc3ccccc3C2)c1] | 410.2318 | 411.1 |
| 118 | 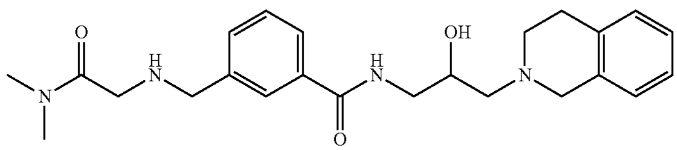 [SMILES: CN(C)C(=O)CNCc1cccc(C(=O)NCC(O)CN2CCc3ccccc3C2)c1] | 424.2474 | 425.1 |
| 119 | 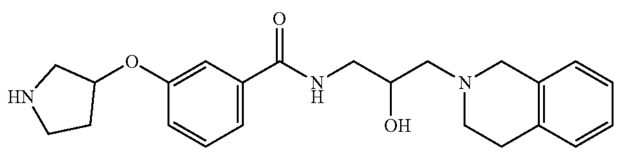 [SMILES: O=C(NCC(O)CN1CCc2ccccc2C1)c1cccc(OC2CCNC2)c1] | 395.2209 | 396.2 |
| 120 | 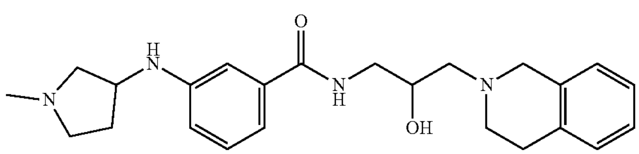 [SMILES: CN1CCC(Nc2cccc(C(=O)NCC(O)CN3CCc4ccccc4C3)c2)C1] | 408.2525 | 409.2 |
| 121 | 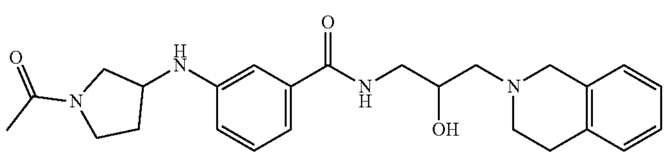 | 436.2474 | 437.2 |
| 122 | 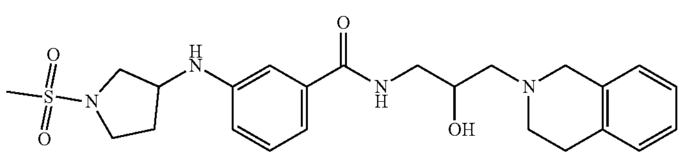 [SMILES: CS(=O)(=O)N1CCC(Nc2cccc(C(=O)NCC(O)CN3CCc4ccccc4C3)c2)C1] | 472.2144 | 473 |
| 123 | 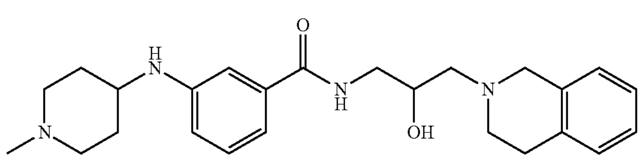 [SMILES: CN1CCC(Nc2cccc(C(=O)NCC(O)CN3CCc4ccccc4C3)c2)CC1] | 422.2682 | 423.2 |
| 124 | 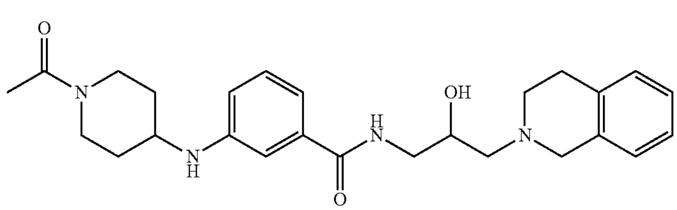 [SMILES: CC(=O)N1CCC(Nc2cccc(C(=O)NCC(O)CN3CCc4ccccc4C3)c2)CC1] | 450.2631 | 451.3 |

TABLE 1-continued

Exemplary Compounds

| Cmpd No | Structure | Exact Mass | LCMS m/z (M + H) |
|---|---|---|---|
| 125 | 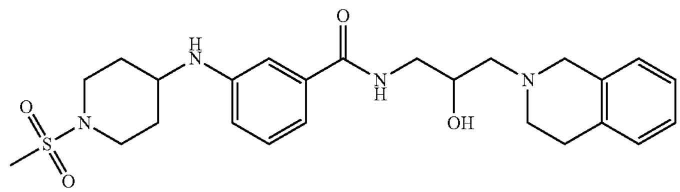 [SMILES: CS(=O)(=O)N1CCC(Nc2cccc(C(=O)NCC(O)CN3CCc4ccccc4C3)c2)CC1] | 486.2301 | 487.2 |
| 126 | 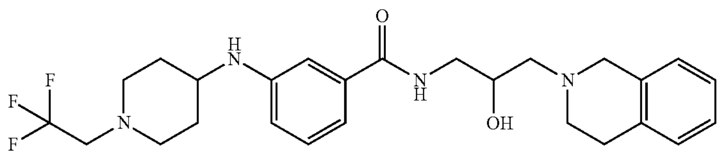 [SMILES: O=C(NCC(O)CN1CCc2ccccc2C1)c1cccc(NC2CCN(CC(F)(F)F)CC2)c1] | 490.2556 | 491.2 |
| 127 | 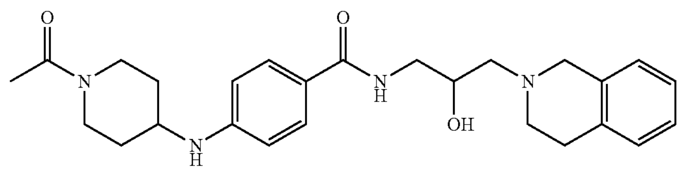 [SMILES: CC(=O)N1CCC(Nc2ccc(C(=O)NCC(O)CN3CCc4ccccc4C3)cc2)CC1] | 450.2631 | 451.3 |
| 128 | 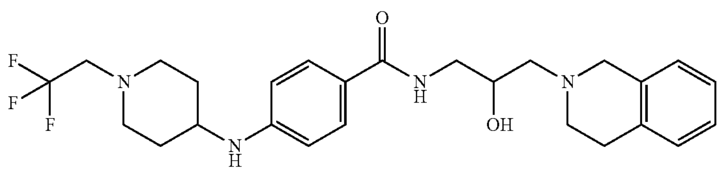 [SMILES: O=C(NCC(O)CN1CCc2ccccc2C1)c1ccc(NC2CCN(CC(F)(F)F)CC2)cc1] | 490.2556 | 491.2 |
| 129 | 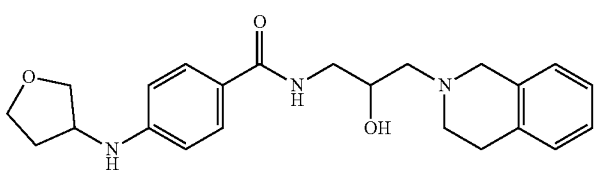 [SMILES: O=C(NCC(O)CN1CCc2ccccc2C1)c1ccc(NC2CCOC2)cc1] | 395.2209 | 396.2 |
| 130 | 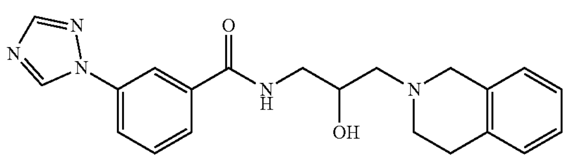 [SMILES: O=C(NCC(O)CN1CCc2ccccc2C1)c1cccc(-n2cncn2)c1] | 377.1852 | 378.2 |
| 131 | 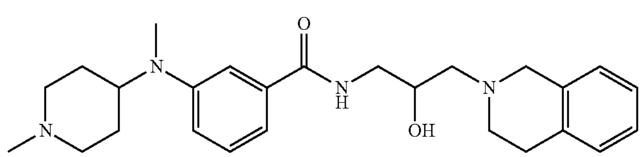 [SMILES: CN1CCC(N(C)c2cccc(C(=O)NCC(O)CN3CCc4ccccc4C3)c2)CC1] | 436.2838 | 437.2 |
| 132 | 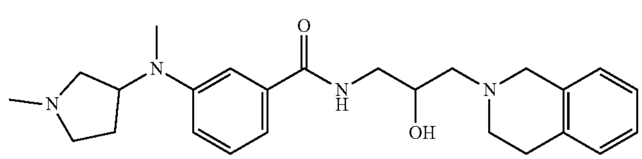 [SMILES: CN1CCC(N(C)c2cccc(C(=O)NCC(O)CN3CCc4ccccc4C3)c2)C1] | 422.2682 | 423.2 |
| 133 | 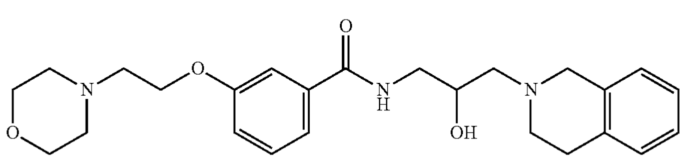 [SMILES: O=C(NCC(O)CN1CCc2ccccc2C1)c1cccc(OCCN2CCOCC2)c1] | 439.2471 | 440.2 |

TABLE 1-continued

Exemplary Compounds

| Cmpd No | Structure | Exact Mass | LCMS m/z (M + H) |
|---|---|---|---|
| 134 | 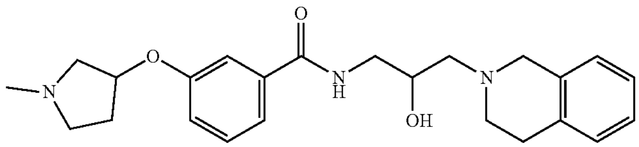 [SMILES: CN1CCC(Oc2cccc(C(=O)NCC(O)CN3CCc4ccccc4C3)c2)C1] | 409.2365 | 410.3 |
| 135 | 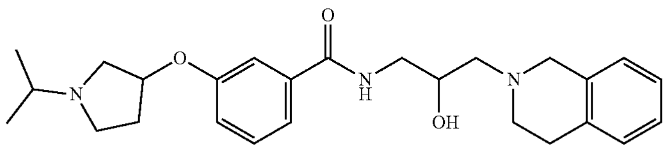 [SMILES: CC(C)N1CCC(Oc2cccc(C(=O)NCC(O)CN3CCc4ccccc4C3)c2)C1] | 437.2678 | 438.3 |
| 136 | 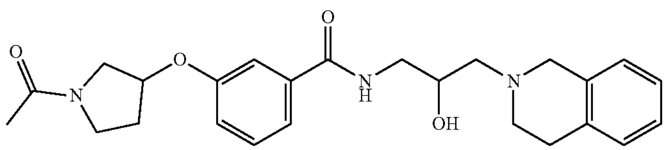 [SMILES: CC(=O)N1CCC(Oc2cccc(C(=O)NCC(O)CN3CCc4ccccc4C3)c2)C1] | 437.2315 | 438.2 |
| 137 | 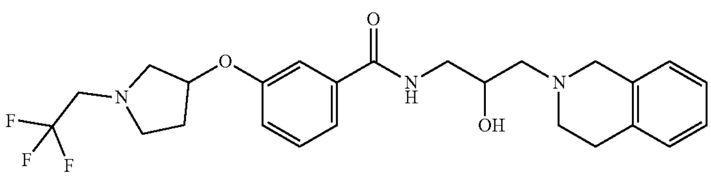 [SMILES: O=C(NCC(O)CN1CCc2ccccc2C1)c1cccc(OC2CCN(CC(F)(F)F)C2)c1] | 477.2239 | 478.3 |
| 138 | 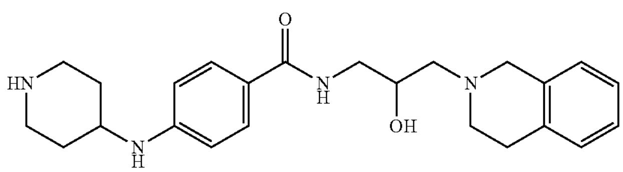 [SMILES: O=C(NCC(O)CN1CCc2ccccc2C1)c1ccc(NC2CCNCC2)cc1] | 408.2525 | 409.3 |
| 139 | 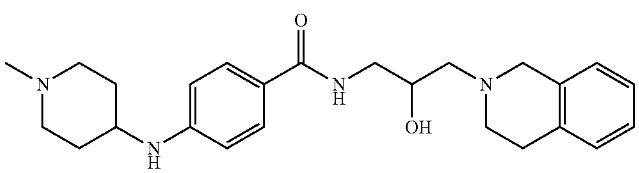 [SMILES: CN1CCC(Nc2ccc(C(=O)NCC(O)CN3CCc4ccccc4C3)cc2)CC1] | 422.2682 | 423.2 |
| 140 | 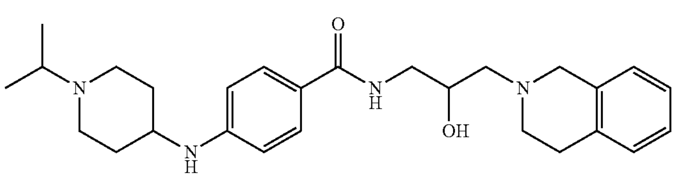 [SMILES: CC(C)N1CCC(Nc2ccc(C(=O)NCC(O)CN3CCc4ccccc4C3)cc2)CC1] | 450.2995 | 451.2 |
| 141 | 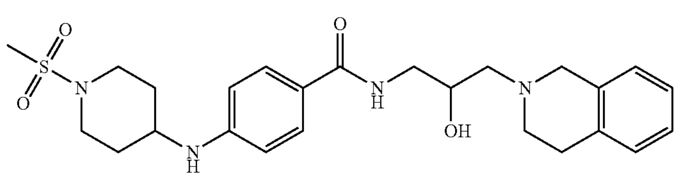 [SMILES: CS(=O)(=O)N1CCC(Nc2ccc(C(=O)NCC(O)CN3CCc4ccccc4C3)cc2)CC1] | 486.2301 | 487.2 |
| 142 | 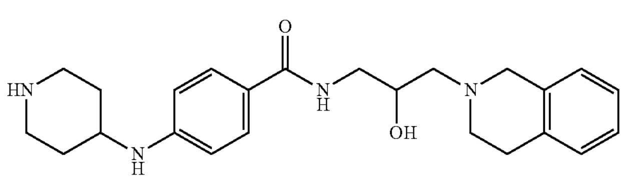 [SMILES: O=C(NCC(O)CN1CCc2ccccc2C1)c1ccc(NC2CCNCC2)cc1] | 396.2049 | 397.2 |

TABLE 1-continued

Exemplary Compounds

| Cmpd No | Structure | Exact Mass | LCMS m/z (M + H) |
|---|---|---|---|
| 143 | 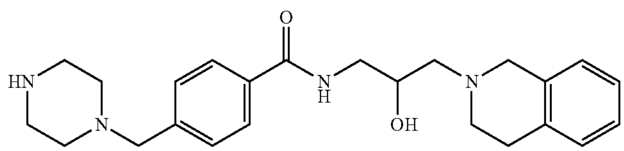 [SMILES: O=C(NCC(O)CN1CCc2ccccc2C1)c1ccc(CN2CCNCC2)cc1] | 408.2525 | 409.3 |
| 144 | 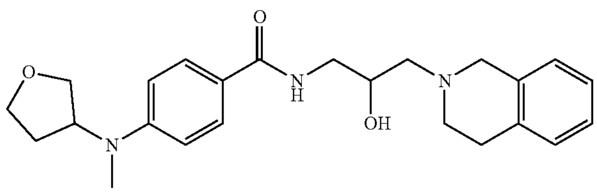 [SMILES: CN(c1ccc(C(=O)NCC(O)CN2CCc3ccccc3C2)cc1)C1CCOC1] | 409.2365 | 410.2 |
| 145 | 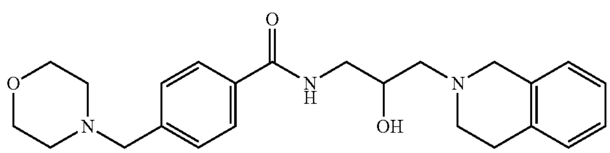 [SMILES: O=C(NCC(O)CN1CCc2ccccc2C1)c1ccc(CN2CCOCC2)cc1] | 409.2365 | 410.2 |
| 146 | 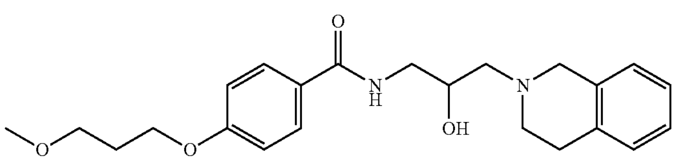 [SMILES: COCCCOc1ccc(C(=O)NCC(O)CN2CCc3ccccc3C2)cc1] | 398.2206 | 399.2 |
| 147 | 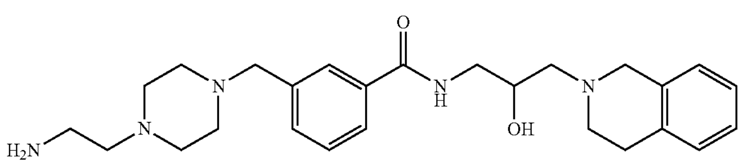 [SMILES: NCCN1CCN(Cc2cccc(C(=O)NCC(O)CN3CCc4ccccc4C3)c2)CC1] | 451.2947 | 452.2 |
| 148 | 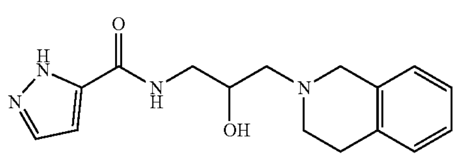 [SMILES: O=C(NCC(O)CN1CCc2ccccc2C1)c1ccn[nH]1] | 300.1586 | 315.2 |
| 149 | 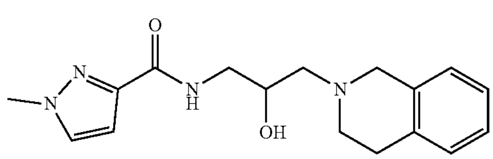 [SMILES: Cn1ccc(C(=O)NCC(O)CN2CCc3ccccc3C2)n1] | 314.1743 | 315.1 |
| 150 | 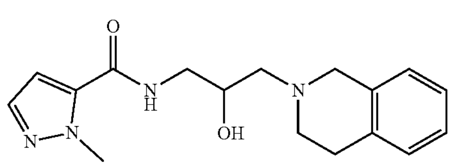 [SMILES: Cn1nccc1C(=O)NCC(O)CN1CCc2ccccc2C1] | 314.1743 | 315.1 |
| 151 | 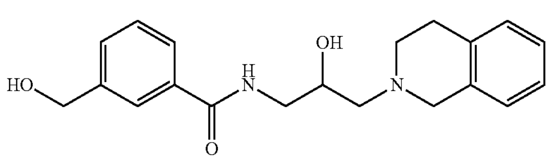 [SMILES: O=C(NCC(O)CN1CCc2ccccc2C1)c1cccc(CO)c1] | 340.1787 | 341.1 |

TABLE 1-continued
Exemplary Compounds
| Cmpd No | Structure | Exact Mass | LCMS m/z (M + H) |
|---|---|---|---|
| 152 | 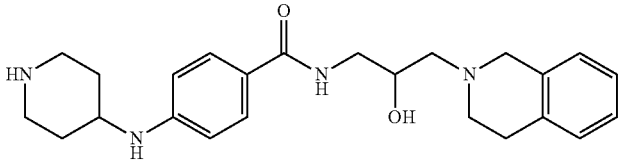 [SMILES: O=C(NCC(O)CN1CCc2ccccc2C1)c1ccc(NC2CCNCC2)cc1] | 437.2678 | 438.3 |
| 153 | 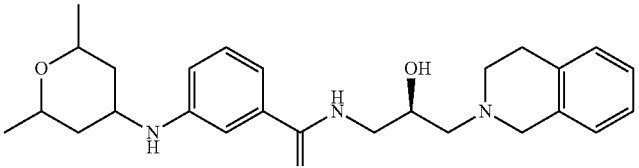 | 437.2678 | 438.3 |
| 154 | 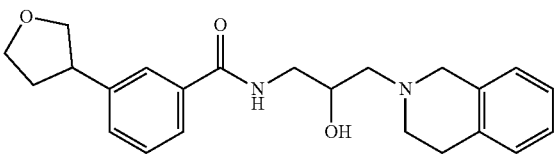 [SMILES: O=C(NCC(O)CN1CCc2ccccc2C1)c1cccc(C2CCOC2)c1] | 380.21 | 381.2 |
| 155 | 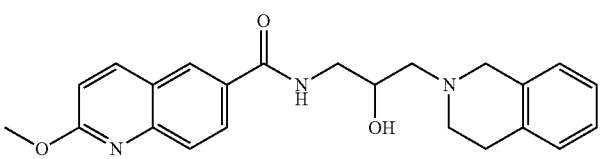 [SMILES: COc1ccc2cc(C(=O)NCC(O)CN3CCc4ccccc4C3)ccc2n1] | 391.1896 | 392.2 |
| 156 | 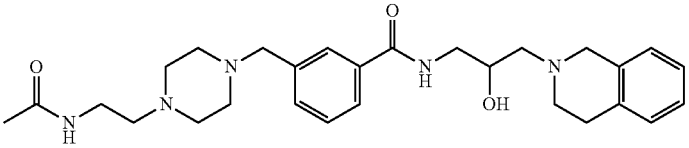 [SMILES: CC(=O)NCCN1CCN(Cc2cccc(C(=O)NCC(O)CN3CCc4ccccc4C3)c2)CC1] | 493.3053 | 494.2 |
| 157 | 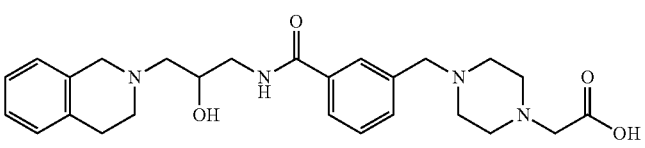 [SMILES: O=C(O)CN1CCN(Cc2cccc(C(=O)NCC(O)CN3CCc4ccccc4C3)c2)CC1] | 466.258 | 467.2 |
| 158 | 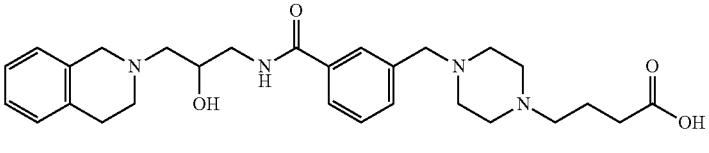 [SMILES: O=C(O)CCCN1CCN(Cc2cccc(C(=O)NCC(O)CN3CCc4ccccc4C3)c2)CC1] | 494.2893 | 495.3 |
| 159 | 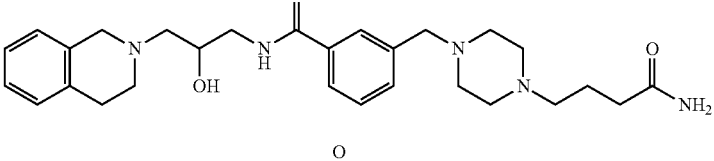 | 493.3053 | 494.2 |
| 160 | 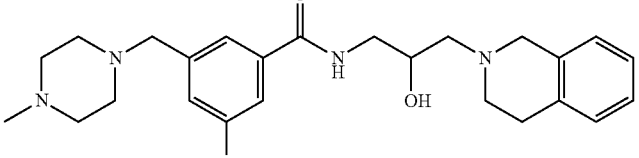 | 452.2787 | 453.3 |

TABLE 1-continued

Exemplary Compounds

| Cmpd No | Structure | Exact Mass | LCMS m/z (M + H) |
|---|---|---|---|
| 161 | | 436.2838 | 437.2 |
| 162 | | 473.1984 | 474.2 |
| 163 | | 422.2682 | 423.3 |
| 164 | | 443.1879 | 444.2 |
| 165 | | 494.2893 | 495.2 |
| 166 | | 383.1957 | 384.1 |
| 167 | | 423.2522 | 424.2 |
| 168 | | 423.2522 | 424.2 |
| 169 | | 399.227 | 400.2 |

TABLE 1-continued

Exemplary Compounds

| Cmpd No | Structure | Exact Mass | LCMS m/z (M + H) |
|---|---|---|---|
| 170 | 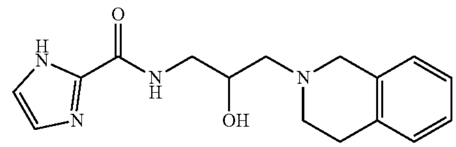 [SMILES: O=C(NCC(O)CN1CCc2ccccc2C1)c1ncc[nH]1] | 300.1586 | 301.1 |
| 171 | 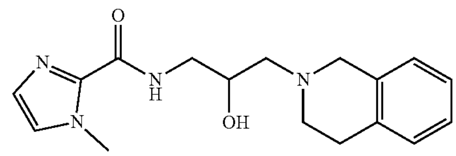 [SMILES: Cn1ccnc1C(=O)NCC(O)CN1CCc2ccccc2C1] | 314.1743 | 315.1 |
| 172 | 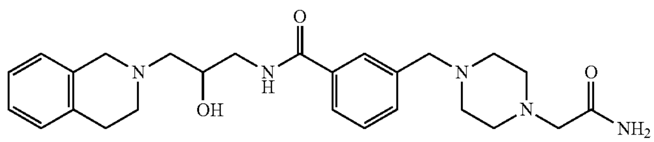 [SMILES: NC(=O)CN1CCN(Cc2cccc(C(=O)NCC(O)CN3CCc4ccccc4C3)c2)CC1] | 465.274 | 466.2 |
| 173 | 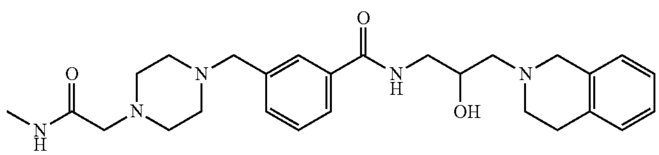 [SMILES: CNC(=O)CN1CCN(Cc2cccc(C(=O)NCC(O)CN3CCc4ccccc4C3)c2)CC1] | 479.2896 | 480.3 |
| 174 | 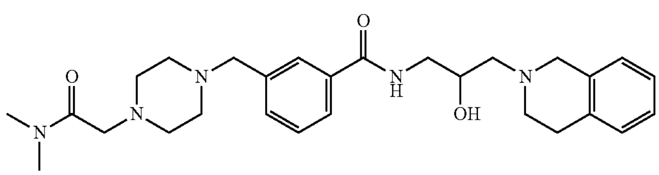 [SMILES: CN(C)C(=O)CN1CCN(Cc2cccc(C(=O)NCC(O)CN3CCc4ccccc4C3)c2)CC1] | 493.3053 | 494.4 |
| 175 | 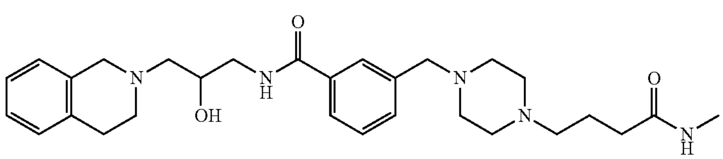 [SMILES: CNC(=O)CCCN1CCN(Cc2cccc(C(=O)NCC(O)CN3CCc4ccccc4C3)c2)CC1] | 507.3209 | 508.3 |
| 176 | 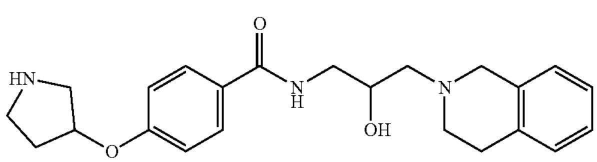 [SMILES: O=C(NCC(O)CN1CCc2ccccc2C1)c1ccc(OC2CCNC2)cc1] | 395.2209 | 396.2 |
| 177 | 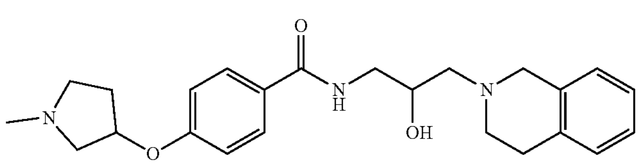 [SMILES: CN1CCC(Oc2ccc(C(=O)NCC(O)CN3CCc4ccccc4C3)cc2)C1] | 409.2365 | 410.2 |
| 178 | 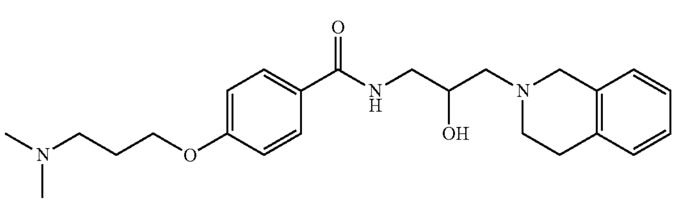 [SMILES: CN(C)CCCOc1ccc(C(=O)NCC(O)CN2CCc3ccccc3C2)cc1] | 411.2522 | 412.2 |

TABLE 1-continued

Exemplary Compounds

| Cmpd No | Structure | Exact Mass | LCMS m/z (M + H) |
|---|---|---|---|
| 179 | 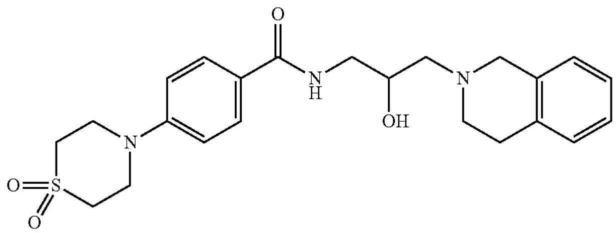 [SMILES: O=C(NCC(O)CN1CCc2ccccc2C1)c1ccc(N2CCS(=O)(=O)CC2)cc1] | 443.1879 | 444.2 |
| 180 | 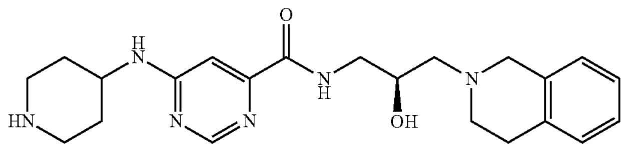 [SMILES: O=C(NC[C@H](O)CN1CCc2ccccc2C1)c1cc(NC2CCNCC2)ncn1] | 410.243 | 411.2 |
| 181 | 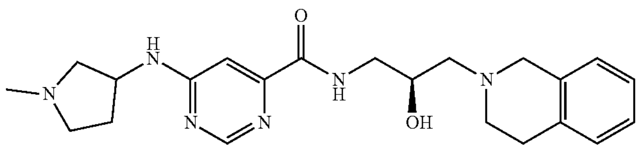 [SMILES: CN1CCC(Nc2cc(C(=O)NC[C@H](O)CN3CCc4ccccc4C3)ncn2)C1] | 410.243 | 411.3 |
| 182 | 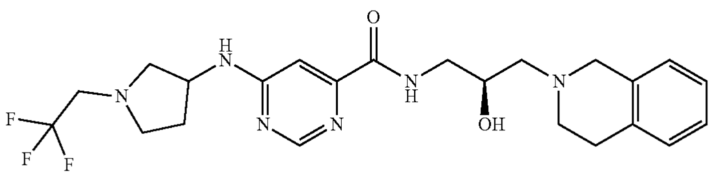 [SMILES: O=C(NC[C@H](O)CN1CCc2ccccc2C1)c1cc(NC2CCN(CC(F)(F)F)C2)ncn1] | 478.2304 | 479.3 |
| 183 | 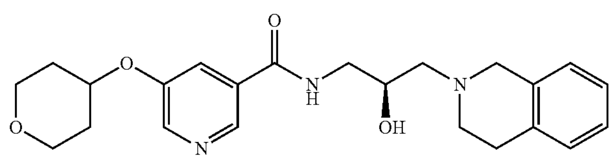 [SMILES: O=C(NC[C@H](O)CN1CCc2ccccc2C1)c1cncc(OC2CCOCC2)c1] | 411.2158 | 412.3 |
| 184 | 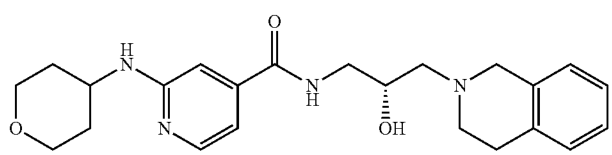 | 410.2318 | 411.3 |
| 185 | 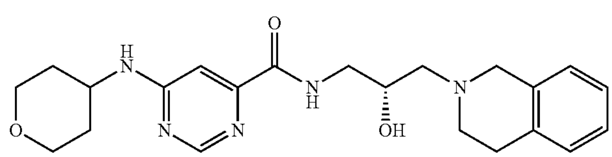 | 411.227 | 412.1 |
| 186 | 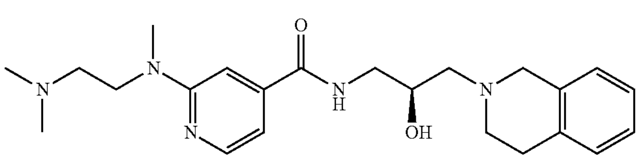 [SMILES: CN(C)CCN(C)c1cc(C(=O)NC[C@H](O)CN2CCc3ccccc3C2)ccn1] | 411.2634 | 412.3 |
| 187 | 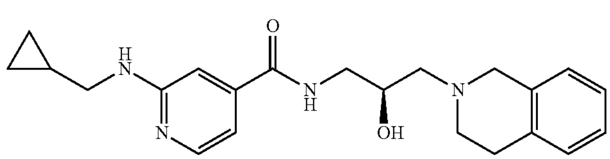 [SMILES: O=C(NC[C@H](O)CN1CCc2ccccc2C1)c1ccnc(NCC2CC2)c1] | 380.2212 | 381.3 |

TABLE 1-continued

Exemplary Compounds

| Cmpd No | Structure | Exact Mass | LCMS m/z (M + H) |
|---|---|---|---|
| 188 | 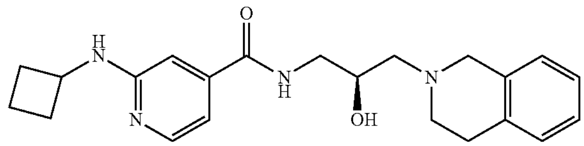 [SMILES: O=C(NC[C@H](O)CN1CCc2ccccc2C1)c1ccnc(NC2CCC2)c1] | 380.2212 | 381.2 |
| 189 | 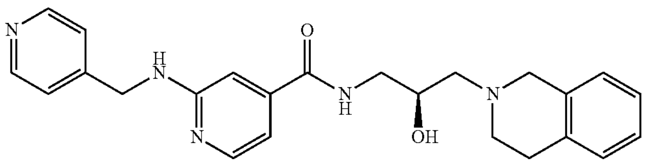 [SMILES: O=C(NC[C@H](O)CN1CCc2ccccc2C1)c1ccnc(NCc2ccncc2)c1] | 417.2165 | 418.2 |
| 190 | 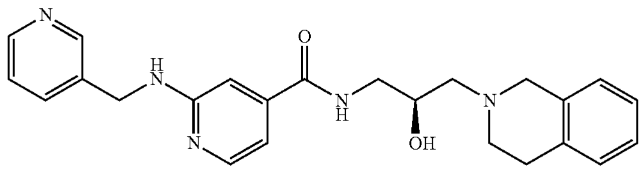 [SMILES: O=C(NC[C@H](O)CN1CCc2ccccc2C1)c1ccnc(NCc2cccnc2)c1] | 417.2165 | 418.3 |
| 191 | 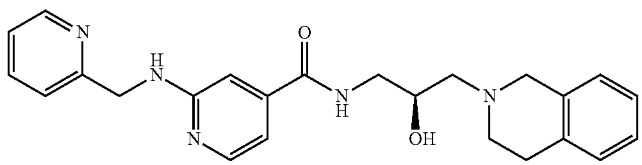 [SMILES: O=C(NC[C@H](O)CN1CCc2ccccc2C1)c1ccnc(NCc2ccccn2)c1] | 417.2165 | 418.2 |
| 192 | 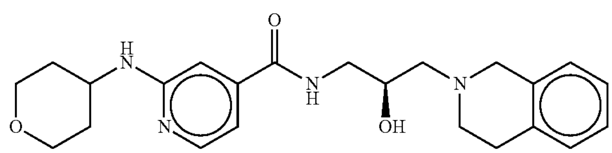 | 410.2318 | 411.3 |
| 193 | 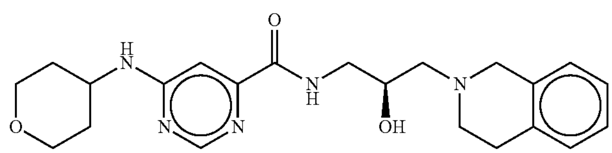 | 411.227 | 412.2 |
| 194 | 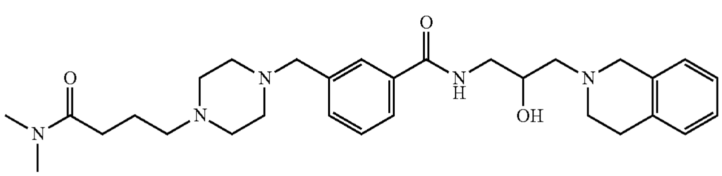 [SMILES: CN(C)C(=O)CCCN1CCN(Cc2cccc(C(=O)NCC(O)CN3CCc4ccccc4C3)c2)CC1] | 521.3366 | 522.3 |
| 195 | 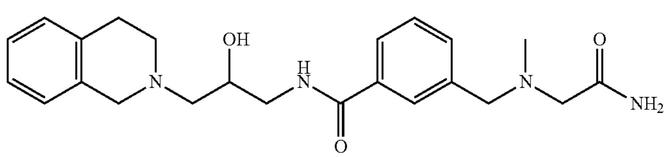 [SMILES: CN(CC(N)=O)Cc1cccc(C(=O)NCC(O)CN2CCc3ccccc3C2)c1] | 410.2318 | 411.2 |
| 196 | 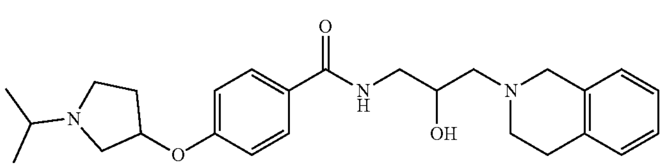 [SMILES: CC(C)N1CCC(Oc2ccc(C(=O)NCC(O)CN3CCc4ccccc4C3)cc2)C1] | 437.2678 | 438.3 |

TABLE 1-continued

Exemplary Compounds

| Cmpd No | Structure | Exact Mass | LCMS m/z (M + H) |
|---|---|---|---|
| 197 | 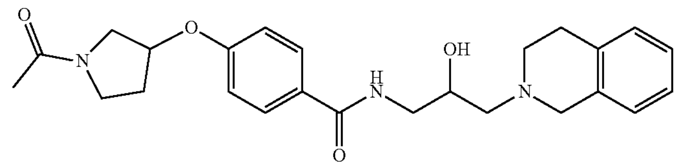 [SMILES: CC(=O)N1CCC(Oc2ccc(C(=O)NCC(O)CN3CCc4ccccc4C3)cc2)C1] | 437.2315 | 438.2 |
| 198 | 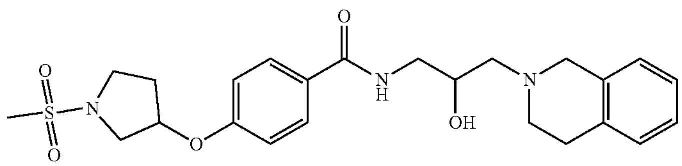 [SMILES: CS(=O)(=O)N1CCC(Oc2ccc(C(=O)NCC(O)CN3CCc4ccccc4C3)cc2)C1] | 473.1984 | 474.2 |
| 199 | 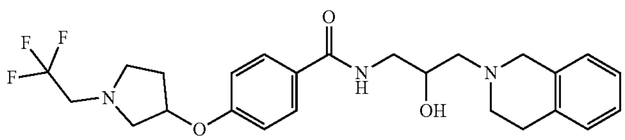 [SMILES: O=C(NCC(O)CN1CCc2ccccc2C1)c1ccc(OC2CCN(CC(F)(F)F)C2)cc1] | 477.2239 | 478.3 |
| 200 | 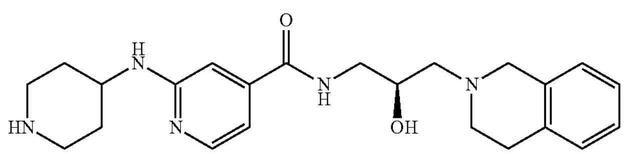 [SMILES: O=C(NC[C@H](O)CN1CCc2ccccc2C1)c1ccnc(NC2CCNCC2)c1] | 409.2478 | 410.3 |
| 201 | 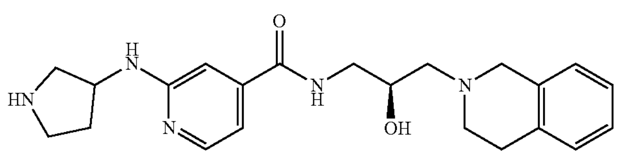 [SMILES: O=C(NC[C@H](O)CN1CCc2ccccc2C1)c1ccnc(NC2CCNC2)c1] | 395.2321 | 396.2 |
| 202 | 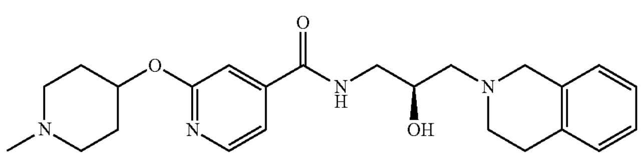 [SMILES: CN1CCC(Oc2cc(C(=O)NC[C@H](O)CN3CCc4ccccc4C3)ccn2)CC1] | 424.2474 | 425.3 |
| 203 | 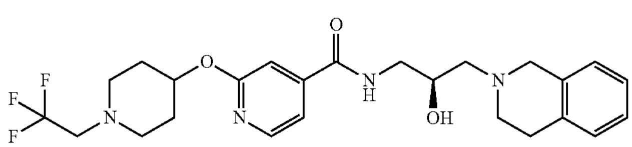 [SMILES: O=C(NC[C@H](O)CN1CCc2ccccc2C1)c1ccnc(OC2CCN(CC(F)(F)F)CC2)c1] | 492.2348 | 493.3 |
| 204 | 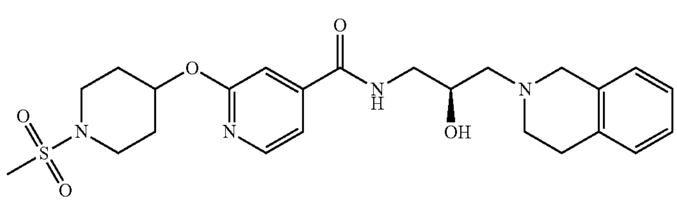 [SMILES: CS(=O)(=O)N1CCC(Oc2cc(C(=O)NC[C@H](O)CN3CCc4ccccc4C3)ccn2)CC1] | 488.2093 | 489.3 |
| 205 | 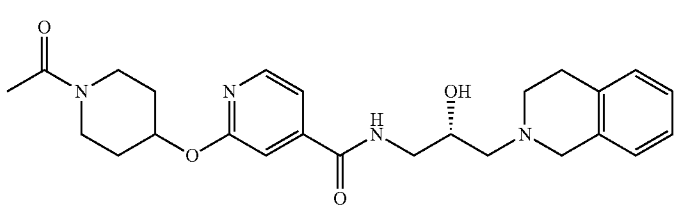 [SMILES: CC(=O)N1CCC(Oc2cc(C(=O)NC[C@H](O)CN3CCc4ccccc4C3)ccn2)CC1] | 452.2424 | 453.3 |

TABLE 1-continued

Exemplary Compounds

| Cmpd No | Structure | Exact Mass | LCMS m/z (M + H) |
|---|---|---|---|
| 206 | 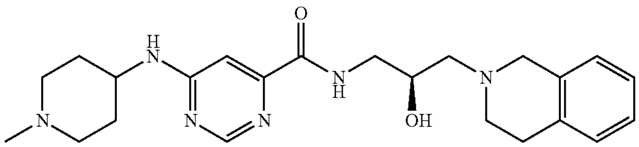 [SMILES: CN1CCC(Nc2cc(C(=O)NC[C@H](O)CN3CCc4ccccc4C3)ncn2)CC1] | 424.2587 | 425.2 |
| 207 | 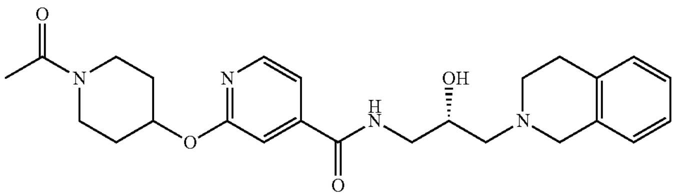 [SMILES: CC(=O)N1CCC(Oc2cc(C(=O)NC[C@H](O)CN3CCc4ccccc4C3)ccn2)CC1] | 492.2461 | 493.3 |
| 208 | 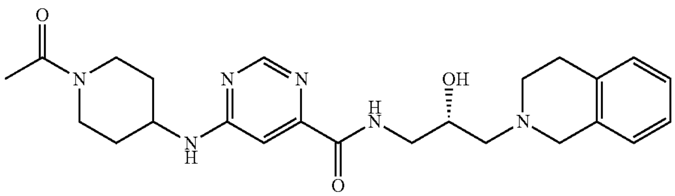 [SMILES: CC(=O)N1CCC(Nc2cc(C(=O)NC[C@H](O)CN3CCc4ccccc4C3)ncn2)CC1] | 452.2536 | 453.3 |
| 209 | 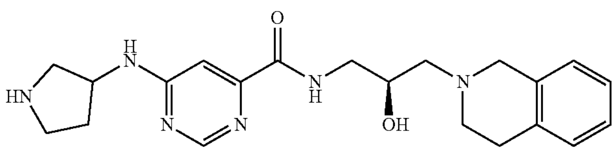 [SMILES: O=C(NC[C@H](O)CN1CCc2ccccc2C1)c1cc(NC2CCNC2)ncn1] | 396.2274 | 397.3 |
| 210 | 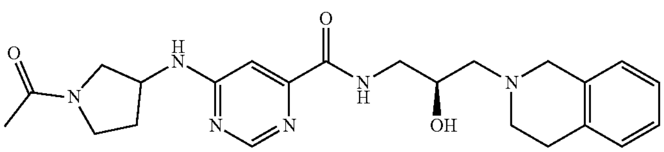 [SMILES: CC(=O)N1CCC(Nc2cc(C(=O)NC[C@H](O)CN3CCc4ccccc4C3)ncn2)C1] | 438.2379 | 439.3 |
| 211 | 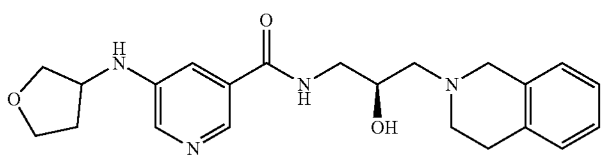 [SMILES: O=C(NC[C@H](O)CN1CCc2ccccc2C1)c1cncc(NC2CCOC2)c1] | 396.2161 | 397.1 |
| 212 | 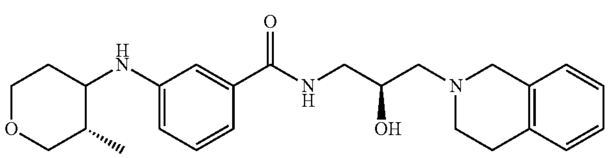 [SMILES: C[C@@H]1COCCC1Nc1cccc(C(=O)NC[C@H](O)CN2CCc3ccccc3C2)c1] | 423.2522 | 424.3 |
| 213 | 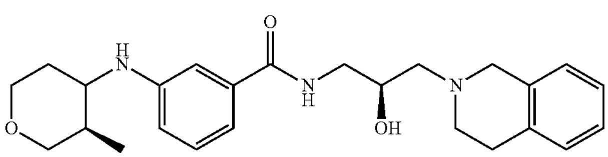 [SMILES: C[C@H]1COCCC1Nc1cccc(C(=O)NC[C@H](O)CN2CCc3ccccc3C2)c1] | 423.2522 | 424.3 |
| 214 | 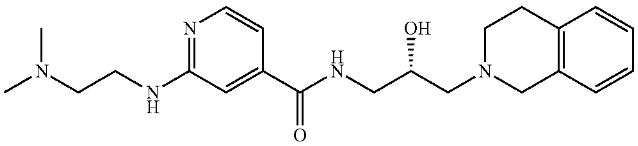 [SMILES: CN(C)CCNc1cc(C(=O)NC[C@H](O)CN2CCc3ccccc3C2)ccn1] | 397.2478 | 398.2 |

TABLE 1-continued

Exemplary Compounds

| Cmpd No | Structure | Exact Mass | LCMS m/z (M + H) |
|---|---|---|---|
| 215 | | 450.2631 | 451.3 |
| 216 | | 486.2301 | 487.3 |
| 217 | | 490.2556 | 491.3 |
| 218 | | 361.179 | 362.1 |
| 219 | | 375.1947 | 376.1 |
| 220 | | 361.179 | 362.1 |
| 221 | | 375.1947 | 376.1 |
| 222 | | 426.2267 | 427.1 |
| 223 | | 423.2634 | 424.1 |

TABLE 1-continued

Exemplary Compounds

| Cmpd No | Structure | Exact Mass | LCMS m/z (M + H) |
|---|---|---|---|
| 224 | 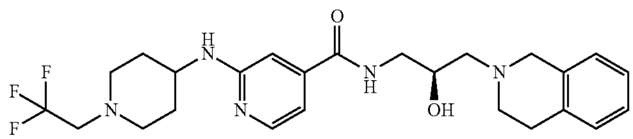 [SMILES: O=C(NC[C@H](O)CN1CCc2ccccc2C1)c1ccnc(NC2CCN(CC(F)(F)F)CC2)c1] | 491.2508 | 492.2 |
| 225 | 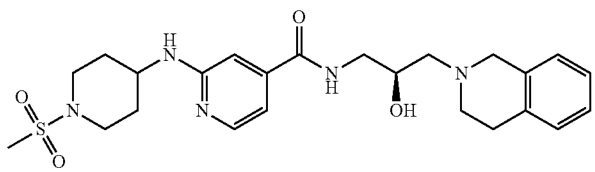 [SMILES: CS(=O)(=O)N1CCC(Nc2cc(C(=O)NC[C@H](O)CN3CCc4ccccc4C3)ccn2)CC1] | 487.2253 | 488.3 |
| 226 | 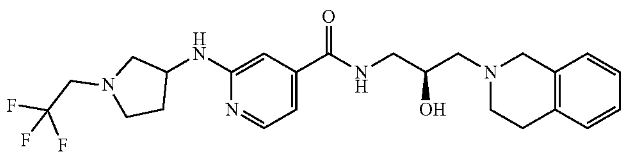 [SMILES: O=C(NC[C@H](O)CN1CCc2ccccc2C1)c1ccnc(NC2CCN(CC(F)(F)F)C2)c1] | 477.2352 | 478.3 |
| 227 | 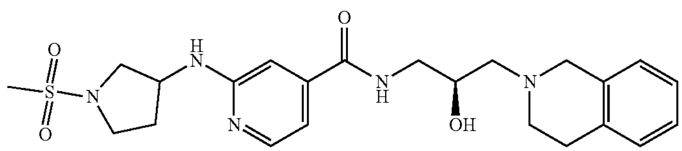 [SMILES: CS(=O)(=O)N1CCC(Nc2cc(C(=O)NC[C@H](O)CN3CCc4ccccc4C3)ccn2)C1] | 473.2097 | 474.2 |
| 228 | 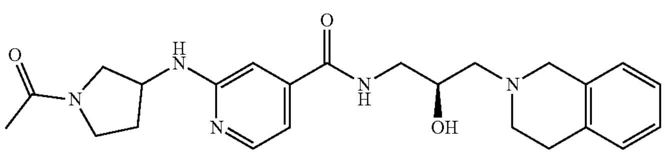 [SMILES: CC(=O)N1CCC(Nc2cc(C(=O)NC[C@H](O)CN3CCc4ccccc4C3)ccn2)C1] | 437.2427 | 438.3 |
| 229 | 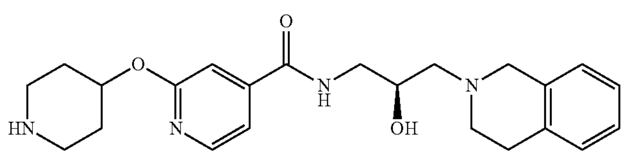 [SMILES: O=C(NC[C@H](O)CN1CCc2ccccc2C1)c1ccnc(OC2CCNCC2)c1] | 410.2318 | 411.3 |
| 230 | 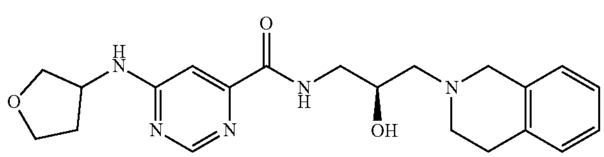 [SMILES: O=C(NC[C@H](O)CN1CCc2ccccc2C1)c1cc(NC2CCOC2)ncn1] | 397.2114 | 398.1 |
| 231 | 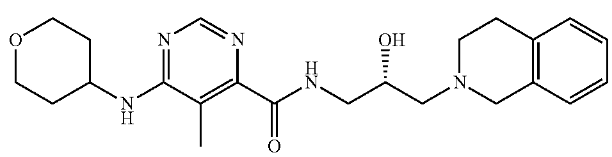 [SMILES: Cc1c(NC2CCOCC2)ncnc1C(=O)NC[C@H](O)CN1CCc2ccccc2C1] | 425.2427 | 426.1 |
| 232 | 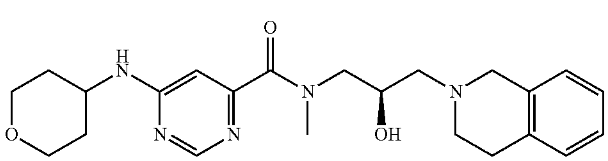 [SMILES: CN(C[C@H](O)CN1CCc2ccccc2C1)C(=O)c1cc(NC2CCOCC2)ncn1] | 425.2427 | 426.3 |

TABLE 1-continued

Exemplary Compounds

| Cmpd No | Structure | Exact Mass | LCMS m/z (M + H) |
|---|---|---|---|
| 233 | 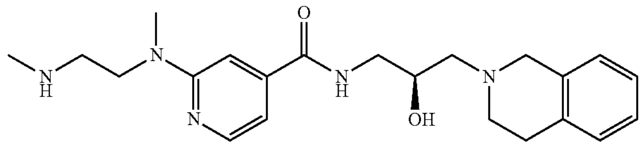 [SMILES: CNCCN(C)c1cc(C(=O)NC[C@H](O)CN2CCc3ccccc3C2)ccn1] | 397.2478 | 398.3 |
| 234 | 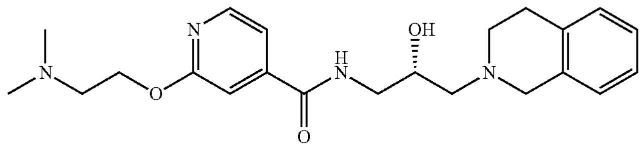 [SMILES: CN(C)CCOc1cc(C(=O)NC[C@H](O)CN2CCc3ccccc3C2)ccn1] | 398.2318 | 399.3 |
| 235 | 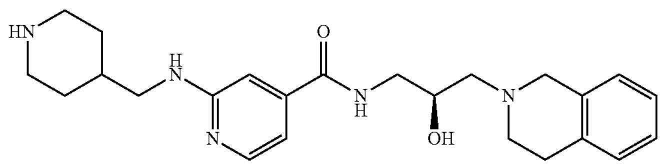 [SMILES: O=C(NC[C@H](O)CN1CCc2ccccc2C1)c1ccnc(NCC2CCNCC2)c1] | 423.2634 | 424.3 |
| 236 | 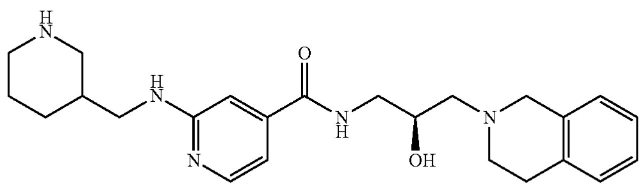 [SMILES: O=C(NC[C@H](O)CN1CCc2ccccc2C1)c1ccnc(NCC2CCCNC2)c1] | 423.2634 | 424.3 |
| 237 | 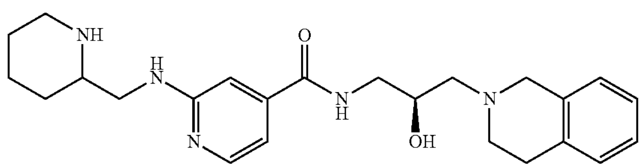 [SMILES: O=C(NC[C@H](O)CN1CCc2ccccc2C1)c1ccnc(NCC2CCCCN2)c1] | 423.2634 | 424.3 |
| 238 | 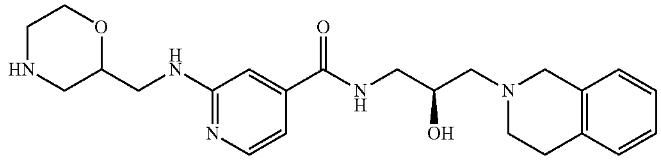 [SMILES: O=C(NC[C@H](O)CN1CCc2ccccc2C1)c1ccnc(NCC2CNCCO2)c1] | 425.2427 | 426.3 |
| 239 | 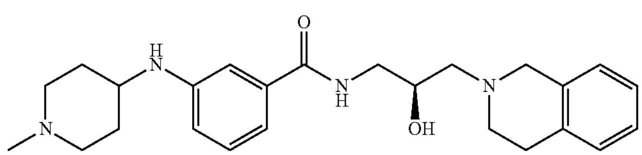 [SMILES: CN1CCC(Nc2cccc(C(=O)NC[C@H](O)CN3CCc4ccccc4C3)c2)CC1] | 422.2682 | 423.1 |
| 240 | 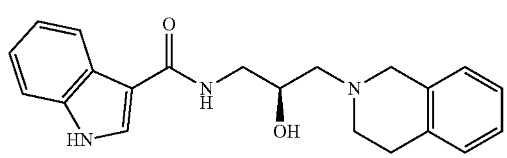 [SMILES: O=C(NC[C@H](O)CN1CCc2ccccc2C1)c1c[nH]c2ccccc12] | 349.179 | 350.1 |
| 241 | 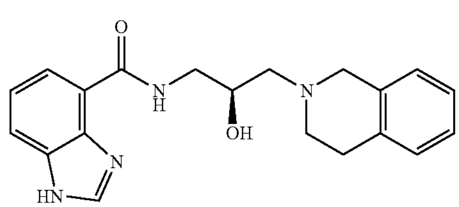 [SMILES: O=C(NC[C@H](O)CN1CCc2ccccc2C1)c1cccc2[nH]cnc12] | 350.1743 | 351.1 |

TABLE 1-continued

Exemplary Compounds

| Cmpd No | Structure | Exact Mass | LCMS m/z (M + H) |
|---|---|---|---|
| 242 | 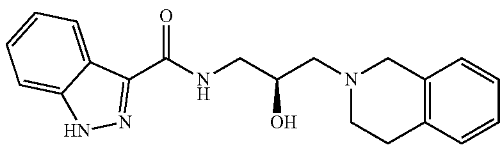 [SMILES: O=C(NC[C@H](O)CN1CCc2ccccc2C1)c1n[nH]c2ccccc12] | 350.1743 | 351.1 |
| 243 | 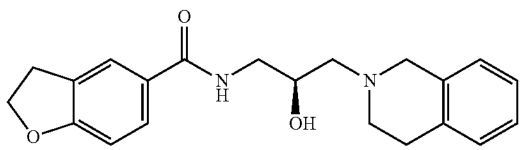 [SMILES: O=C(NC[C@H](O)CN1CCc2ccccc2C1)c1ccc2c(c1)CCO2] | 352.1787 | 353.2 |
| 244 | 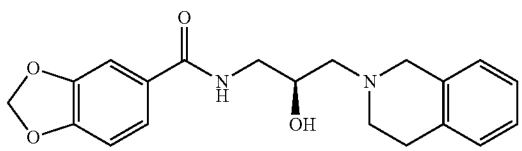 [SMILES: O=C(NC[C@H](O)CN1CCc2ccccc2C1)c1ccc2c(c1)OCO2] | 354.158 | 355 |
| 245 | 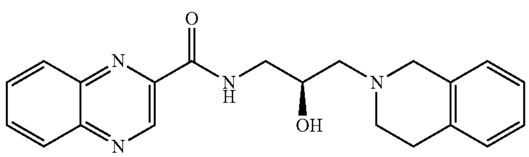 [SMILES: O=C(NC[C@H](O)CN1CCc2ccccc2C1)c1cnc2ccccc2n1] | 362.1743 | 363.1 |
| 246 | 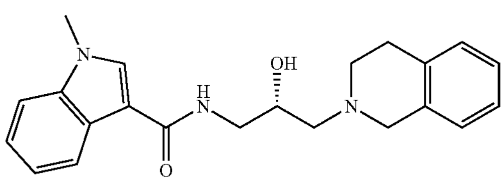 [SMILES: Cn1cc(C(=O)NC[C@H](O)CN2CCc3ccccc3C2)c2ccccc21] | 363.1947 | 364.1 |
| 247 | 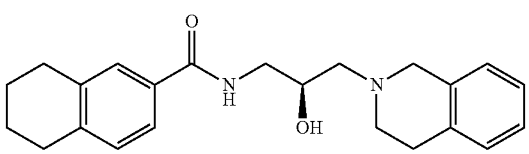 [SMILES: O=C(NC[C@H](O)CN1CCc2ccccc2C1)c1ccc2c(c1)CCCC2] | 364.2151 | 365.1 |
| 248 | 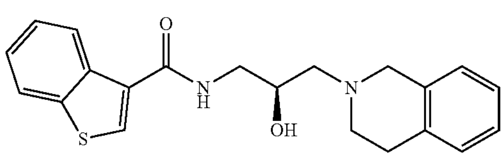 [SMILES: O=C(NC[C@H](O)CN1CCc2ccccc2C1)c1csc2ccccc12] | 366.1402 | 367 |
| 249 | 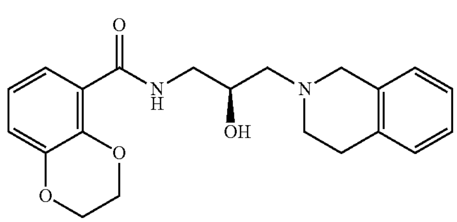 [SMILES: O=C(NC[C@H](O)CN1CCc2ccccc2C1)c1cccc2c1OCCO2] | 368.1736 | 369.1 |

TABLE 1-continued

Exemplary Compounds

| Cmpd No | Structure | Exact Mass | LCMS m/z (M + H) |
|---|---|---|---|
| 250 | 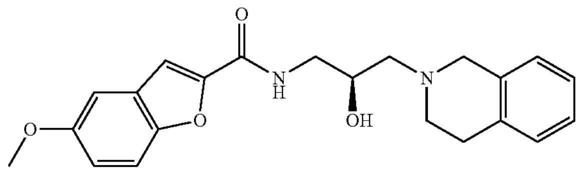 [SMILES: COc1ccc2oc(C(=O)NC[C@H](O)CN3CCc4ccccc4C3)cc2c1] | 380.1736 | 381.1 |
| 251 | 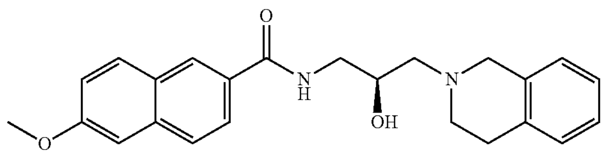 [SMILES: COc1ccc2cc(C(=O)NC[C@H](O)CN3CCc4ccccc4C3)ccc2c1] | 390.1943 | 391.1 |
| 252 | 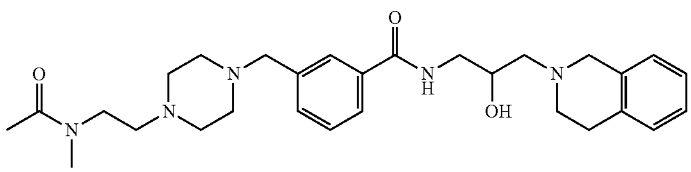 [SMILES: CC(=O)N(C)CCN1CCN(Cc2cccc(C(=O)NCC(O)CN3CCc4ccccc4C3)c2)CC1] | 507.3209 | 508.2 |
| 253 | 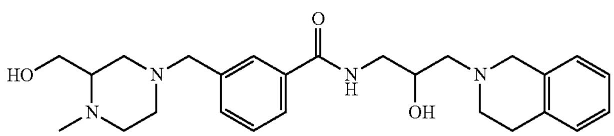 [SMILES: CN1CCN(Cc2cccc(C(=O)NCC(O)CN3CCc4ccccc4C3)c2)CC1CO] | 452.2787 | 453.2 |
| 254 | 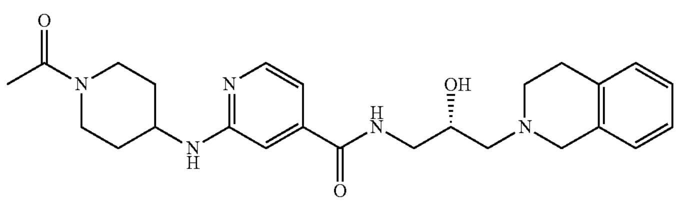 [SMILES: CC(=O)N1CCC(Nc2cc(C(=O)NC[C@H](O)CN3CCc4ccccc4C3)ccn2)CC1] | 451.2583 | 452.3 |
| 255 | 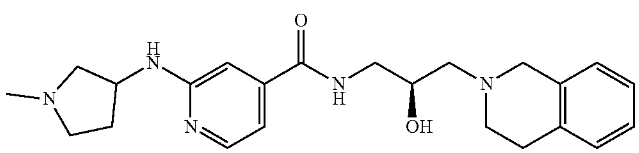 [SMILES: CN1CCC(Nc2cc(C(=O)NC[C@H](O)CN3CCc4ccccc4C3)ccn2)C1] | 409.2478 | 410.3 |
| 256 | 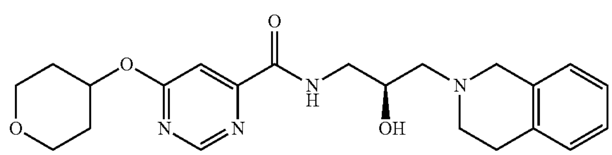 [SMILES: O=C(NC[C@H](O)CN1CCc2ccccc2C1)c1cc(OC2CCOCC2)ncn1] | 412.2111 | 413.1 |
| 257 | 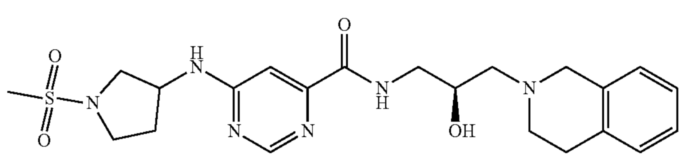 [SMILES: CS(=O)(=O)N1CCC(Nc2cc(C(=O)NC[C@H](O)CN3CCc4ccccc4C3)ncn2)C1] | 474.2049 | 475.3 |
| 258 | 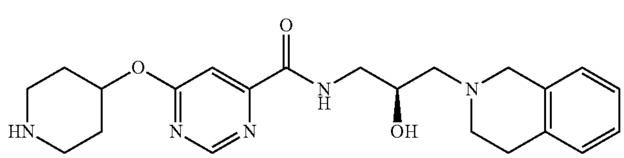 [SMILES: O=C(NC[C@H](O)CN1CCc2ccccc2C1)c1cc(OC2CCNCC2)ncn1] | 411.227 | 412.2 |

TABLE 1-continued

Exemplary Compounds

| Cmpd No | Structure | Exact Mass | LCMS m/z (M + H) |
|---|---|---|---|
| 259 | 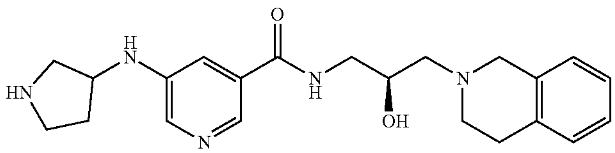 [SMILES: O=C(NC[C@H](O)CN1CCc2ccccc2C1)c1cncc(NC2CCNC2)c1] | 395.2321 | 396.1 |
| 260 | 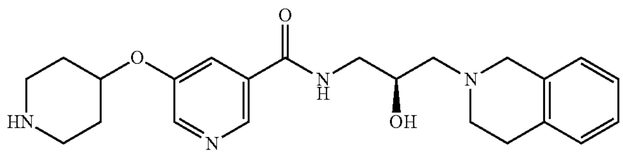 [SMILES: O=C(NC[C@H](O)CN1CCc2ccccc2C1)c1cncc(OC2CCNCC2)c1] | 410.2318 | 411.1 |
| 261 | 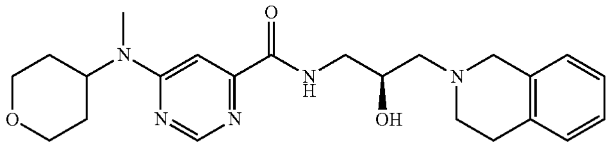 | 425.2427 | 426.3 |
| 262 | 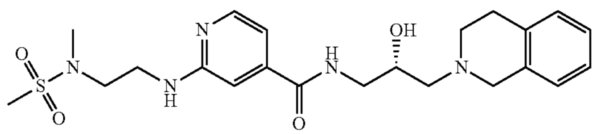 [SMILES: CN(CCNc1cc(C(=O)NC[C@H](O)CN2CCc3ccccc3C2)ccn1)S(C)(=O)=O] | 461.2097 | 462.3 |
| 263 | 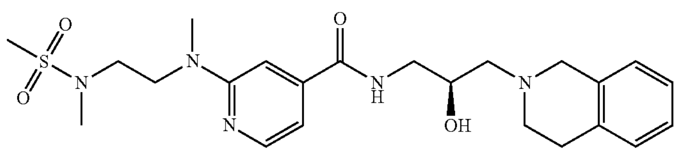 [SMILES: CN(CCN(C)S(C)(=O)=O)c1cc(C(=O)NC[C@H](O)CN2CCc3ccccc3C2)ccn1] | 475.2253 | 476.3 |
| 264 | 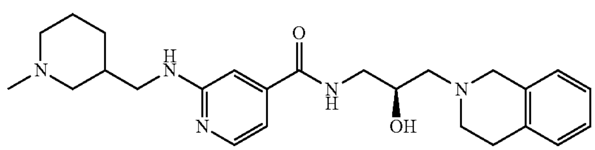 [SMILES: CN1CCCC(CNc2cc(C(=O)NC[C@H](O)CN3CCc4ccccc4C3)ccn2)C1] | 437.2791 | 438.3 |
| 265 | 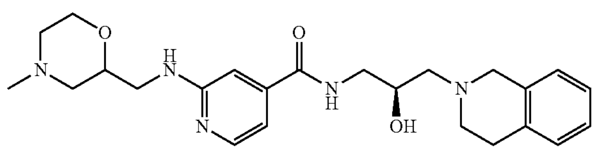 [SMILES: CN1CCOC(CNc2cc(C(=O)NC[C@H](O)CN3CCc4ccccc4C3)ccn2)C1] | 439.2583 | 440.3 |
| 266 | 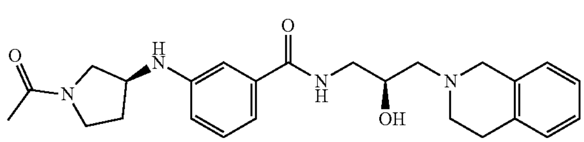 [SMILES: CC(=O)N1CC[C@H](Nc2cccc(C(=O)NC[C@H](O)CN3CCc4ccccc4C3)c2)C1] | 436.2474 | 437.3 |
| 267 | 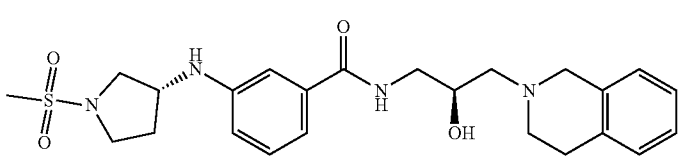 | 472.2144 | 473.3 |
| 268 | 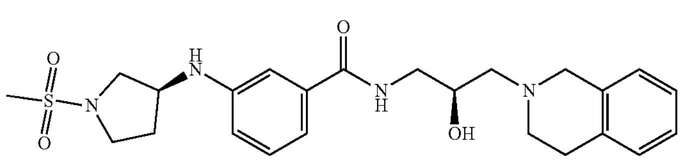 [SMILES: CS(=O)(=O)N1CC[C@H](Nc2cccc(C(=O)NC[C@H](O)CN3CCc4ccccc4C3)c2)C1] | 472.2144 | 473.3 |

TABLE 1-continued

Exemplary Compounds

| Cmpd No | Structure | Exact Mass | LCMS m/z (M + H) |
|---|---|---|---|
| 269 | 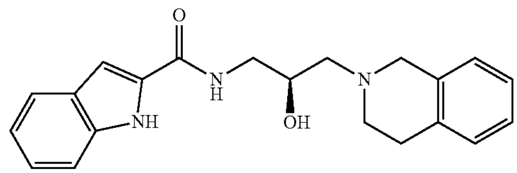 [SMILES: O=C(NC[C@H](O)CN1CCc2ccccc2C1)c1cc2ccccc2[nH]1] | 349.179 | 350.2 |
| 270 | 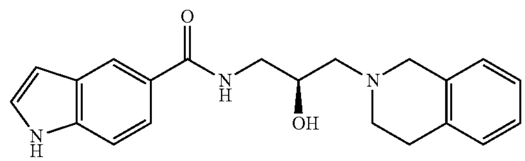 [SMILES: O=C(NC[C@H](O)CN1CCc2ccccc2C1)c1ccc2[nH]ccc2c1] | 349.179 | 350 |
| 271 | 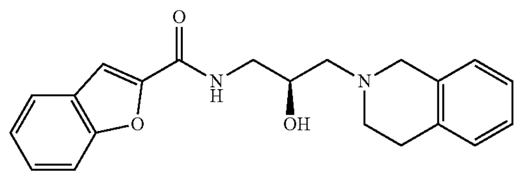 [SMILES: O=C(NC[C@H](O)CN1CCc2ccccc2C1)c1cc2ccccc2o1] | 350.163 | 351 |
| 272 | 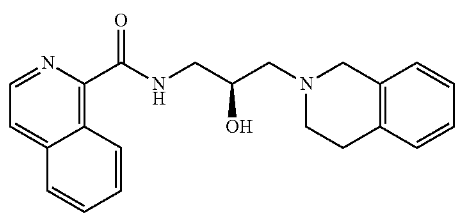 [SMILES: O=C(NC[C@H](O)CN1CCc2ccccc2C1)c1nccc2ccccc12] | 361.179 | 362.1 |
| 273 | 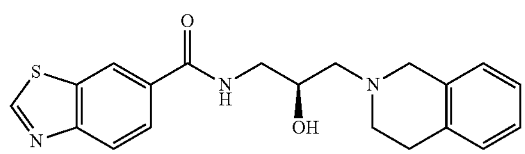 [SMILES: O=C(NC[C@H](O)CN1CCc2ccccc2C1)c1ccc2ncsc2c1] | 367.1354 | 368 |
| 274 | 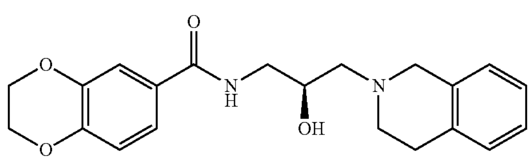 [SMILES: O=C(NC[C@H](O)CN1CCc2ccccc2C1)c1ccc2c(c1)OCCO2] | 368.1736 | 369.1 |
| 275 | 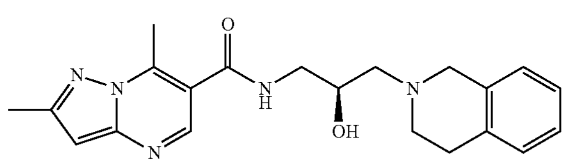 [SMILES: Cc1cc2ncc(C(=O)NC[C@H](O)CN3CCc4ccccc4C3)c(C)n2n1] | 379.2008 | 380.1 |
| 276 | 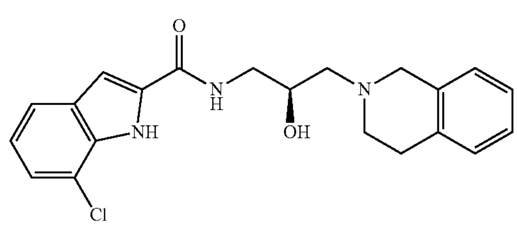 [SMILES: O=C(NC[C@H](O)CN1CCc2ccccc2C1)c1cc2cccc(Cl)c2[nH]1] | 383.1401 | 384.2 |

TABLE 1-continued

Exemplary Compounds

| Cmpd No | Structure | Exact Mass | LCMS m/z (M + H) |
|---|---|---|---|
| 277 | 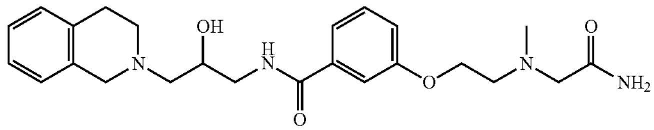 [SMILES: CN(CCOc1cccc(C(=O)NCC(O)CN2CCc3ccccc3C2)c1)CC(N)=O] | 440.2424 | 441.1 |
| 278 | 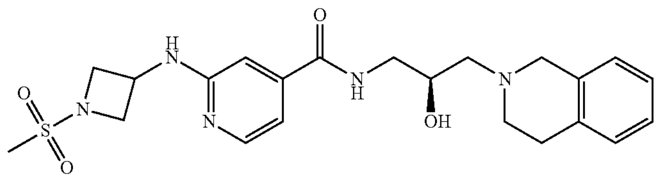 [SMILES: CS(=O)(=O)N1CC(Nc2cc(C(=O)NC[C@H](O)CN3CCc4ccccc4C3)ccn2)C1] | 459.194 | 460.2 |
| 279 | 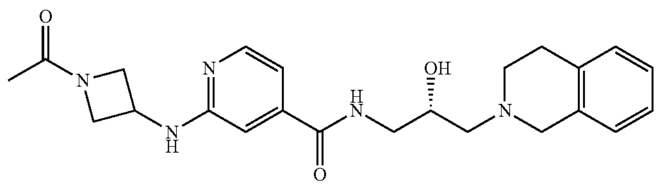 [SMILES: CC(=O)N1CC(Nc2cc(C(=O)NC[C@H](O)CN3CCc4ccccc4C3)ccn2)C1] | 423.227 | 424.3 |
| 280 | 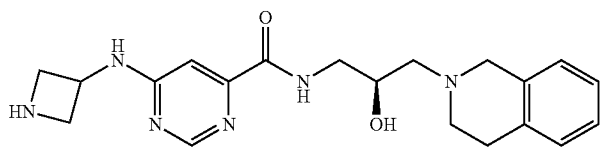 [SMILES: O=C(NC[C@H](O)CN1CCc2ccccc2C1)c1cc(NC2CNC2)ncn1] | 382.2117 | 383.1 |
| 281 | 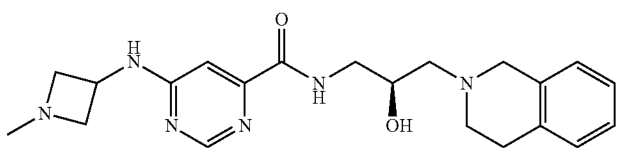 [SMILES: CN1CC(Nc2cc(C(=O)NC[C@H](O)CN3CCc4ccccc4C3)ncn2)C1] | 396.2274 | 397.2 |
| 282 | 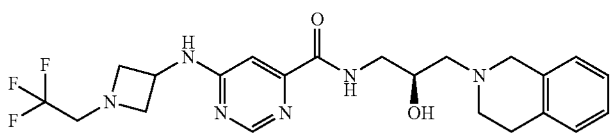 [SMILES: O=C(NC[C@H](O)CN1CCc2ccccc2C1)c1cc(NC2CN(CC(F)(F)F)C2)ncn1] | 464.2148 | 465.1 |
| 283 | 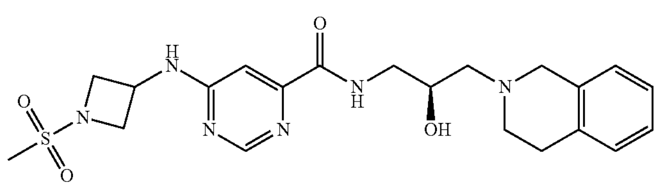 [SMILES: CS(=O)(=O)N1CC(Nc2cc(C(=O)NC[C@H](O)CN3CCc4ccccc4C3)ncn2)C1] | 460.1893 | 461.2 |
| 284 | 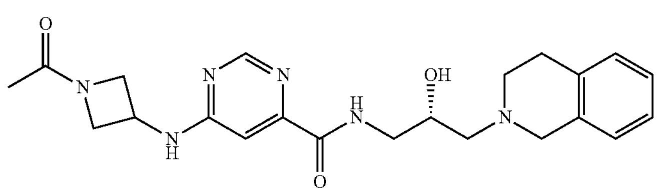 [SMILES: CC(=O)N1CC(Nc2cc(C(=O)NC[C@H](O)CN3CCc4ccccc4C3)ncn2)C1] | 424.2223 | 425.3 |
| 285 | 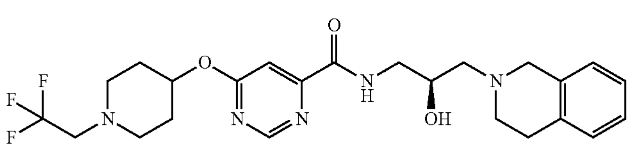 [SMILES: O=C(NC[C@H](O)CN1CCc2ccccc2C1)c1cc(OC2CCN(CC(F)(F)F)CC2)ncn1] | 493.2301 | 494.1 |

TABLE 1-continued

Exemplary Compounds

| Cmpd No | Structure | Exact Mass | LCMS m/z (M + H) |
|---|---|---|---|
| 286 | 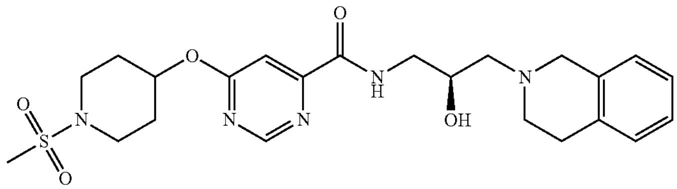 | 489.2046 | 490.3 |
| 287 | 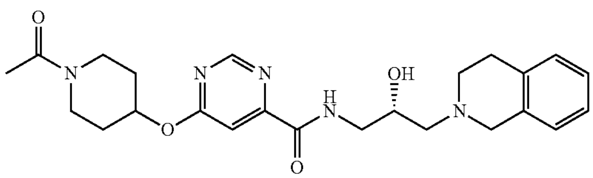 [SMILES: CC(=O)N1CCC(Oc2cc(C(=O)NC[C@H](O)CN3CCc4ccccc4C3)ncn2)CC1] | 453.2376 | 454.3 |
| 288 | 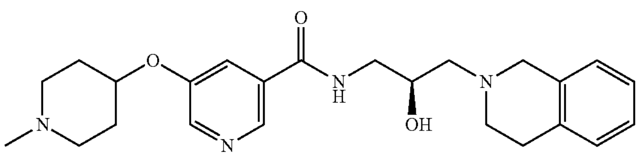 [SMILES: CN1CCC(Oc2cncc(C(=O)NC[C@H](O)CN3CCc4ccccc4C3)c2)CC1] | 424.2474 | 425.3 |
| 289 | 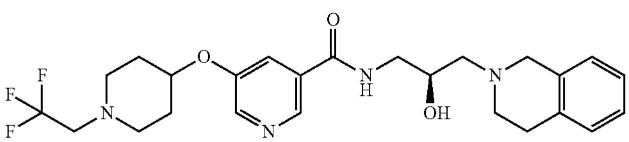 [SMILES: O=C(NC[C@H](O)CN1CCc2ccccc2C1)c1cncc(OC2CCN(CC(F)(F)F)CC2)c1] | 492.2348 | 493.3 |
| 290 | 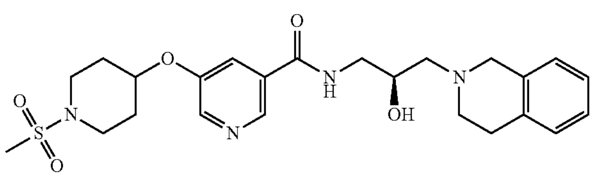 [SMILES: CS(=O)(=O)N1CCC(Oc2cncc(C(=O)NC[C@H](O)CN3CCc4ccccc4C3)c2)CC1] | 488.2093 | 489.2 |
| 291 | 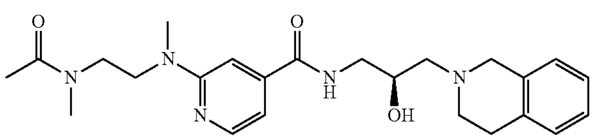 [SMILES: CC(=O)N(C)CCN(C)c1cc(C(=O)NC[C@H](O)CN2CCc3ccccc3C2)ccn1] | 439.2583 | 440.3 |
| 292 | 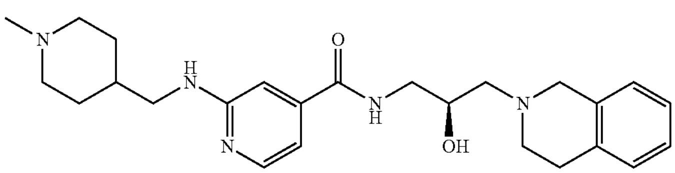 [SMILES: CN1CCC(CNc2cc(C(=O)NC[C@H](O)CN3CCc4ccccc4C3)ccn2)CC1] | 437.2791 | 438.3 |
| 293 | 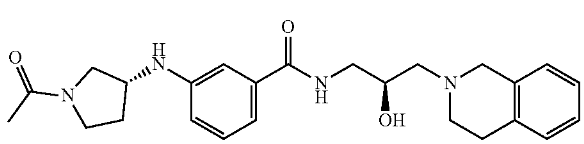 [SMILES: CC(=O)N1CC[C@@H](Nc2cccc(C(=O)NC[C@H](O)CN3CCc4ccccc4C3)c2)C1] | 436.2474 | 437.3 |
| 294 | 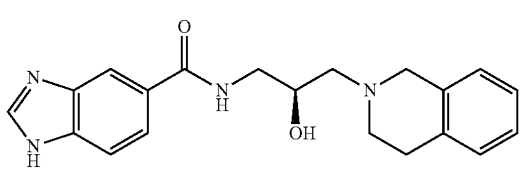 [SMILES: O=C(NC[C@H](O)CN1CCc2ccccc2C1)c1ccc2[nH]cnc2c1] | 350.1743 | 351.1 |

TABLE 1-continued

Exemplary Compounds

| Cmpd No | Structure | Exact Mass | LCMS m/z (M + H) |
|---|---|---|---|
| 295 | 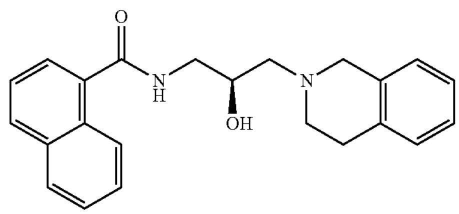 [SMILES: O=C(NC[C@H](O)CN1CCc2ccccc2C1)c1cccc2ccccc12] | 360.1838 | 361.1 |
| 296 | 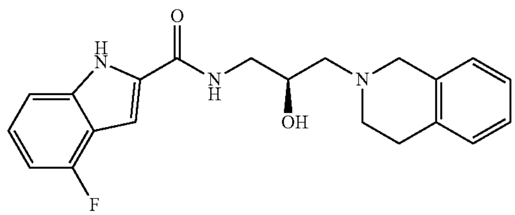 [SMILES: O=C(NC[C@H](O)CN1CCc2ccccc2C1)c1cc2c(F)cccc2[nH]1] | 367.1696 | 368.2 |
| 297 | 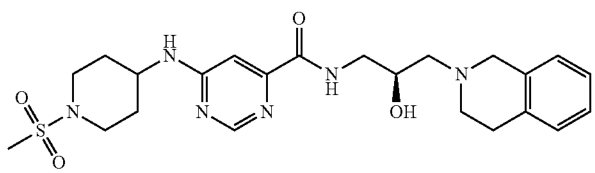 [SMILES: CS(=O)(=O)N1CCC(Nc2cc(C(=O)NC[C@H](O)CN3CCc4ccccc4C3)ncn2)CC1] | 488.2206 | 489.3 |
| 298 | 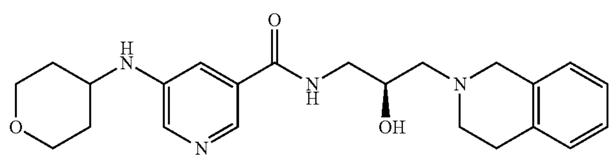 [SMILES: O=C(NC[C@H](O)CN1CCc2ccccc2C1)c1cncc(NC2CCOCC2)c1] | 410.2318 | 411.1 |
| 299 | 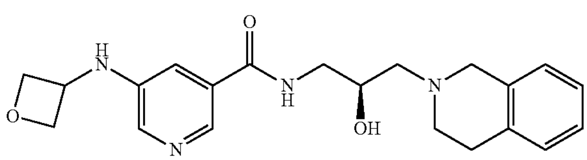 [SMILES: O=C(NC[C@H](O)CN1CCc2ccccc2C1)c1cncc(NC2COC2)c1] | 382.2005 | 383.1 |
| 300 | 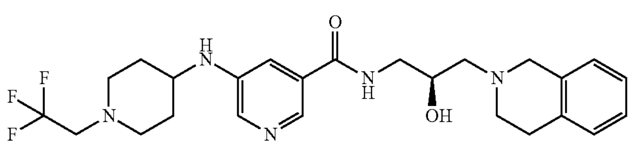 [SMILES: O=C(NC[C@H](O)CN1CCc2ccccc2C1)c1cncc(NC2CCN(CC(F)(F)F)CC2)c1] | 491.2508 | 492.1 |
| 301 | 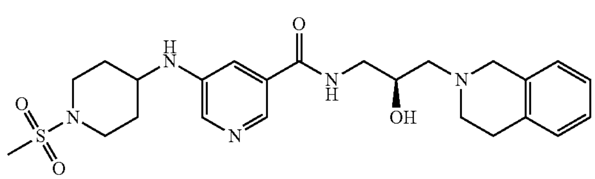 [SMILES: CS(=O)(=O)N1CCC(Nc2cncc(C(=O)NC[C@H](O)CN3CCc4ccccc4C3)c2)CC1] | 487.2253 | 488.1 |
| 302 | 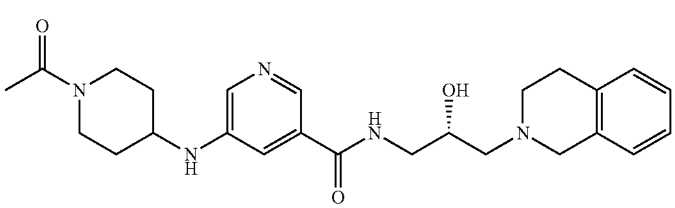 [SMILES: CC(=O)N1CCC(Nc2cncc(C(=O)NC[C@H](O)CN3CCc4ccccc4C3)c2)CC1] | 451.2583 | 452.3 |

TABLE 1-continued

Exemplary Compounds

| Cmpd No | Structure | Exact Mass | LCMS m/z (M + H) |
|---|---|---|---|
| 303 | 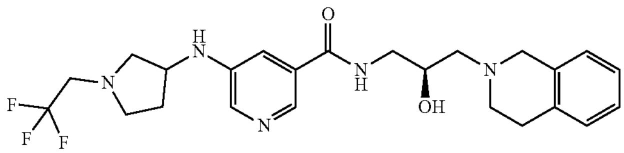 [SMILES: O=C(NC[C@H](O)CN1CCc2ccccc2C1)c1cncc(NC2CCN(CC(F)(F)F)C2)c1] | 477.2352 | 478.1 |
| 304 | 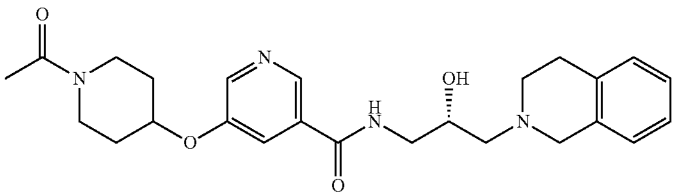 [SMILES: CC(=O)N1CCC(Oc2cncc(C(=O)NC[C@H](O)CN3CCc4ccccc4C3)c2)CC1] | 452.2424 | 453.3 |
| 305 | 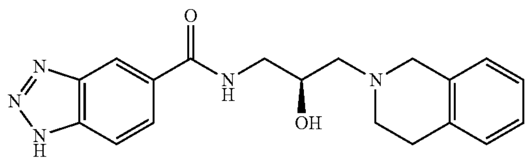 [SMILES: O=C(NC[C@H](O)CN1CCc2ccccc2C1)c1ccc2[nH]nnc2c1] | 351.1695 | 352.1 |
| 306 | 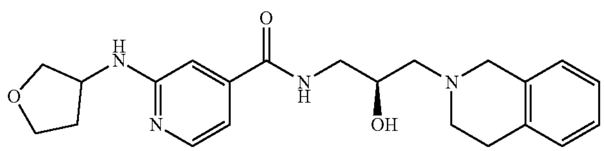 [SMILES: O=C(NC[C@H](O)CN1CCc2ccccc2C1)c1ccnc(NC2CCOC2)c1] | 396.2161 | 397.2 |
| 307 | 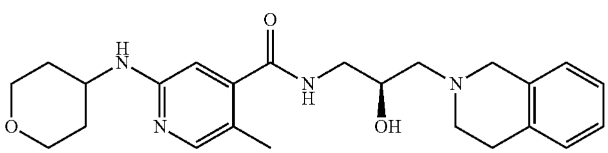 [SMILES: Cc1cnc(NC2CCOCC2)cc1C(=O)NC[C@H](O)CN1CCc2ccccc2C1] | 424.2474 | 425.1 |
| 308 | 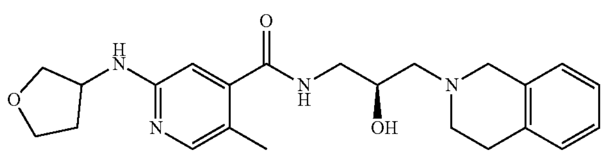 [SMILES: Cc1cnc(NC2CCOC2)cc1C(=O)NC[C@H](O)CN1CCc2ccccc2C1] | 410.2318 | 411.1 |
| 309 | 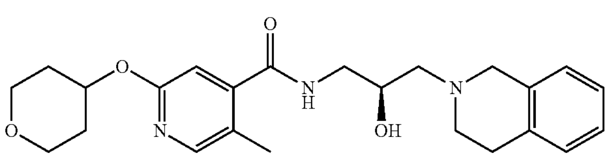 [SMILES: Cc1cnc(OC2CCOCC2)cc1C(=O)NC[C@H](O)CN1CCc2ccccc2C1] | 425.2315 | 426.1 |
| 310 | 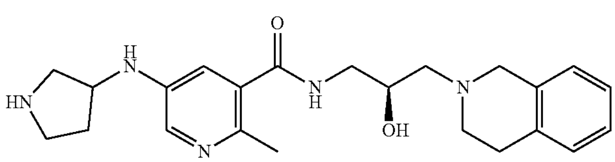 [SMILES: Cc1ncc(NC2CCNC2)cc1C(=O)NC[C@H](O)CN1CCc2ccccc2C1] | 409.2478 | 410.3 |
| 311 | 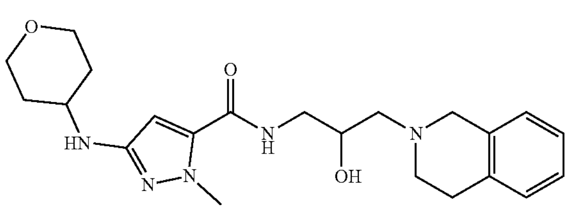 [SMILES: Cn1nc(NC2CCOCC2)cc1C(=O)NCC(O)CN1CCc2ccccc2C1] | 413.2427 | 414.3 |

TABLE 1-continued

Exemplary Compounds

| Cmpd No | Structure | Exact Mass | LCMS m/z (M + H) |
|---|---|---|---|
| 312 | 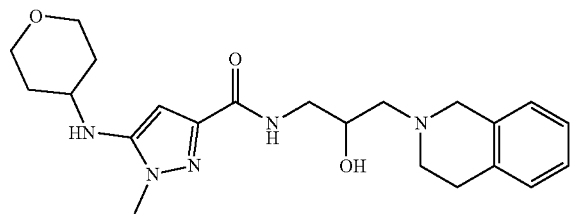 [SMILES: Cn1nc(C(=O)NCC(O)CN2CCc3ccccc3C2)cc1NC1CCOCC1] | 413.2427 | 301.1 |
| 313 | 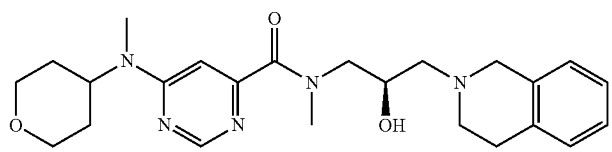 [SMILES: CN(C[C@H](O)CN1CCc2ccccc2C1)C(=O)c1cc(N(C)C2CCOCC2)ncn1] | 439.2583 | 440.1 |
| 314 | 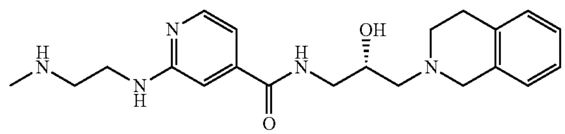 [SMILES: CNCCNc1cc(C(=O)NC[C@H](O)CN2CCc3ccccc3C2)ccn1] | 383.2321 | 384.1 |
| 315 | 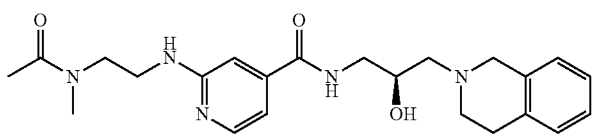 [SMILES: CC(=O)N(C)CCNc1cc(C(=O)NC[C@H](O)CN2CCc3ccccc3C2)ccn1] | 425.2427 | 426.1 |
| 316 | 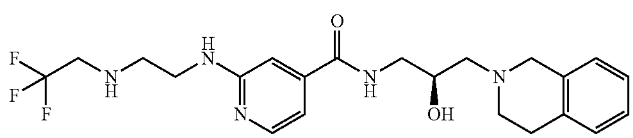 [SMILES: O=C(NC[C@H](O)CN1CCc2ccccc2C1)c1ccnc(NCCNCC(F)(F)F)c1] | 451.2195 | 452.3 |
| 317 | 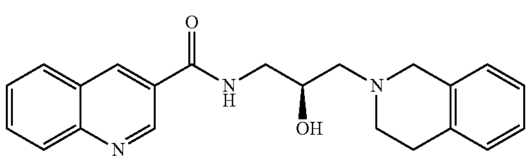 [SMILES: O=C(NC[C@H](O)CN1CCc2ccccc2C1)c1cnc2ccccc2c1] | 361.179 | 362.1 |
| 318 | 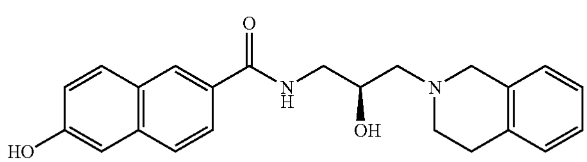 [SMILES: O=C(NC[C@H](O)CN1CCc2ccccc2C1)c1ccc2cc(O)ccc2c1] | 376.1787 | 377.1 |
| 319 | 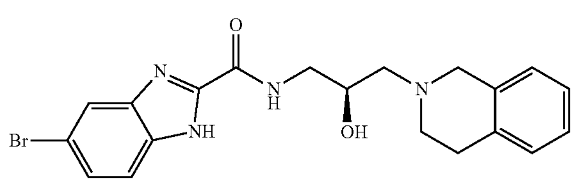 [SMILES: O=C(NC[C@H](O)CN1CCc2ccccc2C1)c1nc2cc(Br)ccc2[nH]1] | 428.0848 | 429 |
| 320 | 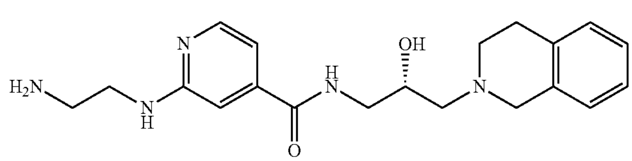 [SMILES: NCCNc1cc(C(=O)NC[C@H](O)CN2CCc3ccccc3C2)ccn1] | 369.2165 | 370.1 |

TABLE 1-continued

Exemplary Compounds

| Cmpd No | Structure | Exact Mass | LCMS m/z (M + H) |
|---|---|---|---|
| 321 | 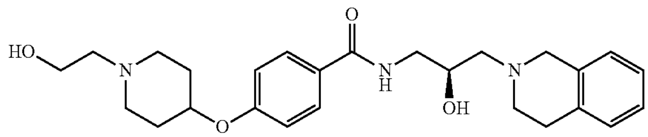 [SMILES: O=C(NC[C@H](O)CN1CCc2ccccc2C1)c1ccc(OC2CCN(CCO)CC2)cc1] | 453.2628 | 454.2 |
| 322 | 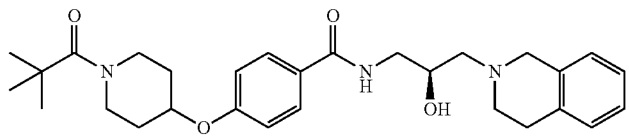 [SMILES: CC(C)(C)C(=O)N1CCC(Oc2ccc(C(=O)NC[C@H](O)CN3CCc4ccccc4C3)cc2)CC1] | 493.2941 | 494.2 |
| 323 | 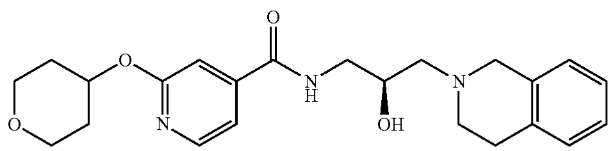 | 411.2158 | 412.3 |
| 324 | 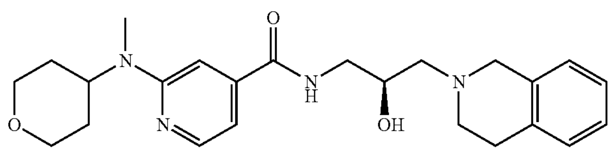 [SMILES: CN(c1cc(C(=O)NC[C@H](O)CN2CCc3ccccc3C2)ccn1)C1CCOCC1] | 424.2474 | 425.1 |
| 325 | 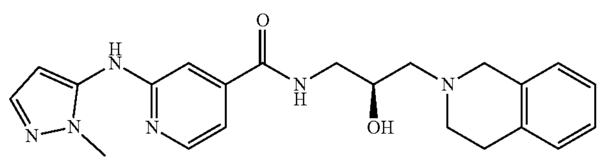 [SMILES: Cn1nccc1Nc1cc(C(=O)NC[C@H](O)CN2CCc3ccccc3C2)ccn1] | 406.2117 | 407.3 |
| 326 | 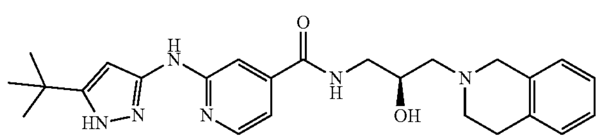 [SMILES: CC(C)(C)c1cc(Nc2cc(C(=O)NC[C@H](O)CN3CCc4ccccc4C3)ccn2)n[nH]1] | 448.2587 | 449.3 |
| 327 | 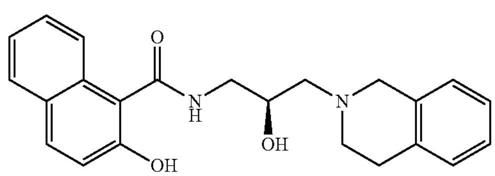 [SMILES: O=C(NC[C@H](O)CN1CCc2ccccc2C1)c1c(O)ccc2ccccc12] | 376.1787 | 377.2 |
| 328 | 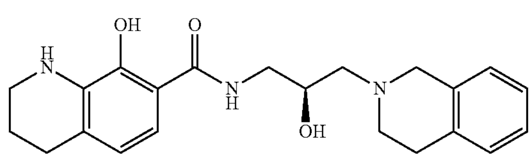 [SMILES: O=C(NC[C@H](O)CN1CCc2ccccc2C1)c1ccc2c(c1O)NCCC2] | 381.2052 | 382.2 |
| 329 | 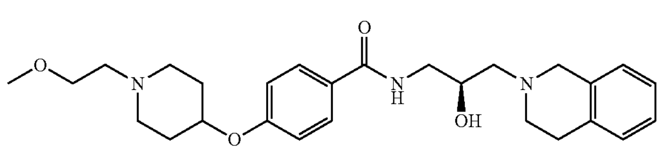 [SMILES: COCCN1CCC(Oc2ccc(C(=O)NC[C@H](O)CN3CCc4ccccc4C3)cc2)CC1] | 467.2784 | 468.2 |
| 330 | 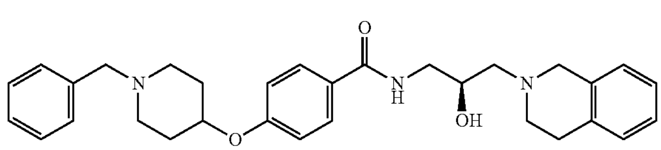 [SMILES: O=C(NC[C@H](O)CN1CCc2ccccc2C1)c1ccc(OC2CCN(Cc3ccccc3)CC2)cc1] | 499.2835 | 500.2 |

TABLE 1-continued

Exemplary Compounds

| Cmpd No | Structure | Exact Mass | LCMS m/z (M + H) |
|---|---|---|---|
| 331 | 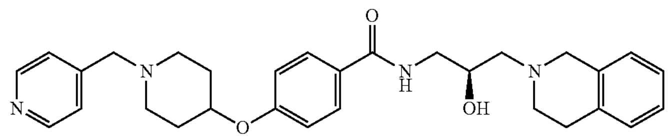 [SMILES: O=C(NC[C@H](O)CN1CCc2ccccc2C1)c1ccc(OC2CCN(Cc3ccncc3)CC2)cc1] | 500.2787 | 501.2 |
| 332 | 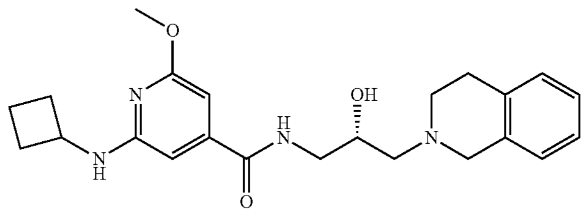 [SMILES: COc1cc(C(=O)NC[C@H](O)CN2CCc3ccccc3C2)cc(NC2CCC2)n1] | 410.2318 | 411.1 |
| 333 | 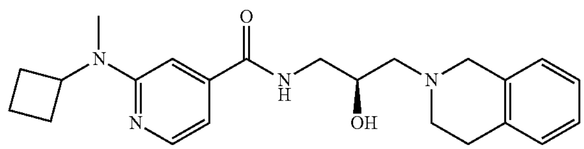 [SMILES: CN(c1cc(C(=O)NC[C@H](O)CN2CCc3ccccc3C2)ccn1)C1CCC1] | 394.2369 | 395.3 |
| 334 | 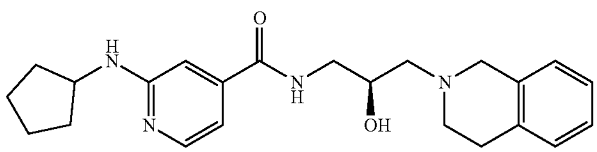 [SMILES: O=C(NC[C@H](O)CN1CCc2ccccc2C1)c1ccnc(NC2CCCC2)c1] | 394.2369 | 395.3 |
| 335 | 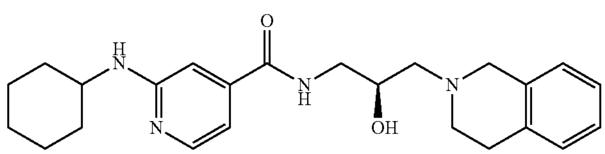 [SMILES: O=C(NC[C@H](O)CN1CCc2ccccc2C1)c1ccnc(NC2CCCCC2)c1] | 408.2525 | 409.1 |
| 336 | 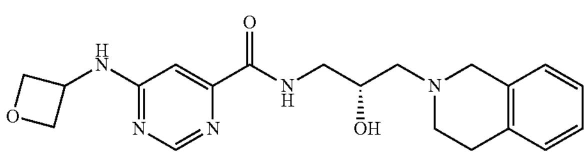 [SMILES: O=C(NC[C@@H](O)CN1CCc2ccccc2C1)c1cc(NC2COC2)ncn1] | 383.1957 | |

In certain embodiments, a provided compound inhibits PRMT5. In certain embodiments, a provided compound inhibits wild-type PRMT5. In certain embodiments, a provided compound inhibits a mutant PRMT5. In certain embodiments, a provided compound inhibits PRMT5, e.g., as measured in an assay described herein. In certain embodiments, the PRMT5 is from a human. In certain embodiments, a provided compound inhibits PRMT5 at an $IC_{50}$ less than or equal to 10 µM. In certain embodiments, a provided compound inhibits PRMT5 at an $IC_{50}$ less than or equal to 1 µM. In certain embodiments, a provided compound inhibits PRMT5 at an $IC_{50}$ less than or equal to 0.1 µM. In certain embodiments, a provided compound inhibits PRMT5 in a cell at an $EC_{50}$ less than or equal to 10 µM. In certain embodiments, a provided compound inhibits PRMT5 in a cell at an $EC_{50}$ less than or equal to 1 µM. In certain embodiments, a provided compound inhibits PRMT5 in a cell at an $EC_{50}$ less than or equal to 0.1 µM. In certain embodiments, a provided compound inhibits cell proliferation at an $EC_{50}$ less than or equal to 10 µM. In certain embodiments, a provided compound inhibits cell proliferation at an $EC_{50}$ less than or equal to 1 µM. In certain embodiments, a provided compound inhibits cell proliferation at an $EC_{50}$ less than or equal to 0.1 µM. In some embodiments, a provided compound is selective for PRMT5 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective for PRMT5 relative to one or more other methyltransferases.

It will be understood by one of ordinary skill in the art that the PRMT5 can be wild-type PRMT5, or any mutant or variant of PRMT5.

In certain embodiments, the PRMT5 is isoform A (GenBank accession no. NP006100) (SEQ ID NO:1):

```
MAAMAVGGAG GSRVSSGRDL NCVPEIADTL GAVAKQGFDF

LCMPVFHPRF KREFIQEPAK NRPGPQTRSD LLLSGRDWNT

LIVGKLSPWI RPDSKVEKIR RNSEAAMLQE LNFGAYLGLP

AFLLPLNQED NTNLARVLTN HIHTGHHSSM FWMRVPLVAP

EDLRDDIIEN APTTHTEEYS GEEKTWMWWH NFRTLCDYSK

RIAVALEIGA DLPSNHVIDR WLGEPIKAAI LPTSIFLTNK

KGFPVLSKMH QRLIFRLLKL EVQFIITGTN HHSEKEFCSY

LQYLEYLSQN RPPPNAYELF AKGYEDYLQS PLQPLMDNLE

SQTYEVFEKD PIKYSQYQQA IYKCLLDRVP EEEKDTNVQV

LMVLGAGRGP LVNASLRAAK QADRRIKLYA VEKNPNAVVT

LENWQFEEWG SQVTVVSSDM REWVAPEKAD IIVSELLGSF

ADNELSPECL DGAQHFLKDD GVSIPGEYTS FLAPISSSKL

YNEVRACREK DRDPEAQFEM PYVVRLHNFH QLSAPQPCFT

FSHPNRDPMI DNNRYCTLEF PVEVNTVLHG FAGYFETVLY

QDITLSIRPE THSPGMFSWF PILFPIKQPI TVREGQTICV

RFWRCSNSKK VWYEWAVTAP VCSAIHNPTG RSYTIGL
```

In certain embodiments, the PRMT5 is isoform B (GenBank accession no. NP001034708) (SEQ ID NO:2)

```
MRGPNSGTEK GRLVIPEKQG FDFLCMPVFH PRFKREFIQE

PAKNRPGPQT RSDLLLSGRD WNTLIVGKLS PWIRPDSKVE

KIRRNSEAAM LQELNFGAYL GLPAFLLPLN QEDNTNLARV

LTNHIHTGHH SSMFWMRVPL VAPEDLRDDI IENAPTTHTE

EYSGEEKTWM WWHNFRTLCD YSKRIAVALE IGADLPSNHV

IDRWLGEPIK AAILPTSIFL TNKKGFPVLS KMHQRLIFRL

LKLEVQFIIT GTNHHSEKEF CSYLQYLEYL SQNRPPPNAY

ELFAKGYEDY LQSPLQPLMD NLESQTYEVF EKDPIKYSQY

QQAIYKCLLD RVPEEEKDTN VQVLMVLGAG RGPLVNASLR

AAKQADRRIK LYAVEKNPNA VVTLENWQFE EWGSQVTVVS

SDMREWVAPE KADIIVSELL GSFADNELSP ECLDGAQHFL

KDDGVSIPGE YTSFLAPISS SKLYNEVRAC REKDRDPEAQ

FEMPYVVRLH NFHQLSAPQP CFTFSHPNRD PMIDNNRYCT

LEFPVEVNTV LHGFAGYFET VLYQDITLSI RPETHSPGMF

SWFPILFPIK QPITVREGQT ICVRFWRCSN SKKVWYEWAV

TAPVCSAIHN PTGRSYTIGL
```

In certain embodiments, the PRMT5 is transcript variant 1 (GenBank accession no. NM_006109).

The present disclosure provides pharmaceutical compositions comprising a compound described herein, e.g., a compound of Formula (I), or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting PRMT5. In certain embodiments, the effective amount is an amount effective for treating a PRMT5-mediated disorder. In certain embodiments, the effective amount is a prophylactically effective amount. In certain embodiments, the effective amount is an amount effective to prevent a PRMT5-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytouened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I). In certain embodiments, the additional therapeutically active agent is not a compound of Formula (I). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of PRMT5. In some embodiments, methods of treating PRMT5-mediated disorder in a subject are provided which comprise administering an effective amount of a compound described herein (e.g., a compound of Formula (I)), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a PRMT5-mediated disorder. In certain embodiments, the subject is susceptible to a PRMT5-mediated disorder.

As used herein, the term "PRMT5-mediated disorder" means any disease, disorder, or other pathological condition in which PRMT5 is known to play a role. Accordingly, in some embodiments, the present disclosure relates to treating or lessening the severity of one or more diseases in which PRMT5 is known to play a role.

In some embodiments, the present disclosure provides a method of inhibiting PRMT5 comprising contacting PRMT5 with an effective amount of a compound described herein (e.g., a compound of Formula (I)), or a pharmaceutically acceptable salt thereof. The PRMT5 may be purified or crude, and may be present in a cell, tissue, or subject. Thus, such methods encompass both inhibition of in vitro and in vivo PRMT5 activity. In certain embodiments, the method is an in vitro method, e.g., such as an assay method. It will be understood by one of ordinary skill in the art that inhibition of PRMT5 does not necessarily require that all of the PRMT5 be occupied by an inhibitor at once. Exemplary levels of inhibition of PRMT5 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting PRMT5 activity in a subject in need thereof comprising administering to the subject an effective amount of a compound described herein (e.g., a compound of Formula (I)), or a pharmaceutically acceptable salt thereof, or a pharmaceutical composition thereof.

In certain embodiments, provided is a method of altering gene expression in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, provided is a method of altering transcription in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, a method is provided of selecting a therapy for a subject having a disease associated with PRMT5-mediated disorder or mutation comprising the steps of determining the presence of PRMT5-mediated disorder or gene mutation in the PRMT5 gene or and selecting, based on the presence of PRMT5-mediated disorder a gene mutation in the PRMT5 gene a therapy that includes the administration of a provided compound. In certain embodiments, the disease is cancer.

In certain embodiments, a method of treatment is provided for a subject in need thereof comprising the steps of determining the presence of PRMT5-mediated disorder or a gene mutation in the PRMT5 gene and treating the subject in need thereof, based on the presence of a PRMT5-mediated disorder or gene mutation in the PRMT5 gene with a therapy that includes the administration of a provided compound. In certain embodiments, the subject is a cancer patient.

In some embodiments, a provided compound is useful in treating a proliferative disorder, such as cancer, a benign neoplasm, an autoimmune disease, or an inflammatory disease. For example, while not being bound to any particular mechanism, PRMT5 has been shown to be involved in cyclin D1 dysregulated cancers. Increased PRMT5 activity mediates key events associated with cyclin D1-dependent neoplastic growth including CUL4 repression, CDT1 overexpression, and DNA re-replication. Further, human cancers harboring mutations in Fbx4, the cyclin D1 E3 ligase, exhibit nuclear cyclin D1 accumulation and increased PRMT5 activity (Aggarwal et al., *Cancer Cell.* 2010 18(4): 329-40). Additionally, PRMT5 has also been implicated in accelerating cell cycle progression through G1 phase and modulating regulators of G1; for example, PRMT5 may upregulate cyclin-dependent kinase (CDK) 4, CDK6, and cyclins D1, D2 and E1. Moreover, PRMT5 may activate phosphoinositide 3-kinase (PI3K)/AKT signaling (Wei et al., *Cancer Sci.* 2012 103(9):1640-50). Thus in some embodiments, the inhibition of PRMT5 by a provided compound is useful in treating the following non-limiting list of cancers: breast cancer, esophageal cancer, bladder cancer, lung cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenocarcinoma.

In some embodiments, the inhibition of PRMT5 by a provided compound is useful in treating prostate cancer and lung cancer, in which PRMT5 has been shown to play a role (Gu et al., *PLoS One* 2012; 7(8):e44033; Gu et al., *Biochem. J.* (2012) 446 (235-241)). In some embodiments, a provided compound is useful to delay the onset of, slow the progression of, or ameliorate the symptoms of cancer. In some embodiments, a provided compound is administered in combination with other compounds, drugs, or therapeutics to treat cancer.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrim's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomal-leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a provided compound is useful in treating a metabolic disorder, such as diabetes or obesity. For example, while not being bound to any particular mechanism, a role for PRMT5 has been recognized in adipogenesis. Inhibition of PRMT5 expression in multiple cell culture models for adipogenesis prevented the activation of adipogenic genes, while overexpression of PRMT5 enhanced adipogenic gene expression and differentiation (LeBlanc et al., *Mol Endocrinol.* 2012 April; 26(4):583-97). Additionally, it has been shown that adipogenesis plays a pivotal role in the etiology and progression of diabetes and obesity (Camp et al., *Trends Mol Med.* 2002 September; 8(9):442-7). Thus in some embodiments, the inhibition of PRMT5 by a provided compound is useful in treating diabetes and/or obesity.

In some embodiments, a provided compound is useful to delay the onset of, slow the progression of, or ameliorate the symptoms of, diabetes. In some embodiments, the diabetes is Type 1 diabetes. In some embodiments, the diabetes is Type 2 diabetes. In some embodiments, a provided compound is useful to delay the onset of, slow the progression of, or ameliorate the symptoms of, obesity. In some embodiments, a provided compound is useful to make a subject lose weight. In some embodiments, a provided compound could be used in combination with other compounds, drugs, or therapeutics, such as metformin and insulin, to treat diabetes and/or obesity.

In some embodiments, a provided compound is useful in treating a blood disorder, e.g., a hemoglobinopathy, such as sickle cell disease or β-thalassemia. For example, while not being bound to any particular mechanism, PRMT5 is a known repressor of γ-globin gene expression, and increased fetal γ-globin (HbF) levels in adulthood are associated with symptomatic amelioration in sickle cell disease and β-thalassemia (Xu et al., *Haematologica.* 2012 November; 97(11): 1632-40). Thus in some embodiments, the inhibition of PRMT5 by a provided compound is useful in treating a blood disorder, such as a hemoglobinopathy such as sickle cell disease or β-thalassemia.

In some embodiments, a provided compound is useful to delay the onset of, slow the progression of, or ameliorate the symptoms of, sickle cell disease. In some embodiments, a provided compound is useful to delay the onset of, slow the progression of, or ameliorate the symptoms of, β-thalassemia. In some embodiments, a provided compound could be used in combination with other compounds, drugs, or therapeutics, to treat a hemoglobinopathy such as sickle cell disease or β-thalassemia.

In some embodiments, compounds described herein can prepared using methods shown in general Scheme 1. Compound B can be prepared via ring opening of a chiral or racemic epoxide group. This amino alcohol intermediate can be coupled to form an amide via normal amide coupling methodology using a carboxylic acid A wherein Z is hydrogen or via amination of an ester of intermediate A when Z is an optionally substituted aliphatic group.

Scheme 1
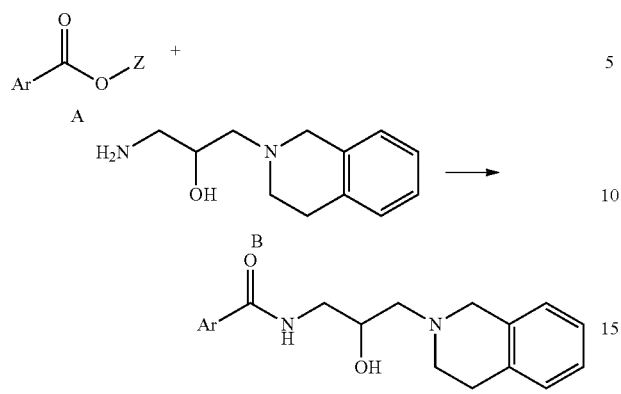
Analogous reactions may be performed to form a carbamate or urea bond using methods known to one of ordinary skill in the art.
In some embodiments, such couplings can be used to provide a key intermediate for further synthesis, as shown, for example, in exemplary Scheme 2.

Scheme 2
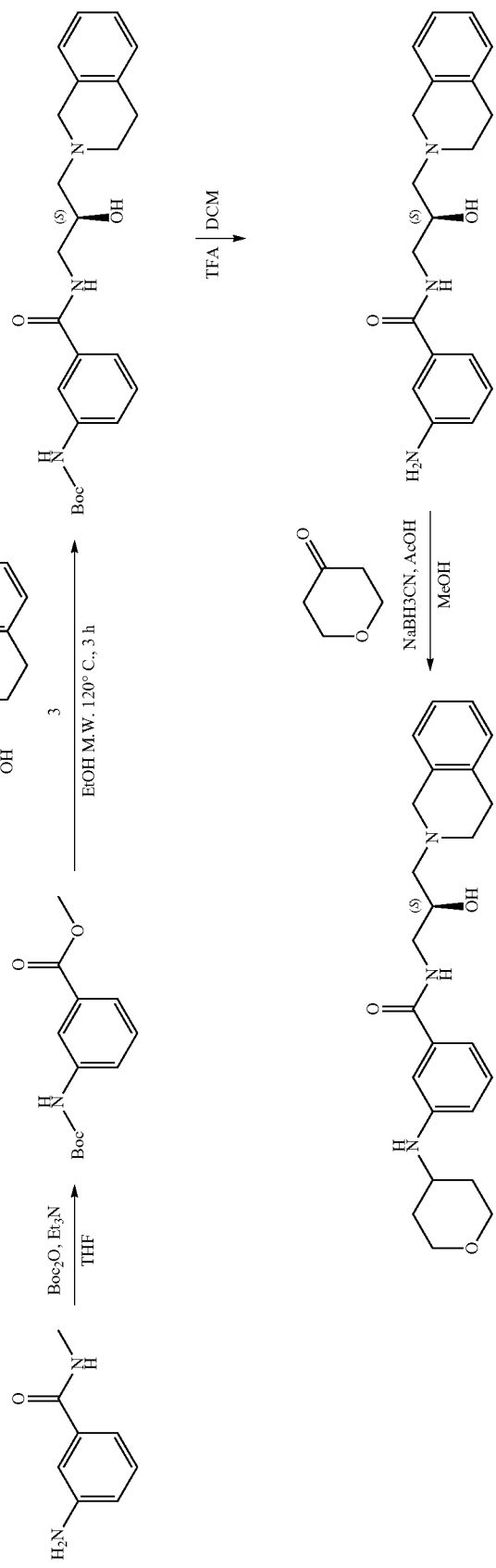

In other embodiments, an amide coupling step is the final synthetic step as shown in exemplary Scheme 3.

Scheme 3

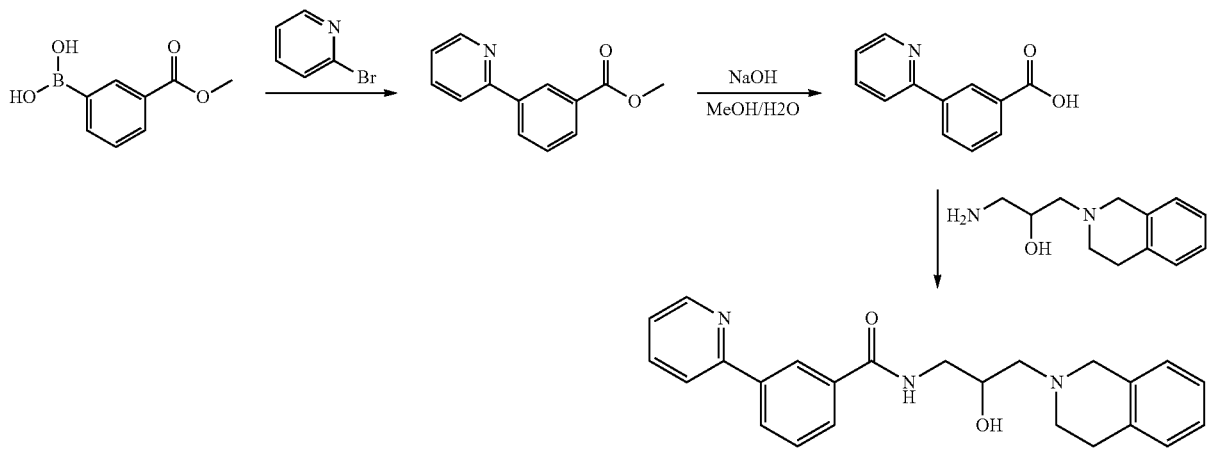

EXAMPLES

In order that the invention described herein may be more fully understood, the following examples are set forth. It should be understood that these examples are for illustrative purposes only and are not to be construed as limiting this invention in any manner.

Synthetic Methods

Compound 1

N-(3-(3,4-dihydroisoquinolin-2(1H)-yl)-2-hydroxypropyl)-3-(pyridin-2-yl)benzamide

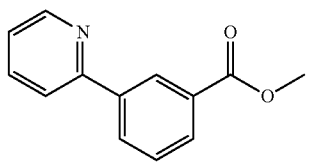

Step 1: methyl 3-(pyridin-2-yl)benzoate

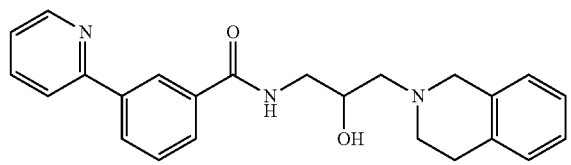 [SMILES: O=C(NCC(O)CN1CCc2ccccc2C1)c1cccc(-c2ccccn2)c1]

A mixture of (3-(methoxycarbonyl)phenyl)boronic acid (500 mg, 2.78 mmol), 2-bromopyridine (399 mg, 2.53 mmol), $K_2CO_3$ (1.0 g, 7.6 mmol) and Pd(dppf)Cl$_2$ (20 mg) in a mixture solution of dioxane (10 mL) and $H_2O$ (2.5 mL) was stirred at 120° C. for 30 min under microwave heating. The catalyst was removed by filtration and the filtrate was concentrated. The residue was purified by column chromatography to give the desired product (530 mg, Yield: 90%) and this was used directly in the next step. LCMS (m/z): 214.1.

Step 2: 3-(pyridin-2-yl)benzoic Acid

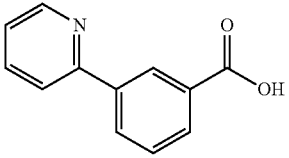 [SMILES: O=C(O)c1cccc(-c2ccccn2)c1]

To a solution of methyl 3-(pyridin-2-yl)benzoate (300 mg, 1.40 mmol) in MeOH (3 mL) was added aqueous NaOH (1 mL, 0.4M). The mixture was stirred at room temperature for 3 h. The reaction solution was concentrated and the residue dissolved in water and adjust pH to 5-6 with 2N of HCl. The solution was extracted with EtOAc (3×20 mL) and the combined organic layers concentrated to give the desired crude product (450 mg, Yield 90%) which was used in the next step without further purification. LCMS (m/z): 200.1 (M+1).

Step 3: N-(3-(3,4-dihydroisoquinolin-2(1H)-yl)-2-hydroxypropyl)-3-(pyridin-2-yl)benzamide

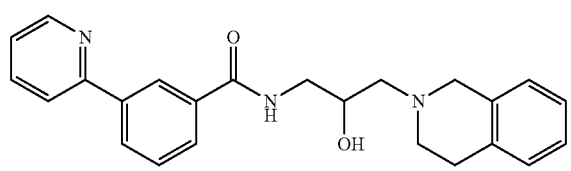 [SMILES: O=C(NCC(O)CN1CCc2ccccc2C1)c1cccc(-c2ccccn2)c1]

To a solution of 3-(pyridin-2-yl)benzoic acid (200 mg, 1.00 mmol) in DCM (6 mL) was added EDCI (383 mg, 2.00 mmol), HOBt (270 mg, 2 mmol), Et$_3$N (303 mg, 3 mmol) and 1-amino-3-(3,4-dihydroisoquinolin-2(1H)-yl)propan-2- ol (206 mg, 1.00 mmol). The mixture was stirred at room temperature for 16 h. The reaction mixture was diluted with water (10 mL) and extracted with DCM (3×10 mL). The combined organic layers were then dried and concentrated. The residue was purified by Prep-HPLC to give the product as the formate salt (70 mg, Yield 18%). $^1$H NMR (400 MHz, MeOD): 8.64 (d, J=4.8 Hz, 1H), 8.46 (s, 1H), 8.13 (d, J=8.4 Hz, 1H), 7.93-7.90 (m. 3H), 7.60 (dd, J=8.0 Hz, 1H), 7.40-7.37 (m, 1H), 7.26-7.14 (m, 4H), 4.44 (s, 2H), 4.38 (br. s, 1H), 3.57-3.56 (m, 4H), 3.36-3.16 (m, 4H). LCMS (m/z): 388.2 (M+1).
Compound 2

N-(3-(3,4-dihydroisoquinolin-2(1H)-yl)-2-hydroxypropyl)-3-(1-methyl-1H-pyrazol-5-yl)benzamide

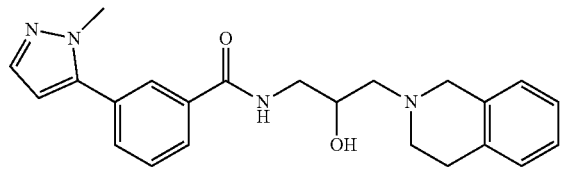 [SMILES: Cn1nccc1-c1cccc(C(=O)NCC(O)CN2CCc3ccccc3C2)c1]

Step 1: methyl 3-(1-methyl-1H-pyrazol-5-yl)benzoate

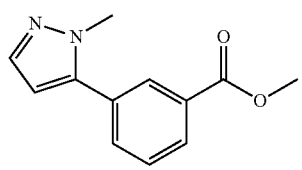 [SMILES: COC(=O)c1cccc(-c2ccnn2C)c1]

A mixture of (3-(methoxycarbonyl)phenyl)boronic acid (270 mg, 1.5 mmol), 5-bromo-1-methyl-1H-pyrazole (200 mg, 1.25 mmol), K$_2$CO$_3$ (518 mg, 3.75 mmol) and Pd(dppf)Cl$_2$ (10 mg) in a mixture solution of dioxane (8 mL) and H$_2$O (2 mL) was stirred at 120° C. for 30 min under microwave heating. The catalyst was filtered and the filtrate concentrated. The residue was then purified by column chromatography to give provide the desired product as a colorless oil (226 mg, Yield 60%). It was used directly in the next step. LCMS (m/z): 217.1.

Step 2: 3-(1-methyl-1H-pyrazol-5-yl)benzoic Acid

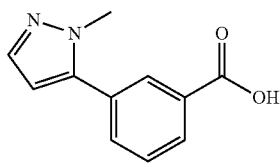

To a solution of methyl 3-(1-methyl-1H-pyrazol-5-yl)benzoate (200 mg, 0.93 mmol) in MeOH (3 mL) was added aqueous NaOH (1 mL, 0.4M). The mixture was stirred at room temperature for 2 h. The reaction solution was concentrated and the residue was dissolved in water and adjusted pH to 5~6 with 2N of HCl. The solution was extracted with EtOAc (2×20 mL). The combined organic layers were dried and concentrated to give the target crude product which was used directly in the next step. LCMS (m/z): 203.1 (M+1).

Step 3: N-(3-(3,4-dihydroisoquinolin-2(1H)-yl)-2-hydroxypropyl)-3-(1-methyl-1H-pyrazol-5-yl)benzamide

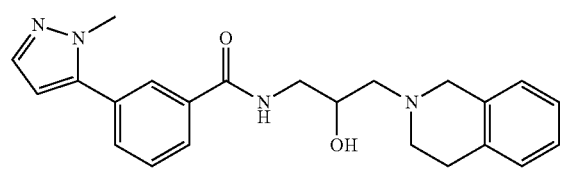 [SMILES: Cn1nccc1-c1cccc(C(=O)NCC(O)CN2CCc3ccccc3C2)c1]

To a solution of 3-(1-methyl-1H-pyrazol-5-yl)benzoic acid (130 mg, 0.64 mmol) in DCM (6 mL) was added EDCI (245 mg, 1.28 mmol), HOBt (173 mg, 1.28 mmol), Et$_3$N (195 mg, 1.93 mmol) and 1-amino-3-(3,4-dihydroisoquinolin-2(1H)-yl)propan-2-ol (132 mg, 0.64 mmol). The mixture was stirred at room temperature for 16 h until completion of the reaction was indicated by which TLC. The reaction solution was then diluted with water (10 mL) and extracted with DCM (2×10 mL) then the combined organic layers were concentrated. The residue was purified by prep-HPLC to give the desired product (60 mg, Yield 25%). $^1$H NMR (400 MHz, MeOD): 7.55 (s, 1H), 7.52 (s, 1H), 7.24-7.15 (m, 3H), 6.85-6.73 (m, 4H), 6.03 (s, 1H), 4.22 (br. s, 1H), 4.03-3.99 (m, 1H), 3.45 (s, 3H), 3.17-2.73 (m, 7H). LCMS (m/z): 391.2 (M+1).
Compound 3

(S)—N-(3-(3,4-dihydroisoquinolin-2(1H)-yl)-2-hydroxypropyl)benzamide

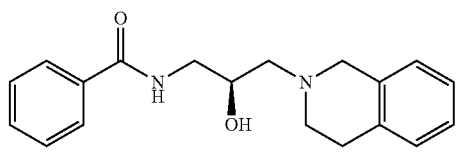 [SMILES: O=C(NC[C@H](O)CN1CCc2ccccc2C1)c1ccccc1]

Step 1: (R)-2-(oxiran-2-ylmethyl)-1,2,3,4-tetrahydroisoquinoline

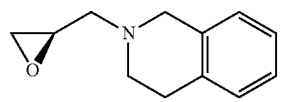

To a solution of 1,2,3,4-tetrahydroisoquinoline (1 g, 7.52 mmol) in MeOH (40 mL) was added K$_2$CO$_3$ (5.19 g, 37.6 mmol) under 0° C. After stirring for 30 minutes, (R)-2-(chloromethyl) oxirane (0.692 g, 7.52 mmol) was added the reaction. The mixture was then stirred at 0° C. overnight before filtration and washing of the solid by with MeOH. The solution was concentrated and the residue purified by column separation to give the title compound as a colorless oil (70% purity). This crude was used directly in the next step. LCMS (m/z): 190.1 (M+1).

Step 2: (S)-1-amino-3-(3,4-dihydroisoquinolin-2 (1H)-yl)propan-2-ol

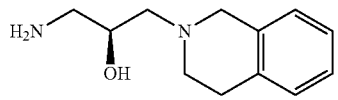 [SMILES: NC[C@H](O)CN1CCc2ccccc2C1]

To a solution of (R)-2-(oxiran-2-ylmethyl)-1,2,3,4-tetrahydroisoquinoline (200 mg, 5.2 mmol) in EtOH (20 mL) was added NH₄OH (600 mg, 35.2 mmol) at −78° C. The reaction mixture was then warmed and heated at 100° C. for 3 h in a seal tube. The reaction mixture was concentrated and the crude product was used in next step without further purification. LCMS (m/z): 207.1 (M+1).

Step 3: (S)—N-(3-(3,4-dihydroisoquinolin-2(1H)-yl)-2-hydroxypropyl)benzamide

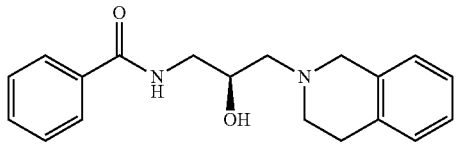 [SMILES: O=C(NC[C@H](O)CN1CCc2ccccc2C1)c1ccccc1]

A solution of (S)-1-amino-3-(3,4-dihydroisoquinolin-2 (1H)-yl)propan-2-ol (200 mg, 0.97 mmol), benzoic acid (122.5 mg, 1.07 mmol), HATU (387.6 mg, 1.02 mmol) and TEA (196.1 mg, 1.94 mmol) in DCM (20 mL) was stirred at room temperature for 2 h until completion of the reaction. The reaction mixture was then diluted with water and extracted with DCM (20 ml×2). The combined organic layers were dried and concentrated with the residue purified by pre-HPLC and SFC separation to give the desired compound (55 mg, Yield 18%). ¹H NMR (400 MHz, MeOD): 7.66 (d, J=8.0 Hz, 2H), 7.36-7.34 (m, 1H), 7.26 (d, J=7.6 Hz, 2H), 6.99-6.89 (m, 4H), 4.01-3.96 (m, 1H), 3.61 (s, 2H), 3.43-3.37 (m, 2H), 2.77-2.72 (m, 4H), 2.56-2.53 (m, 2H). LCMS (m/z): 311.1 (M+1).

Compound 8

N-(3-(3,4-dihydroisoquinolin-2(1H)-yl)-2-hydroxypropyl)-3-(pyridin-3-yl)benzamide

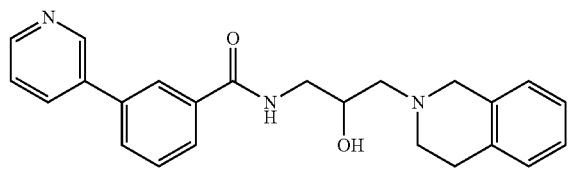 [SMILES: O=C(NCC(O)CN1CCc2ccccc2C1)c1cccc(-c2cccnc2)c1]

Step 1: methyl 3-(pyridin-3-yl)benzoate

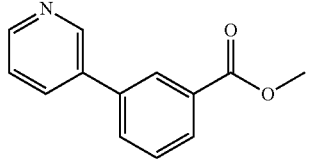 [SMILES: COC(=O)c1cccc(-c2cccnc2)c1]

A mixture of (3-(methoxycarbonyl)phenyl)boronic acid (600 mg, 3.33 mmol), 3-bromopyridine (479 mg, 3.0 mmol), K₂CO₃ (1.2 g, 9.0 mmol) and Pd(dppf)Cl₂ (50 mg) in a solution of dioxane (10 mL) and H₂O (2.5 mL) was stirred at 120° C. for 30 minutes with microwave heating under N₂. The catalyst was then filtered and the filtrate concentrated. The residue was then purified by column chromatography to give the desired product and used directly in the next step. (630 mg Yield 90%).

Step 2: 3-(pyridin-3-yl)benzoic Acid

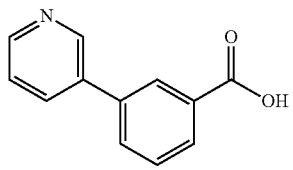 [SMILES: O=C(O)c1cccc(-c2cccnc2)c1]

To a solution of methyl 3-(pyridin-3-yl)benzoate (450 mg, 2.1 mmol) in MeOH (5 mL) was added aqueous of NaOH (1.5 mL, 0.4M). The mixture was stirred at room temperature for 2 h then reaction solution was concentrated and the resulting residue dissolved in water and adjusted pH to 5-6 with 2N HCl. Extracted was then performed using EtOAc with the organic layer dried and concentrated to give the target product which was used without further purification (600 mg, Yield 90%). LCMS (m/z): 200.1 (M+1).

Step 3: N-(3-(3,4-dihydroisoquinolin-2(1H)-yl)-2-hydroxypropyl)-3-(pyridin-3-yl)benzamide

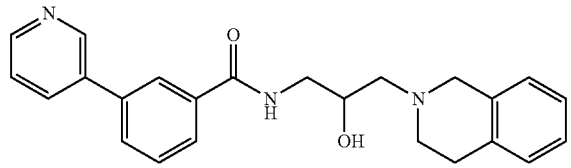 [SMILES: O=C(NCC(O)CN1CCc2ccccc2C1)c1cccc(-c2cccnc2)c1]

To a solution of 3-(pyridin-3-yl)benzoic acid (150 mg, 0.75 mmol) in DCM (6 mL) was added EDCI (215 mg, 1.10 mmol), HOBt (148 mg, 1.10 mmol), Et₃N (228 mg, 2.25 mmol) and 1-amino-3-(3,4-dihydroisoquinolin-2(1H)-yl) propan-2-ol (185 mg, 0.90 mmol). The mixture was stirred at room temperature for 16 h. The reaction solution was then washed with water and extracted with DCM. The organic layer was concentrated, dried and the residue purified by prep-HPLC to give the desired title product (110 mg, Yield 34%). ¹H NMR (400 MHz, MeOD) δ 8.80 (d, J=2.0 Hz, 1H), 8.52 (dd, J=4.8 Hz, J₂=3.6 Hz, 1H), 8.10 (s, 1H), 8.09 (dd, J=8.8 Hz, J$_2$=1.6 Hz, 1H), 7.83 (d, J=7.6 Hz, 1H), 7.77 (d, J=7.6 Hz, 1H), 7.51-7.46 (m, 2H), 7.06-6.95 (m, 4H), 4.15-4.10 (m, 1H), 3.69 (s, 2H), 3.60-3.47 (m, 2H), 2.85-2.79 (m, 4H), 2.69-2.59 (m, 2H). LCMS (m/z): 388.2 (M+1).

Compound 9

N-(3-(3,4-dihydroisoquinolin-2(1H)-yl)-2-hydroxypropyl)-3-(pyridin-4-yl)benzamide

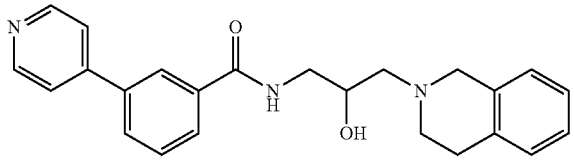 [SMILES: O=C(NCC(O)CN1CCc2ccccc2C1)c1cccc(-c2ccncc2)c1]

Step 1: methyl 3-(pyridin-4-yl)benzoate

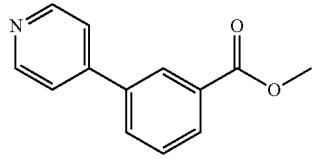 [SMILES: COC(=O)c1cccc(-c2ccncc2)c1]

A mixture of (3-(methoxycarbonyl)phenyl)boronic acid (600 mg, 3.33 mmol), 4-bromopyridine (583.5 mg, 3.0 mmol), K$_2$CO$_3$ (1.2 g, 9.0 mmol) and Pd(dppf)Cl$_2$ (50 mg) in a solution of dioxane (10 mL) and H$_2$O (2.5 mL) was stirred at 120° C. for 30 min with microwave heating. The catalyst was filtered and the filtrate concentrated. The residue was then purified by column chromatography to give the title product (630 mg Yield 90%).

Step 2: 3-(pyridin-4-yl)benzoic Acid

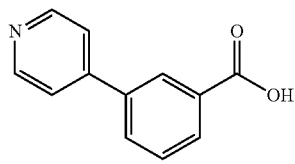 [SMILES: O=C(O)c1cccc(-c2ccncc2)c1]

To a solution of methyl 3-(pyridin-4-yl)benzoate (450 mg, 2.1 mmol) in MeOH (5 mL) was added an aqueous solution of NaOH (1.5 mL, 0.4M). The mixture was stirred at room temperature for 2 h. The reaction solution was then concentrated, the residue was next dissolved in water and adjusted pH to 5~6 with the 2N HCl. After extraction with EtOAc, the organic layers were dried and concentrated to give the product desired (600 mg, Yield 90%). LCMS (m/z): 200.1 (M+1).

Step 3: N-(3-(3,4-dihydroisoquinolin-2(1H)-yl)-2-hydroxypropyl)-3-(pyridin-4-yl)benzamide

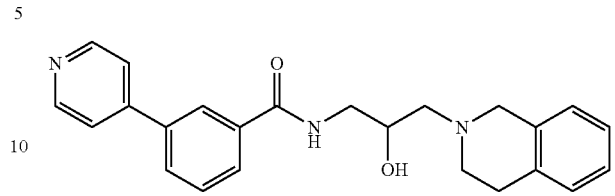

To a solution of 3-(pyridin-4-yl)benzoic acid (300 mg, 1.5 mmol) in DCM (6 mL) was added EDCI (430 mg, 2.20 mmol), HOBt (296 mg, 2.20 mmol), Et$_3$N (556 mg, 4.50 mmol) and 1-amino-3-(3,4-dihydroisoquinolin-2(1H)-yl)propan-2-ol (370 mg, 1.80 mmol). The mixture was stirred at room temperature for 16 h, then the reaction mixture was washed with water and extracted with DCM. The organic layer was then dried, concentrated and the residue purified by prep-HPLC to give the title product (230 mg, Yield 40%). $^1$H NMR (400 MHz, MeOD) δ 8.54 (d, J=4.0 Hz, 2H), 8.16 (s, 1H), 7.85-7.80 (m, 2H), 7.64 (dd J=4.0 Hz, 2H), 7.48 (dd, J=7.6 Hz, 1H), 7.03-6.95 (m, 4H), 4.13 (br. s, 1H), 3.66 (s, 2H), 3.60-3.48 (m, 2H), 2.80-2.77 (m, 4H), 2.63-2.59 (m, 2H). LCMS (m/z): 388.2 (M+1).

Compound 11

(R)-phenyl (3-(3,4-dihydroisoquinolin-2(1H)-yl)-2-hydroxypropyl)carbamate

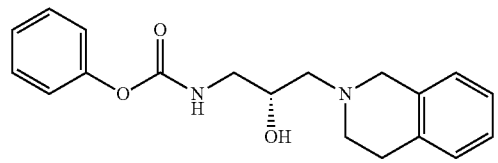 [SMILES: O=C(NC[C@@H](O)CN1CCc2ccccc2C1)Oc1ccccc1]

Step 1: (S)-2-(oxiran-2-ylmethyl)-1,2,3,4-tetrahydroisoquinoline

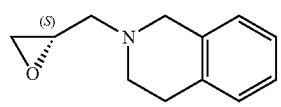

To a solution of 1,2,3,4-tetrahydroisoquinoline (5 g, 7.52 mmol) in THF (100 mL) was added KF (8.57 g, 150.4 mmol) at 0° C. (R)-oxiran-2-ylmethyl 3-nitrobenzenesulfonate (10.7 g, 41.4 mmol) was added to the reaction in 1 h. The solution was stirred at room temperature overnight. The solid was removed by filtration and washed with THF. The solution was then concentrated and the residue used for next step without further purification (11.3 g Yield 80%). LCMS (m/z): 190.1 (M+1).

165

Step 2: (R)-1-amino-3-(3,4-dihydroisoquinolin-2 (1H)-yl)propan-2-ol

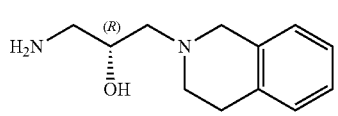

To a solution of (S)-2-(oxiran-2-ylmethyl)-1,2,3,4-tetrahydroisoquinoline (2.2 g, 0.012 mol) in EtOH (30 mL), NH₃ was bubbled to the solution under −78° C. The reaction mixture was then sealed and heated at 80° C. for 3 h. After LCMS indicated completion of the reaction, the mixture was concentrated and the crude product was used in next step without further purification (2.2 g, Yield 90%). LCMS (m/z): 207.1 (M+1).

Step 3: (R)-phenyl (3-(3,4-dihydroisoquinolin-2 (1H)-yl)-2-hydroxypropyl)carbamate

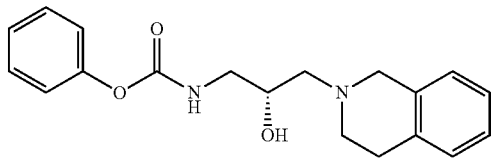 [SMILES: O=C(NC[C@@H](O)CN1CCc2ccccc2C1)Oc1ccccc1]

To the stirring solution of (R)-1-amino-3-(3,4-dihydroisoquinolin-2(1H)-yl)propan-2-ol (200 mg, 0.97 mmol) in 15 mL dry DCM was added TEA (1 mL) and the solution was cooled to 0° C. Phenyl carbonochloridate (151.3 mg, 1.02 mmol) in DCM (10 mL) was then added drop wise to the reaction over 20 minutes and the solution was then stirred at room temperature overnight. The solution was then diluted with water, extracted with DCM, the organic layer was concentrated, purified by pre-HPLC to give the product as formate salt (125 mg, Yield 40%). ¹H NMR (400 MHz, MeOD) δ 7.35 (dd, J=7.6 Hz, 2H), 7.31-7.18 (m, 5H), 7.08 (d, J=7.6 Hz, 2H), 4.33 (s, 2H), 4.22-4.19 (m, 1H), 3.48 (t, J=6.0 Hz, 2H), 3.27-3.10 (m, 6H). LCMS (m/z): 327.2 (M+1).

Compound 12

N-(3-(3,4-dihydroisoquinolin-2(1H)-yl)-2-hydroxypropyl)-2-(pyridin-2-yl)benzamide

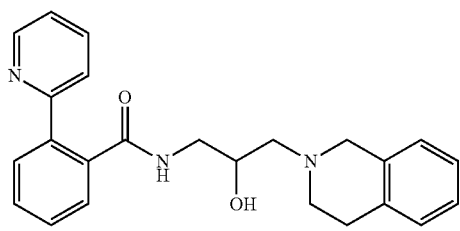 [SMILES: O=C(NCC(O)CN1CCc2ccccc2C1)c1ccccc1-c1ccccn1]

166

Step 1: 2-(pyridin-2-yl)benzoic Acid

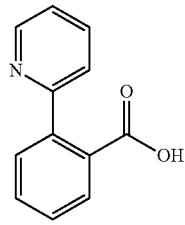

A mixture of 2-boronobenzoic acid (400 mg, 2.4 mmol), 2-bromopyridine (416 mg, 2.6 mmol), K₂CO₃ (994 mg, 7.2 mmol) and Pd(dppf)Cl₂ (20 mg) in dioxane (8 mL) and H₂O (2 mL) was stirred at 125° C. for 30 min. under microwave heating under N₂. The catalyst was filtered, and the filtrate was acidified with 2N HCl to pH 5~6. The solution was concentrated, and the residue was dissolved in MeOH and filtered. The filtrate was concentrated, and the residue was purified by prep-TLC to give the title compound (205 mg, Yield 42.9%). LCMS (m/z): 200.0 (M+1).

Step 2: N-(3-(3,4-dihydroisoquinolin-2(1H)-yl)-2-hydroxypropyl)-2-(pyridin-2-yl) benzamide

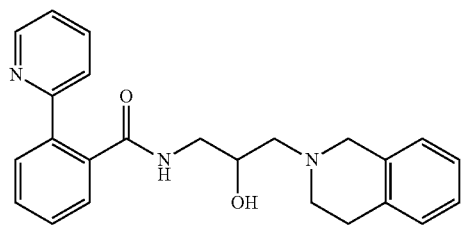 [SMILES: O=C(NCC(O)CN1CCc2ccccc2C1)c1ccccc1-c1ccccn1]

To a solution of 2-(pyridin-2-yl)benzoic acid (150 mg, 0.75 mmol) in DCM (6 mL) was added EDCI (215 mg, 1.1 mmol), HOBt (148 mg, 1.1 mmol), Et3N (228 mg, 2.25 mmol) and 1-amino-3-(3,4-dihydroisoquinolin-2(1H)-yl) propan-2-ol (185 mg, 0.9 mmol). The mixture was stirred at 25° C. for 16 h. The reaction solution was washed with water and extracted with DCM. The organic layer was then concentrated, and the residue was purified by prep-HPLC to give the title compound (80 mg, Yield 27.5%). ¹H NMR (CD₃OD, 400 MHz): δ 8.60-8.53 (m, 1H), 7.89-7.81 (m, 1H), 7.63-7.51 (m, 4H), 7.48-7.43 (m, 1H), 7.39-7.32 (m, 1H), 7.12-7.05 (m, 3H), 7.05-6.98 (m, 1H), 4.05-3.93 (m, 1H), 3.73-3.63 (s, 2H), 3.46-3.37 (m, 1H), 3.31-3.23 (m, 1H), 2.92-2.75 (m, 4H), 2.56 (s, 2H). LCMS (m/z): 388.2 (M+1).

Compound 13

N-(3-(3,4-dihydroisoquinolin-2(1H)-yl)-2-hydroxy-propyl)-4-(pyridin-2-yl)benzamide

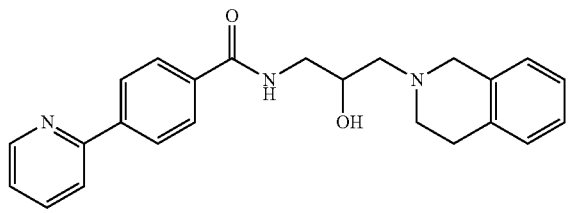 [SMILES: O=C(NCC(O)CN1CCc2ccccc2C1)c1ccc(-c2ccccn2)cc1]

Step 1: 4-(pyridin-2-yl)benzoic Acid

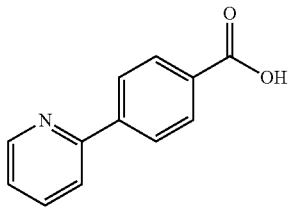 [SMILES: O=C(O)c1ccc(-c2ccccn2)cc1]

A mixture of 4-boronobenzoic acid (200 mg, 1.2 mmol), 2-bromopyridine (208 mg, 1.3 mmol), $K_2CO_3$ (497 mg, 3.6 mmol) and Pd(dppf)Cl$_2$ (10 mg) in dioxane (4 mL) and H$_2$O (1 mL) was stirred at 125° C. for 30 min with microwave heating under N$_2$. The catalyst was filtered, and the filtrate was acidified with 2N HCl to pH 5~6. The solution was concentrated, and the residue was dissolved in MeOH and filtered. The filtrate was concentrated, and the residue was purified by prep-TLC to give the title compound (100 mg, Yield 41.8%). LCMS (m/z): 200.1 (M+1).

Step 2: N-(3-(3,4-dihydroisoquinolin-2(1H)-yl)-2-hydroxypropyl)-4-(pyridin-2-yl)benzamide

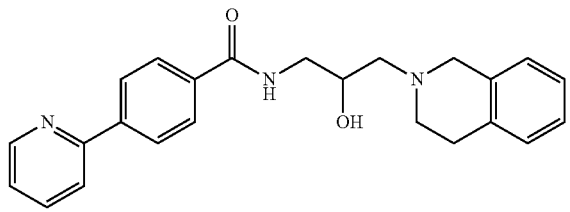 [SMILES: O=C(NCC(O)CN1CCc2ccccc2C1)c1ccc(-c2ccccn2)cc1]

To a solution of 4-(pyridin-2-yl)benzoic acid (100 mg, 0.5 mmol) in DCM (5 mL) was added EDCI (144 mg, 0.75 mmol), HOBt (101 mg, 0.75 mmol), Et$_3$N (152 mg, 1.5 mmol) and 1-amino-3-(3,4-dihydroisoquinolin-2(1H)-yl) propan-2-ol (103 mg, 0.5 mmol). The mixture was stirred at 25° C. for 16 h. The reaction solution was washed with water and extracted with DCM. The organic layer was concentrated, and the residue was purified by prep-HPLC to give the title compound (30 mg, Yield 15.5%). $^1$H NMR (CD$_3$OD, 400 MHz): δ 8.70-8.60 (m, 1H), 8.01-7.84 (m, 6H), 7.45-7.36 (m, 1H), 7.16-6.99 (m, 4H), 4.20-4.10 (m, 1H), 3.79 (s, 2H), 3.62-3.46 (m, 2H), 2.92 (s, 4H), 2.78-2.65 (m, 2H). LCMS (m/z): 388.2 (M+1).

Compound 14

N-(3-(3,4-dihydroisoquinolin-2(1H)-yl)-2-hydroxy-propyl)-3-morpholinobenzamide

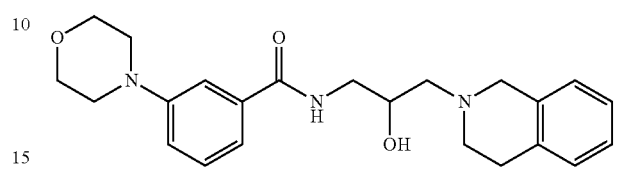

Step 1: 3-bromo-N-(3-(3,4-dihydroisoquinolin-2 (1H)-yl)-2-hydroxypropyl) benzamide

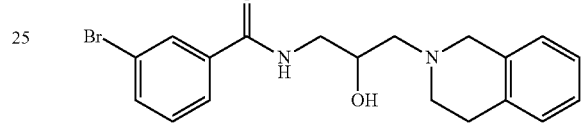

To a solution of 3-bromobenzoic acid (200 mg, 1.0 mmol) in DCM (8 mL) was added Et$_3$N (303 mg, 3.0 mmol), EDCI (383 mg, 2.0 mmol), HOBt (270 mg, 2.0 mmol) and 1-amino-3-(3,4-dihydroisoquinolin-2(1H)-yl)propan-2-ol (247 mg, 1.2 mmol). The mixture was stirred at 25° C. for 6 h. The mixture was treated with water and extracted with EA. The organic layer was washed with NaHCO$_3$, brine, dried over Na$_2$SO$_4$ and concentrated to give the title compound which was used in next step without further purification (300 mg, Yield 77%). LCMS (m/z): 390.1 (M+1).

Step 2: N-(3-(3,4-dihydroisoquinolin-2(1H)-yl)-2-hydroxypropyl)-3-morpholino benzamide

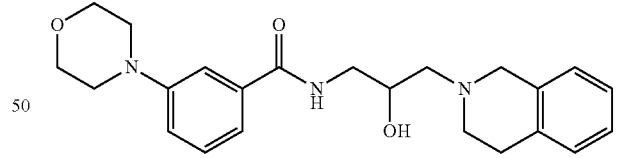

A mixture of 3-bromo-N-(3-(3,4-dihydroisoquinolin-2 (1H)-yl)-2-hydroxypropyl) benzamide (200 mg, 0.51 mmol), morpholine (44 mg, 0.51 mmol), Pd$_2$(dba)$_3$ (46 mg, 0.05 mmol), BINAP (62 mg, 0.1 mmol) and NaOtBu (73 mg, 0.77 mmol) in toluene (6 mL) was stirred at reflux for 16 h under N$_2$. The reaction solution was concentrated, and the residue was dissolved in EA and filtered. The filtrate was concentrated, and the residue was purified by prep-HPLC to give the title compound (15 mg, Yield 7.5%). $^1$H NMR (CD$_3$OD, 400 MHz): δ 8.48 (brs, 1H), 7.42 (s, 1H), 7.37-7.28 (m, 2H), 7.27-7.19 (m, 3H), 7.18-7.11 (m, 2H), 4.31-4.23 (m, 1H), 4.19 (s, 2H), 3.86 (dd, J=5.1, 4.8 Hz, 4H), 3.61-3.44 (m, 2H), 3.32-3.29 (m, 2H), 3.25-3.16 (m, 4H), 3.14-2.97 (m, 4H). LCMS (m/z): 396.2 (M+1).

Compound 15

N-(3-(3,4-dihydroisoquinolin-2(1H)-yl)-2-hydroxypropyl)-3-(((tetrahydro-2H-pyran-4-yl)amino)methyl)benzamide

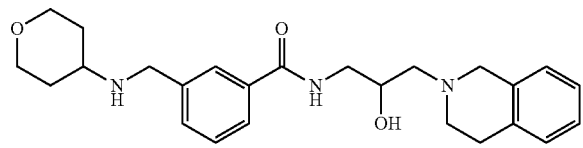 [SMILES: O=C(NCC(O)CN1CCc2ccccc2C1)c1cccc(CNC2CCOCC2)c1]

Step 1: methyl 3-(((tetrahydro-2H-pyran-4-yl)amino)methyl)benzoate

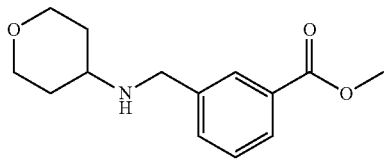 [SMILES: COC(=O)c1cccc(CNC2CCOCC2)c1]

To a solution of methyl 3-formylbenzoate (492 mg, 3.0 mmol) in MeOH (10 mL) was added tetrahydro-2H-pyran-4-amine (303 mg, 3.0 mmol) and AcOH (0.05 mL). The mixture was stirred at 25° C. for 2 h. NaBH$_3$CN (945 mg, 15.0 mmol) was added, and the resulting mixture was stirred at 25° C. for 16 h. The reaction solution was concentrated and the residue was dissolved in water and extracted with DCM. The organic layer was concentrated, and the residue was purified by prep-TLC to give the title product (500 mg, Yield 67%). LCMS (m/z): 250.1 (M+1).

Step 2: methyl 3-(((tert-butoxycarbonyl)(tetrahydro-2H-pyran-4-yl)amino)-methyl)benzoate

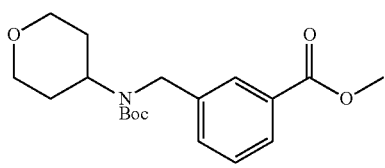 [SMILES: COC(=O)c1cccc(CN(C(=O)OC(C)(C)C)C2CCOCC2)c1]

To a solution of methyl 3-(((tetrahydro-2H-pyran-4-yl)amino)methyl)benzoate (400 mg, 1.6 mmol) in a mixture solution of THF (10 mL) and H$_2$O (1 mL) was added Boc$_2$O (418 mg, 1.9 mmol) and Et$_3$N (243 mg, 2.4 mmol). The mixture was stirred at 25° C. for 16 h. The reaction solution was concentrated to remove THF, and the residue was dissolved in water and extracted with EA. The organic layer was concentrated, and the residue was purified by column chromatography to give the title product (550 mg, 98%). LCMS (m/z): 350.1 (M+1).

Step 3: 3-(((tert-butoxycarbonyl)(tetrahydro-2H-pyran-4-yl)amino)methyl) benzoic Acid

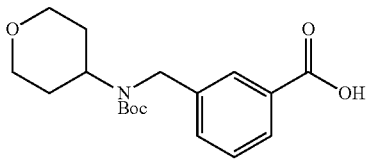 [SMILES: CC(C)(C)OC(=O)N(Cc1cccc(C(=O)O)c1)C1CCOCC1]

To a solution of methyl 3-(((tert-butoxycarbonyl)(tetrahydro-2H-pyran-4-yl)amino)methyl)benzoate (550 mg, 1.57 mmol) in MeOH (5 mL) was added aqueous of NaOH (2.0 mL, 40% w/w). The mixture was stirred at 25° C. for 4 h. The reaction solution was concentrated, and the residue was dissolved in water and adjusted pH to 5~6 with 2N of HCl and extracted with EA. The organic layer was concentrated to give the desired product (300 mg, Yield 57%). LCMS (m/z): 336.1 (M+1).

Step 4: tert-butyl 3-((3-(3,4-dihydroisoquinolin-2(1H)-yl)-2-hydroxypropyl) carbamoyl)benzyl(tetrahydro-2H-pyran-4-yl)carbamate

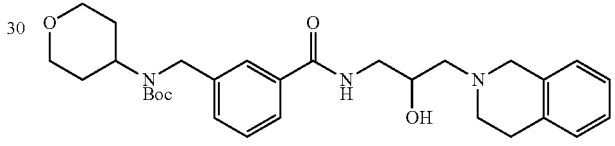

To a solution of 3-(((tert-butoxycarbonyl)(tetrahydro-2H-pyran-4-yl)amino)methyl)benzoic acid (300 mg, 0.89 mmol) in DCM (8 mL) was added EDCI (257 mg, 1.34 mmol), HOBt (181 mg, 1.34 mmol), Et$_3$N (270 mg, 2.67 mmol) and 1-amino-3-(3,4-dihydroisoquinolin-2(1H)-yl)propan-2-ol (183 mg, 0.89 mmol). The mixture was stirred at 25° C. for 16 h. The reaction solution was washed with water and extracted with DCM. The organic layer was concentrated to give the title product (350 mg, Yield 65%). LCMS (m/z): 524.3 (M+1).

Step 5: N-(3-(3,4-dihydroisoquinolin-2(1H)-yl)-2-hydroxypropyl)-3-(((tetrahydro-2H-pyran-4-yl)amino)methyl)benzamide

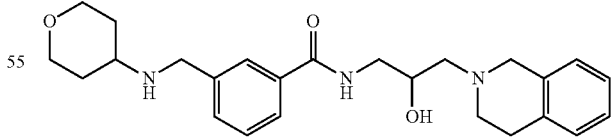

To a solution of tert-butyl 3-((3-(3,4-dihydroisoquinolin-2(1H)-yl)-2-hydroxypropyl)carbamoyl)benzyl(tetrahydro-2H-pyran-4-yl)carbamate (450 mg, crude) in DCM (6 mL) was added TFA (6 mL). The mixture was stirred at 25° C. for 16 h. The reaction solution was concentrated, and the residue was purified by prep-HPLC to give the title product (200 mg, 54.9%). $^1$H NMR (CD$_3$OD, 400 MHz): δ 8.08 (s, 1H), 8.00-7.89 (m, 1H), 7.81-7.68 (m, 1H), 7.58 (s, 1H), 7.39-

7.15 (m, 4H), 4.75-4.47 (m, 2H), 4.46-4.39 (m, 1H), 4.34 (s, 2H), 4.05 (dd, J=11.6, 3.6 Hz, 2H), 3.98-3.70 (brs, 1H), 3.62-3.55 (m, 2H), 3.55-3.45 (m, 4H), 3.45-3.32 (m, 2H), 3.32-3.06 (m, 2H), 2.22-2.07 (m, 2H), 1.89-1.72 (m, 2H). LCMS (m/z): 424.2 (M+1).

Compound 16

N-(3-(3,4-dihydroisoquinolin-2(1H)-yl)-2-hydroxypropyl)-3-((tetrahydro-2H-pyran-4-yl)amino)benzamide

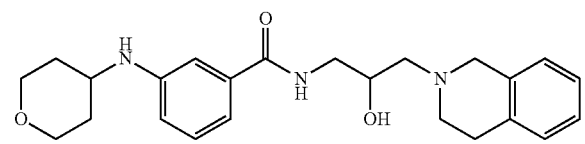 [SMILES: O=C(NCC(O)CN1CCc2ccccc2C1)c1cccc(NC2CCOCC2)c1]

Step 1: 3-((tert-butoxycarbonyl)amino)benzoic Acid

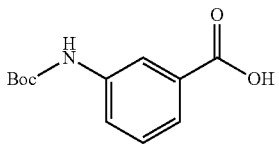 [SMILES: CC(C)(C)OC(=O)Nc1cccc(C(=O)O)c1]

To a solution of 3-aminobenzoic acid (1.37 g, 10 mmol) in a mixture solution of THF (20 mL) and $H_2O$ (2 mL) was added $Boc_2O$ (2.18 g, 10 mmol) and $Et_3N$ (1.52 g, 15 mmol). The mixture was stirred at 25° C. for 16 h. The reaction solution was concentrated and the residue was dissolved in water and extracted with EA. The organic layer was concentrated to give the title product (2.3 g, Yield 97%). LCMS (m/z): 260.0 (M+23).

Step 2: tert-butyl (3-((3-(3,4-dihydroisoquinolin-2(1H)-yl)-2-hydroxypropyl) carbamoyl)phenyl)carbamate

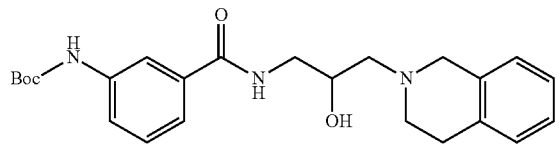 [SMILES: CC(C)(C)OC(=O)Nc1cccc(C(=O)NCC(O)CN2CCc3ccccc3C2)c1]

To a solution of 3-((tert-butoxycarbonyl)amino)benzoic acid (2.5 g, 10.5 mmol) in DCM (25 mL) was added EDCI (3.0 g, 15.7 mmol), HOBt (2.1 g, 15.7 mmol), $Et_3N$ (2.1 g, 21 mmol) and 1-amino-3-(3,4-dihydroisoquinolin-2(1H)-yl)propan-2-ol (2.2 g, 10.5 mmol). The mixture was stirred at 25° C. for 16 h. The reaction solution was washed with water, extracted with DCM and the organic layer was concentrated, and the residue was purified by column chromatography to give the desired product (3.2 g, Yield 71%). LCMS (m/z): 426.3 (M+1).

Step 3: 3-amino-N-(3-(3,4-dihydroisoquinolin-2(1H)-yl)-2-hydroxypropyl) benzamide

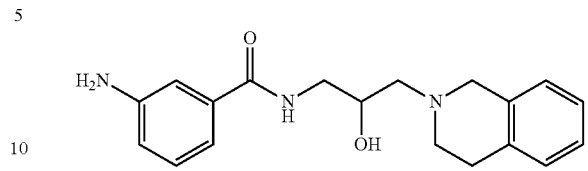

To a solution of tert-butyl (3-((3-(3,4-dihydroisoquinolin-2(1H)-yl)-2-hydroxypropyl)carbamoyl)phenyl)carbamate (500 mg, 1.18 mmol) in DCM (5 mL) was added TFA (5 mL). The mixture was stirred at 25° C. for 16 h. The reaction solution was concentrated, and the residue was dissolved in water, pH was adjusted to 7-7.5 with saturated aqueous $NaHCO_3$ and extracted with EA. The organic layer was concentrated to give the title product (360 mg, Yield 94%). The crude product was used in next step without further purification. LCMS (m/z): 326.2 (M+1).

Step 4: N-(3-(3,4-dihydroisoquinolin-2(1H)-yl)-2-hydroxypropyl)-3-((tetrahydro-2H-pyran-4-yl)amino)benzamide

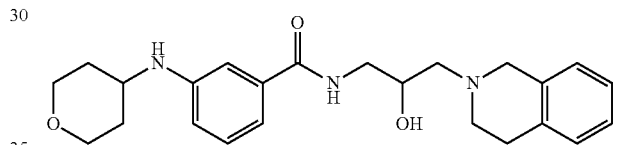

To a solution of 3-amino-N-(3-(3,4-dihydroisoquinolin-2(1H)-yl)-2-hydroxypropyl)benzamide (325 mg, 1.0 mmol) in MeOH (10 mL) was added dihydro-2H-pyran-4(3H)-one (88 mg, 1.0 mmol) and AcOH (0.05 mL). The mixture was stirred at 25° C. for 2 h. $NaBH_3CN$ (630 mg, 10.0 mmol) was added, and the resulting mixture was stirred at 25° C. for 16 h. The reaction solution was concentrated, and the residue was dissolved in water, extracted with EA. The organic layer was concentrated, and the residue was purified by prep-HPLC to give the title compound (200 mg, Yield 48.9%). $^1$H NMR (CD$_3$OD, 400 MHz): δ 8.44 (brs, 1H), 7.32-7.20 (m, 3H), 7.20-7.13 (m, 2H), 7.13-7.09 (m, 1H), 7.08-7.00 (m, 1H), 6.86-6.77 (m, 1H), 4.39 (s, 2H), 4.35-4.25 (m, 1H), 4.03-3.89 (m, 2H), 3.63-3.40 (m, 7H), 3.31-3.07 (m, 4H), 2.06-1.92 (m, 2H), 1.55-1.40 (m, 2H). LCMS (m/z): 410.2 (M+1).

Compound 17

N-(3-(3,4-dihydroisoquinolin-2(1H)-yl)-2-hydroxypropyl)picolinamide

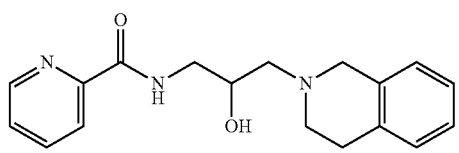 [SMILES: O=C(NCC(O)CN1CCc2ccccc2C1)c1ccccn1]

Step 1: N-(3-(3,4-dihydroisoquinolin-2(1H)-yl)-2-hydroxypropyl)picolinamide

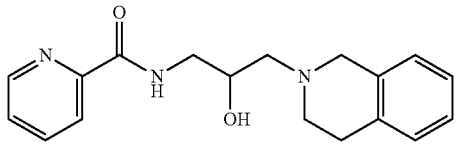

To a solution of picolinic acid (100 mg, 0.81 mmol) in DCM (10 mL), was added EDCI (187 mg, 0.97 mmol) and HOBT (132 mg, 0.98 mmol), which was stirred at 25° C. for 0.5 h before 1-amino-3-(3,4-dihydroisoquinolin-2(1H)-yl)propan-2-ol (167 mg, 0.81 mmol) was added and the resulting mixture was stirred at 25° C. for 2 h. The solution was concentrated in vacuo and the residue was purified by prep-HPLC to provide the title compound (68 mg, Yield 26.9%). $^1$H NMR (CD$_3$OD, 400 MHz): δ 8.61 (d, J=3.9 Hz, 1H), 8.49 (brs, 1H), 8.10 (d, J=7.8 Hz, 1H), 8.01-7.92 (m, 1H), 7.56 (dd, J=5.1, 6.8 Hz, 1H), 7.31-7.20 (m, 3H), 7.19-7.13 (m, 1H), 4.44-4.27 (m, 3H), 3.66-3.47 (m, 4H), 3.31-3.12 (m, 4H). LCMS (m/z): 312.1 (M+1).
Compound 21

N-(3-(3,4-dihydroisoquinolin-2(1H)-yl)-2-hydroxypropyl)-4-sulfamoylbenzamide

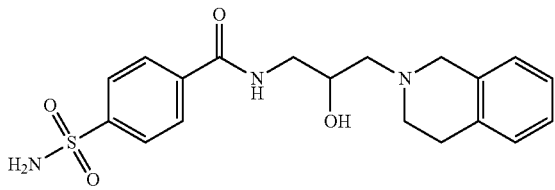 [SMILES: NS(=O)(=O)c1ccc(C(=O)NCC(O)CN2CCc3ccccc3C2)cc1]

Step 1: N-(3-(3,4-dihydroisoquinolin-2(1H)-yl)-2-hydroxypropyl)-4-sulfamoylbenzamide

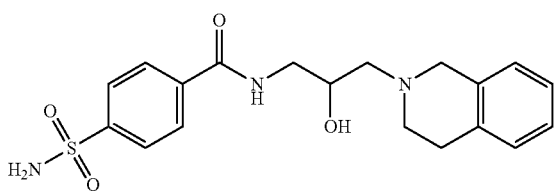 [SMILES: NS(=O)(=O)c1ccc(C(=O)NCC(O)CN2CCc3ccccc3C2)cc1]

A solution of 4-sulfamoylbenzoic acid (88.4 mg, 0.44 mmol), HATU (182.4 mg, 0.48 mmol) and TEA (48.48 mg, 0.48 mmol) in DCM (10 mL) was stirred at 22° C. for 10 min. 1-amino-3-(3,4-dihydroisoquinolin-2(1H)-yl)propan-2-ol (100 mg, 0.48 mmol) was then added and the solution was stirred at 22° C. for another 3 h. The reaction mixture was diluted with water and extracted with DCM. The organic layers were combined, dried over anhydrous Na$_2$SO$_4$, filtered and concentrated. The residue was purified by prep-HPLC to give the title compound (49.5 mg, Yield 29%). $^1$H NMR (CD$_3$OD, 400 MHz): δ 7.92 (s, 4H), 7.16-7.09 (m, 3H), 7.05-7.02 (m, 1H), 4.14-4.12 (m, 1H), 3.77 (s, 2H), 3.58-3.39 (m, 2H), 2.94-2.91 (m, 2H), 2.90-2.86 (m, 2H), 2.75-2.66 (m, 2H). LCMS (m/z): 390.1 (M+1).
Compound 23

4-acetamido-N-(3-(3,4-dihydroisoquinolin-2(1H)-yl)-2-hydroxypropyl)benzamide

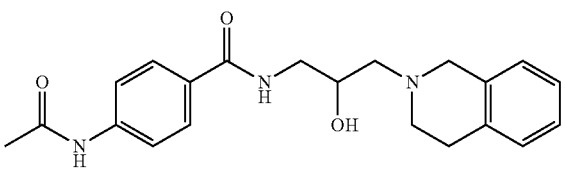 [SMILES: CC(=O)Nc1ccc(C(=O)NCC(O)CN2CCc3ccccc3C2)cc1]

Step 1: 4-acetamido-N-(3-(3,4-dihydroisoquinolin-2(1H)-yl)-2-hydroxypropyl)benzamide

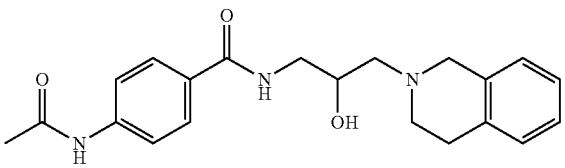 [SMILES: CC(=O)Nc1ccc(C(=O)NCC(O)CN2CCc3ccccc3C2)cc1]

A solution of 4-acetamidobenzoic acid (100 mg, 0.56 mmol), HATU (234 mg, 0.62 mmol) and TEA (63 mg, 0.62 mmol) in DCM (10 mL) was stirred at 22° C. for 10 min. 1-amino-3-(3,4-dihydroisoquinolin-2(1H)-yl)propan-2-ol (116 mg, 0.56 mmol) was then added and the solution was stirred at 22° C. for another 3 h. The reaction mixture was then diluted with water and extracted with DCM. The organic layers were combined and dried over anhydrous Na$_2$SO$_4$, filtered and concentrated and the residue was purified by prep-HPLC to give the title compound (48.5 mg, Yield 24%). $^1$H NMR (CD$_3$OD, 400 MHz): δ 7.77-7.72 (m, 2H), 7.63-7.57 (m, 2H), 7.17-7.08 (m, 3H), 7.04 (d, J=7.0 Hz, 1H), 4.12 (t, J=6.0 Hz, 1H), 3.75 (s, 2H), 3.58-3.46 (m, 2H), 2.92-2.85 (m, 4H), 2.74-2.63 (m, 2H), 2.16 (s, 3H). LCMS (m/z): 368.1 (M+1).
Compound 28

N-(3-(3,4-dihydroisoquinolin-2(1H)-yl)-2-hydroxypropyl)-3-(2-(dimethylamino)ethoxy)benzamide

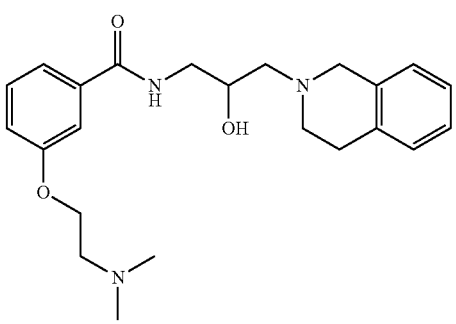 [SMILES: CN(C)CCOc1cccc(C(=O)NCC(O)CN2CCc3ccccc3C2)c1]

Step 1: methyl 3-(2-(dimethylamino)ethoxy)benzoate

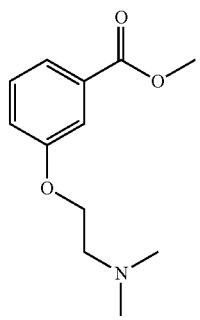 [SMILES: COC(=O)c1cccc(OCCN(C)C)c1]

To a stirred mixture of methyl 3-hydroxybenzoate (200 mg, 1.32 mmol), and $K_2CO_3$ (169 mg, 1.58 mmol) in MeCN (50 mL) was added 2-chloro-N,N-dimethylethanamine (137 mg, 1.58 mmol). The mixture was stirred at 60° C. for 16 h. The reaction mixture was filtered and the filtrate was concentrated to give the title compound that was used without further purification (300 mg, Yield 98%). $^1$H NMR (CDCl$_3$, 400 MHz): δ 7.61-7.53 (m, 1H), 7.53-7.47 (m, 1H), 7.26-7.23 (m, 1H), 7.06-7.04 (m, 1H), 4.05 (t, J=5.6 Hz, 2H), 3.84 (s, 3H), 2.69 (t, J=5.6 Hz, 2H), 2.28 (s, 6H). LCMS (m/z): 224.2 (M+1).

Step 2: N-(3-(3,4-dihydroisoquinolin-2(1H)-yl)-2-hydroxypropyl)-3-(2-(dimethylamino)ethoxy)benzamide

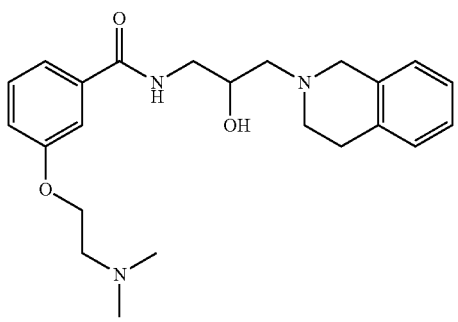 [SMILES: CN(C)CCOc1cccc(C(=O)NCC(O)CN2CCc3ccccc3C2)c1]

A mixture of crude methyl 3-(2-(dimethylamino)ethoxy)benzoate (300 mg, 1.34 mmol) and 1-amino-3-(3,4-dihydroisoquinolin-2(1H)-yl)propan-2-ol (332 mg, 1.61 mmol) in EtOH (2 mL) was heated at 120° C. in a microwave reactor for 3 h. After evaporation of the solvent, the residue was purified by prep-HPLC to give the title compound (34 mg, Yield 6.4%). $^1$H NMR (CD$_3$OD, 400 MHz): δ 7.43-7.42 (m, 1H), 7.34-7.29 (m, 2H), 7.12-7.10 (m, 4H), 7.09-7.03 (m, 1H), 4.20-4.10 (m, 3H), 3.75 (brs, 2H), 3.59-3.42 (m, 2H), 2.95-2.85 (m, 4H), 2.82-2.77 (m, 2H), 2.72-2.65 (m, 2H), 2.37 (s, 6H). LCMS (m/z): 398.1 (M+1).

Compound 30

N-(3-(3,4-dihydroisoquinolin-2(1H)-yl)-2-hydroxypropyl)-3-((4-methylpiperazin-1-yl)methyl)benzamide

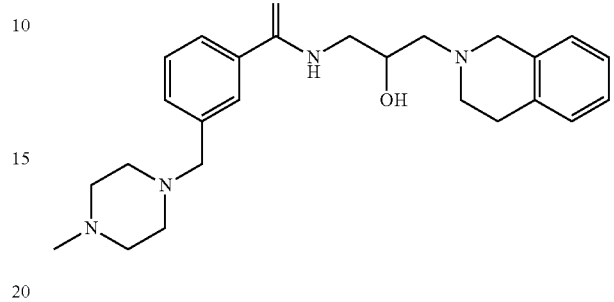

Step 1: 3-((4-(tert-butoxycarbonyl)piperazin-1-yl)methyl)benzoic Acid

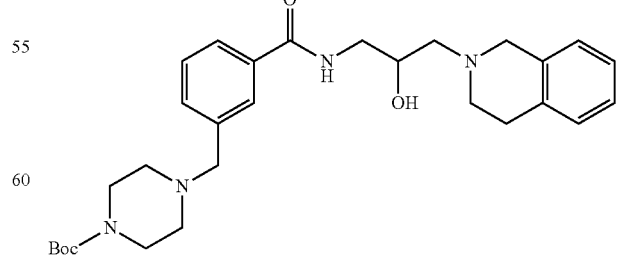

The solution of 3-formylbenzoic acid (300 mg, 1.83 mmol) and tert-butyl piperazine-1-carboxylate (340 mg, 1.83 mmol) in MeOH (10 mL) was stirred at 27° C. for 1 h. Then NaBH$_3$CN (138 mg, 2.19 mmol) was added to the solution and stirred at 27° C. for 6 h. The solution was concentrated and the residue was purified by column to give the title product (320 mg, Yield 50%). LCMS (m/z): 321.2 (M+1).

Step 2: tert-butyl 4-(3-((3-(3,4-dihydroisoquinolin-2(1H)-yl)-2-hydroxypropyl) carbamoyl)benzyl)piperazine-1-carboxylate The solution of 3-((4-(tert-butoxycarbonyl)piperazin-1-yl)methyl)benzoic acid (100 mg, 0.31 mmol) and HATU (119 mg, 0.31 mmol) in DCM (10 mL) was stirred at 28° C.

for 30 min. Then 1-amino-3-(3,4-dihydroisoquinolin-2(1H)-yl)propan-2-ol (64.4 mg, 0.31 mmol) and DIPEA (48.4 mg, 0.38 mmol) was added and the resulting solution was stirred at 28° C. for 16 h. The solution was concentrated and the residue was purified by column chromatography to give the crude title product (150 mg, Yield 94%). LCMS (m/z): 509.2 (M+1).

Step 3: N-(3-(3,4-dihydroisoquinolin-2(1H)-yl)-2-hydroxypropyl)-3-(piperazin-1-ylmethyl)benzamide

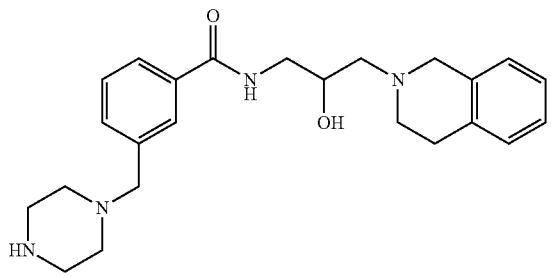 [SMILES: O=C(NCC(O)CN1CCc2ccccc2C1)c1cccc(CN2CCNCC2)c1]

The solution of tert-butyl 4-(3-((3-(3,4-dihydroisoquinolin-2(1H)-yl)-2-hydroxypropyl)carbamoyl)benzyl)piperazine-1-carboxylate (160 mg, 0.314 mmol) in DCM (2 mL) and TFA (2 mL) was stirred at 27° C. for 16 h. The solution was concentrated and the residue was purified by prep-HPLC to give the title product (89 mg, Yield 69.0%). $^1$H NMR (D$_2$O, 400 MHz): δ 7.66-7.56 (m, 2H), 7.51-7.44 (m, 1H), 7.44-7.37 (m, 1H), 7.16-7.06 (m, 3H), 7.02 (d, J=7.3 Hz, 1H), 4.11 (quin, J=5.9 Hz, 1H), 3.73-3.60 (m, 2H), 3.56-3.49 (m, 2H), 3.49-3.42 (m, 1H), 3.41-3.32 (m, 1H), 2.86-2.75 (m, 8H), 2.68-2.58 (m, 2H), 2.56-2.32 (m, 4H). LCMS (m/z): 409.2 (M+1).

Step 4: N-(3-(3,4-dihydroisoquinolin-2(1H)-yl)-2-hydroxypropyl)-3-((4-methyl piperazin-1-yl)methyl) benzamide

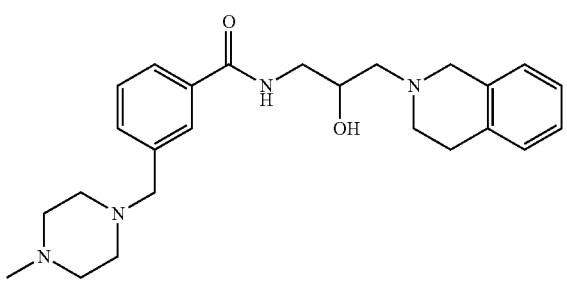 [SMILES: CN1CCN(Cc2cccc(C(=O)NCC(O)CN3CCc4ccccc4C3)c2)CC1]

The solution of N-(3-(3,4-dihydroisoquinolin-2(1H)-yl)-2-hydroxypropyl)-3-(piperazin-1-ylmethyl)benzamide (78 mg, 0.19 mmol) and HCHO solution (0.5 mL) in MeOH (10 mL) was stirred at 27° C. for 1 h. Then NaBH$_3$CN (14.5 mg, 0.23 mmol) was added to the solution and stirred at 27° C. for 4 h. The solution was concentrated and the residue was purified by column chromatography to give the title product (14.1 mg, Yield 17.5%). $^1$H NMR (CD$_3$OD, 400 MHz): δ 7.79 (s, 1H), 7.70 (d, J=7.8 Hz, 1H), 7.50 (d, J=7.5 Hz, 1H), 7.39-7.32 (m, 1H), 7.20-7.07 (m, 3H), 7.06-6.98 (m, 1H), 4.13 (quin, J=6.0 Hz, 1H), 3.75 (s, 2H), 3.63-3.44 (m, 4H), 2.95-2.83 (m, 4H), 2.78-2.62 (m, 3H), 2.62-2.30 (m, 7H), 2.28 (s, 3H). LCMS (m/z): 423.2 (M+1).

Compound 34

N-(3-(3,4-dihydroisoquinolin-2(1H)-yl)-2-hydroxypropyl)-3-(1-methylpyrrolidin-2-yl) benzamide

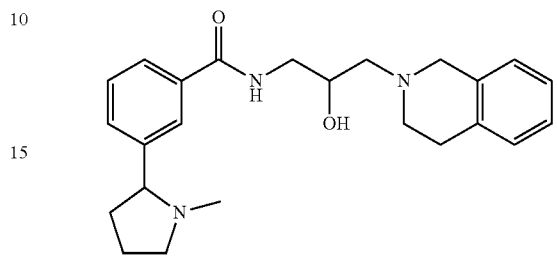

To a solution of N-(3-(3,4-dihydroisoquinolin-2(1H)-yl)-2-hydroxypropyl)-3-(pyrrolidin-2-yl)benzamide (20 mg, 0.13 mmol) in MeOH (20 mL) was added HCHO (1 mL) and AcOH (0.05 mL). The reaction mixture was stirred at room temperature for 30 min at which time NaBH$_3$CN (200 mg, 3.22 mmol) was added. The reaction mixture was stirred at room temperature for 2 h. The solvent was removed and the crude product was purified by prep-HPLC to give the desired product (8.5 mg, Yield 16.8%). $^1$H NMR (CD$_3$OD, 400 MHz): δ 7.80 (brs, 1H), 7.67 (d, J=7.6 Hz, 1H), 7.52 (d, J=7.6 Hz, 1H), 7.35-7.41 (m, 1H), 7.09-7.15 (m, 3H), 7.09-7.15 (m, 1H), 7.02-7.08 (m, 1H), 4.10-4.16 (m, 1H), 3.73-3.81 (m, 2H), 3.49-3.58 (m, 2H), 3.20-3.28 (m, 1H), 3.08-3.16 (m, 1H), 2.84-2.97 (m, 4H), 2.64-2.75 (m, 2H), 2.33-2.40 (m, 1H), 2.20-2.27 (m, 1H), 2.16 (s, 3H), 1.95-2.05 (m, 1H), 1.77-1.93 (m, 2H). LCMS (m/z): 394.1 (M+1).

Compound 35

N-(3-(3,4-dihydroisoquinolin-2(1H)-yl)-2-hydroxypropyl)-3-(piperazin-1-yl)benzamide

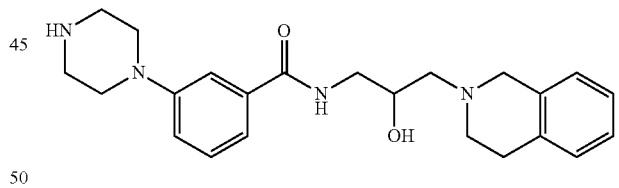

Step 1:
3-(4-(tert-butoxycarbonyl)piperazin-1-yl)benzoic Acid

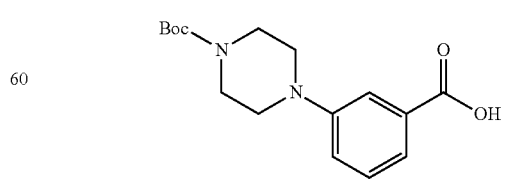

The mixture of ethyl 3-bromobenzoate (500 mg, 2.33 mmol), tert-butyl piperazine-1-carboxylate (433 mg, 2.33 mmol) and NaOtBu (268 mg, 2.78 mmol), Pd₂(dba)₃ (20 mg, 0.034 mmol) and Xantphos (20 mg, 0,034 mmol) in anhydrous dioxane (10 mL) was heated to 110° C. for 10 h. The mixture was concentrated and the residue was partitioned in water, the solution was adjusted to pH=5, and extracted with DCM. The organic layer was washed with water and brine, dried over anhydrous Na₂SO₄, filtered and concentrated to afford the title compound that was used for next step (300 mg, Yield 42.2%). LCMS (m/z): 307.1 (M+1).

Step 2: tert-butyl 4-(3-(3-(3,4-dihydroisoquinolin-2 (1H)-yl)-2-hydroxypropyl carbamoyl)phenyl)piperazine-1-carboxylate

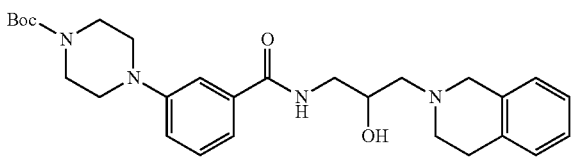 [SMILES: CC(C)(C)OC(=O)N1CCN(c2cccc(C(=O)NCC(O)CN3CCc4ccccc4C3)c2)CC1]

The solution of 3-(4-(tert-butoxycarbonyl)piperazin-1-yl) benzoic acid (300 mg, 1.0 mmol) and HATU (381 mg, 1.0 mmol) in DCM (10 mL) was stirred at 25° C. for 30 min. Then 1-amino-3-(3,4-dihydroisoquinolin-2(1H)-yl)propan-2-ol (200 mg, 1.0 mmol) and DIPEA (259 mg, 2.00 mmol) was added and the resulting solution was stirred at 25° C. for 16 h. The solution was concentrated and the residue was purified by column chromatography to give the title product (140 mg, Yield 28.8%). LCMS (m/z): 495.2 (M+1).

Step 3: N-(3-(3,4-dihydroisoquinolin-2(1H)-yl)-2-hydroxypropyl)-3-(piperazin-1-yl)benzamide

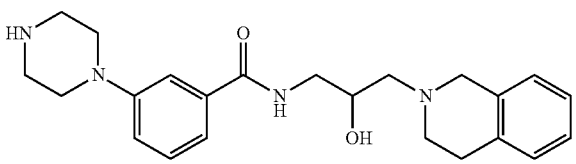 [SMILES: O=C(NCC(O)CN1CCc2ccccc2C1)c1cccc(N2CCNCC2)c1]

To a solution of tert-butyl 4-(3-(3-(3,4-dihydroisoquinolin-2(1H)-yl)-2-hydroxy propylcarbamoyl)phenyl)piperazine-1-carboxylate (140 mg, 0.28 mmol) in DCM (2 mL) was added TFA (2 mL). The resulting solution was stirred at 27° C. for 4 h. The solution was concentrated and the residue was purified by prep-HPLC to give the title product (64.0 mg, Yield 57%). ¹H NMR (CD₃OD, 400 MHz): δ 7.47-7.38 (s, 1H), 7.31-7.21 (m, 2H), 7.19-7.08 (m, 4H), 7.08-7.01 (m, 1H), 4.13 (quin, J=6.0 Hz, 1H), 3.77 (s, 2H), 3.62-3.52 (m, 1H), 3.51-3.43 (m, 1H), 3.31-3.19 (m, 4H), 3.15-3.00 (m, 4H), 2.98-2.83 (m, 4H), 2.75-2.62 (m, 2H). LCMS (m/z): 395.2 (M+1).

Compound 38

N-(3-(3,4-dihydroisoquinolin-2(1H)-yl)-2-hydroxypropyl)-3-(1-methylpyrrolidin-3-yl)benzamide

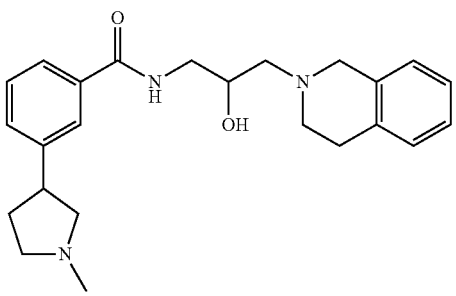 [SMILES: CN1CCC(c2cccc(C(=O)NCC(O)CN3CCc4ccccc4C3)c2)C1]

Step 1: tert-butyl 3-(((trifluoromethyl)sulfonyl)oxy)-2,5-dihydro-1H-pyrrole-1-carboxylate

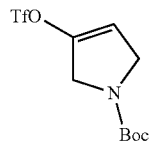

A solution of tert-butyl 3-oxopyrrolidine-1-carboxylate (5 g, 27.0 mmol) in THF (50 ml) was slowly added to a stirring solution of NaHMDS (1M THF, 32.4 ml, 32.4 mmol) at −78° C. After 10 min a solution of N-phenyl-O-((trifluoromethyl)sulfonyl)-N-(((trifluoromethyl) sulfonyl)oxy)hydroxylamine (10.6 g, 29.7 mmol) in THF (50 ml) was slowly added. Stirring at −78° C. was continued for 30 min and the cooling bath was removed. The reaction mixture was stirred at room temperature for 1.5 h. The mixture was cooled to 0° C., quenched with sat. NaHCO₃, and extracted with MTBE. The organic layer was washed with 5% citric acid, 1M NaOH, H₂O, brine, dried over Na₂SO₄, concentrated and the residue was purified by flash column chromatography to give the title compound (1.5 g, Yield 17.4%). ¹H NMR (CDCl₃, 400 MHz): δ 5.77 (s, 1H), 4.14-4.30 (m, 4H), 1.48 (s, 9H).

Step 2: tert-butyl 3-(3-(methoxycarbonyl)phenyl)-2,5-dihydro-1H-pyrrole-1-carboxylate

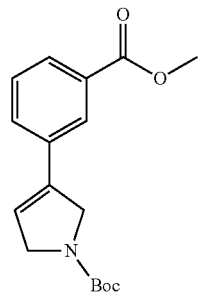 [SMILES: COC(=O)c1cccc(C2=CCN(C(=O)OC(C)(C)C)C2)c1]

To a solution of tert-butyl 3-(((trifluoromethyl)sulfonyl)oxy)-2,5-dihydro-1H-pyrrole-1-carboxylate (300 mg, 0.95 mmol) in dioxane (4 mL) and H₂O (1 mL) was added methyl 3-(4,4,5,5-tetramethyl-1,3,2-dioxaborolan-2-yl)benzoate (298 mg, 1.13 mmol), Pd(dppf)Cl₂ (66 mg, 0.09 mmol) and K₂CO₃ (392 mg, 2.84 mmol) at 27° C. The mixture was stirred at 100° C. for 16 h. The catalyst was filtered, the filtrate was concentrated and the residue was purified by column chromatography to give the title compound (213 mg, Yield 74.2%). ¹H NMR (CDCl₃, 400 MHz): δ 8.03 (d, J=19.6 Hz, 1H), 7.94 (d, J=7.8 Hz, 1H), 7.55 (dd, J=15.7, 7.8 Hz, 1H), 7.38-7.45 (m, 1H), 6.22 (dt, J=16.4, 1.8 Hz, 1H), 4.43-4.58 (m, 2H), 4.24-4.38 (m, 2H), 3.88-3.96 (m, 3H), 1.51 (d, J=7.9 Hz, 9H).

Step 3: tert-butyl 3-(3-(methoxycarbonyl)phenyl)pyrrolidine-1-carboxylate

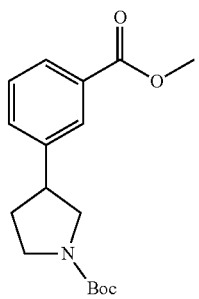 [SMILES: COC(=O)c1cccc(C2CCN(C(=O)OC(C)(C)C)C2)c1]

To a solution of tert-butyl 3-(3-(methoxycarbonyl)phenyl)-2,5-dihydro-1H-pyrrole-1-carboxylate (213 mg, 0.7 mmol) in MeOH (10 mL) was added Pd/C (20 mg). The mixture was stirred for 30 min at 30° C. under H₂ atmosphere. The mixture was filtered and the filtrate was concentrated to give the title compound which was used in next step without further purification (210 mg, Yield 98.1%). ¹H NMR (CDCl₃, 400 MHz): δ 7.88-7.97 (m, 2H), 7.36-7.48 (m, 2H), 3.92 (s, 3H), 3.77-3.90 (m, 1H), 3.53-3.72 (m, 1H), 3.25-3.47 (m, 3H), 2.29 (d, J=5.27 Hz, 1H), 2.01 (quin, J=10.2 Hz, 1H), 1.42-1.55 (m, 10H).

Step 4:
3-(1-(tert-butoxycarbonyl)pyrrolidin-3-yl)benzoic Acid

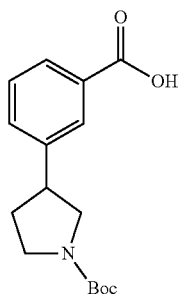 [SMILES: CC(C)(C)OC(=O)N1CCC(c2cccc(C(=O)O)c2)C1]

To a solution of tert-butyl 3-(3-(methoxycarbonyl)phenyl) pyrrolidine-1-carboxylate (210 mg, 0.7 mmol) in EtOH (4 ml) was added a solution of NaOH (56 mg, 1.4 mmol) in H₂O (1 ml) at 29° C. The mixture was stirred for 30 min at 29° C. The mixture was concentrated and the residue was treated with water and extracted with EA. The water layer was treated with 2N HCl until pH=3, extracted with EA and the combined organic layers were washed with brine, dried over Na₂SO₄ and concentrated to give the title compound which was used in next step without further purification (200 mg, Yield 98.0%).

Step 5: tert-butyl 3-(3-((3-(3,4-dihydroisoquinolin-2(1H)-yl)-2-hydroxypropyl)carbamoyl) phenyl)pyrrolidine-1-carboxylate

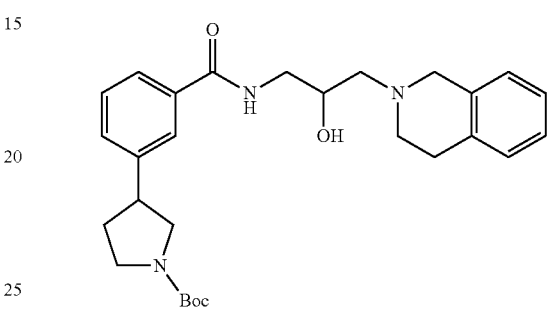

To a solution of 3-(1-(tert-butoxycarbonyl)pyrrolidin-3-yl)benzoic acid (200 mg, 0.69 mmol) in DMF (4 ml) was added TEA (208 mg, 2.06 mmol), HOBt (139 mg, 1.03 mmol), EDCI (197 mg, 1.03 mmol) and 1-amino-3-(3,4-dihydroisoquinolin-2(1H)-yl)propan-2-ol (170 mg, 0.82 mmol) at 33° C. The reaction mixture was stirred for 16 h at 31° C. The mixture was treated with water and extracted with EA. The organic layer was washed with brine, dried over Na₂SO₄ and concentrated to give the title compound which was used in next step without further purification (300 mg, Yield 92%).

Step 6: N-(3-(3,4-dihydroisoquinolin-2(1H)-yl)-2-hydroxypropyl)-3-(pyrrolidin-3-yl) benzamide

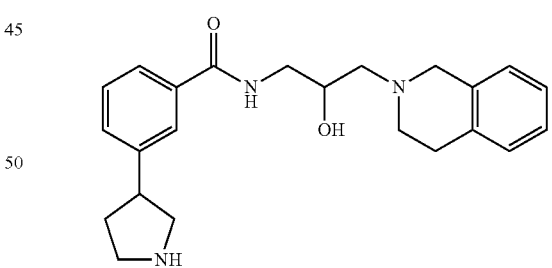

To a solution of tert-butyl 3-(3-((3-(3, 4-dihydroisoquinolin-2(1H)-yl)-2-hydroxypropyl) carbamoyl)phenyl)pyrrolidine-1-carboxylate (400 mg, 0.83 mmol) in CH₂Cl₂ (5 mL) was added TFA (1 mL) at 29° C. The mixture was stirred for 2 h at 29° C. The mixture was concentrated and the residue was purified by prep-HPLC to give the title compound (79.1 mg, Yield 25.0%). ¹H NMR (CD₃OD, 400 MHz): δ 7.75-7.93 (m, 2H), 7.45-7.62 (m, 2H), 7.17-7.37 (m, 4H), 4.45-4.74 (m, 2H), 4.40 (dd, J=6.3, 3.3 Hz, 1H), 3.71-4.04 (m, 2H), 3.49-3.70 (m, 5H), 3.35-3.49 (m, 3H), 3.08-3.32 (m, 3H), 2.52 (qd, J=6.6, 4.2 Hz, 1H), 2.09-2.27 (m, 1H). LCMS (m/z): 380.2 (M+1).

Step 7: N-(3-(3,4-dihydroisoquinolin-2(1H)-yl)-2-hydroxypropyl)-3-(1-methylpyrrolidin-3-yl)benzamide

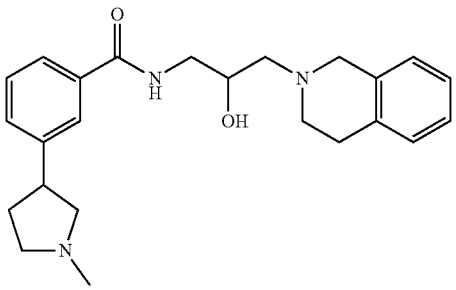 [SMILES: CN1CCC(c2cccc(C(=O)NCC(O)CN3CCc4ccccc4C3)c2)C1]

To a solution of N-(3-(3,4-dihydroisoquinolin-2(1H)-yl)-2-hydroxypropyl)-3-(pyrrolidin-3-yl)benzamide (200 mg, 0.53 mmol) in MeOH (4 ml) was added HCHO (31.9 mg, 1.05 mmol) and NaBH$_3$CN (66.1 mg, 1.05 mmol) at 29° C. The mixture was then added AcOH (0.5 ml) at 29° C. and stirred for 16 h. The mixture was purified by prep-HPLC to give the title compound (29.6 mg, Yield 14.3%). $^1$H NMR (CD$_3$OD, 400 MHz): δ 8.52 (brs, 2H), 7.88 (s, 1H), 7.78 (d, J=7.7 Hz, 1H), 7.53-7.60 (m, 1H), 7.43-7.52 (m, 1H), 7.22-7.33 (m, 3H), 7.15-7.21 (m, 1H), 4.36 (s, 3H), 3.78 (brs, 2H), 3.46-3.67 (m, 6H), 3.41 (brs, 1H), 3.07-3.19 (m, 3H), 3.01 (s, 3H), 2.50-2.64 (m, 1H), 2.19-2.34 (m, 1H). LCMS (m/z): 394.2 (M+1).

Compound 40

N-(3-(3,4-dihydroisoquinolin-2(1H)-yl)-2-hydroxypropyl)-2-methyl-3-((tetrahydro-2H-pyran-4-yl)amino)benzamide

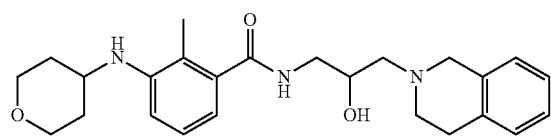 [SMILES: Cc1c(NC2CCOCC2)cccc1C(=O)NCC(O)CN1CCc2ccccc2C1]

Step 1: N-(3-(3,4-dihydroisoquinolin-2(1H)-yl)-2-hydroxypropyl)-2-methyl-3-nitrobenzamide

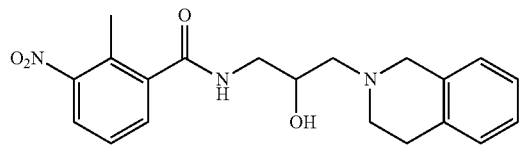 [SMILES: Cc1c(C(=O)NCC(O)CN2CCc3ccccc3C2)cccc1[N+](=O)[O-]]

To a solution of 2-methyl-3-nitrobenzoic acid (1.0 g, 5.5 mmol) in DCM (20 mL) was added EDCI (1.58 g, 8.25 mmol), HOBt (1.11 g, 8.25 mmol), Et$_3$N (1.11 g, 11.0 mmol) and 1-amino-3-(3,4-dihydroisoquinolin-2(1H)-yl)propan-2-ol (1.36 g, 6.6 mmol). The mixture was stirred at 25° C. for 16 h. The reaction solution was washed with water and extracted with DCM. The organic layer was concentrated, and the residue was purified by column chromatography to give the title product (1.6 g, 78.8%). LCMS (m/z): 370.2 (M+1).

Step 2: 3-amino-N-(3-(3,4-dihydroisoquinolin-2(1H)-yl)-2-hydroxypropyl)-2-methyl benzamide

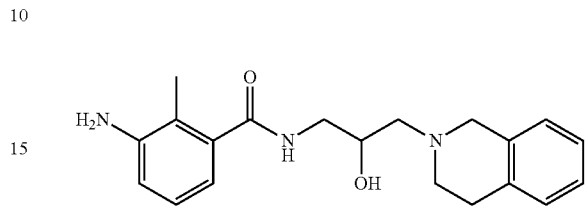

To a solution of N-(3-(3,4-dihydroisoquinolin-2(1H)-yl)-2-hydroxypropyl)-2-methyl-3-nitrobenzamide (1.6 g, 4.3 mmol) in EtOH (15 mL) and H$_2$O (15 mL) was added Fe powder (1.45 g, 25.8 mmol) and NH$_4$Cl (1.38 g, 25.8 mmol). The mixture was stirred at 60° C. for 4 h. The reaction solution was filtered, and the filtrate was concentrated to remove EtOH. The residue was diluted with water and extracted with DCM. The organic layer was concentrated to give the desired product (1.4 g, Yield 95.9%). The crude product was used in next step without further purification. LCMS (m/z): 340.1 (M+H).

Step 3: N-(3-(3,4-dihydroisoquinolin-2(1H)-yl)-2-hydroxypropyl)-2-methyl-3-((tetrahydro-2H-pyran-4-yl)amino)benzamide

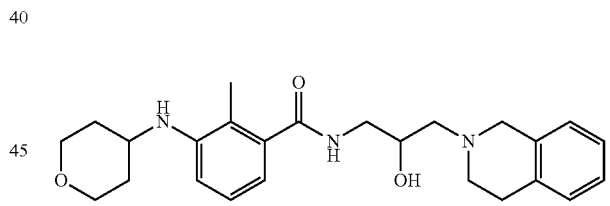

To a solution of 3-amino-N-(3-(3,4-dihydroisoquinolin-2(1H)-yl)-2-hydroxypropyl)-2-methylbenzamide (200 mg, 0.59 mmol) in MeOH (8 mL) was added AcOH (0.05 mL) and dihydro-2H-pyran-4(3H)-one (118 mg, 1.18 mmol). The mixture was stirred at 25° C. for 2 h. NaBH$_3$CN (186 mg, 2.95 mmol) was added and the resulting mixture was stirred at 25° C. for 2 h. The reaction solution was concentrated and the residue was washed with water and extracted with EA. The organic layer was concentrated, and the residue was purified by prep-HPLC to give the title compound (24 mg, Yield 9.6%). $^1$H NMR (CD$_3$OD, 400 MHz): δ 8.41 (s, 1H), 7.35-7.23 (m, 3H), 7.20 (d, J=7.0 Hz, 1H), 7.11 (t, J=7.8 Hz, 1H), 6.81 (d, J=8.3 Hz, 1H), 6.70 (d, J=7.3 Hz, 1H), 4.44 (s, 2H), 4.33 (brs, 1H), 3.99 (d, J=11.5 Hz, 2H), 3.66-3.43 (m, 7H), 3.38-3.16 (m, 4H), 2.15 (s, 3H), 2.01 (d, J=12.8 Hz, 2H), 1.63-1.48 (m, 2H). LCMS (m/z): 424.2 (M+1).

Compound 42

N-(3-(3,4-dihydroisoquinolin-2(1H)-yl)-2-hydroxypropyl)-3-(pyrrolidin-2-yl)benzamide

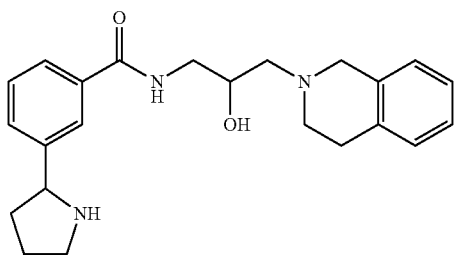 [SMILES: O=C(NCC(O)CN1CCc2ccccc2C1)c1cccc(C2CCCN2)c1]

Step 1: tert-butyl 2-(3-((3-(3,4-dihydroisoquinolin-2(1H)-yl)-2-hydroxypropyl)carbamoyl) phenyl)pyrrolidine-1-carboxylate

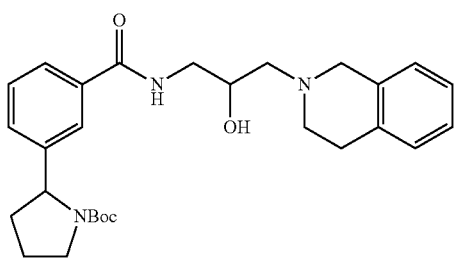 [SMILES: CC(C)(C)OC(=O)N1CCCC1c1cccc(C(=O)NCC(O)CN2CCc3ccccc3C2)c1]

A mixture of compound 3-(1-(tert-butoxycarbonyl)pyrrolidin-2-yl)benzoic acid (100 mg, 0.34 mmol), 1-amino-3-(3,4-dihydroisoquinolin-2(1H)-yl)propan-2-ol (70 mg, 0.34 mmol), BOPCl (100 mg, 0.41 mmol) and DIPEA (1 mL) in DCM (10 mL) was stirred at 25° C. for 4 h. The reaction mixture was diluted with water and extracted with DCM. The combined organic layers were washed with brine, dried over Na₂SO₄, concentrated and the residue was purified by prep-TLC to give the title product which was used directly in next step (150 mg, Yield 93%). LCMS (m/z): 480.2 (M+1).

Step 2: N-(3-(3,4-dihydroisoquinolin-2(1H)-yl)-2-hydroxypropyl)-3-(pyrrolidin-2-yl) benzamide

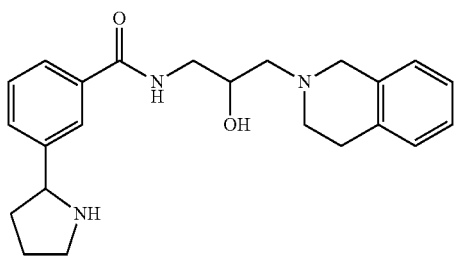

To a solution of tert-butyl 2-(3-((3-(3,4-dihydroisoquinolin-2(1H)-yl)-2-hydroxypropyl)carbamoyl)phenyl)pyrrolidine-1-carboxylate (100 mg, 0.11 mmol) in EA (10 mL) was added HCl (1M in EA, 4 mL). The reaction mixture was stirred at 25° C. for 16 h. The solvent was then removed by in vacuo and the crude product was purified by prep-HPLC to give the title compound (39.4 mg, Yield 52%). ¹H NMR (CD₃OD, 400 MHz): δ 7.80 (brs, 1H), 7.66 (d, J=7. Hz, 1H), 7.53 (d, J=7.6 Hz, 1H), 7.32-7.43 (m, 1H), 7.00-7.17 (m, 4H), 4.05-4.24 (m, 2H), 3.73-3.81 (m, 2H), 3.48-3.60 (m, 2H), 3.17-3.27 (m, 1H), 2.96-3.07 (m, 1H), 2.81-2.95 (m, 4H), 2.64-2.75 (m, 2H), 2.20-2.32 (m, 1H), 1.87-2.05 (m, 2H), 1.70-1.84 (m, 1H). LCMS (m/z): 380.2 (M+1).

Compound 44

(S)—N-(3-(3,4-dihydroisoquinolin-2(1H)-yl)-2-hydroxypropyl)-3-((tetrahydro-2H-pyran-4-yl)amino)benzamide

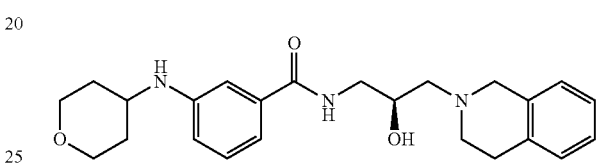

Step 1: (R)-2-(oxiran-2-ylmethyl)-1,2,3,4-tetrahydroisoquinoline

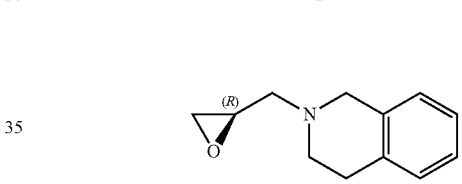

To a solution of 1,2,3,4-tetrahydroisoquinoline (10 g, 0.15 mol) in THF (100 mL) at 0° C. was added KF (22 g, 0.3 mmol). After 1 h, (S)-oxiran-2-ylmethyl 3-nitrobenzenesulfonate (21.4 g, 0.17 mmol) was added and the resulting solution was stirred at 22° C. for 16 h. The solid was removed by filtration and washed with THF. The solution was concentrated and the crude compound was used for next step without further purification (15 g, Yield 53%). LCMS (m/z): 190.1 (M+1).

Step 2: (S)-1-amino-3-(3,4-dihydroisoquinolin-2(1H)-yl)propan-2-ol

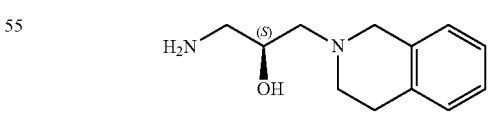

To a solution of (R)-2-(oxiran-2-ylmethyl)-1,2,3,4-tetrahydroisoquinoline (15 g, 0.08 mol) in EtOH (100 mL) at −78° C. was slowly bubbled NH₃ (g). The reaction mixture was then sealed and heated at 80° C. for 3 h. The reaction mixture was concentrated and the crude product was used in next step without further purification (15 g, Yield 92%). LCMS (m/z): 207.1 (M+1).

Step 3: Methyl 3-((tert-butoxycarbonyl)amino)benzoate

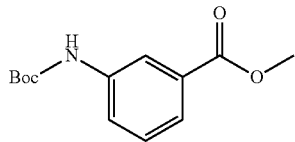 [SMILES: COC(=O)c1cccc(NC(=O)OC(C)(C)C)c1]

To a solution of methyl 3-aminobenzoate (2.0 g, 13.2 mmol) in THF (20 mL) was added Et$_3$N (2.67 g, 26.4 mmol) and Boc$_2$O (3.16 g, 14.5 mmol) at 0° C. The mixture was stirred at 25° C. for 16 h. The reaction solution was concentrated to remove THF, and the residue was washed with water and extracted with EA. The organic layer was concentrated, and the residue was purified by column chromatography to give the title product (1.6 g, Yield 48.5%). $^1$H NMR (CD$_3$OD, 400 MHz): δ 8.12 (s, 1H), 7.64-7.60 (m, 2H), 7.37-7.33 (t, J=8 Hz, 1H), 3.89 (s, 3H), 1.52 (s, 9H). LCMS (m/z): 251.1 (M+1).

Step 4: (S)-tert-butyl(3-((3-(3,4-dihydroisoquinolin-2(1H)-yl)-2-hydroxypropyl) carbamoyl) phenyl) carbamate

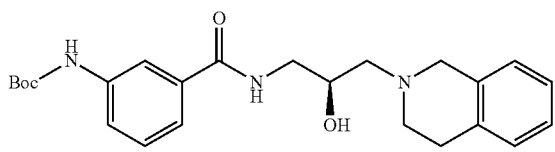 [SMILES: CC(C)(C)OC(=O)Nc1cccc(C(=O)NC[C@H](O)CN2CCc3ccccc3C2)c1]

A mixture of methyl 3-((tert-butoxycarbonyl)amino)benzoate (500 mg, 2 mmol) and (S)-1-amino-3-(3,4-dihydroisoquinolin-2(1H)-yl)propan-2-ol (618 mg, 3 mmol) in EtOH (1 mL) was heated at 120° C. for 3 h in a microwave reactor under N$_2$. The reaction solution was concentrated and the residue was purified by column chromatography to give the title product (500 mg, Yield 58.8%). LCMS (m/z): 426.2 (M+1).

Step 5: (S)-3-amino-N-(3-(3,4-dihydroisoquinolin-2(1H)-yl)-2-hydroxypropyl) benzamide

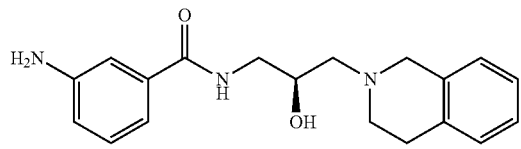

To a solution of (S)-tert-butyl-(3-((3-(3,4-dihydroisoquinolin-2(1H)-yl)-2-hydroxyl propyl)carbamoyl)phenyl)carbamate (500 mg, 1.18 mmol) in DCM (8 mL) was added TFA (8 mL). The mixture was stirred at 25° C. for 16 h. The reaction solution was concentrated to give the crude title product that was used without further purification (400 mg). LCMS (m/z): 326.2 (M+1).

Step 6: (S)—N-(3-(3,4-dihydroisoquinolin-2(1H)-yl)-2-hydroxypropyl)-3-((tetrahydro-2H-pyran-4-yl)amino)benzamide

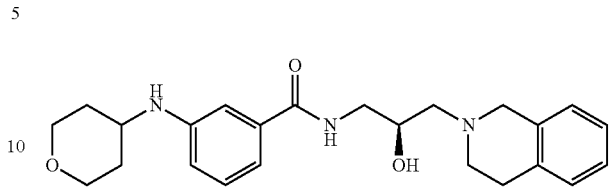

To a solution of (S)-3-amino-N-(3-(3,4-dihydroisoquinolin-2(1H)-yl)-2-hydroxylpropyl)benzamide (400 mg, 1.23 mmol) in MeOH (8 mL) was added AcOH (0.05 mL) and dihydro-2H-pyran-4(3H)-one (123 mg, 1.23 mmol). The mixture was stirred at 25° C. for 2 h. NaBH$_3$CN (387 mg, 6.15 mmol) was added and the resulting mixture was stirred at 25° C. for 2 h. The reaction solution was concentrated, and the residue was washed with water and extracted with EA. The organic layer was concentrated, and the residue was purified by prep-HPLC to give the title compound (160 mg, Yield 31.8%). $^1$H NMR (CD$_3$OD, 400 MHz): δ 7.94-7.76 (m, 2H), 7.63-7.56 (m, 1H), 7.56-7.49 (m, 1H), 7.32-7.24 (m, 3H), 7.21-7.15 (m, 1H), 4.71-4.55 (m, 1H), 4.52-4.28 (m, 2H), 4.05-3.95 (m, 2H), 3.92-3.70 (m, 2H), 3.62-3.46 (m, 3H), 3.46-3.33 (m, 4H), 3.28-3.02 (m, 2H), 1.99-1.85 (m, 2H), 1.82-1.66 (m, 2H). LCMS (m/z): 410.2 (M+1).

Compound 45

N-(3-(3,4-dihydroisoquinolin-2(1H)-yl)-2-hydroxypropyl)-3-((tetrahydrofuran-3-yl)amino)benzamide

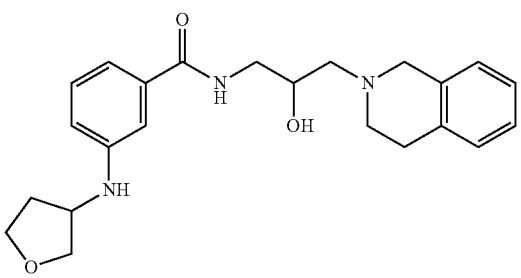 [SMILES: O=C(NCC(O)CN1CCc2ccccc2C1)c1cccc(NC2CCOC2)c1]

Step 1: 2-(oxiran-2-ylmethyl)-1,2,3,4-tetrahydroisoquinoline

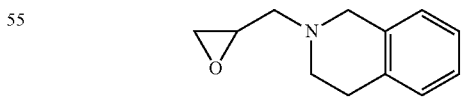

To a solution of 1,2,3,4-tetrahydroisoquinoline (15 g, 0.11 mol) in MeCN (100 mL) was added K$_2$CO$_3$ (30.7 g, 0.23 mol) at 0° C. 2-(bromomethyl)oxirane (17 g, 0.12 mol) was added to the reaction after 1 h. The solution was stirred at 22° C. for 16 h at which time the solids were filtered and washed with MeCN. The solution was concentrated and the residue was used in the next step without further purification (17 g, Yield 78%). LCMS (m/z): 190.1 (M+1).

Step 2: 1-amino-3-(3,4-dihydroisoquinolin-2(1H)-yl)propan-2-ol

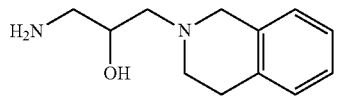 [SMILES: NCC(O)CN1CCc2ccccc2C1]

To a solution of 2-(oxiran-2-ylmethyl)-1,2,3,4-tetrahydroisoquinoline (17 g, 0.09 mol) in EtOH (300 mL) at −78° C. was slowly bubbled NH$_3$ (g). The reaction mixture was then sealed and heated at 80° C. for 3 h. The reaction mixture was concentrated and the crude product was used in next step without further purification (18 g, Yield 96%). LCMS (m/z): 207.1 (M+1).

Step 3: tert-butyl (3-((3-(3,4-dihydroisoquinolin-2(1H)-yl)-2-hydroxypropyl) carbamoyl)phenyl)carbamate

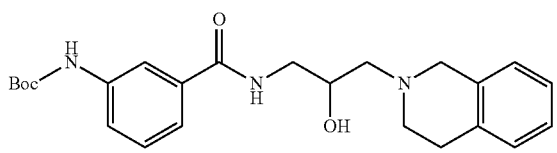 [SMILES: CC(C)(C)OC(=O)Nc1cccc(C(=O)NCC(O)CN2CCc3ccccc3C2)c1]

To a solution of 3-((tert-butoxycarbonyl)amino)benzoic acid (2.5 g, 10.5 mmol) in DCM (25 mL) was added EDCI (3.0 g, 15.7 mmol), HOBt (2.1 g, 15.7 mmol), Et$_3$N (2.1 g, 21 mmol) and 1-amino-3-(3,4-dihydroisoquinolin-2(1H)-yl)propan-2-ol (2.2 g, 10.5 mmol). The mixture was stirred at 25° C. for 16 h. The reaction solution was washed with water and extracted with DCM. The organic layer was concentrated, and the residue was purified by column chromatography to give the title product (3.2 g, 71%). LCMS (m/z): 426.3 (M+1).

Step 5: 3-amino-N-(3-(3,4-dihydroisoquinolin-2(1H)-yl)-2-hydroxypropyl) benzamide

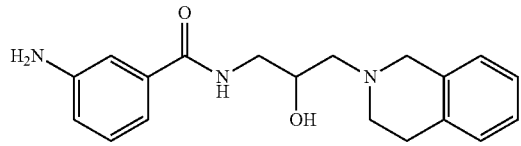

To a solution of tert-butyl (3-((3-(3,4-dihydroisoquinolin-2(1H)-yl)-2-hydroxypropyl)carbamoyl)phenyl)carbamate (500 mg, 1.18 mmol) in DCM (5 mL) was added TFA (5 mL). The mixture was stirred at 25° C. for 16 h. The reaction solution was concentrated, and the residue was dissolved in water, the pH was adjusted to 7-7.5 with saturated aqueous of NaHCO$_3$ and extracted with EA. The organic layer was concentrated to give the title product that was used in the next step without further purification (450 mg). LCMS (m/z): 326.2 (M+1).

Step 6: N-(3-(3,4-dihydroisoquinolin-2(1H)-yl)-2-hydroxypropyl)-3-((tetrahydrofuran-3-yl)amino)benzamide

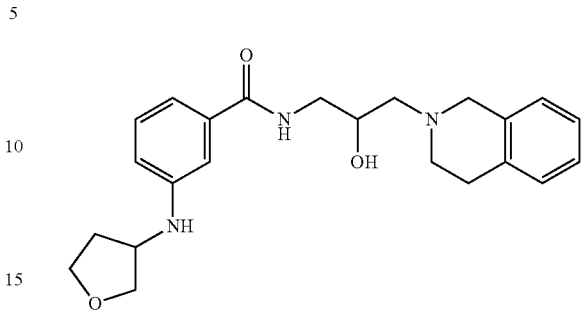

To a solution of 3-amino-N-(3-(3,4-dihydroisoquinolin-2(1H)-yl)-2-hydroxypropyl)benzamide (100 mg, 0.31 mmol) in MeOH (5 mL) was added AcOH (0.05 mL) and dihydrofuran-3(2H)-one (27 mg, 0.31 mmol). The mixture was stirred at 22° C. for 2 h. NaBH$_3$CN (98 mg, 1.55 mmol) was added and the resulting mixture was stirred at 22° C. for 2 h. The reaction solution was concentrated, and the residue was washed with water, extracted with EA, the organic layer was concentrated, and the residue was purified by prep-HPLC to give the title compound (22 mg, Yield 18.0%). $^1$H NMR (CD$_3$OD, 400 MHz): δ 7.14-6.95 (m, 7H), 6.80-6.71 (m, 1H), 4.14-4.03 (m, 2H), 3.99-3.89 (m, 2H), 3.87-3.78 (m, 1H), 3.75-3.69 (m, 2H), 3.67-3.61 (m, 1H), 3.55-3.41 (m, 2H), 2.91-2.79 (m, 4H), 2.71-2.57 (m, 2H), 2.32-2.19 (m, 1H), 1.91-1.79 (m, 1H). LCMS (m/z): 396.2 (M+1).

Compound 46

N-(3-(3,4-dihydroisoquinolin-2(1H)-yl)-2-hydroxypropyl)-3-(morpholine-4-carbonyl)benzamide

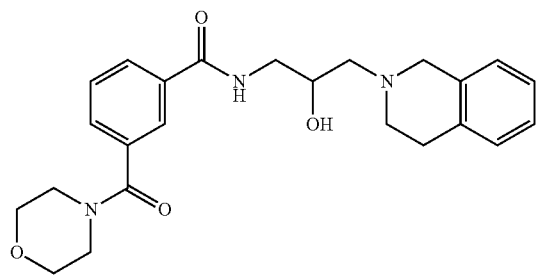 [SMILES: O=C(NCC(O)CN1CCc2ccccc2C1)c1cccc(C(=O)N2CCOCC2)c1]

Step 1: methyl 3-(morpholine-4-carbonyl)benzoate

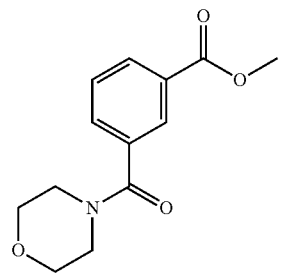 [SMILES: COC(=O)c1cccc(C(=O)N2CCOCC2)c1]

To a solution of 3-(methoxycarbonyl)benzoic acid (200 mg, 1.11 mmol) in DCM (10 mL) were added morpholine (200 mg, 2.30 mmol) and TEA (300 mg, 2.96 mmol) and the resulting solution was stirred for 10 min at 20° C. To the mixture was added HATU (500 mg, 1.31 mmol) and the reaction mixture was stirred at 20° C. for 1 h. The mixture was concentrated and the residue was purified via column chromatography to obtain the title product (250 mg, Yield 90.5%). LCMS (m/z): 250.1 (M+1).

Step 2: 3-(morpholine-4-carbonyl)benzoic Acid

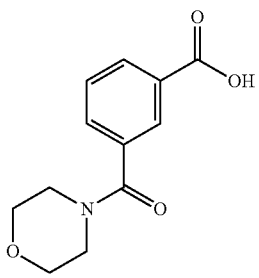 [SMILES: O=C(O)c1cccc(C(=O)N2CCOCC2)c1]

To a solution of methyl methyl-3-(morpholine-4-carbonyl)benzoate (300 mg, 1.11 mmol) in MeOH (2 mL) and water (2 mL) was added LiOH (100 mg, 2.38 mmol) at 20° C. The mixture was heated to 60° C. for 1 h under N$_2$. The reaction solution was concentrated in vacuo and diluted with water. The pH was adjusted to 4 with 2N HCl and the aqueous layer was extracted with DCM. The organic layer was concentrated to dryness and obtained the title product that was used in the next reaction without further purification (250 mg, Yield 96%). LCMS (m/z): 236.2 (M+1).

Step 3: N-(3-(3,4-dihydroisoquinolin-2(1H)-yl)-2-hydroxypropyl)-3-(morpholine-4-carbonyl)benzamide

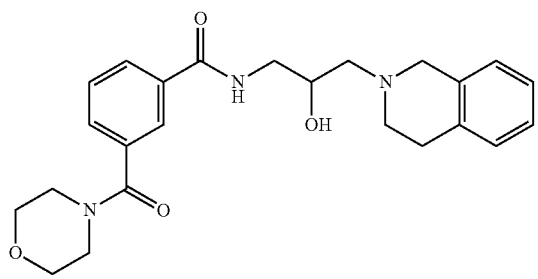 [SMILES: O=C(NCC(O)CN1CCc2ccccc2C1)c1cccc(C(=O)N2CCOCC2)c1]

To a solution of 3-(morpholine-4-carbonyl)benzoic acid (300 mg crude, 0.48 mmol) in MeCN (5 mL) was added 1-amino-3-(3,4-dihydroisoquinolin-2(1H)-yl)-propan-2-ol (100 mg, 0.49 mmol), and TEA (250 mg, 2.48 mmol) and the resulting mixture was stirred at 20° C. for 10 min. BOPCl (120 mg, 0.49 mmol) was added and the reaction mixture was stirred at 20° C. for 1 h. After evaporation of the solvent, the residue was purified by prep-HPLC to give the title compound (15.2 mg, Yield 7.5%). $^1$H NMR (CD$_3$OD, 400 MHz): δ 7.85-7.94 (m, 2H), 7.60 (d, J=7.8 Hz, 1H), 7.50 (t, J=7.7 Hz, 1H), 7.08-7.16 (m, 3H), 7.01-7.07 (m, 1H), 4.14 (quin, J=6.0 Hz, 1H), 3.76 (s, 6H), 3.54-3.68 (m, 3H), 3.47 (dd, J=6.8, 13.6 Hz, 3H), 2.80-2.98 (m, 4H), 2.63-2.74 (m, 2H). LCMS (m/z): 424.2 (M+1).

Compound 49

N-(3-(3,4-dihydroisoquinolin-2(1H)-yl)-2-hydroxypropyl)-3-(methyl(tetrahydro-2H-pyran-4-yl)amino)benzamide

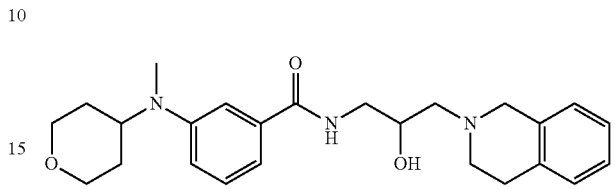

Step 1: tert-butyl-(3-((3-(3,4-dihydroisoquinolin-2(1H)-yl)-2-hydroxypropyl) carbamoyl)phenyl)carbamate

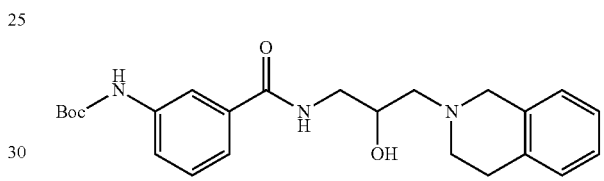

To a solution of 3-((tert-butoxycarbonyl)amino)benzoic acid (2.5 g, 10.5 mmol) in DCM (25 mL) was added EDCI (3.0 g, 15.7 mmol), HOBt (2.1 g, 15.7 mmol), Et$_3$N (2.1 g, 21 mmol) and 1-amino-3-(3,4-dihydroisoquinolin-2(1H)-yl) propan-2-ol (2.2 g, 10.5 mmol). The mixture was stirred at 25° C. for 16 h. The reaction solution was washed with water and extracted with DCM. The organic layer was concentrated, and the residue was purified by column chromatography to give the title product (3.2 g, Yield 71%). LCMS (m/z): 426.3 (M+1).

Step 3: 3-amino-N-(3-(3,4-dihydroisoquinolin-2(1H)-yl)-2-hydroxypropyl) benzamide

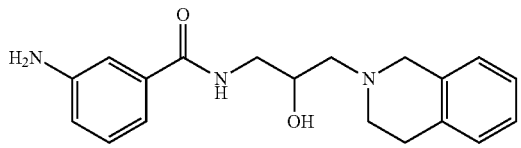

To a solution of tert-butyl (3-((3-(3,4-dihydroisoquinolin-2(1H)-yl)-2-hydroxypropyl) carbamoyl)phenyl)carbamate (500 mg, 1.18 mmol) in DCM (5 mL) was added TFA (5 mL). The mixture was stirred at 25° C. for 16 h. The reaction solution was concentrated, and the residue was dissolved in water, the pH was adjusted to 7-7.5 with saturated aqueous of NaHCO$_3$ and extracted with EA. The organic layer was concentrated to give the title product that was used in the next step without further purification (450 mg, crude). LCMS (m/z): 326.2 (M+1).

Step 4. N-(3-(3,4-dihydroisoquinolin-2(1H)-yl)-2-hydroxypropyl)-3-(methyl (tetrahydro-2H-pyran-4-yl)amino)benzamide

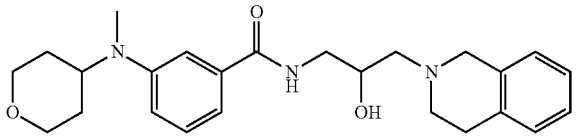 [SMILES: CN(c1cccc(C(=O)NCC(O)CN2CCc3ccccc3C2)c1)C1CCOCC1]

To a solution of N-(3-(3,4-dihydroisoquinolin-2(1H)-yl)-2-hydroxypropyl)-3-((tetrahydro-2H-pyran-4-yl)amino) benzamide (300 mg, 0.73 mmol) in MeOH (6 mL) was added AcOH (0.05 mL) and HCHO (548 mg, 7.3 mmol, 40% w/w). The mixture was stirred at 20° C. for 2 h. NaBH$_3$CN (276 mg, 4.38 mmol) was added and the resulting mixture was stirred at 20° C. for 16 h. The reaction solution was concentrated, the residue was washed with water and extracted with EA. The organic layer was concentrated, and the residue was purified by prep-HPLC to give the title compound (105 mg, Yield 33.9%). $^1$H NMR (CD$_3$OD, 400 MHz): δ 7.37-7.29 (m, 1H), 7.23-7.17 (m, 1H), 7.17-6.97 (m, 6H), 4.18-4.08 (m, 1H), 4.07-3.90 (m, 3H), 3.80-3.68 (m, 2H), 3.62-3.51 (m, 3H), 3.51-3.43 (m, 1H), 2.99-2.79 (m, 7H), 2.75-2.58 (m, 2H), 1.94-1.79 (m, 2H), 1.72-1.59 (m, 2H). LCMS (m/z): 424.1 (M+1).

Compound 50

N-(3-(3,4-dihydroisoquinolin-2(1H)-yl)-2-hydroxypropyl)-3-(oxetan-3-ylamino)benzamide

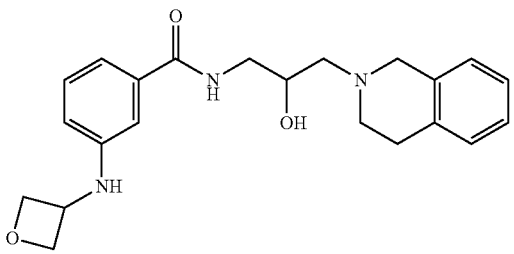 [SMILES: O=C(NCC(O)CN1CCc2ccccc2C1)c1cccc(NC2COC2)c1]

Step 1: N-(3-(3,4-dihydroisoquinolin-2(1H)-yl)-2-hydroxypropyl)-3-(oxetan-3-ylamino)benzamide

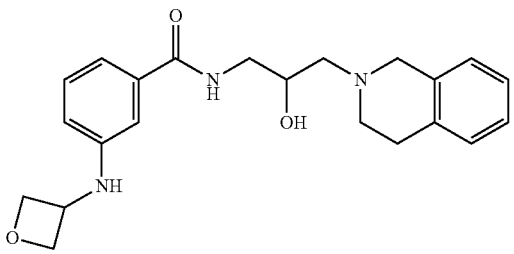 [SMILES: O=C(NCC(O)CN1CCc2ccccc2C1)c1cccc(NC2COC2)c1]

To a solution of 3-amino-N-(3-(3,4-dihydroisoquinolin-2 (1H)-yl)-2-hydroxypropyl)benzamide (100 mg, 0.31 mmol) in MeOH (5 mL) was added AcOH (0.05 mL) and oxetan-3-one (22 mg, 0.31 mmol). The mixture was stirred at 22° C. for 2 h. NaBH$_3$CN (98 mg, 1.55 mmol) was added, and the resulting mixture was stirred at 22° C. for 2 h. The reaction solution was concentrated, the residue was washed with water, extracted with EA, the organic layer was concentrated, and the residue was purified by prep-HPLC to give the title compound (17 mg, Yield 14.4%). $^1$H NMR (CD$_3$OD, 400 MHz): δ 7.17-6.97 (m, 6H), 6.96-6.88 (m, 1H), 6.72-6.62 (m, 1H), 5.03-4.95 (m, 2H), 4.67-4.59 (m, 1H), 4.59-4.49 (m, 2H), 4.15-4.04 (m, 1H), 3.80-3.69 (m, 2H), 3.56-3.40 (m, 2H), 2.96-2.79 (m, 4H), 2.73-2.58 (m, 2H). LCMS (m/z): 382.2 (M+1).

Compound 51

N-(3-(3,4-dihydroisoquinolin-2(1H)-yl)-2-hydroxypropyl)-3-(morpholinomethyl)benzamide

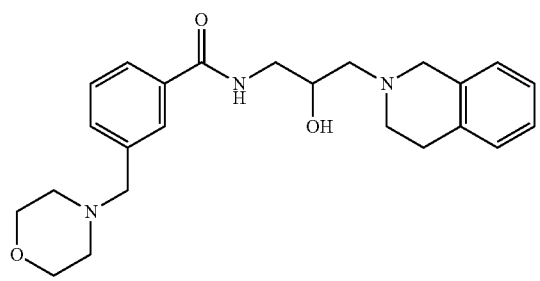 [SMILES: O=C(NCC(O)CN1CCc2ccccc2C1)c1cccc(CN2CCOCC2)c1]

Step 1: methyl 3-(morpholinomethyl)benzoate

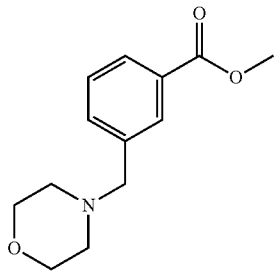 [SMILES: COC(=O)c1cccc(CN2CCOCC2)c1]

To a solution of methyl 3-formylbenzoate (100 mg, 0.61 mmol) in MeOH (5 mL) was added morpholine (100 mg, 1.15 mmol) and the resulting mixture was stirred for 10 min at 20° C. To the mixture was added NaBH$_3$CN (100 mg, 1.59 mmol) and the reaction mixture was stirred for 30 min at 20° C. The solution was concentrated and the residue was purified by prep-TLC to afford the title compound (130 g, Yield 90.9%). $^1$H NMR (CD$_3$OD, 400 MHz): δ 7.98-8.05 (m, 1H), 7.92 (td, J=1.4, 7.7 Hz, 1H), 7.57-7.62 (m, 1H), 7.37-7.53 (m, 1H), 3.90 (s, 3H), 3.66-3.71 (m, 4H), 3.57 (s, 2H), 2.41-2.49 (m, 4H).

Step 2: 3-(morpholinomethyl)benzoic Acid

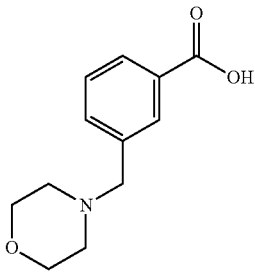 [SMILES: O=C(O)c1cccc(CN2CCOCC2)c1]

To a solution of methyl 3-(morpholinomethyl)benzoate (150 mg, 0.64 mmol) in MeOH (2 mL) and water (2 mL) was added LiOH (55 mg, 1.31 mmol) at 20° C. The mixture was heated to 60° C. for 1 h. The reaction solution was concentrated and purified via prep-HPLC to give the title compound (60 mg, Yield 42.5%). LCMS (m/z): 222 (M+1).

Step 3: N-(3-(3,4-dihydroisoquinolin-2(1H)-yl)-2-hydroxypropyl)-3-(morpholinomethyl)benzamide

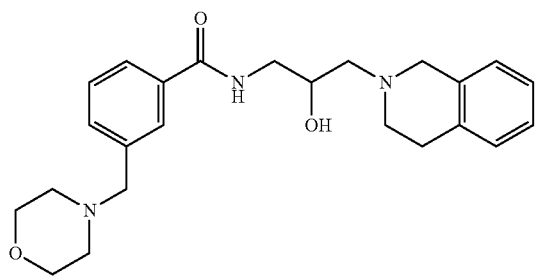 [SMILES: O=C(NCC(O)CN1CCc2ccccc2C1)c1cccc(CN2CCOCC2)c1]

To a solution of 3-(morpholinomethyl)benzoic acid (60 mg, 0.27 mmol) in MeCN (3 mL) were added 1-amino-3-(3,4-dihydroisoquinolin-2(1H)-yl)propan-2-ol (60 mg, 0.29 mmol), TEA (70 mg, 0.69 mmol) and the resulting mixture was stirred at 20° C. for 10 min. BOPCl (70 mg, 0.28 mmol) was added and the reaction mixture was stirred at 20° C. for 16 h. The reaction solution was concentrated and the residue was purified by prep-HPLC to give the title compound (4 mg, Yield 3.6%). ¹H NMR (CD₃OD, 400 MHz): δ 7.77 (s, 1H), 7.68 (d, J=7.8 Hz, 1H), 7.50 (d, J=7.7 Hz, 1H), 7.35 (t, J=7.7 Hz, 1H), 7.07-7.14 (m, 3H), 7.00-7.06 (m, 1H), 4.11 (quin, J=6.0 Hz, 1H), 3.75 (s, 2H), 3.64-3.72 (m, 4H), 3.43-3.59 (m, 4H), 2.83-2.93 (m, 4H), 2.61-2.74 (m, 2H), 2.44 (brs, 4H). LCMS (m/z): 410.1 (M+1).
Compound 52

N-(3-(3,4-dihydroisoquinolin-2(1H)-yl)-2-hydroxypropyl)-3-((1-(tetrahydro-2H-pyran-4-yl)ethyl)amino)benzamide

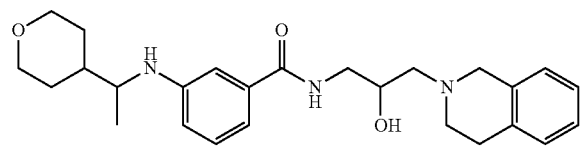 [SMILES: CC(Nc1cccc(C(=O)NCC(O)CN2CCc3ccccc3C2)c1)C1CCOCC1]

Step 1: N-(3-(3,4-dihydroisoquinolin-2(1H)-yl)-2-hydroxypropyl)-3-((1-(tetrahydro-2H-pyran-4-yl)ethyl)amino)benzamide

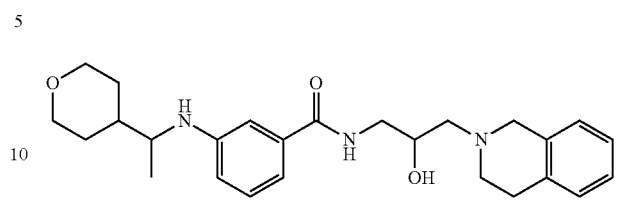

A solution of 3-amino-N-(3-(3,4-dihydroisoquinolin-2(1H)-yl)-2-hydroxypropyl) benzamide (130 mg, 0.4 mmol), 1-(tetrahydro-2H-pyran-4-yl)ethanone (52 mg, 0.4 mmol) and AcOH (0.1 mL) in MeOH (10 mL). The mixture was stirred at 22° C. for 1 h, then NaBH₃CN (76 mg, 1.2 mmol) was added. The mixture was stirred at 22° C. for 4 h. The reaction mixture was concentrated and quenched with water. The mixture solution was extracted with DCM, the combined organic layers were concentrated and the residue was purified by prep-TLC to give the desired compound (14.0 mg, Yield 8%). ¹H NMR (CD₃OD, 400 MHz): δ 6.90-7.07 (m, 6H), 6.81 (d, J=7.5 Hz, 1H), 6.64 (d, J=8.03 Hz, 1H), 3.98-4.04 (m, 1H), 3.87 (d, J=11.3 Hz, 2H), 3.70 (s, 2H), 3.28-3.45 (m, 5H), 2.82 (brs, 4H), 2.56-2.65 (m, 2H), 1.70 (d, J=13.8 Hz, 1H), 1.57 (brs, 1H), 1.17-1.37 (m, 3H), 1.04 (d, J=6.3 Hz, 3H). LCMS (m/z): 438.3 (M+1).
Compound 53

N-(3-(3,4-dihydroisoquinolin-2(1H)-yl)-2-hydroxypropyl)-3-((2,2-dimethyltetrahydro-2H-pyran-4-yl)amino)benzamide

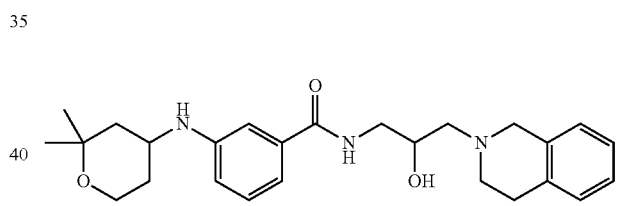

Step 1: N-(3-(3,4-dihydroisoquinolin-2(1H)-yl)-2-hydroxypropyl)-3-((2,2-dimethyltetrahydro-2H-pyran-4-yl)amino)benzamide

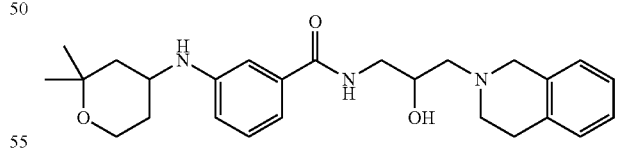

A solution of 3-amino-N-(3-(3,4-dihydroisoquinolin-2(1H)-yl)-2-hydroxypropyl) benzamide (130 mg, 0.4 mmol), 2,2-dimethyldihydro-2H-pyran-4(3H)-one (52 mg, 0.4 mmol) and AcOH (0.1 mL) in MeOH (10 mL). The mixture was stirred at 22° C. for 12 h, then NaBH₃CN (76 mg, 1.2 mmol) was added and the resulting mixture was stirred at 22° C. for 2 h. The reaction mixture was concentrated and quenched with water. The aqueous mixture was extracted with DCM, the combined organic layers were concentrated and the residue was purified by prep-HPLC to give the title compound (5.5 mg, Yield 3.1%). ¹H NMR (CD₃OD, 400

MHz): δ 8.42 (brs, 1H) 7.00-7.33 (m, 7H) 6.84 (d, J=7.8 Hz, 1H) 4.21-4.41 (m, 3H) 3.40-3.92 (m, 8H) 3.11-3.20 (m, 3H) 1.91-2.07 (m, 2H) 1.18-1.44 (m, 8H). LCMS (m/z): 438.3 (M+1).

Compound 54

N-(3-(3,4-dihydroisoquinolin-2(1H)-yl)-2-hydroxypropyl)-5-((tetrahydro-2H-pyran-4-yl)amino)nicotinamide

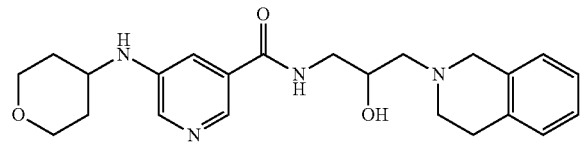 [SMILES: O=C(NCC(O)CN1CCc2ccccc2C1)c1cncc(NC2CCOCC2)c1]

Step 1. 5-bromo-N-(3-(3,4-dihydroisoquinolin-2(1H)-yl)-2-hydroxypropyl)nicotinamide

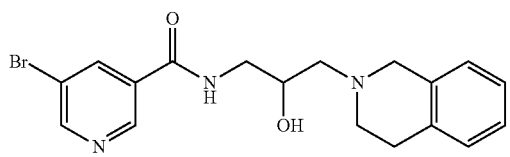 [SMILES: O=C(NCC(O)CN1CCc2ccccc2C1)c1cncc(Br)c1]

A solution of 1-amino-3-(3,4-dihydroisoquinolin-2(1H)-yl)propan-2-ol (326 mg, 1.58 mmol), 5-bromonicotinic acid (300 mg, 1.5 mmol), HATU (627 mg, 1.65 mmol) and TEA (181.8 mg, 1.8 mmol) in DCM (15 mL) was stirred at 22° C. for 2 h, at which time the reaction mixture was diluted with water and extracted with DCM. The combined organic layers were dried and concentrated and the residue was purified by column chromatography to give title compound that was used in the next step without further purification (200 mg, Yield 34%). LCMS (m/z): 390/392 (M+1/M+2).

Step 2: N-(3-(3,4-dihydroisoquinolin-2(1H)-yl)-2-hydroxypropyl)-5-((tetrahydro-2H-pyran-4-yl)amino)nicotinamide

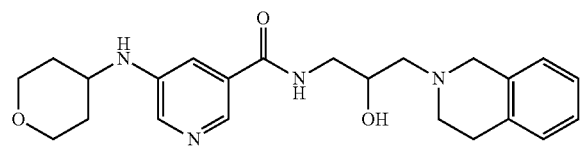 [SMILES: O=C(NCC(O)CN1CCc2ccccc2C1)c1cncc(NC2CCOCC2)c1]

To a solution of 5-bromo-N-(3-(3,4-dihydroisoquinolin-2(1H)-yl)-2-hydroxypropyl) nicotinamide (100 mg, 0.26 mmol) in dioxane (10 mL) were added tetrahydro-2H-pyran-4-amine (39.4 mg, 0.29 mmol), Pd$_2$(dba)$_3$ (20 mg, 0.02 mmol), NaOtBu (24 mg, 0.52 mmol) and BINAP (26 mg, 0.04 mmol). The reaction mixture was heated at 110° C. for 6 h under N$_2$. The mixture was concentrated and the residue was dissolved in EA, washed with water, the organic layer was collected, dried, and the residue purified by prep-HPLC to give the title compound (25.9 mg, Yield 24%). $^1$H NMR (CD$_3$OD, 400 MHz): δ 8.17 (d, J=1.5 Hz, 1H), 8.05 (d, J=2.5 Hz, 1H), 7.43-7.35 (m, 1H), 7.13-7.06 (m, 3H), 7.04-6.99 (m, 1H), 4.17-4.07 (m, 1H), 4.02-3.93 (m, 2H), 3.73 (s, 2H), 3.63-3.50 (m, 4H), 3.41 (dd, J=6.8, 13.6 Hz, 1H), 2.94-2.82 (m, 4H), 2.70-2.57 (m, 2H), 2.03-1.93 (m, 2H), 1.57-1.45 (m, 2H). LCMS (m/z): 411.1 (M+1).

Compound 55

N-(3-(3,4-dihydroisoquinolin-2(1H)-yl)-2-hydroxypropyl)-4-((tetrahydro-2H-pyran-4-yl)amino)picolinamide

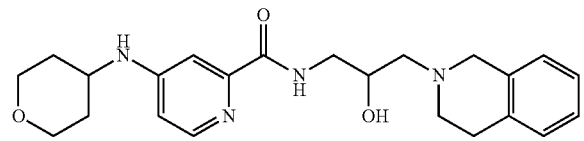 [SMILES: O=C(NCC(O)CN1CCc2ccccc2C1)c1cc(NC2CCOCC2)ccn1]

Step 1: methyl 4-((tetrahydro-2H-pyran-4-yl)amino)picolinate

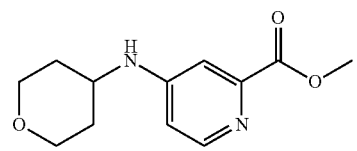 [SMILES: COC(=O)c1cc(NC2CCOCC2)ccn1]

To a solution of compound methyl 4-chloropicolinate (100 mg, 0.59 mmol), tetrahydro-2H-pyran-4-amine hydrochloride (121 mg, 0.88 mmol), Cs$_2$CO$_3$ (762 mg, 2.34 mmol), Pd$_2$(dba)$_3$ (54 mg, 0.059 mmol) and XPhos (28 mg, 0.06 mmol) in toluene (10 mL) was stirred and heated at 110° C. under N$_2$ for 16 h. The catalyst was filtered and the filtrate was washed with EA, concentrated in vacuo and the residue was purified by prep-TLC to give the title product (50 mg, Yield 36.2%). LCMS (m/z): 237.2 (M+1).

Step 2: N-(3-(3,4-dihydroisoquinolin-2(1H)-yl)-2-hydroxypropyl)-4-((tetrahydro-2H-pyran-4-yl)amino)picolinamide To a solution of compound methyl 4-((tetrahydro-2H-pyran-4-yl)amino)picolinate (50 mg, 0.21 mmol) and 1-amino-3-(3,4-dihydroisoquinolin-2(1H)-yl)propan-2-ol (44 mg, 0.21 mmol) in MeOH (2 mL) was stirred at 100° C. under microwave heating for 3 h. The reaction mixture was purified by prep-HPLC to give the title compound (29.9 mg, Yield 34.4%). $^1$H NMR (400 MHz, CD$_3$OD): δ 7.95 (d, J=5.6 Hz, 1H), 7.26 (d, J=2.4 Hz, 1H), 7.13-7.05 (m, 3H), 7.03-6.98 (m, 1H), 6.62 (dd, J=2.4, 5.6 Hz, 1H), 4.07 (quin, J=6.0 Hz, 1H), 4.01-3.93 (m, 2H), 3.72 (s, 2H), 3.66-3.60 (m, 1H), 3.60-3.57 (m, 1H), 3.57-3.52 (m, 2H), 3.49-3.42 (m, 1H), 2.95-2.89 (m, 2H), 2.87-2.81 (m, 2H), 2.65 (d, J=6.0 Hz, 2H), 1.97 (d, J=12.8 Hz, 2H), 1.59-1.47 (m, 2H). LCMS (m/z): 411.1 (M+1).

Compound 57

N-(3-(3,4-dihydroisoquinolin-2(1H)-yl)-2-hydroxy-propyl)-2-fluoro-5-((tetrahydro-2H-pyran-4-yl)amino)benzamide

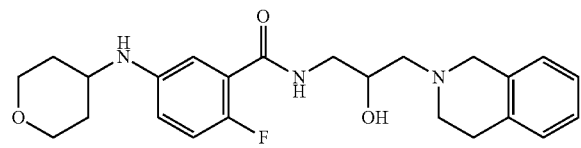 [SMILES: O=C(NCC(O)CN1CCc2ccccc2C1)c1cc(NC2CCOCC2)ccc1F]

Step 1: 5-amino-N-(3-(3,4-dihydroisoquinolin-2(1H)-yl)-2-hydroxypropyl)-2-fluorobenzamide

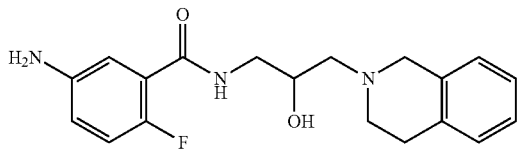 [SMILES: Nc1ccc(F)c(C(=O)NCC(O)CN2CCc3ccccc3C2)c1]

The solution of 5-amino-2-fluorobenzoic acid (200 mg, 1.29 mmol) and HATU (490 mg, 1.29 mmol) in DCM (15 mL) was stirred at 17° C. for 30 min. Then 1-amino-3-(3,4-dihydroisoquinolin-2(1H)-yl)propan-2-ol (265 mg, 1.29 mmol) and DIPEA (333 mg, 2.58 mmol) was added and the resulting solution was stirred at 17° C. for 16 h. The solution was concentrated and the residue was purified by column chromatography to give desired product (372 mg, Yield 84%).

Step 2: N-(3-(3,4-dihydroisoquinolin-2(1H)-yl)-2-hydroxypropyl)-2-fluoro-5-((tetrahydro-2H-pyran-4-yl)amino)benzamide

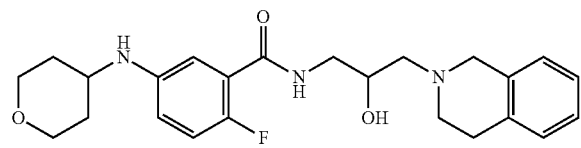 [SMILES: O=C(NCC(O)CN1CCc2ccccc2C1)c1cc(NC2CCOCC2)ccc1F]

A solution of 5-amino-N-(3-(3,4-dihydroisoquinolin-2(1H)-yl)-2-hydroxypropyl)-2-fluorobenzamide (372 mg, 1.08 mmol), dihydro-2H-pyran-4(3H)-one (108 mg, 1.08 mmol) and AcOH (0.05 mL) in MeOH (20 mL) was stirred at 17° C. for 2 h. Then NaBH$_3$CN (109 mg, 1.63 mmol) was added and the resulting solution was stirred at 17° C. for 4 h. The solution was concentrated and the residue was purified by column chromatography to afford the title product (121.5 mg, Yield 17.5%). $^1$H NMR (CD$_3$OD, 400 MHz): δ 7.16-7.07 (m, 3H), 7.03 (dd, J=2.9, 5.9 Hz, 2H), 6.95 (dd, J=8.9, 10.7 Hz, 1H), 6.79 (td, J=3.6, 8.8 Hz, 1H), 4.11 (quin, J=6.0 Hz, 1H), 3.98 (d, J=11.5 Hz, 2H), 3.80-3.69 (m, 2H), 3.64-3.40 (m, 5H), 2.98-2.81 (m, 4H), 2.72-2.60 (m, 2H), 1.99 (d, J=12.8 Hz, 2H), 1.56-1.39 (m, 2H). LCMS (m/z): 428.2 (M+1).

Compound 58

N-(3-(3,4-dihydroisoquinolin-2(1H)-yl)-2-hydroxy-propyl)-4-((tetrahydro-2H-pyran-4-yl)oxy)benzamide

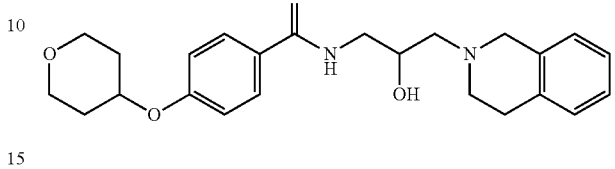

Step 1: methyl 4-((tetrahydro-2H-pyran-4-yl)oxy)benzoate

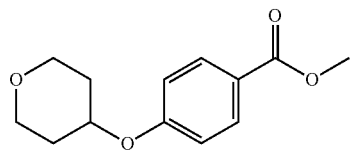 [SMILES: COC(=O)c1ccc(OC2CCOCC2)cc1]

To a solution of ethyl 4-hydroxybenzoate (500 mg, 3.0 mmol), tetrahydro-2H-pyran-4-ol (307.3 mg, 3.0 mmol) and PPh$_3$ (944 mg, 3.6 mmol) in THF (15 mL) was added DEAD (627 mg, 3.6 mmol) at 0° C. The mixture was the warmed to 21° C. and stirred for 16 h. The mixture was treated with water and the organic layer was washed with brine, dried over Na$_2$SO$_4$, concentrated and the residue was purified by column chromatography to give the title compound (320 mg, Yield 45%). $^1$H NMR (CDCl$_3$, 400 MHz): δ 7.92 (d, J=8.9 Hz, 1H), 6.75-6.94 (m, 1H), 4.44-4.59 (m, 1H), 4.28 (d, J=7.2 Hz, 2H), 3.83-4.00 (m, 2H), 3.46-3.60 (m, 2H), 1.88-2.05 (m, 2H), 1.67-1.83 (m, 2H), 1.31 (t, J=7.2 Hz, 3H).

Step 2: 4-((tetrahydro-2H-pyran-4-yl)oxy)benzoic Acid

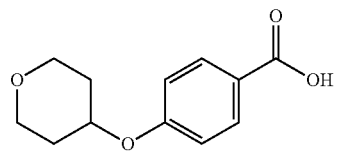 [SMILES: O=C(O)c1ccc(OC2CCOCC2)cc1]

To a solution of methyl 4-((tetrahydro-2H-pyran-4-yl)oxy)benzoate (400 mg, 1.6 mmol) in MeOH (10 ml) was added a solution of NaOH (128 mg, 3.2 mmol) in H$_2$O (4 mL) at 22° C. The mixture was stirred at 50° C. for 4 h. The mixture was concentrated and the residue was treated with water and extracted with EA. The water layer was treated with 2N HCl to pH=3. The water layer was then extracted with EA. The organic layer was washed with brine, dried over Na$_2$SO$_4$ and concentrated to give the title product which was used in next step without further purification (350 mg, Yield 98.6%). $^1$H NMR (CDCl$_3$, 400 MHz): δ 8.08 (d, J=8.9 Hz, 2H), 6.98 (d, J=8.9 Hz, 2H), 4.64 (tt, J=7.7, 3.8

Hz, 1H), 3.95-4.09 (m, 2H), 3.64 (ddd, J=11.6, 8.2, 3.3 Hz, 2H), 2.01-2.13 (m, 2H), 1.78-1.93 (m, 2H).

Step 3: N-(3-(3,4-dihydroisoquinolin-2(1H)-yl)-2-hydroxypropyl)-4-((tetrahydro-2H-pyran-4-yl)oxy) benzamide

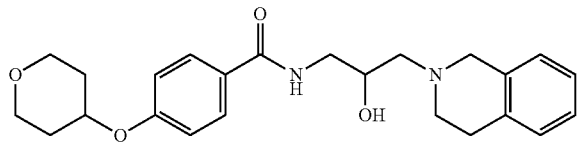 [SMILES: O=C(NCC(O)CN1CCc2ccccc2C1)c1ccc(OC2CCOCC2)cc1]

To a solution of 4-((tetrahydro-2H-pyran-4-yl)oxy)benzoic acid (150 mg, 0.67 mmol) in DMF (4 mL) was added DIEA (260 mg, 2.01 mmol), HATU (384 mg, 1.01 mmol) and 1-amino-3-(3,4-dihydroisoquinolin-2(1H)-yl)propan-2-ol (170 mg, 0.81 mmol). The reaction mixture was stirred at 22° C. for 16 h. The mixture was treated with water and extracted with EA. The organic layer was washed with brine, dried over Na$_2$SO$_4$, concentrated and the residue was was purified by prep-HPLC to give the title compound (206.1 mg, Yield 74.9%). $^1$H NMR (CD$_3$OD, 400 MHz): δ 7.84 (d, J=8.8 Hz, 2H), 7.26-7.37 (m, 3H), 7.19-7.25 (m, 1H), 7.05 (d, J=8.8 Hz, 2H), 4.59-4.74 (m, 2H), 4.31-4.49 (m, 2H), 3.93-4.01 (m, 2H), 3.86 (brs, 1H), 3.63 (ddd, J=11.7, 8.8, 3.0 Hz, 2H), 3.53 (qd, J=14.0, 5.7 Hz, 3H), 3.37-3.44 (m, 1H), 3.11-3.32 (m, 3H), 2.02-2.12 (m, 2H), 1.69-1.81 (m, 2H). LCMS (m/z): 411.2 (M+1).

Compound 166

(S)—N-(3-(3,4-dihydroisoquinolin-2(1H)-yl)-2-hydroxypropyl)-6-(oxetan-3-ylamino)pyrimidine-4-carboxamide

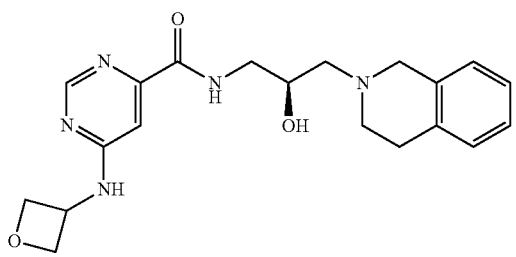 [SMILES: O=C(NC[C@H](O)CN1CCc2ccccc2C1)c1cc(NC2COC2)ncn1]

Step 1: 6-Hydroxypyrimidine-4-carboxylic Acid

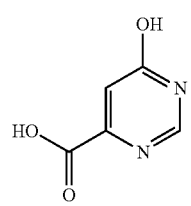

To a solution of sodium (Z)-1,4-diethoxy-1,4-dioxobut-2-en-2-olate (55.0 g, 262 mmol) in H$_2$O (500 mL) was added formimidamide acetate (27.3 g, 262 mmol) and NaOH (10.5 g). After addition, the resulting mixture was stirred at 25° C. for 16 h then concentrated and then acidified by added aqueous HCl (1N) until pH=1. The resulting solid was collected by filtration, washed with H$_2$O and ether to give 6-hydroxypyrimidine-4-carboxylic acid (6.0 g, yield: 16.3%). $^1$H NMR (400 MHz, DMSO-d$_6$) δ 12.89 (s, 1H), 8.24 (s, 1H), 6.83 (s, 1H).

Step 2: 6-chloropyrimidine-4-carboxylic Acid

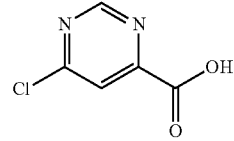

To a solution of 6-hydroxypyrimidine-4-carboxylic acid (6.0 g, 42.8 mmol) in EtOAc (90 mL) was added (COCl)$_2$ (12 mL) dropwise, followed by a few drops of DMF. The mixture was stirred at 75° C. for 3 h, and then at 25° C. for 16 h. The solvent was evaporated to give the crude 6-chloropyrimidine-4-carboxylic acid (6.3 g, yield: 92.9%). $^1$H NMR (400 MHz, DMSO-d$_6$) δ 8.31 (s, 1H), 6.88 (s, 1H).

Step 3: 6-chloropyrimidine-4-carbonyl chloride

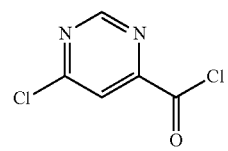

A drop of DMF was added to a stirred solution of 6-chloropyrimidine-4-carboxylic acid (5.5 g, 34.7 mmol) and (COCl)$_2$ (12 mL) in DCM (100 mL). The mixture was stirred at 25° C. for 2 h. The solvent was evaporated under reduced pressure to give crude 6-chloropyrimidine-4-carbonyl chloride (6.0 g, yield: 97.7%). $^1$H NMR (400 MHz, DMSO-d$_6$) δ 9.20 (s, 1H), 8.10 (s, 1H).

Step 4: (S)-6-chloro-N-(3-(3,4-dihydroisoquinolin-2(1H)-yl)-2-hydroxypropyl)pyrimidine-4-carboxamide

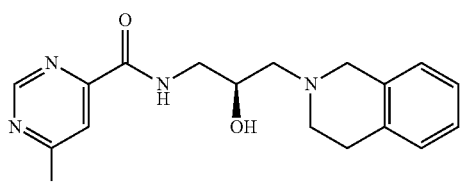

To a stirred and cooled (0° C.) solution of (S)-1-amino-3-(3,4-dihydroisoquinolin-2(1H)-yl) propan-2-ol (7.15 g, 34.7 mmol) and Et$_3$N (14.0 g, 138.8 mmol) in DCM (100 mL) was added 6-chloropyrimidine-4-carbonyl chloride (5.5 g, 34.7 mmol). After addition, the resulting mixture was stirred at 25° C. for 16 h, at which time LCMS showed the completion of the reaction. The solvent was evaporated and the residue purified by flash chromatography to give the (S)-6-chloro-N-(3-(3,4-dihydroisoquinolin-2(1H)-yl)-2-hydroxypropyl)pyrimidine-4-carboxamide (7.2 g, yield: 60%). LCMS (m/z): 347.0 [M+H]+

Step 5: (S)—N-(3-(3,4-dihydroisoquinolin-2(1H)-yl)-2-hydroxypropyl)-6-(oxetan-3-ylamino)pyrimidine-4-carboxamide

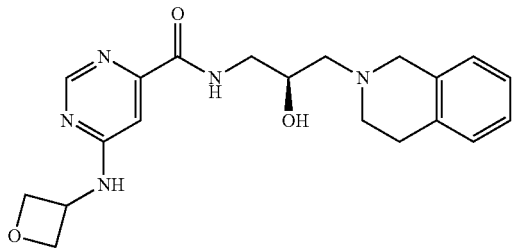 [SMILES: O=C(NC[C@H](O)CN1CCc2ccccc2C1)c1cc(NC2COC2)ncn1]

To a solution of (S)-6-chloro-N-(3-(3,4-dihydroisoquinolin-2(1H)-yl)-2-hydroxy propyl)pyrimidine-4-carboxamide (347 mg, 1 mmol) in i-PrOH (5 mL) was added oxetan-3-amine (73.1 mg, 1 mmol) and DIPEA (129 mg, 1 mmol). The resulting mixture was stirred at 110° C. for 16 hours, at which time LCMS showed the completion of the reaction. After evaporation of the solvent, the residue was purified by preparative HPLC to give the target compound (S)—N-(3-(3,4-dihydroisoquinolin-2(1H)-yl)-2-hydroxypropyl)-6-(oxetan-3-ylamino)pyrimidine-4-carboxamide (62.5 mg, yield: 16.3%). $^1$H NMR (400 MHz, MeOD-d$_4$) δ 8.24 (s, 1H), 7.15-7.05 (m, 4H), 7.02-6.98 (m, 1H), 5.09 (s, 1H), 4.95 (t, J=6.8 Hz, 2H), 4.59 (t, J=6.3 Hz, 2H), 4.10-4.03 (m, 1H), 3.72 (s, 2H), 3.56-3.46 (m, 2H), 2.96-2.91 (m, 2H), 2.87-2.80 (m, 2H), 2.65 (d, J=6.3 Hz, 2H). LCMS (m/z): 384.1 [M+H]+.
Compound 84

N-(3-(3,4-dihydroisoquinolin-2(1H)-yl)-2-hydroxypropyl)-2-methylquinoline-6-carboxamide

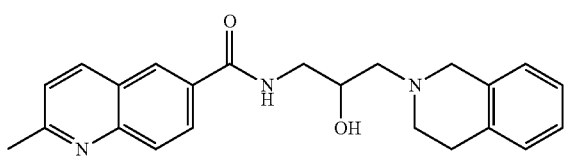 [SMILES: Cc1ccc2cc(C(=O)NCC(O)CN3CCc4ccccc4C3)ccc2n1]

Step 1: 2-(oxiran-2-ylmethyl)-1,2,3,4-tetrahydroisoquinoline

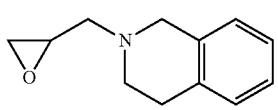 [SMILES: c1ccc2c(c1)CCN(CC1CO1)C2]

To a stirring solution of 1,2,3,4-tetrahydroisoquinoline (15 g, 0.11 mol) in MeCN (100 mL) at 0° C. was added K$_2$CO$_3$ (30.7 g, 0.23 mol), then 2-(bromomethyl) oxirane (17 g, 0.12 mol) added slowly over a period of 1 h. After the addition the solution was stirred at 21° C. for 12 h. The resulting solid was then removed by filtration and washed with MeCN and the combined organic filtrate was concentrated under reduced pressure to give the crude product. This residue was used into next step without further purification (17 g, Yield: 78%). LCMS (m/z): 190.1 (M+1).

Step 2: 1-amino-3-(3,4-dihydroisoquinolin-2(1H)-yl)propan-2-ol

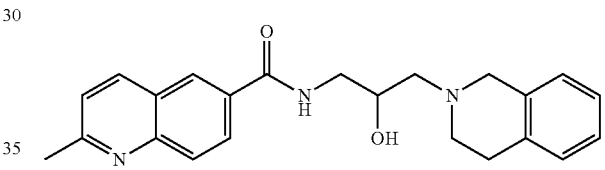

NH$_3$ was bubbled into a stirred and cooled (−78° C.) solution of 2-(oxiran-2-ylmethyl)-1,2,3,4-tetrahydroisoquinoline (17 g, 0.09 mol) in EtOH (300 mL). After saturation, the reaction mixture was then sealed and heated at 80° C. for 3 h. After LCMS indicated the reaction to be complete, the reaction mixture was concentrated and the crude product used in the next step without further purification (18 g, Yield 96%). LCMS (m/z): 207.1 (M+1).

Step 3: N-(3-(3,4-dihydroisoquinolin-2(1H)-yl)-2-hydroxypropyl)-2-methylquinoline-6-carboxamide

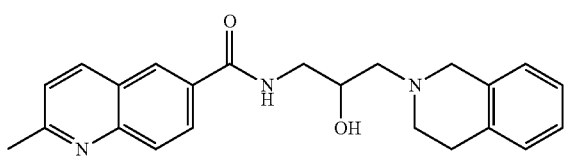 [SMILES: Cc1ccc2cc(C(=O)NCC(O)CN3CCc4ccccc4C3)ccc2n1]

To a solution of 2-methylquinoline-6-carboxylic acid (100 mg, 0.535 mmol) in DCM (20 mL) was added HATU (244 mg, 0.642 mmol) and TEA (162 mg, 1.604 mmol). The mixture was stirred at 15° C. for 30 minutes before 1-amino-3-(3,4-dihydro isoquinolin-2(1H)-yl)propan-2-ol (110 mg, 0.535 mmol) was added. The resulting mixture was stirred for another 16 h at 15° C., at which point LCMS showed the completion of the reaction. The mixture was concentrated and the residue was purified by Preparation HPLC to give the desired title compound (106.2 mg, 53%). $^1$H NMR (400 MHz, METHANOL-d$_4$) δ=8.32 (d, J=1.9 Hz, 1H), 8.14 (d, J=8.4 Hz, 1H), 8.09 (dd, J=2.1, 8.8 Hz, 1H), 7.93 (d, J=8.8 Hz, 1H), 7.49 (d, J=8.4 Hz, 1H), 7.16-7.08 (m, 3H), 7.08-7.03 (m, 1H), 4.18 (quin, J=6.1 Hz, 1H), 3.79 (s, 2H), 3.59 (d, J=5.8 Hz, 2H), 2.94-2.88 (m, 4H), 2.79-2.68 (m, 5H). LCMS (m/z): 376.0 (M+1).
Compound 219

(R)—N-(3-(3,4-dihydroisoquinolin-2(1H)-yl)-2-hydroxypropyl)-2-methylquinoline-6-carboxamide

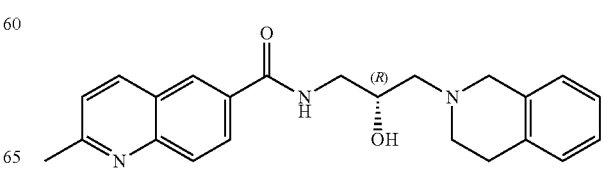

To a solution of 2-methylquinoline-6-carboxylic acid (200 mg, 1.070 mmol) in DCM (30 mL), was added HATU (489 mg, 1.283 mmol) and TEA (324 mg, 3.208 mmol). The solution was stirred at 15° C. for 30 minutes before (R)-1-amino-3-(3,4-dihydro isoquinolin-2(1H)-yl)propan-2-ol (264 mg, 1.283 mmol) was added. The resulting solution was stirred for another 16 h at 15° C., until the reaction was complete by LCMS analysis. The mixture was then concentrated under vacuum to give the crude material which was purified by Preparative HPLC to give the title compound (118 mg, 29%). $^1$H NMR (400 MHz, METHANOL-d$_4$) δ 8.33 (d, J=1.9 Hz, 1H), 8.15 (d, J=8.5 Hz, 1H), 8.09 (dd, J=2.1, 8.8 Hz, 1H), 7.93 (d, J=8.8 Hz, 1H), 7.49 (d, J=8.4 Hz, 1H), 7.15-7.05 (m, 4H), 4.18 (quin, J=6.1 Hz, 1H), 3.79 (s, 2H), 3.63-3.55 (m, 2H), 2.95-2.90 (m, 4H), 2.76 (s, 3H), 2.76-2.68 (m, 2H). LCMS (m/z): 376.1 [M+H]

Compound 221

(S)—N-(3-(3,4-dihydroisoquinolin-2(1H)-yl)-2-hydroxypropyl)-2-methylquinoline-6-carboxamide

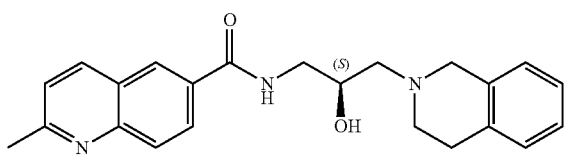

To a solution of 2-methylquinoline-6-carboxylic acid (1 g, 5.35 mmol) in DCM (100 mL), was added HATU (2.44 g, 6.42 mmol) and TEA (1620 mg, 16.043 mmol). The solution was stirred at 15° C. for 30 minutes before (S)-1-amino-3-(3,4-dihydro isoquinolin-2(1H)-yl)propan-2-ol (1.76 g, 8.55 mmol) was added. The resulting solution was stirred for 16 h at 15° C. until LCMS analysis showed the reaction to be complete. The mixture was then concentrated under vacuum and the residue purified by Preparative HPLC to give the desired title compound (502.1 mg, 25%). $^1$H NMR (400 MHz, METHANOL-d$_4$) δ 8.31 (br. s., 1H), 8.08 (d, J=8.8 Hz, 1H), 8.12 (d, J=8.4 Hz, 1H), 7.91 (d, J=8.8 Hz, 1H), 7.47 (d, J=8.3 Hz, 1H), 7.17-7.03 (m, 4H), 4.23-4.11 (m, 1H), 3.78 (br. s., 2H), 3.59 (d, J=5.5 Hz, 2H), 2.91 (br. s., 4H), 2.78-2.69 (m, 5H). LCMS (m/z): 376.1 [M+H]$^+$.

Compound 208

(S)-6-((1-acetylpiperidin-4-yl)amino)-N-(3-(3,4-dihydroisoquinolin-2(1H)-yl)-2-hydroxypropyl)pyrimidine-4-carboxamide

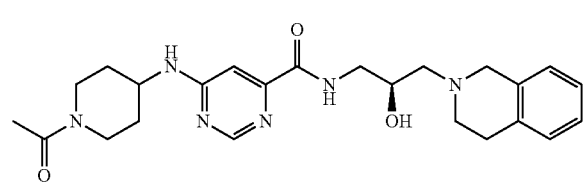 [SMILES: CC(=O)N1CCC(Nc2cc(C(=O)NC[C@H](O)CN3CCc4ccccc4C3)ncn2)CC1]

Step 1: tert-butyl (1-acetylpiperidin-4-yl)carbamate

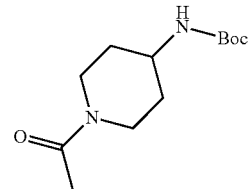 [SMILES: CC(=O)N1CCC(NC(=O)OC(C)(C)C)CC1]

To a solution of tert-butyl piperidin-4-ylcarbamate (200 g, 1 mol) and Et$_3$N (150 g, 1.5 mol) in DCM (3000 mL) was added Ac$_2$O (102 g, 1 mol) dropwise over 1 h, while maintained the temperature at 0° C. After addition, the mixture was stirred 0° C. for another 2 h, at which time TLC showed the reaction was completed. The solution was quenched by addition of water (1 L). The organic phase was collected and washed with saturated aqueous NaHCO$_3$ (1 L), dried (Na$_2$SO$_4$) and concentrated to give crude product. Four batches were run in parallel and produced a combined crude product weight of 670 g. This crude was used directly in the step. LCMS (m/z): 243.1 (M+1).

Step 2: 1-(4-aminopiperidin-1-yl)ethanone hydrochloride

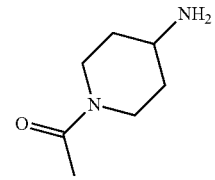

To a solution of tert-butyl (1-acetylpiperidin-4-yl)carbamate (330 g, 1.36 mol) in MeOH (1000 mL) was added HCl/MeOH (4M, 300 mL) over 30 min to maintain the temperature at 0° C. After addition, the mixture was stirred at 0° C. for another 2 h and then concentrated to give the crude product. Two batches were run in parallel and produced a combined crude product weight of 310 g. This crude was used in next step without further purification. $^1$H NMR (400 MHz, D$_2$O) δ 4.35 (dd, J=2.0, 12.0 Hz, 1H), 3.98-3.85 (m, 1H), 3.44-3.30 (m, 1H), 3.18-3.05 (m, 1H), 2.75-2.58 (m, 1H), 2.06-1.92 (m, 5H), 1.61-1.31 (m, 2H); LCMS (m/z): 143.1 (M+1).

Step 3: 6-chloropyrimidine-4-carbonyl chloride

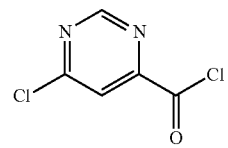

To a stirred mixture of 6-hydroxypyrimidine-4-carboxylic acid (300 g, 2.14 mol) in EA (3000 mL), oxalyl dichloride (1356 g, 10.68 mol) was dropped slowly to maintain a reaction temperature below 30° C. After addition, the mixture was stirred at 20° C. for 30 min and then 2 mL of DMF was added to the mixture. The mixture was then stirred at 80° C. for 16 hours and concentrated to give the crude product as black solid. Three batches were run in parallel and produced a combined crude product weight of 787 g. This crude was used directly in the next step.

Step 4: (S)-6-chloro-N-(3-(3,4-dihydroisoquinolin-2 (1H)-yl)-2-hydroxypropyl)pyrimidine-4-carboxamide

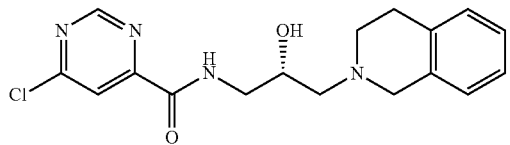 [SMILES: O=C(NC[C@H](O)CN1CCc2ccccc2C1)c1cc(Cl)ncn1]

To a stirred mixture of (S)-1-amino-3-(3,4-dihydroisoquinolin-2(1H)-yl)propan-2-ol (247 g, 1.20 mol), and TEA (250 g, 2.5 mol) in DCM (3500 mL) was added 6-chloropyrimidine-4-carbonyl chloride (190 g in 100 mL of DCM) slowly at −60° C. over 1 h. After addition, the mixture was then allowed to warm to 10° C. Stirring was continued for 1 h, at which time TLC showed the reaction was completed. The reaction was quenched by addition of water (1.5 L). The organic phase was collected, dried (Na$_2$SO$_4$) and evaporated. The residue was purified by flash chromatography (EtOAc~DCM:MeOH=10:1) to give the desired product as a pale yellow solid. Four batches were run in parallel and produced a combined crude product weight of 800 g, 49% yield. $^1$H NMR (400 MHz, MeOD-d$_4$) δ 8.73 (d, J=1.0 Hz, 1H), 8.07 (d, J=1.0 Hz, 1H), 7.17-7.06 (m, 3H), 7.00 (d, J=7.0 Hz, 1H), 4.12 (q, J=6.0 Hz, 1H), 3.74 (s, 2H), 3.64-3.53 (m, 2H), 2.94 (q, J=5.5 Hz, 2H), 2.92-2.81 (m, 2H), 2.78-2.64 (m, 2H); LCMS (m/z): 347.2 [M+H]$^+$ Step 5: (S)-6-((1-acetylpiperidin-4-yl)amino)-N-(3-(3,4-dihydroisoquinolin-2(1H)-yl)-2-hydroxypropyl) pyrimidine-4-carboxamide

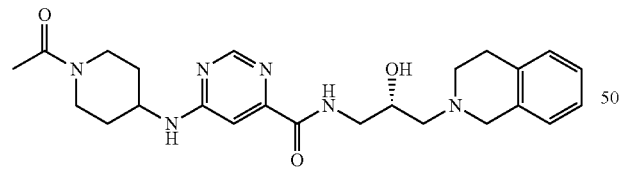

The solution of (S)-6-chloro-N-(3-(3,4-dihydroisoquinolin-2(1H)-yl)-2-hydroxypropyl)pyrimidine-4-carboxamide (190 g, 0.55 mmol) and 1-(4-aminopiperidin-1-yl)ethanone (78 g), Et$_3$N (100 g, 1 mol) in i-PrOH (2000 mL) was stirred at 60° C. for 16 h, at which time LCMS showed completed conversion. The mixture was concentrated and the residue was purified by flash chromatography to give the crude product. Four batches were run in parallel and produced a combined crude product weight of 482 g. This crude was further purified on preparative HPLC to give the title compound (325 g, >98% purity, free base form). $^1$H NMR (400 MHz, MeOD-d$_4$) 8.26 (s, 1H), 7.15-7.02 (m, 5H), 4.46 (m, 1H), 4.15-4.07 (m, 2H), 3.88 (m, 1H), 3.74 (s, 2H), 3.53 (m, 2H), 3.33 (m, 1H), 2.95-2.86 (m, 5H), 2.68 (m, 2H), 2.14-2.01 (m, 5H), 1.48-1.42 (m, 2H); LCMS (m/z): 453.3 [M+H]$^+$ Step 6: (S)-6-((1-acetylpiperidin-4-yl)amino)-N-(3-(3,4-dihydroisoquinolin-2(1H)-yl)-2-hydroxypropyl) pyrimidine-4-carboxamide hydrochloride

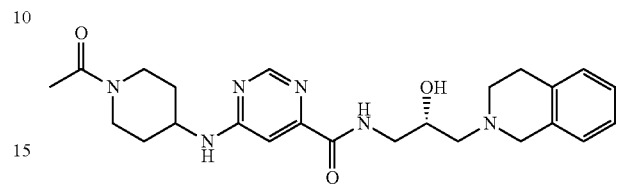

The free base was dissolved in DCM (100 mL) and added dropwise to a stirred and cooled solution of HCl (6N in EtOAc, 1 L) at −30° C. Stirring at −30° C. was continued for another 1 h and the resulting precipitate was collected by filtration. The solid was washed with DCM and EtOAc, dried to give the HCl salt of the target compound (301.4 g, yield: 30.2%) as a white solid. $^1$H NMR (400 MHz, D$_2$O) δ 8.59 (s, 1H), 7.30-7.17 (m, 3H), 7.17-7.07 (m, 2H), 4.55 (dd, J=6.4, 15.4 Hz, 1H), 4.43-4.19 (m, 4H), 3.88 (d, J=13.8 Hz, 1H), 3.82-3.72 (m, 1H), 3.52-3.33 (m, 4H), 3.31-3.08 (m, 4H), 2.86 (t, J=11.6 Hz, 1H), 2.11-1.94 (m, 5H), 1.67-1.40 (m, 2H); LCMS (m/z): 453.2 [M+H]$^+$.

Compound 254

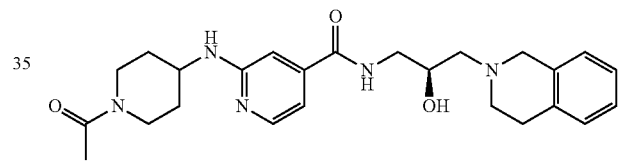

(S)-2-((1-acetylpiperidin-4-yl)amino)-N-(3-(3,4-dihydroisoquinolin-2(1H)-yl)-2-hydroxypropyl) isonicotinamide Step 1: methyl 2-((1-(tert-butoxycarbonyl)piperidin-4-yl)amino)isonicotinate

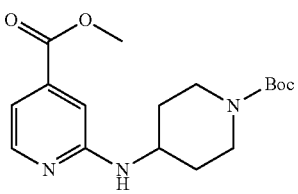 [SMILES: COC(=O)c1ccnc(NC2CCN(C(=O)OC(C)(C)C)CC2)c1]

A mixture of methyl 2-bromoisonicotinate (160 g, 0.69 mol) and tert-butyl 4-amino piperidine-1-carboxylate (200 g, 1.0 mol), Pd$_2$(dba)$_3$ (8 g, 5% w), xantphos (8 g, 5% w), Cs$_2$CO$_3$ (326 g, 1.0 mol) in dioxane (2500 mL) was stirred at 80° C. under N$_2$ for 16 h. After completion of the reaction, the mixture was concentrated and the residue dissolved in water (800 mL) and extracted with DCM (1000 mL×3). The combined organic layers were dried and concentrated. The residue was purified by flash chromatography to give the product. Nine batches were run in parallel and produced a combined product weight of 700 g, Yield: 33.4%. ¹H NMR (400 MHz, CDCl₃) δ 8.19 (d, J=5.2 Hz, 1H), 7.08 (d, J=5.2 Hz, 1H), 6.96 (s, 1H), 4.62 (d, J=8.0 Hz, 1H), 4.05 (br. s., 2H), 3.92 (s, 3H), 2.97 (t, J=12.0 Hz, 2H), 2.11-1.97 (m, 2H), 1.48 (s, 9H), 1.42-1.35 (m, 2H). LCMS (m/z): 336.1 (M+1).

Step 2: 2-((1-(tert-butoxycarbonyl)piperidin-4-yl)amino)isonicotinic Acid

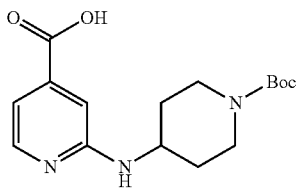 [SMILES: CC(C)(C)OC(=O)N1CCC(Nc2cc(C(=O)O)ccn2)CC1]

To a solution of methyl 2-((1-(tert-butoxycarbonyl)piperidin-4-yl)amino)isonicotinate (230 g, 0.69 mol) in MeOH (1500 mL) was added aq. NaOH (56 g, in 200 mL of water) over 20 min at 0° C. After addition, the mixture was stirred at room temperature for 2 h. MeOH was then removed under reduced pressure and the aqueous solution then pH adjusted to pH=6 by acidifying with the addition of 4N HCl. The resulting precipitate was collected by filtration, washed with water and dried to give the crude product. Three batches were run in parallel and produced a combined crude product weight of 590 g, yield: 89.4%. This crude was used in next step without further purification. LCMS (m/z): 322.2 (M+1).

Step 3: (S)-tert-butyl 4-((4-((3-(3,4-dihydroisoquinolin-2(1H)-yl)-2-hydroxypropyl)carbamoyl)pyridin-2-yl)amino)piperidine-1-carboxylate

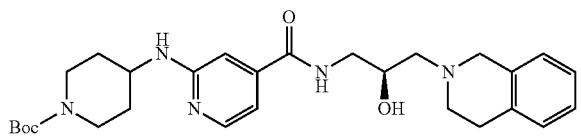 [SMILES: CC(C)(C)OC(=O)N1CCC(Nc2cc(C(=O)NC[C@H](O)CN3CCc4ccccc4C3)ccn2)CC1]

To a solution of 2-((1-(tert-butoxycarbonyl)piperidin-4-yl)amino)isonicotinic acid (150 g, 0.47 mol) in DCM (1500 mL) was added HATU (178 g, 0.47 mol) and TEA (47 g, 0.47 mol) at 20° C., then the mixture was stirred at the temperature for 2 h. (S)-1-amino-3-(3,4-dihydroisoquinolin-2(1H)-yl)propan-2-ol (113 g, 0.55 mol) was added to the solution, and the mixture was stirred at 20° C. for another 16 h, at which time TLC showed the completion of the reaction. The mixture washed with water (200 mL) and the combined organic phases were dried and concentrated. The residue was purified by flash chromatography (EtOAc~DCM:MeOH=10:1) to give the title compound as yellowish oil. Four batches were run in parallel and produced a combined product weight of 510 g, yield: 53.2%. LCMS (m/z): 510.2 [M+H]⁺.

Step 4: (S)—N-(3-(3,4-dihydroisoquinolin-2(1H)-yl)-2-hydroxypropyl)-2-(piperidin-4-ylamino)isonicotinamide hydrochloride

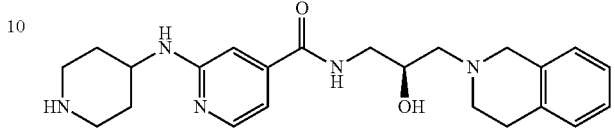

The mixture of (S)-tert-butyl 4-((4-((3-(3,4-dihydroisoquinolin-2(1H)-yl)-2-hydroxypropyl) carbamoyl)pyridin-2-yl)amino)piperidine-1-carboxylate (510 g, 1.0 mol) in DCM (1000 mL) was dropped slowly into a stirred and cooled (−30° C.) solution of HCl (4M in EtOAc, 2000 mL). After addition, the mixture was stirred at −30° C. for 30 min. The resulting solid was then collected by filtration, washed with DCM and dried under reduced pressure to give the title compound (350 g yield: 85.4%, HCl salt) as a white solid. LCMS (m/z): 410.2 [M+H]⁺

Step 5: (S)-2-((1-acetylpiperidin-4-yl)amino)-N-(3-(3,4-dihydroisoquinolin-2(1H)-yl)-2-hydroxypropyl)isonicotinamide

To a stirred mixture of (S)—N-(3-(3,4-dihydroisoquinolin-2(1H)-yl)-2-hydroxypropyl)-2-(piperidin-4-ylamino)isonicotinamide (70 g), and Et₃N (40 g) in DCM (2000 mL) was added Ac₂O (17 g) dropwise over 1 h at 0° C. After addition, the mixture was warmed to 20° C. and stirring was continued for another 1 h, at which time TLC showed the reaction was completed. The reaction mixture was washed with water (500 mL), and the organic phase dried and concentrated. The residue was then purified by flash chromatography (EtOAc~DCM:MeOH=10:1) to give crude product. Five batches were run in parallel and produced a combined crude product weight of 400 g. This crude was further purified by preparative HPLC to give the pure product (310 g, >98% purity, free base form). ¹H NMR (400 MHz, MeOD-d₄) 7.94-7.92 (d, 7.0 Hz, 1H), 7.14-7.05 (m, 4H), 6.87 (s, 1H), 6.76-6.74 (m, 1H), 4.44 (m, 1H), 4.10 (m, 1H), 3.96-3.94 (m, 2H), 3.75 (s, 2H), 3.52 (m, 2H), 3.33-3.32 (m, 1H), 2.92-2.86 (m, 5H), 2.67 (m, 2H), 2.13-2.00 (m, 5H), 1.44-1.37 (m, 2H); LCMS (m/z): 452.3 [M+H]⁺

Step 6: (S)-2-((1-acetylpiperidin-4-yl)amino)-N-(3-(3,4-dihydroisoquinolin-2(1H)-yl)-2-hydroxypropyl)isonicotinamide hydrochloride

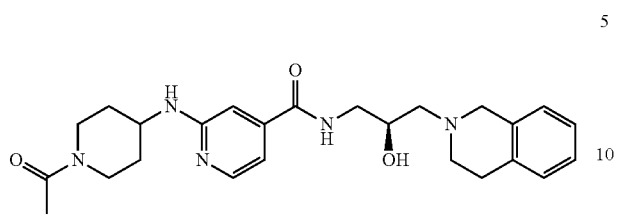

The free base was dissolved in DCM (100 mL) and added dropwise to a stirred and cooled solution of HCl (6N in EtOAc, 1 L) at −30° C. Stirring at −30° C. was continued for another 1 h and the resulting precipitate was collected by filtration. The solid was washed with DCM and EtOAc, dried to give the HCl salt of the product (302.2 g, yield: 78.0%) as a white solid. $^1$H NMR (400 MHz, MeOD-d$_4$) δ 8.00 (d, J=6.8 Hz, 1H), 7.64 (br. s., 1H), 7.36-7.18 (m, 5H), 4.70 (d, J=15.4 Hz, 1H), 4.60-4.39 (m, 3H), 4.19 (br. s., 1H), 4.11 (d, J=13.2 Hz, 1H), 3.98-3.85 (m, 1H), 3.63-3.47 (m, 5H), 3.43-3.25 (m, 3H), 3.25-3.11 (m, 2H), 2.33 (s, 3H), 2.22 (t, J=15.2 Hz, 2H), 1.85-1.61 (m, 2H); LCMS (m/z): 452.2 [M+H]$^+$ Compound 284

(S)-6-((1-acetylazetidin-3-yl)amino)-N-(3-(3,4-dihydroisoquinolin-2(1H)-yl)-2-hydroxypropyl)pyrimidine-4-carboxamide

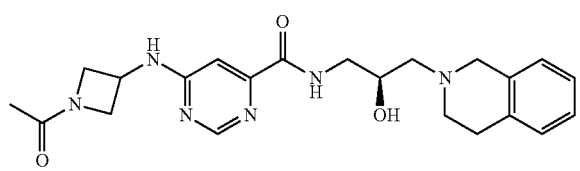 [SMILES: CC(=O)N1CC(Nc2cc(C(=O)NC[C@H](O)CN3CCc4ccccc4C3)ncn2)C1]

Step 1: tert-butyl (1-acetylazetidin-3-yl)carbamate

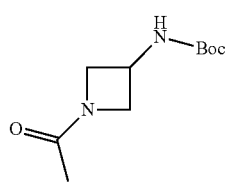

To a solution of tert-butyl azetidin-3-ylcarbamate (100 g, 0.58 mol) and Et$_3$N (88 g, 0.87 mol) in DCM (1500 mL) was added Ac$_2$O (59.6 g, 0.88 mol) dropwise at 0° C. The mixture was then stirred at 0° C. for 2 h, at which time TLC showed the completion of the reaction. The reaction was quenched by addition of water (1000 mL) and then stirred at 20° C. for 30 min. The organic phase was separated, dried (Na$_2$SO$_4$) and concentrated to give the crude product. Seven batches were run in parallel and produced a combined crude product weight of 530 g. This crude was used in next step without the further purification. LCMS (m/z): 215.1 (M+1).

Step 2: 1-(3-aminoazetidin-1-yl)ethanone

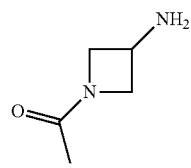

To a solution of tert-butyl (1-acetylazetidin-3-yl)carbamate (250 g) in MeOH (1000 mL) was slowly added HCl/MeOH (4M, 300 mL) at 0° C. After addition, the mixture was stirred at 0° C. for 6 h. The mixture was then concentrated under reduced pressure to give the crude product as a white solid. Two batches were run in parallel and produced a combined crude product weight of 186 g. This crude was used in next step without the further purification. $^1$H NMR (400 MHz, DMSO-d$_6$) δ 4.58-4.49 (m, 1H), 4.35-4.19 (m, 2H), 4.19-4.08 (m, 1H), 3.97 (dd, J=4.2, 11.2 Hz, 1H), 1.83 (s, 3H); LCMS (m/z): 115.1 (M+1).

Step 3: 6-chloropyrimidine-4-carbonyl chloride

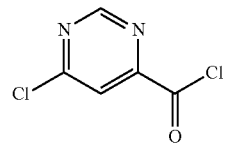

A stirred mixture of 6-hydroxypyrimidine-4-carboxylic acid (75 g, 0.54 mol) in EtOAc (300 mL) had oxalyl dichloride (226 g, 1.79 mol) dropped slowly to maintain the temperature below 30° C. After addition, the mixture was stirred at 20° C. for 30 min and then DMF (2 mL) was added to the mixture. The mixture was then stirred at 80° C. for 16 hours and concentrated to give the crude product as a black solid. Sixteen batches were run in parallel and produced a combined crude product weight of 1035 g. This crude was used directly in the next step.

Step 4: (S)-6-chloro-N-(3-(3,4-dihydroisoquinolin-2(1H)-yl)-2-hydroxypropyl)pyrimidine-4-carboxamide

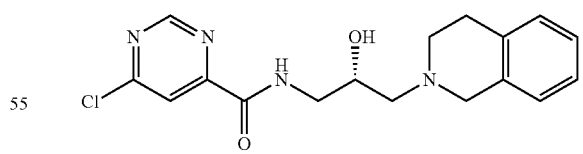

To a stirred mixture of (S)-1-amino-3-(3,4-dihydroisoquinolin-2(1H)-yl)propan-2-ol (300 g, 1.46 mol), and TEA (300 g, 3 mol) in DCM (4 L) was added 6-chloropyrimidine-4-carbonyl chloride (250 g in 2 L of DCM) slowly at −60° C. over 1 h. After the addition was complete, the mixture was then allowed to warm to 10° C. Stirring was continued for 1 h, at which time TLC showed the reaction was completed. The reaction was quenched by addition of water (2 L). The organic phase was collected, dried (Na$_2$SO$_4$) and evaporated. The residue was purified by flash chromatography (EtOAc~DCM:MeOH=10:1) to give the desired product as a pale yellow solid. Four batches were run in parallel and produced a combined product weight of 970 g, yield: 49%. $^1$H NMR (400 MHz, MeOD-$d_4$) δ 8.73 (d, J=1.0 Hz, 1H), 8.07 (d, J=1.2 Hz, 1H), 7.17-7.06 (m, 3H), 7.00 (d, J=7.2 Hz, 1H), 5.51 (s, 1H), 4.12 (q, J=6.0 Hz, 1H), 3.74 (s, 2H), 3.64-3.53 (m, 2H), 2.94 (q, J=5.6 Hz, 2H), 2.92-2.81 (m, 2H), 2.78-2.64 (m, 2H); LCMS (m/z): 347.2 [M+H]$^+$ Step 5: (s)-6-((1-acetylazetidin-3-yl)amino)-N-(3-(3, 4-dihydroisoquinolin-2(1H)-yl)-2-hydroxypropyl) pyrimidine-4-carboxamide

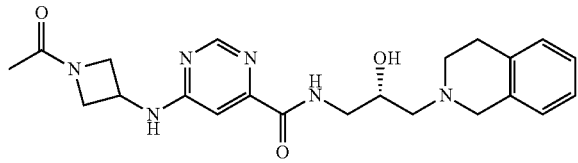 [SMILES: CC(=O)N1CC(Nc2cc(C(=O)NC[C@H](O)CN3CCc4ccccc4C3)ncn2)C1]

To a solution of (S)-6-chloro-N-(3-(3,4-dihydroisoquinolin-2(1H)-yl)-2-hydroxypropyl) pyrimidine-4-carboxamide (240 g, 0.69 mol) in i-PrOH (2.5 L) was added 1-(3-amino azetidin-1-yl)ethanone (120 g) and TEA (100 g). After addition, the solution was heated at 60° C. for 16 h, at which time LCMS showed completion of the reaction. The mixture was concentrated and the residue was purified by flash chromatography to give the crude product. Four batches were run in parallel and produced a combined crude product weight of 420 g, 90% purity. This crude was further purified on preparative HPLC to give the title compound (330 g, >98% purity, free base form). $^1$H NMR (400 MHz, MeOD-$d_4$) 8.27 (s, 1H), 7.12-6.98 (m, 5H), 4.71 (s, 1H), 4.54 (m, 1H), 4.32 (m, 1H), 4.06 (m, 2H), 3.88 (m, 1H), 3.70 (s, 2H), 3.53-3.50 (m, 2H), 2.91-2.83 (m, 4H), 2.65 (m, 2H), 1.88 (s, 3H); LCMS (m/z): 425.2 [M+H]

Step 6: (s)-6-((1-acetylazetidin-3-yl)amino)-N-(3-(3, 4-dihydroisoquinolin-2(1H)-yl)-2-hydroxypropyl) pyrimidine-4-carboxamide hydrochloride

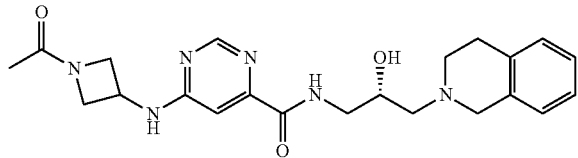 [SMILES: CC(=O)N1CC(Nc2cc(C(=O)NC[C@H](O)CN3CCc4ccccc4C3)ncn2)C1]

The free base was dissolved in DCM (100 mL) and added dropwise to a stirred and cooled solution of HCl (6N in EtOAc, 1 L) at −30° C. Stirring at −30° C. was continued for another 1 h and the resulting precipitate was collected by filtration. The solid was washed with DCM and EtOAc, dried to give the HCl salt of the product (301 g, yield: 26%) as a white solid. $^1$H NMR (400 MHz, D$_2$O) δ 8.65 (s, 1H), 7.30-7.19 (m, 4H), 7.13 (d, J=7.5 Hz, 1H), 4.95-4.85 (m, 1H), 4.63-4.50 (m, 2H), 4.41-4.28 (m, 3H), 4.22 (dd, J=4.8, 9.2 Hz, 1H), 3.97 (dd, J=4.6, 10.0 Hz, 1H), 3.77 (dt, J=5.6, 11.3 Hz, 1H), 3.53-3.35 (m, 4H), 3.34-3.26 (m, 1H), 3.22-3.04 (m, 2H), 1.87-1.79 (m, 3H); LCMS (m/z): 425.2 [M+H]+.

Biological Assays
PRMT5 Biochemical Assay
General Materials.
S-adenosylmethionine (SAM), S-adenosylhomocysteine (SAH), bicine, KCl, Tween20, dimethylsulfoxide (DMSO), bovine skin gelatin (BSG), and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.
Substrates.
Peptide representative of human histone H4 residues 1-15 was synthesized with a C-terminal linker-affinity tag motif and a C-terminal amide cap by 21$^{st}$ Century Biochemicals. The peptide was high high-performance liquid chromatography (HPLC) purified to greater than 95% purity and confirmed by liquid chromatography mass spectrometry (LC-MS). The sequence was Ac-SGRGKGGKGLGKGGA [K-Biot]-amide (SEQ ID NO:3).
Molecular Biology:
Full-length human PRMT5 (NM_006109.3) transcript variant 1 clone was amplified from a fetal brain cDNA library, incorporating flanking 5' sequence encoding a FLAG tag (MDYKDDDDK) (SEQ ID NO:4) fused directly to Ala 2 of PRMT5. Full-length human MEP50 (NM_024102) clone was amplified from a human testis cDNA library incorporating a 5' sequence encoding a 6-histidine tag (MH-HHHHH) (SEQ ID NO:5) fused directly to Arg 2 of MEP50. The amplified genes were sublconed into pENTR/D/TEV (Life Technologies) and subsequently transferred by Gateway™ attL x attR recombination to pDEST8 baculvirus expression vector (Life Technologies).
Protein Expression.
Recombinant baculovirus and Baculovirus-Infected Insect Cells (BIIC) were generated according to Bac-to-Bac kit instructions (Life Technologies) and Wasilko, 2006, respectively. Protein over-expression was accomplished by infecting exponentially growing Spodoptera frugiperda (SF9) cell culture at 1.2×10$^6$ cell/ml with a 5000 fold dilution of BIIC stock. Infections were carried out at 27° C. for 72 hours, harvested by centrifugation, and stored at −80° C. for purification.
Protein Purification.
Expressed full-length human Flag-PRMT5/6His-MeP50 protein complex was purified from cell paste by NiNTA agarose affinity chromatography after a five hour equilibration of the resin with buffer containing 50 mM Tris-HCL, pH 8.0, 25 mM NaCl, and 1 mM TCEP at 4° C., to minimize the adsorption of tubulin impurity by the resin. Flag-PRMT5/6His-MeP50 was eluted with 300 mM Imidazole in the same buffer. The purity of recovered protein was 87%. Reference: Wasilko, D. J. and S. E. Lee: "TIPS: titerless infected-cells preservation and scale-up" Bioprocess J., 5 (2006), pp. 29-32.
Predicted Translations:

```
Flag-PRMT5
                                       (SEQ ID NO.: 6)
MDYKDDDDKA AMAVGGAGGS RVSSGRDLNC VPEIADTLGA

VAKQGFDFLC MPVFHPRFKR EFIQEPAKNR PGPQTRSDLL

LSGRDWNTLI VGKLSPWIRP DSKVEKIRRN SEAAMLQELN

FGAYLGLPAF LLPLNQEDNT NLARVLTNHI HTGHHSSMFW
```

```
             -continued
MRVPLVAPED  LRDDIIENAP  TTHTEEYSGE  EKTWMWWHNF

RTLCDYSKRI  AVALEIGADL  PSNHVIDRWL  GEPIKAAILP

TSIFLTNKKG  FPVLSKMHQR  LIFRLLKLEV  QFIITGTNHH

SEKEFCSYLQ  YLEYLSQNRP  PPNAYELFAK  GYEDYLQSPL

QPLMDNLESQ  TYEVFEKDPI  KYSQYQQAIY  KCLLDRVPEE

EKDTNVQVLM  VLGAGRGPLV  NASLRAAKQA  DRRIKLYAVE

KNPNAVVTLE  NWQFEEWGSQ  VTVVSSDMRE  WVAPEKADII

VSELLGSFAD  NELSPECLDG  AQHFLKDDGV  SIPGEYTSFL

APISSSKLYN  EVRACREKDR  DPEAQFEMPY  VVRLHNFHQL

SAPQPCFTFS  HPNRDPMIDN  NRYCTLEFPV  EVNTVLHGFA

GYFETVLYQD  ITLSIRPETH  SPGMFSWFPI  LFPIKQPITV

REGQTICVRF  WRCSNSKKVW  YEWAVTAPVC  SAIHNPTGRS

YTIG L

6His-MEP50
                                       (SEQ ID NO.: 7)
MHHHHHHRKE  TPPPLVPPAA  REWNLPPNAP  ACMERQLEAA

RYRSDGALLL  GASSLSGRCW  AGSLWLFKDP  CAAPNEGFCS

AGVQTEAGVA  DLTWVGERGI  LVASDSGAVE  LWELDENETL

IVSKFCKYEH  DDIVSTVSVL  SSGTQAVSGS  KDICIKVWDL

AQQVVLSSYR  AHAAQVTCVA  ASPHKDSVFL  SCSEDNRILL

WDTRCPKPAS  QIGCSAPGYL  PTSLAWHPQQ  SEVFVFGDEN

GTVSLVDTKS  TSCVLSSAVH  SQCVTGLVFS  PHSVPFLASL

SEDCSLAVLD  SSLSELFRSQ  AHRDFVRDAT  WSPLNHSLLT

TVGWDHQVVH  HVVPTEPLPA  PGPASVTE
```

General Procedure for PRMT5/MEP50 Enzyme Assays on Peptide Substrates.

The assays were all performed in a buffer consisting of 20 mM Bicine (pH=7.6), 1 mM TCEP, 0.005% BSG, and 0.002% Tween20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT5/MEP50, was added to columns 11, 12, 23, 24, rows I-P for the minimum signal control. A cocktail (40 ul) containing the PRMT5/MEP50 enzyme and the peptide was added by Multidrop Combi (Thermo-Fisher). The compounds were allowed to incubate with PRMT5/MEP50 for 30 min at 25 degrees Celsius, then a cocktail (10 ul) containing $^3$H-SAM was added to initiate the reaction (final volume=51 ul). The final concentrations of the components were as follows: PRMT5/MEP50 was 4 nM, $^3$H-SAM was 75 nM, peptide was 40 nM, SAH in the minimum signal control wells was 100 uM, and the DMSO concentration was 1%. The assays were stopped by the addition of non-radioactive SAM (10 ul) to a final concentration of 600 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed three times with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% inhibition calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-parameter $IC50$ fit $$Y = Bottom + \frac{(Top - Bottom)}{\left(1 + \left(\frac{X}{IC_{50}}\right)\right) Hill \ Coefficient}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

Z-138 Methylation Assay

Z-138 suspension cells were purchased from ATCC (American Type Culture Collection, Manassas, Va.). RPMI/Glutamax medium, penicillin-streptomycin, heat inactivated fetal bovine serum, and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Symmetric di-methyl arginine antibody was purchased from EMD Millipore, Billerica, Mass., USA. 16% Paraformaldehyde was purchased from Electron Microscopy Sciences, Hatfield, Pa., USA.

Z-138 suspension cells were maintained in growth medium (RPMI 1640 supplemented with 10% v/v heat inactivated fetal bovine serum and 100 units/mL penicillin-streptomycin) and cultured at 37° C. under 5% $CO_2$.

Cell Treatment, in Cell Western (ICW) for Detection of Symmetric Di-Methyl Arginine and DNA Content.

Z-138 cells were seeded in assay medium at a concentration of 50,000 cells per mL to a 384-well cell culture plate with 50 μL per well. Compound (100 nL) from 384 well source plates was added directly to 384 well cell plate. Plates were incubated at 37° C., 5% $CO_2$ for 96 hours. After four days of incubation, 40 μL of cells from incubated plates were added to poly-D-lysine coated 384 well culture plates (BD Biosciences 356697). Plates were incubated at room temperature for 30 minutes then incubated at 37° C., 5% $CO_2$ for 5 hours. After the incubation, 40 μL per well of 8% paraformaldehyde in PBS (16% paraformaldehyde was diluted to 8% in PBS) was added to each plate and incubated for 30 minutes. Plates were transferred to a Biotek 405 plate washer and washed 5 times with 100 μL per well of wash buffer (1×PBS with 0.1% Triton X-100 (v/v)). Next 30 μL per well of Odyssey blocking buffer were added to each plate and incubated 1 hour at room temperature. Blocking buffer was removed and 20 μL per well of primary antibody was added (symmetric di-methyl arginine diluted 1:100 in Odyssey buffer with 0.1% Tween 20 (v/v)) and plates were incubated overnight (16 hours) at 4° C. Plates were washed 5 times with 100 µL per well of wash buffer. Next 20 µL per well of secondary antibody was added (1:200 800CW goat anti-rabbit IgG (H+L) antibody, 1:1000 DRAQ5 (Biostatus limited) in Odyssey buffer with 0.1% Tween 20 (v/v)) and incubated for 1 hour at room temperature. The plates were washed 5 times with 100 µL per well wash buffer then 1 time with 100 µL per well of water. Plates were allowed to dry at room temperature then imaged on the Licor Odyssey machine which measures integrated intensity at 700 nm and 800 nm wavelengths. Both 700 and 800 channels were scanned.

Calculations:
First, the ratio for each well was determined by:

$$\left(\frac{\text{symmetric } di\text{-}methyl \text{ Arginine 800 nm value}}{DRAQ5 \text{ 700 nm value}}\right)$$

Each plate included fourteen control wells of DMSO only treatment (minimum inhibition) as well as fourteen control wells for maximum inhibition treated with 3 µM of a reference compound (Background wells). The average of the ratio values for each control type was calculated and used to determine the percent inhibition for each test well in the plate. Reference compound was serially diluted three-fold in DMSO for a total of nine test concentrations, beginning at 3 µM. Percent inhibition was determined and $IC_{50}$ curves were generated using triplicate wells per concentration of compound.

Percent Inhibition = 100 −

$$\left(\left(\frac{\text{(Individual Test Sample Ratio)} - \text{(Background } Avg \text{ Ratio)}}{\text{(Minimum Inhibition Ratio)} - \text{(Background Average Ratio)}}\right) * 100\right)$$

Z-138 Proliferation Assay

Z-138 suspension cells were purchased from ATCC (American Type Culture Collection, Manassas, Va.). RPMI/Glutamax medium, penicillin-streptomycin, heat inactivated fetal bovine serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

Z-138 suspension cells were maintained in growth medium (RPMI 1640 supplemented with 10% v/v heat inactivated fetal bovine serum and cultured at 37° C. under 5% $CO_2$. Under assay conditions, cells were incubated in assay medium (RPMI 1640 supplemented with 10% v/v heat inactivated fetal bovine serum and 100 units/mL penicillin-streptomycin) at 37° C. under 5% $CO_2$.

For the assessment of the effect of compounds on the proliferation of the Z-138 cell line, exponentially growing cells were plated in 384-well white opaque plates at a density of 10,000 cells/ml in a final volume of 50 µl of assay medium. A compound source plate was prepared by performing triplicate nine-point 3-fold serial dilutions in DMSO, beginning at 10 mM (final top concentration of compound in the assay was 20 µM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 5 days at 37° C., 5% $CO_2$, relative humidity >90%. Cell viability was measured by quantitation of ATP present in the cell cultures, adding 35 µl of Cell Titer Glo® reagent to the cell plates. Luminescence was read in the SpectraMax M5 microplate reader. The concentration of compound inhibiting cell viability by 50% was determined using a 4-parametric fit of the normalized dose response curves.

Results for certain compounds described herein are shown in Table 2.

TABLE 2

| | Biological Assay Results | | |
|---|---|---|---|
| Cmpd No | Biochemical $IC_{50}$ | ICW $EC_{50}$ | Proliferation $EC_{50}$ |
| 1 | A | A | C |
| 2 | A | A | C |
| 3 | A | A | C |
| 4 | C | — | — |
| 5 | B | B | ** |
| 6 | C | — | — |
| 7 | C | — | — |
| 8 | A | A | C |
| 9 | A | A | C |
| 10 | A | B | C |
| 11 | A | C | — |
| 12 | B | C | ** |
| 13 | A | A | B |
| 14 | A | B | C |
| 15 | A | B | D |
| 16 | A | A | B |
| 17 | B | B | ** |
| 18 | B | B | D |
| 19 | A | B | D |
| 20 | A | A | B |
| 21 | B | B | ** |
| 22 | B | B | ** |
| 23 | B | B | ** |
| 24 | A | B | C |
| 25 | B | C | ** |
| 26 | B | B | D |
| 27 | C | — | — |
| 28 | A | B | D |
| 29 | A | B | C |
| 30 | A | B | C |
| 31 | B | B | D |
| 32 | B | B | ** |
| 33 | C | — | — |
| 34 | A | B | D |
| 35 | A | B | D |
| 36 | A | B | D |
| 37 | A | B | ** |
| 38 | A | B | D |
| 39 | B | C | ** |
| 40 | A | A | C |
| 41 | A | A | C |
| 42 | B | C | ** |
| 43 | B | B | C |
| 44 | A | — | B |
| 45 | A | B | — |
| 46 | C | — | — |
| 47 | B | B | — |
| 48 | B | B | — |
| 49 | B | — | — |
| 50 | B | — | — |
| 51 | B | — | — |
| 52 | B | — | — |
| 53 | B | — | — |
| 54 | A | — | — |
| 55 | A | — | — |
| 56 | B | — | — |

TABLE 2-continued

Biological Assay Results

| Cmpd No | Biochemical IC$_{50}$ | ICW EC$_{50}$ | Proliferation EC$_{50}$ |
|---|---|---|---|
| 57 | B | — | — |
| 58 | A | — | — |
| 59 | A | A | B |
| 60 | B | B | C |
| 61 | B | B | — |
| 62 | A | B | D |
| 63 | A | A | B |
| 64 | A | B | C |
| 65 | A | A | C |
| 66 | A | B | C |
| 67 | B | B | D |
| 68 | A | A | C |
| 69 | B | C | ** |
| 70 | B | C | ** |
| 71 | B | B | C |
| 72 | B | C | — |
| 73 | A | A | C |
| 74 | A | A | B |
| 75 | B | B | — |
| 76 | B | B | — |
| 77 | A | B | C |
| 78 | A | A | B |
| 79 | A | A | B |
| 80 | A | A | B |
| 81 | A | B | C |
| 82 | A | A | B |
| 83 | B | B | — |
| 84 | A | A | C |
| 85 | B | B | D |
| 86 | B | C | — |
| 87 | C | — | — |
| 88 | B | B | ** |
| 89 | B | B | ** |
| 90 | A | B | D |
| 91 | A | A | C |
| 92 | A | A | C |
| 93 | B | C | ** |
| 94 | A | B | D |
| 95 | B | B | C |
| 96 | A | A | C |
| 97 | A | A | C |
| 98 | A | B | C |
| 99 | A | A | C |
| 100 | A | A | C |
| 101 | A | A | D |
| 102 | A | A | C |
| 103 | A | A | D |
| 104 | A | A | C |
| 105 | A | A | C |
| 106 | A | A | B |
| 107 | A | A | B |
| 108 | A | A | B |
| 109 | A | A | B |
| 110 | A | A | C |
| 111 | A | B | C |
| 112 | B | C | ** |
| 113 | A | B | D |
| 114 | A | B | D |
| 115 | A | B | ** |
| 116 | B | B | ** |
| 117 | B | B | ** |
| 118 | A | B | ** |
| 119 | A | B | C |
| 120 | A | B | C |
| 121 | A | A | B |
| 122 | A | A | B |
| 123 | A | B | C |
| 124 | A | A | A |
| 125 | A | A | B |
| 126 | A | A | C |
| 127 | A | A | C |
| 128 | A | A | C |
| 129 | A | A | C |
| 130 | A | B | D |
| 131 | A | B | C |
| 132 | A | B | C |
| 133 | A | A | C |
| 134 | A | B | D |
| 135 | A | A | D |
| 136 | A | A | C |
| 137 | A | A | C |
| 138 | A | B | D |
| 139 | A | A | C |
| 140 | A | A | C |
| 141 | A | A | C |
| 142 | A | A | C |
| 143 | A | A | C |
| 144 | A | A | C |
| 145 | A | A | C |
| 146 | A | A | C |
| 147 | A | B | D |
| 148 | B | C | ** |
| 149 | B | C | ** |
| 150 | B | B | ** |
| 151 | B | B | ** |
| 152 | A | A | B |
| 153 | A | A | B |
| 154 | A | B | C |
| 155 | B | C | ** |
| 156 | A | B | C |
| 157 | B | C | ** |
| 158 | A | — | ** |
| 159 | A | B | C |
| 160 | A | B | D |
| 161 | A | A | C |
| 162 | A | A | C |
| 163 | A | A | C |
| 164 | A | A | C |
| 165 | A | B | C |
| 166 | A | A | B |
| 167 | A | A | B |
| 168 | A | A | B |
| 169 | A | B | C |
| 170 | B | B | ** |
| 171 | A | B | C |
| 172 | A | A | C |
| 173 | A | A | C |
| 174 | A | A | C |
| 175 | A | B | C |
| 176 | A | A | C |
| 177 | A | A | C |
| 178 | A | A | C |
| 179 | A | A | C |
| 180 | A | B | D |
| 181 | A | B | C |
| 182 | A | A | C |
| 183 | A | A | C |
| 184 | A | A | C |
| 185 | A | B | C |
| 186 | A | A | C |
| 187 | A | A | B |
| 188 | A | A | A |
| 189 | A | A | B |
| 190 | A | A | B |
| 191 | A | A | B |
| 192 | A | A | B |
| 193 | A | A | B |
| 194 | A | B | C |
| 195 | A | B | D |
| 196 | A | A | C |
| 197 | A | A | B |
| 198 | A | A | B |
| 199 | A | A | C |
| 200 | A | B | D |
| 201 | A | B | C |
| 202 | A | A | C |
| 203 | A | A | B |
| 204 | A | A | B |
| 205 | A | A | B |
| 206 | A | B | C |
| 207 | A | A | B |
| 208 | A | A | A |

TABLE 2-continued

Biological Assay Results

| Cmpd No | Biochemical IC$_{50}$ | ICW EC$_{50}$ | Proliferation EC$_{50}$ |
|---|---|---|---|
| 209 | A | A | D |
| 210 | A | A | B |
| 211 | A | A | A |
| 212 | A | A | B |
| 213 | A | A | B |
| 214 | A | A | C |
| 215 | A | A | A |
| 216 | A | A | B |
| 217 | A | A | B |
| 218 | A | B | D |
| 219 | A | B | D |
| 220 | A | A | B |
| 221 | A | A | B |
| 222 | A | B | ** |
| 223 | A | A | C |
| 224 | A | A | B |
| 225 | A | A | A |
| 226 | A | A | B |
| 227 | A | A | B |
| 228 | A | A | B |
| 229 | A | A | C |
| 230 | A | A | B |
| 231 | A | A | C |
| 232 | B | B | C |
| 233 | A | B | C |
| 234 | A | A | C |
| 235 | A | B | ** |
| 236 | A | B | C |
| 237 | A | A | C |
| 238 | A | B | D |
| 239 | A | A | C |
| 240 | B | B | ** |
| 241 | A | B | C |
| 242 | A | B | C |
| 243 | A | B | C |
| 244 | A | B | C |
| 245 | A | B | D |
| 246 | A | B | C |
| 247 | A | B | C |
| 248 | A | B | C |
| 249 | A | B | D |
| 250 | A | A | C |
| 251 | A | A | C |
| 252 | A | B | C |
| 253 | A | B | C |
| 254 | A | A | A |
| 255 | A | A | C |
| 256 | A | A | C |
| 257 | A | A | C |
| 258 | A | B | D |
| 259 | A | B | ** |
| 260 | A | B | ** |
| 261 | A | A | C |
| 262 | A | A | B |
| 263 | A | A | C |
| 264 | A | A | C |
| 265 | A | B | C |
| 266 | A | A | B |
| 267 | A | A | B |
| 268 | A | A | B |
| 269 | A | A | C |
| 270 | C | — | — |
| 271 | A | B | C |
| 272 | A | A | C |
| 273 | A | B | C |
| 274 | A | B | C |
| 275 | B | B | C |
| 276 | A | B | C |
| 277 | A | A | — |
| 278 | A | A | — |
| 279 | A | A | — |
| 280 | A | A | — |
| 281 | A | B | — |
| 282 | A | A | — |
| 283 | A | A | — |
| 284 | A | A | — |
| 285 | B | B | — |
| 286 | A | A | — |
| 287 | A | A | — |
| 288 | A | B | — |
| 289 | B | A | — |
| 290 | A | A | — |
| 291 | A | A | — |
| 292 | A | A | — |
| 293 | A | A | — |
| 294 | B | B | — |
| 295 | B | B | — |
| 296 | A | B | — |
| 297 | A | A | — |
| 298 | A | A | — |
| 299 | A | A | — |
| 300 | A | A | — |
| 301 | A | A | — |
| 302 | A | A | — |
| 303 | A | A | — |
| 304 | A | A | — |
| 305 | B | B | — |
| 306 | A | — | — |
| 307 | A | — | — |
| 308 | A | — | — |
| 309 | B | — | — |
| 310 | B | — | — |
| 311 | A | — | — |
| 312 | B | — | — |
| 313 | — | — | — |
| 314 | A | — | — |
| 315 | A | — | — |
| 316 | A | — | — |
| 317 | A | — | — |
| 318 | A | — | — |
| 319 | A | — | — |
| 320 | A | — | — |
| 321 | A | — | — |
| 322 | A | — | — |
| 323 | A | — | — |
| 324 | A | — | — |
| 325 | A | — | — |
| 326 | A | — | — |
| 327 | B | — | — |
| 328 | C | — | — |
| 329 | A | — | — |
| 330 | A | — | — |
| 331 | A | — | — |
| 332 | A | — | — |
| 333 | A | — | — |
| 334 | A | — | — |
| 335 | A | — | — |

For Table 2, "A" indicates an IC$_{50}$ or EC$_{50}$ < 0.100 μM, "B" indicates an IC$_{50}$ or EC$_{50}$ of 0.101-1.000 μM, "C" indicates an IC$_{50}$ or EC$_{50}$ of 1.001-10.000 μM, "D" indicates an IC$_{50}$ or EC$_{50}$ of 10.001-50 μM, and "E" indicates an IC$_{50}$ or EC$_{50}$ > 50 μM. "—" indicates no data. "**" indicates an IC$_{50}$ or EC$_{50}$ > 20 μM.

OTHER EMBODIMENTS

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of inhibiting PRMT5, altering gene expression, or altering transcription, comprising contacting a cell with an effective amount of a compound of formula (I), or a pharmaceutically acceptable salt thereof:

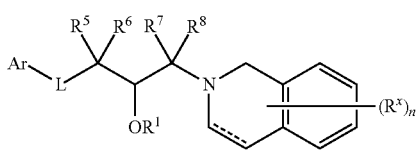

I wherein
- - - - - - represents a single or double bond;

$R^1$ is hydrogen, $R^z$, or $C(O)R^z$, wherein $R^z$ is optionally substituted $C_{1-6}$ alkyl;

L is —N(R)C(O)—, —C(O)N(R)—, —N(R)C(O)N(R)—, —N(R)C(O)O—, or —OC(O)N(R)—;

each R is independently hydrogen or optionally substituted $C_{1-6}$ aliphatic;

Ar is a monocyclic or bicyclic aromatic ring having 0-4 heteroatoms independently selected from nitrogen, oxygen, and sulfur, wherein Ar is substituted with 0, 1, 2, 3, 4, or 5 $R^y$ groups, as valency permits;

each $R^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^5$, $R^6$, $R^7$, and $R^8$ are independently hydrogen, halo, or optionally substituted aliphatic;

each $R^x$ is independently selected from the group consisting of halo, —CN, optionally substituted aliphatic, —OR', and —N(R")$_2$;

R' is hydrogen or optionally substituted aliphatic;

each R" is independently hydrogen or optionally substituted aliphatic, or two R" are taken together with their intervening atoms to form a heterocyclic ring; and n is 0, 1, 2, 3, 4, 5, 6, 7, 8, 9, or 10, as valency permits;

wherein each instance of aliphatic is independently an alkyl, alkenyl, alkynyl, cycloalkyl, or cycloalkenyl group;

each instance of optionally substituted is independently unsubstituted or substituted, and each instance of substituted is, when on a carbon atom, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi ($R^{aa}$)$_3$, —C(=S)N($R^{bb}$)$_2$, —C(=O)S$R^{aa}$, —C(=S) S$R^{aa}$, —SC(=S)S$R^{aa}$, —SC(=O)S$R^{aa}$, —OC(=O) S$R^{aa}$, —SC(=O)O$R^{aa}$, —SC(=O)$R^{aa}$, —P(=O)$_2R^{aa}$, —OP(=O)$_2R^{aa}$, —P(=O)($R^{aa}$)$_2$, —OP(=O) ($R^{aa}$)$_2$, —OP(=O)(O$R^{cc}$)$_2$, —P(=O)$_2$N($R^{bb}$)$_2$, —OP (=O)$_2$N($R^{bb}$)$_2$, —P(=O)(N$R^{bb}$)$_2$, —OP(=O) (N$R^{bb}$)$_2$, —N$R^{bb}$P(=O)(O$R^{cc}$)$_2$, —N$R^{bb}$P(=O) (N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of substituted is, when on a nitrogen, independently hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O) S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$X$^-$, —N(O$R^{cc}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O) $R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$) O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N ($R^{ff}$)$_2$, —C(=O)S$R^{ee}$, —C(=S)S$R^{ee}$, —SC(=S)S$R^{ee}$, —P(=O)$_2R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$ X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC (=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP (=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein $X^-$ is a counterion.

2. A method for the therapeutic treatment of a PRMT5-mediated disorder, comprising administering to a subject in need thereof a therapeutically effective amount of a compound of formula (I), or a pharmaceutically acceptable salt thereof:

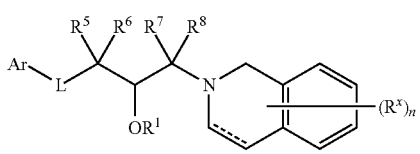

I wherein

----- represents a single or double bond;
$R^1$ is hydrogen, $R^z$, or —C(O)$R^z$, wherein $R^z$ is optionally substituted $C_{1-6}$ alkyl;
L is —N(R)C(O)—, —C(O)N(R)—, —N(R)C(O)N(R)—, —N(R)C(O)O—, or —OC(O)N(R)—;
each R is independently hydrogen or optionally substituted $C_{1-6}$ aliphatic;
Ar is a monocyclic or bicyclic aromatic ring having 0-4 heteroatoms independently selected from nitrogen, oxygen, and sulfur, wherein Ar is substituted with 0, 1, 2, 3, 4, or 5 $R^y$ groups, as valency permits;
each $R^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$;
each $R^A$ is independently selected from the group consisting of hydrogen, optionally substituted aliphatic, optionally substituted carbocyclyl, optionally substituted heterocyclyl, optionally substituted aryl, and optionally substituted heteroaryl;
each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;
$R^5$, $R^6$, $R^7$, and $R^8$ are independently hydrogen, halo, or optionally substituted aliphatic;
each $R^x$ is independently selected from the group consisting of halo, —CN, optionally substituted aliphatic, —OR', and —N(R")$_2$;
R' is hydrogen or optionally substituted aliphatic;
each R" is independently hydrogen or optionally substituted aliphatic, or two R" are taken together with their intervening atoms to form a heterocyclic ring; and
n is 0, 1, 2, 3, 4, 5, 6, 7, 8, 9, or 10, as valency permits;

wherein each instance of aliphatic is independently an alkyl, alkenyl, alkynyl, cycloalkyl, or cycloalkenyl group;
wherein the PRMT5-mediated disorder is diabetes, obesity, a blood disorder, or a hemoglobinopathy; and
each instance of optionally substituted is independently unsubstituted or substituted, and each instance of substituted is, when on a carbon atom, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;
or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;
each instance of substituted is, when on a nitrogen, independently hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two e groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

3. The method of claim 2, wherein the disorder is sickle cell anemia or β-thalessemia.

4. The method of claim 1, wherein the compound is of Formula (I-a) or Formula (I-b):

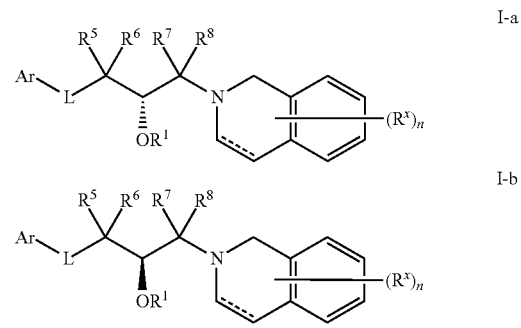

or a pharmaceutically acceptable salt thereof.

5. The method of claim 1, wherein the compound is of Formula (I'), Formula (I'-a), or Formula (I'-b):

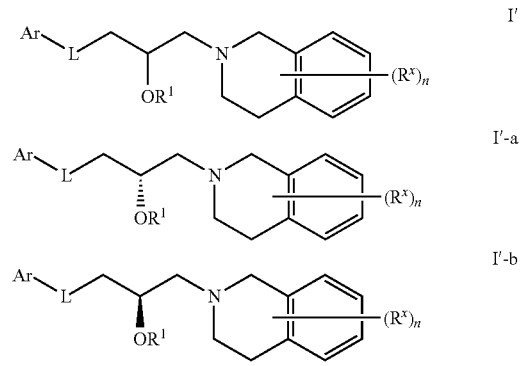

or a pharmaceutically acceptable salt thereof.

6. The method of claim 1, wherein the compound is of Formula (II), Formula (II-a), or Formula (II-b):

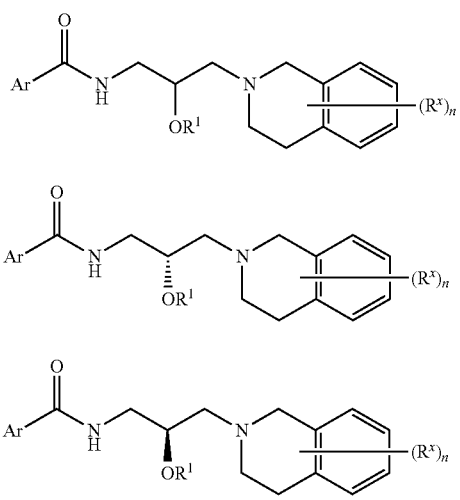

or a pharmaceutically acceptable salt thereof.

7. The method of claim 1, wherein $R^1$ is hydrogen.

8. The method of claim 1, wherein Ar is heteroaryl.

9. The method of claim 8, wherein Ar is a 5- to 6-membered heteroaryl having 1-3 heteroatoms independently selected from nitrogen, oxygen, and sulfur.

10. The method of claim 1, wherein Ar is substituted with 1 or 2 Ry groups.

11. The method of claim 1, wherein the compound is of Formula (VI), Formula (VI-a), or Formula (VI-b):

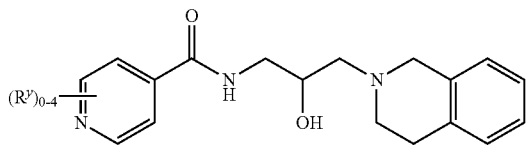

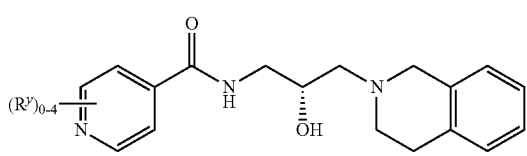

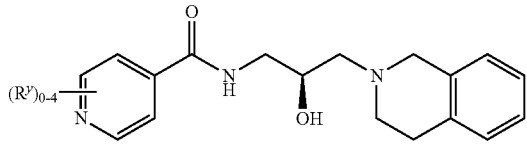

or a pharmaceutically acceptable salt thereof.

12. The method of claim 1, wherein the compound is of Formula (IX), Formula (IX-a), or Formula (IX-b):

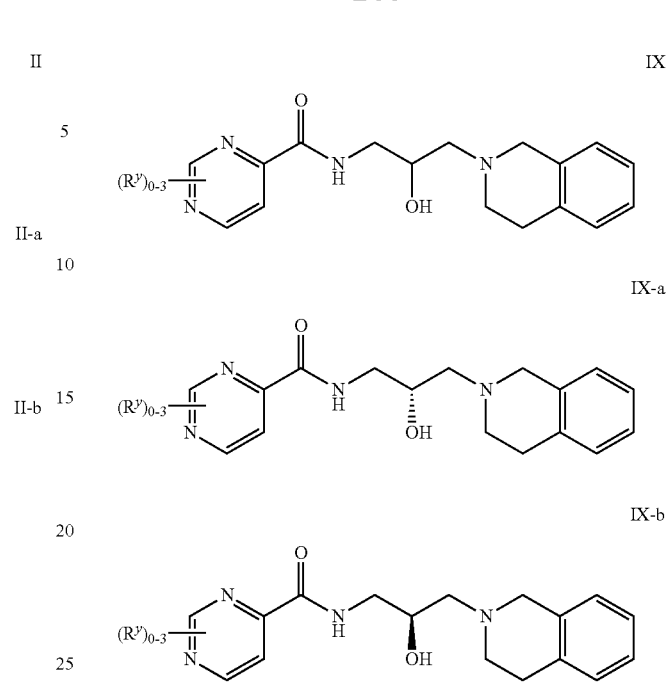

or a pharmaceutically acceptable salt thereof.

13. The method of claim 1, wherein the compound is of Formula (XV-a):

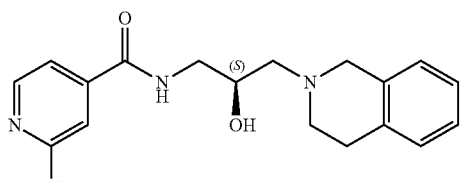

or a pharmaceutically acceptable salt thereof.

14. The method of claim 1, wherein the compound is of Formula (XVII-a):

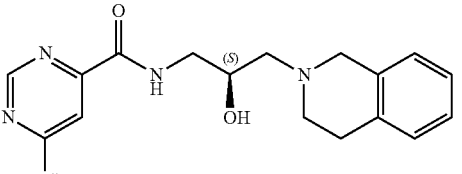

or a pharmaceutically acceptable salt thereof.

15. The method of claim 1, wherein at least one $R^y$ is —$NHR^B$.

16. The method of claim 15, wherein $R^B$ is optionally substituted heterocyclyl.

17. The method of claim 1, wherein Ar is selected from the group consisting of:

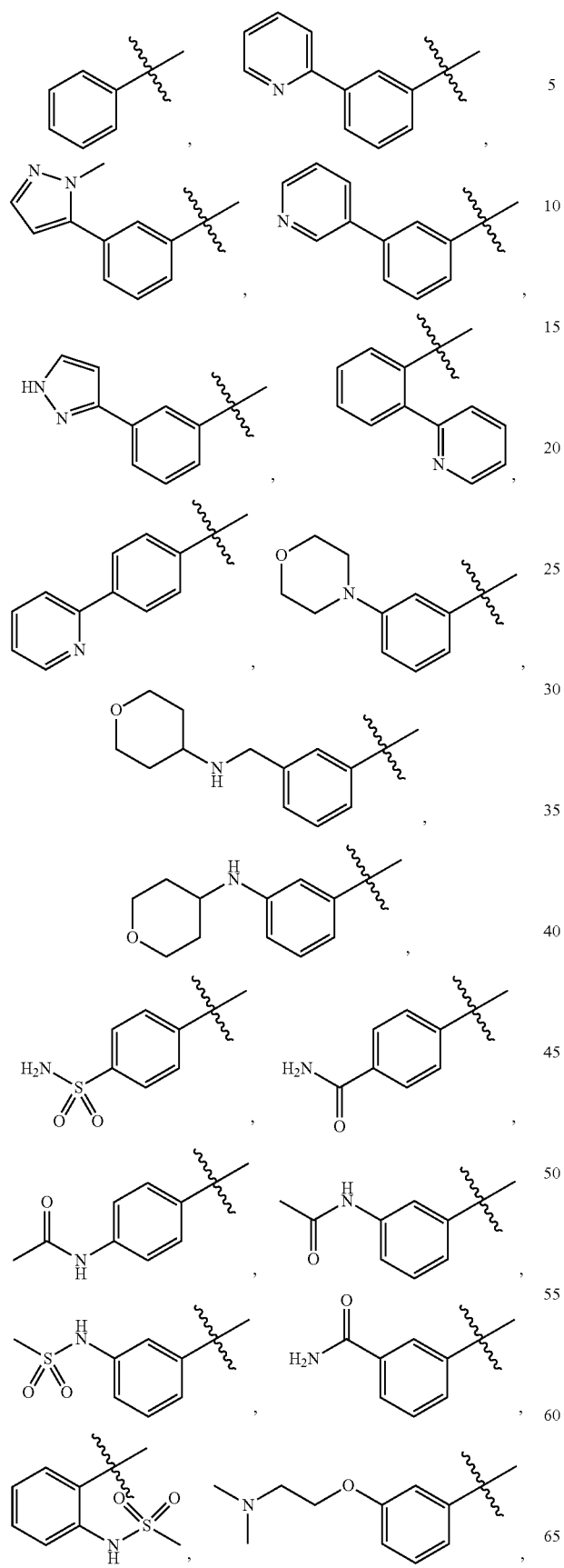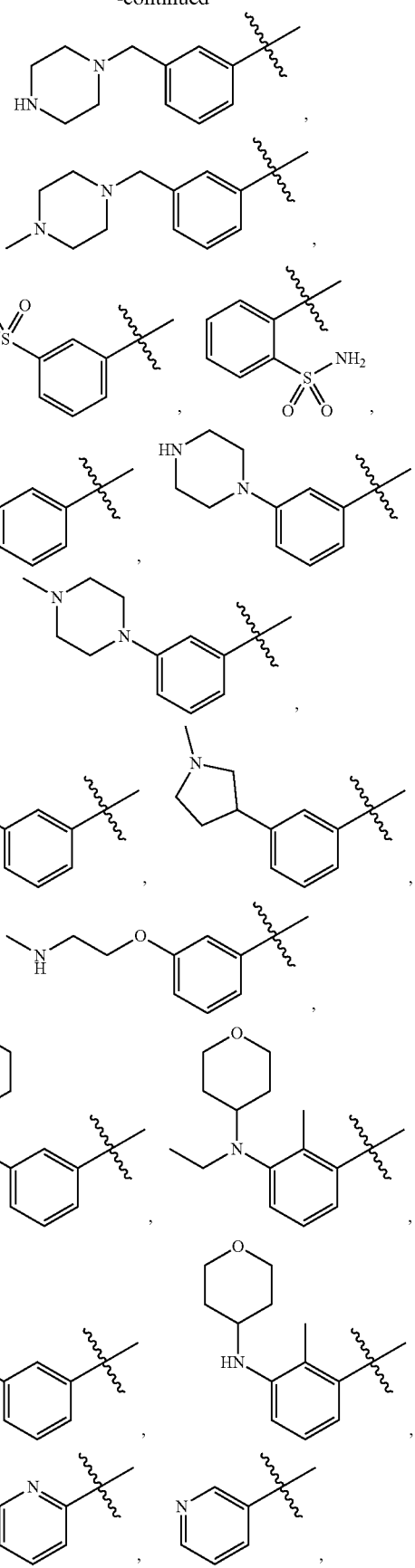

247
-continued
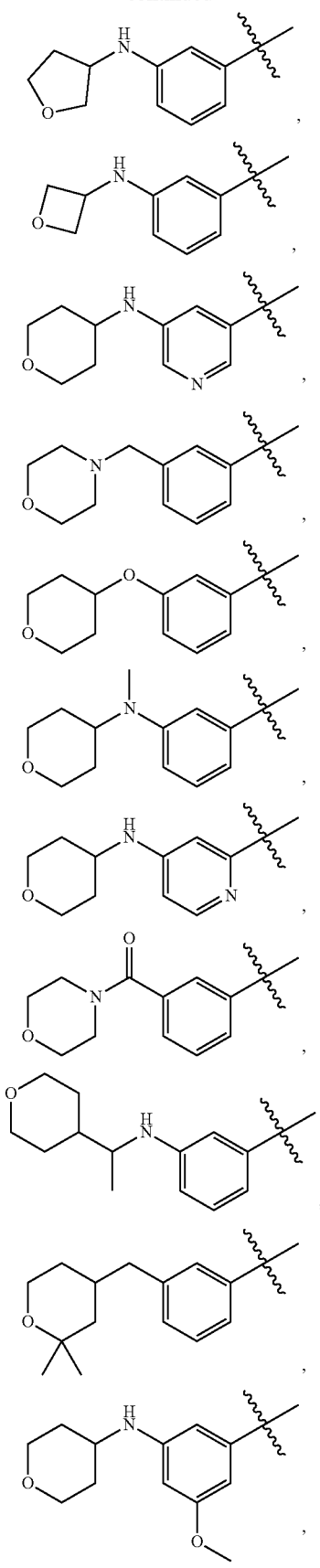
248
-continued
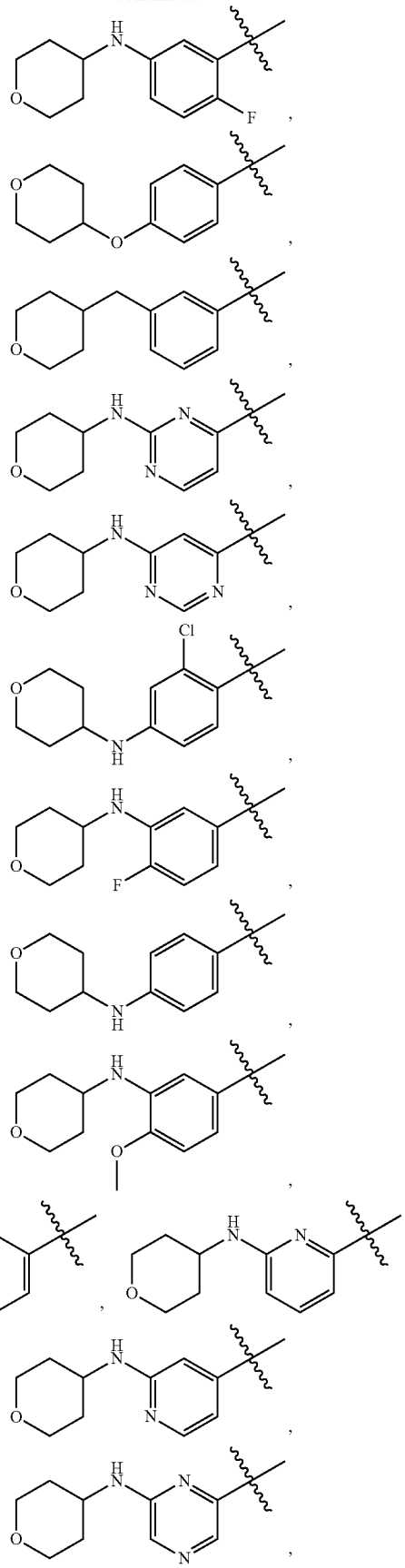

249
-continued
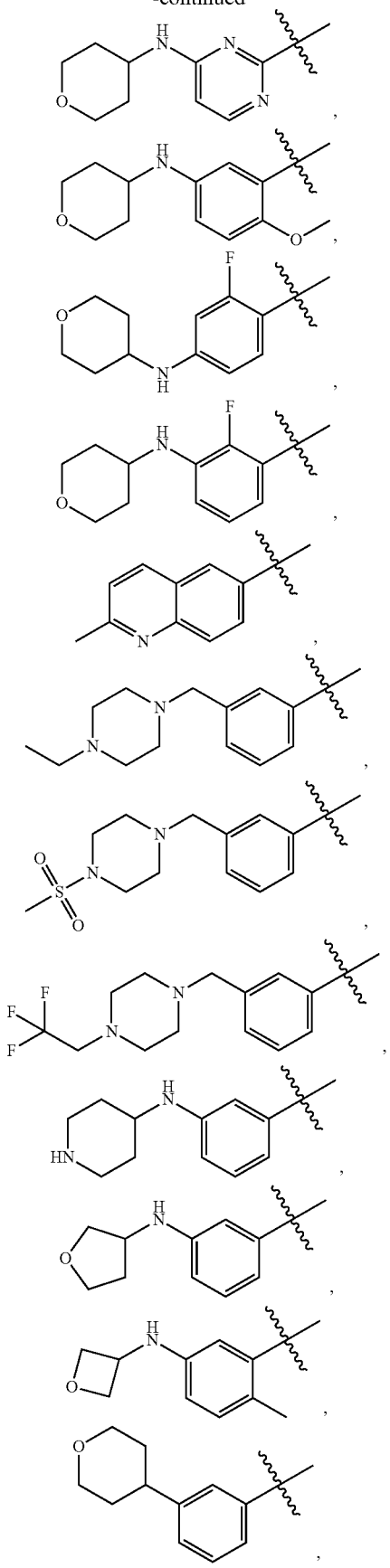
250
-continued
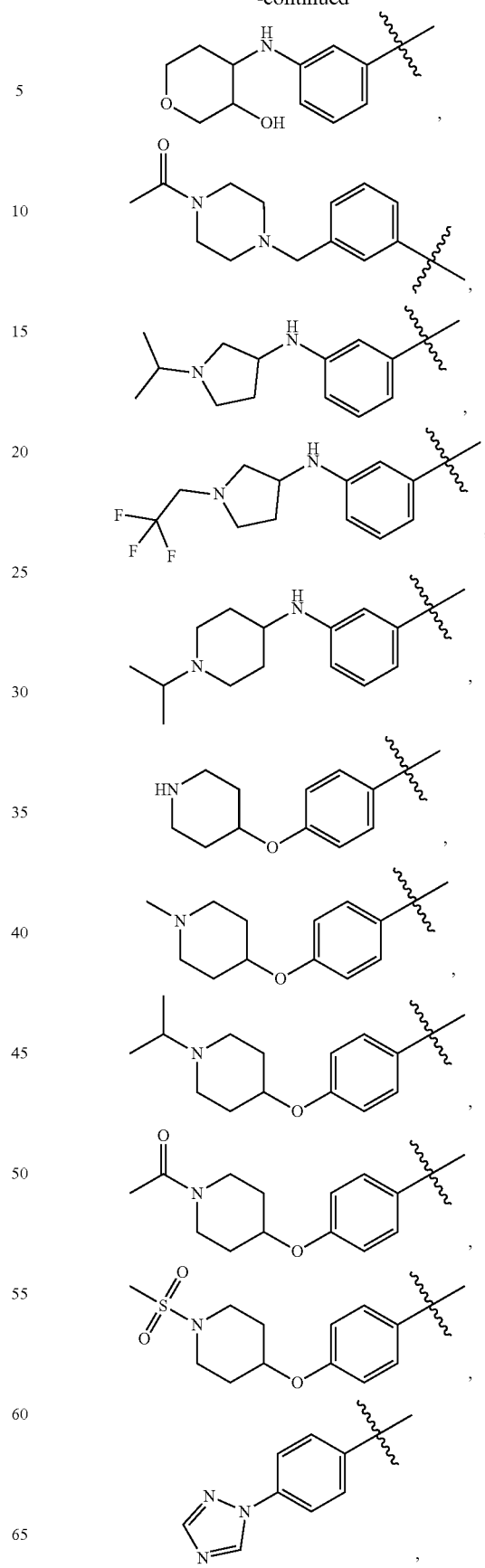

251
-continued
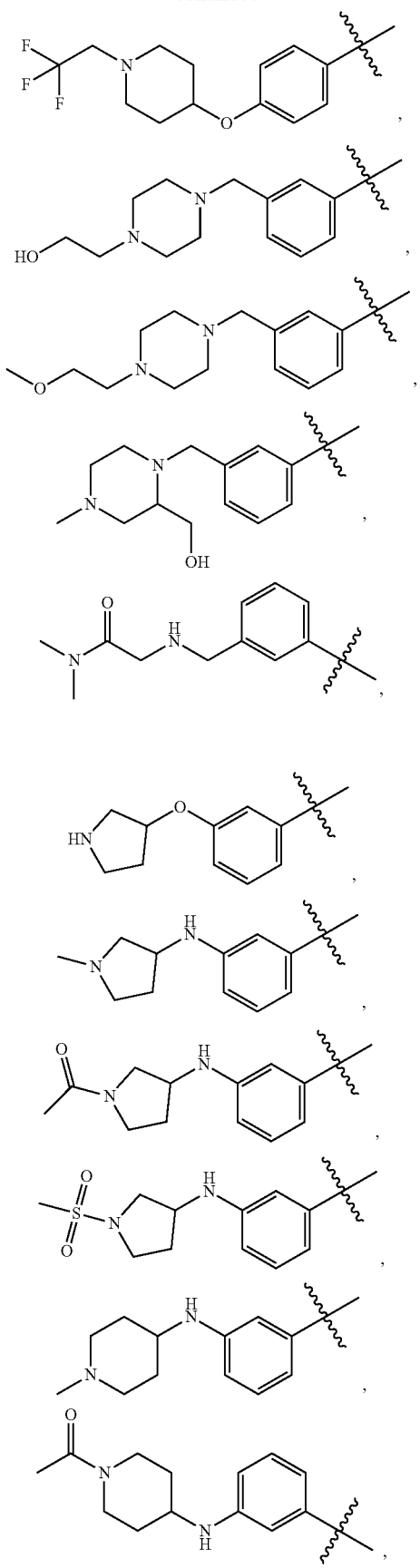
252
-continued
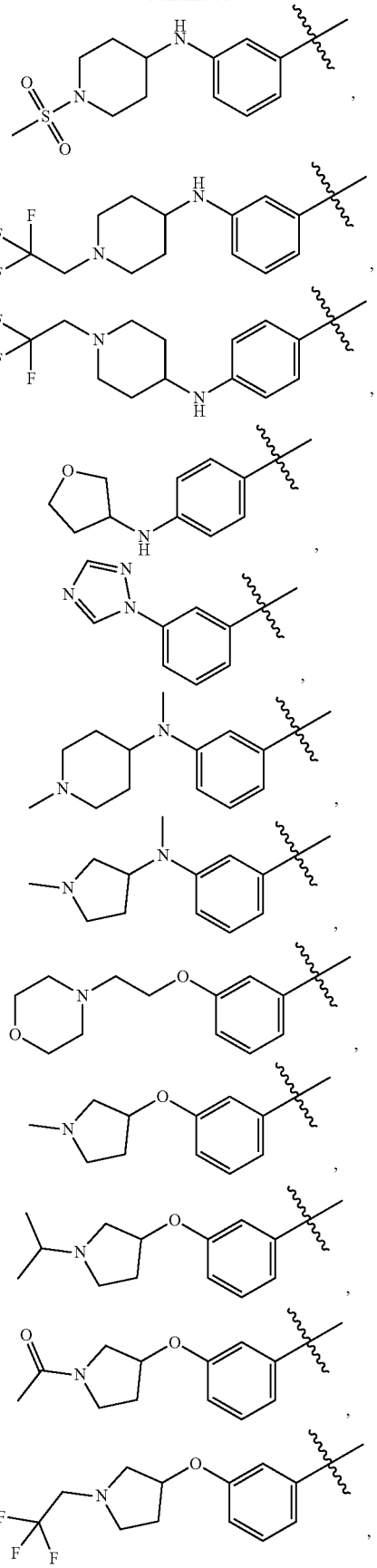

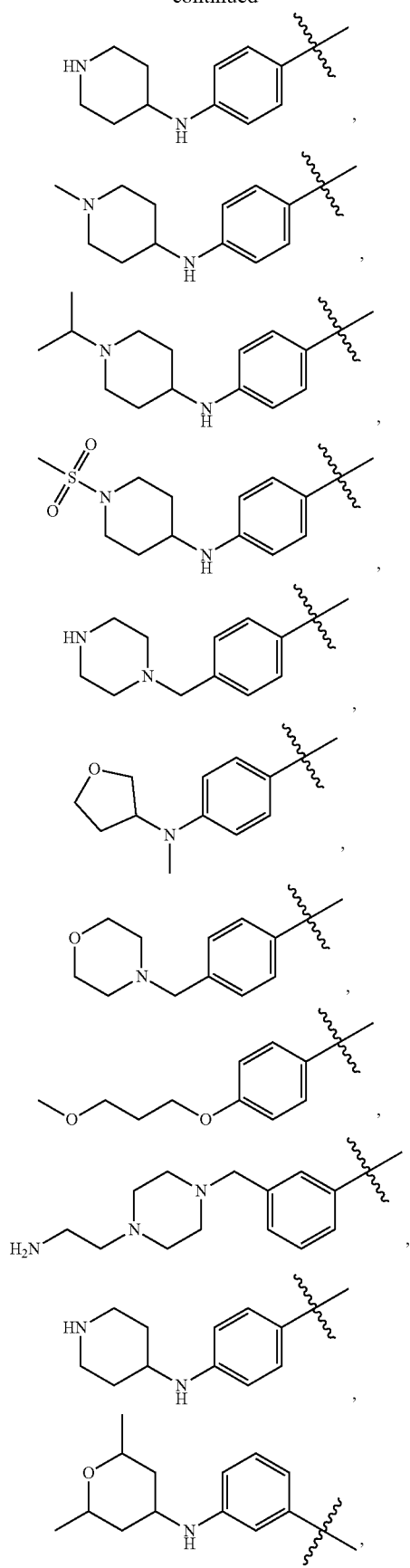
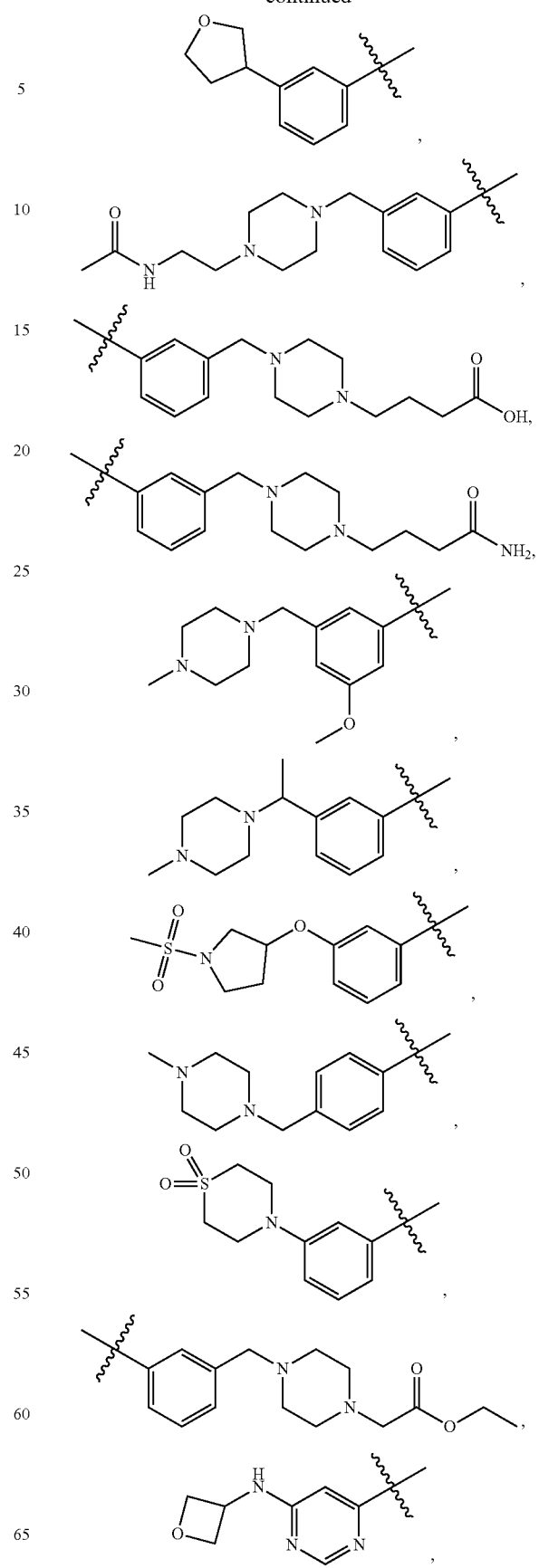

255
-continued
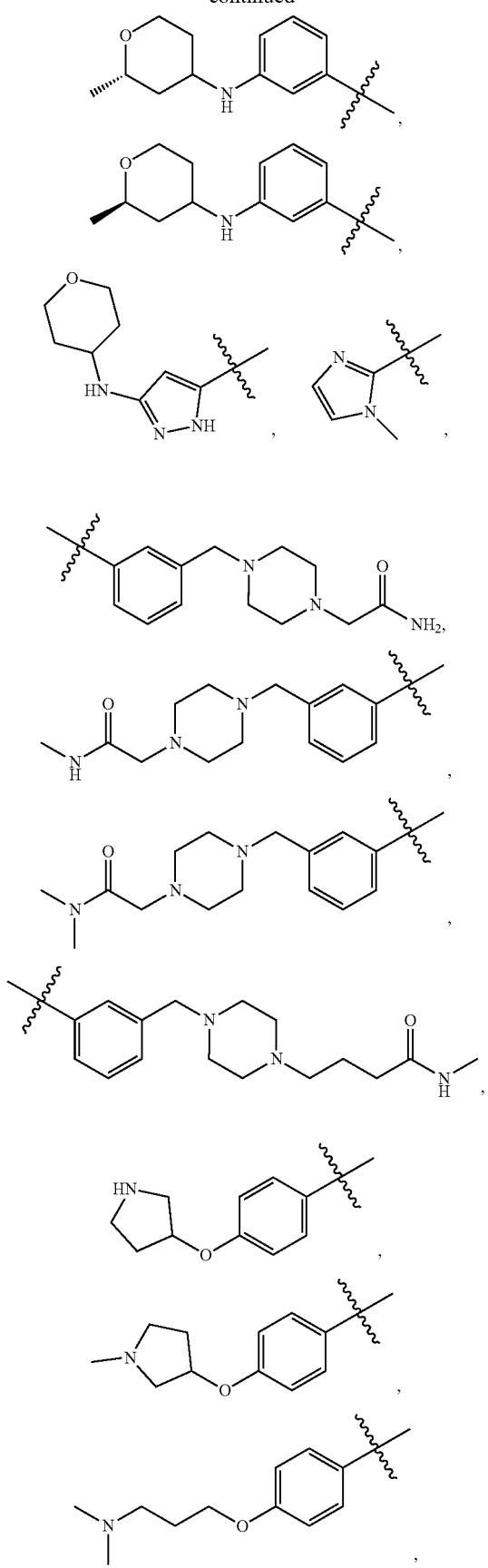
256
-continued
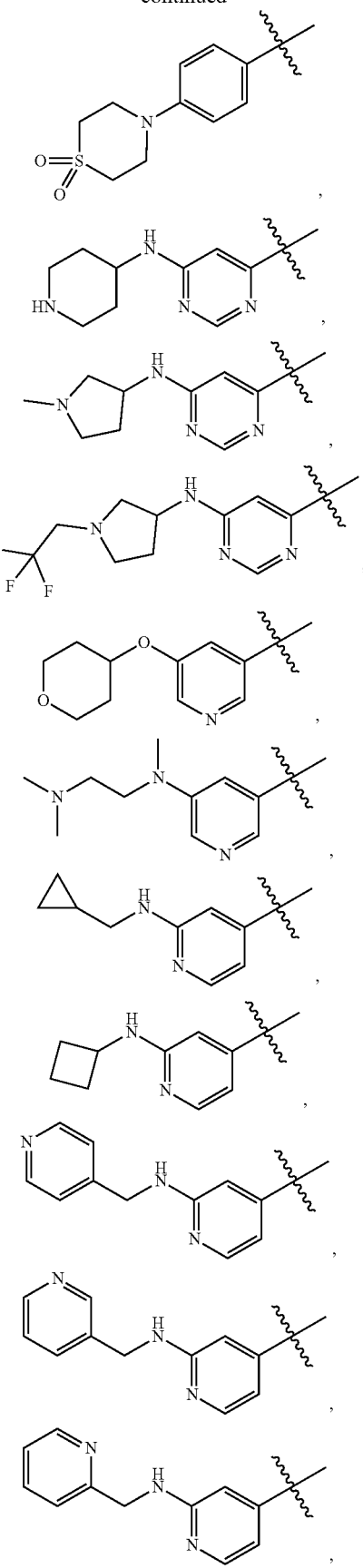

257
-continued
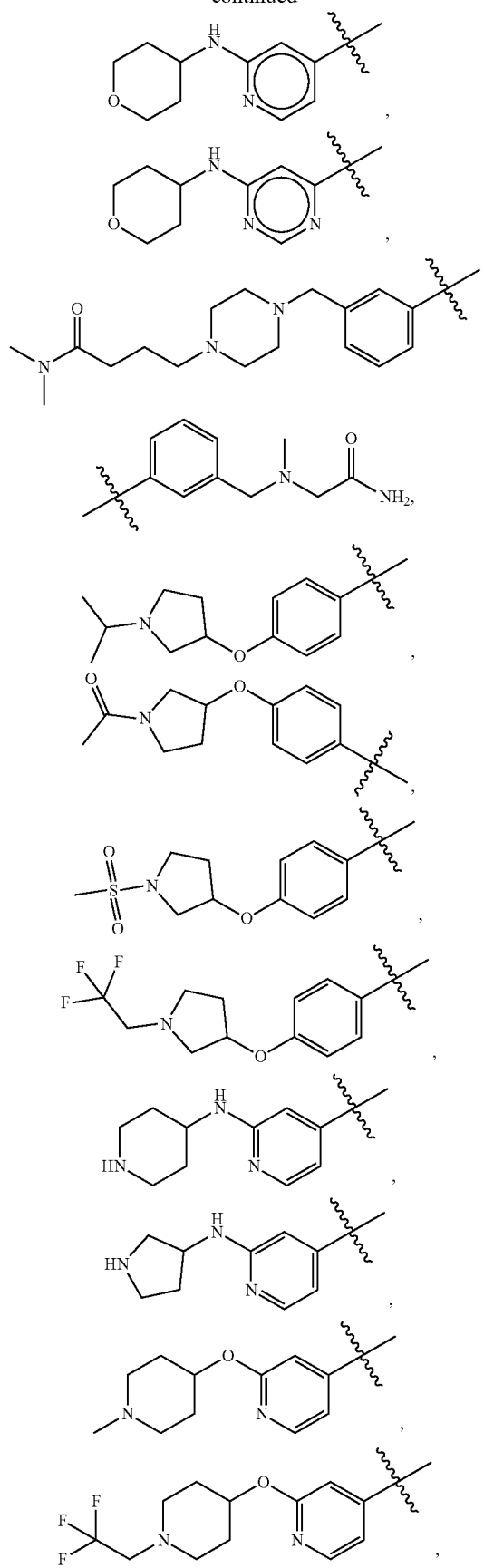
258
-continued
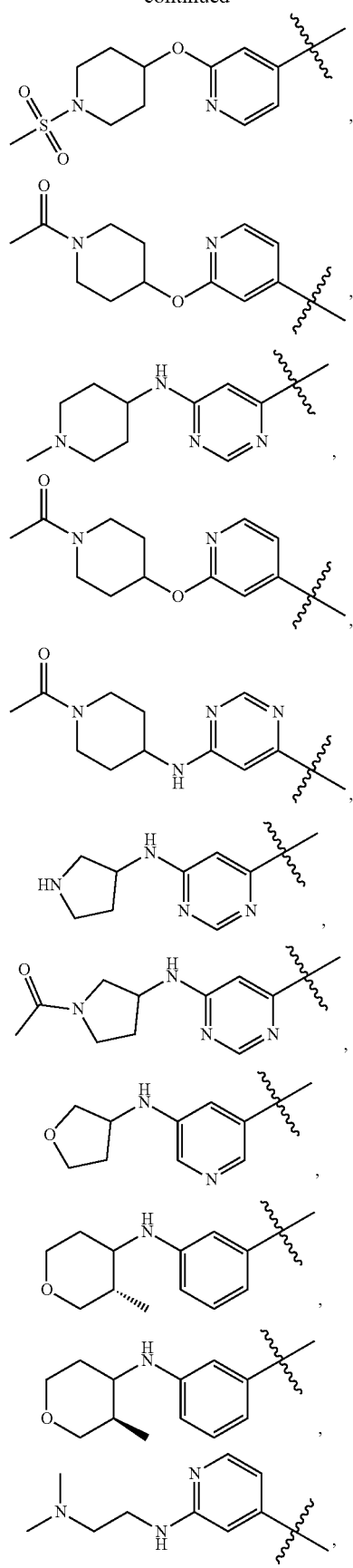

259
-continued
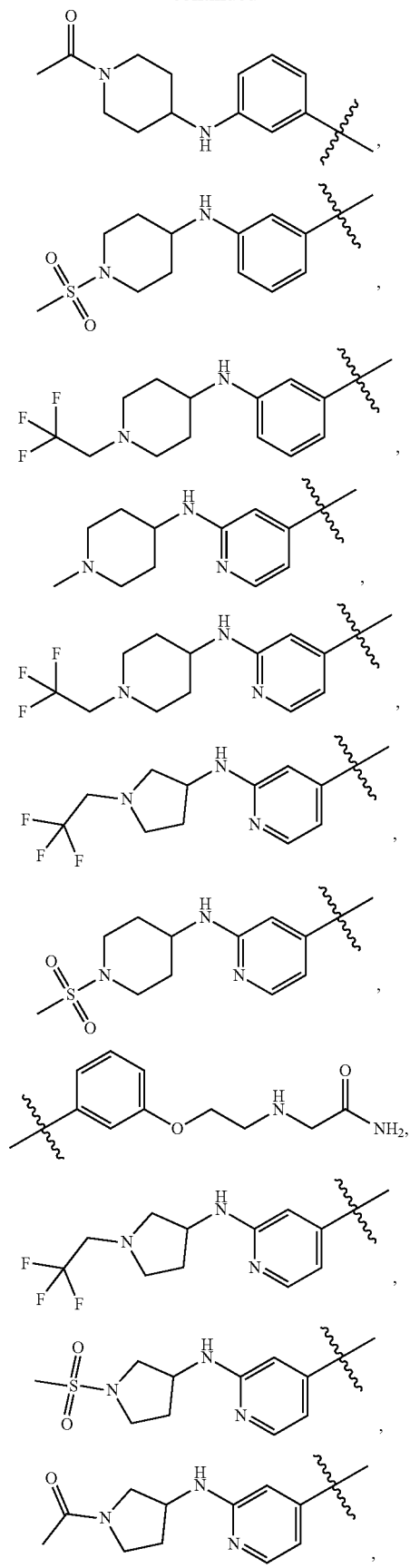
260
-continued
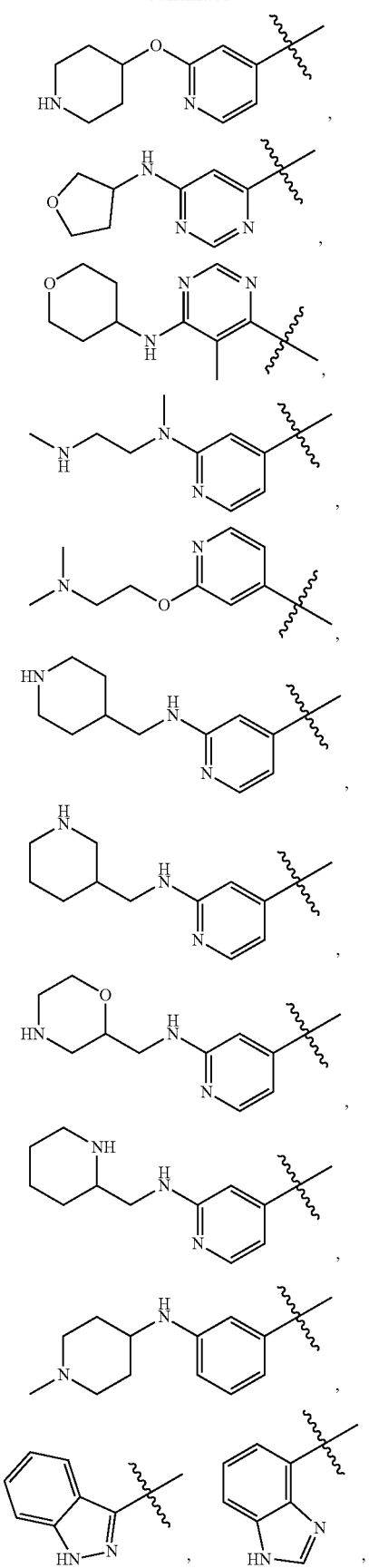

261
-continued
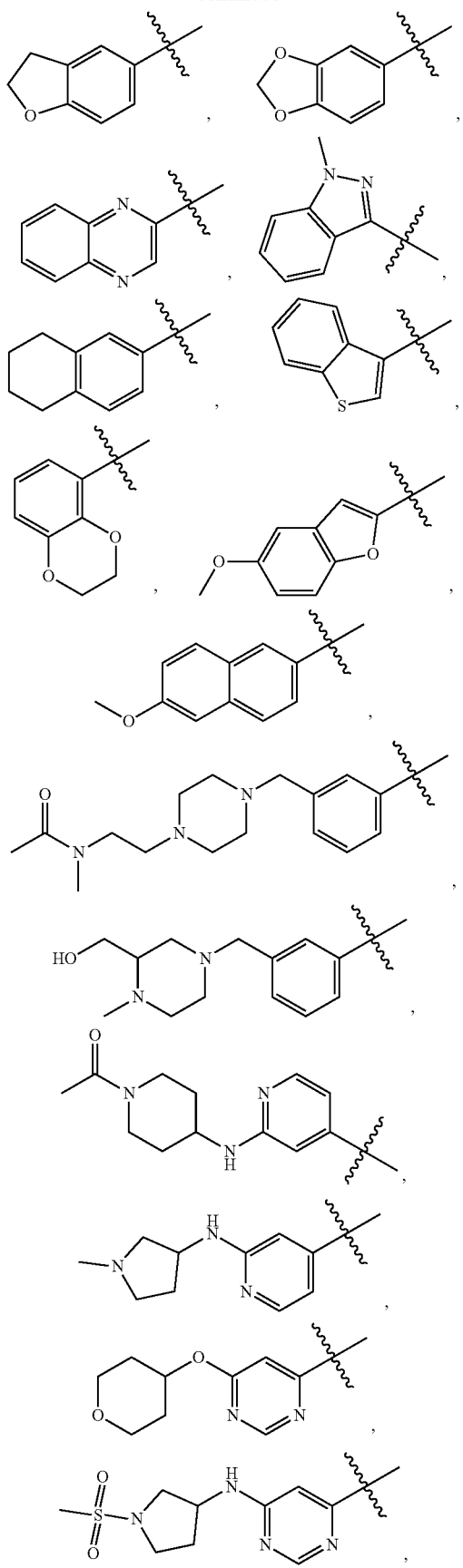
262
-continued
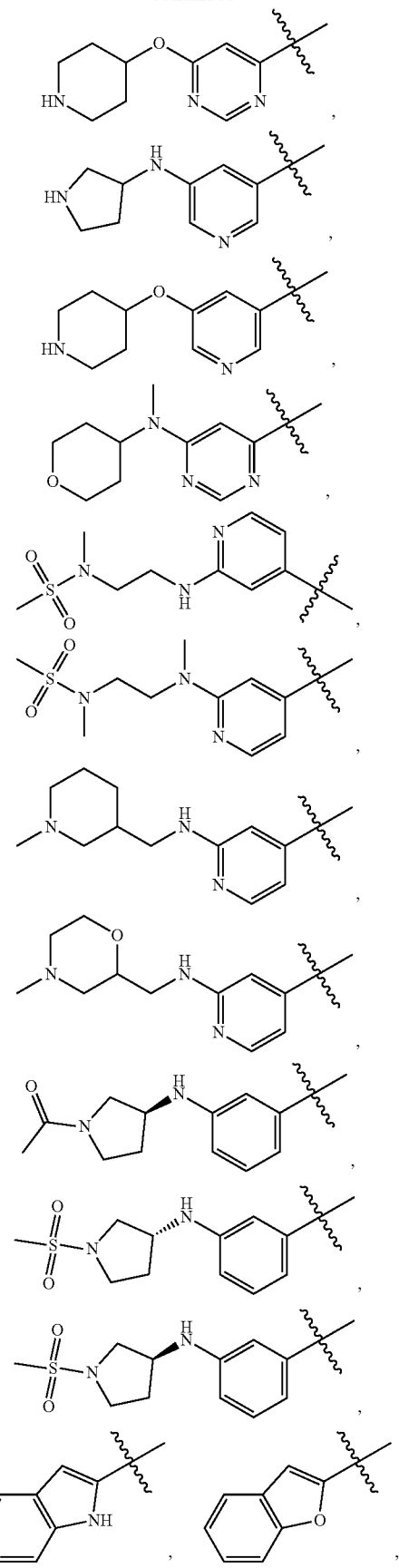

263
-continued
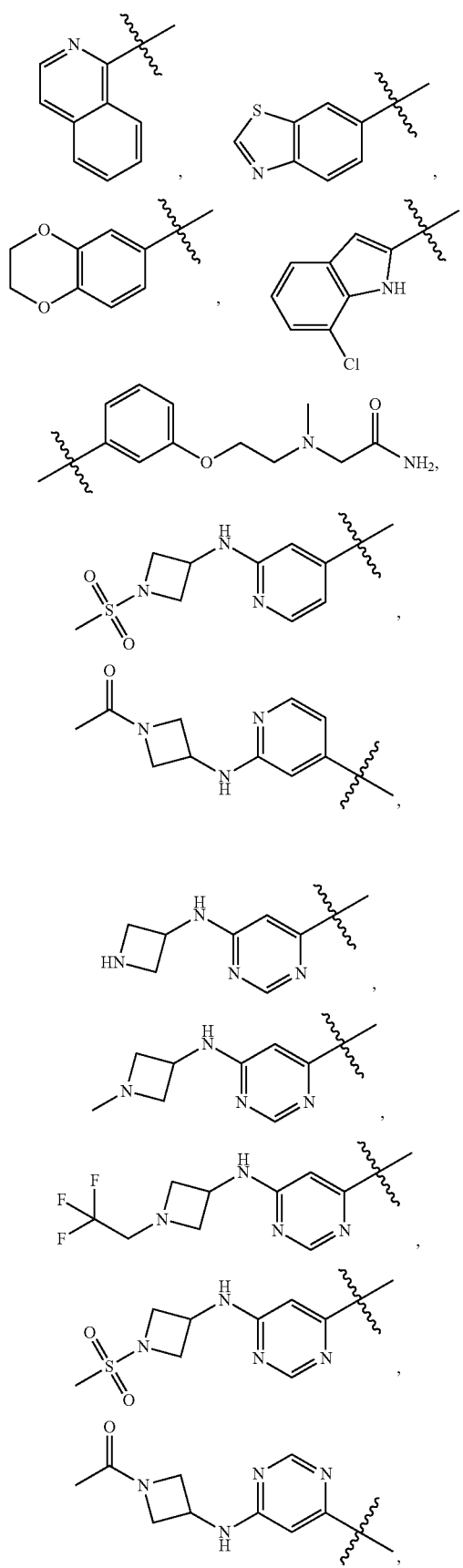
264
-continued
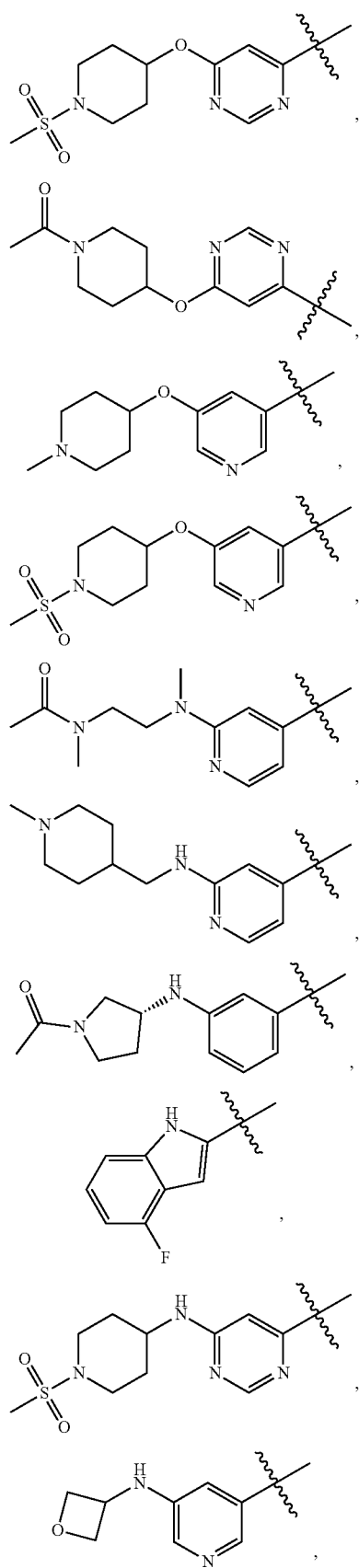

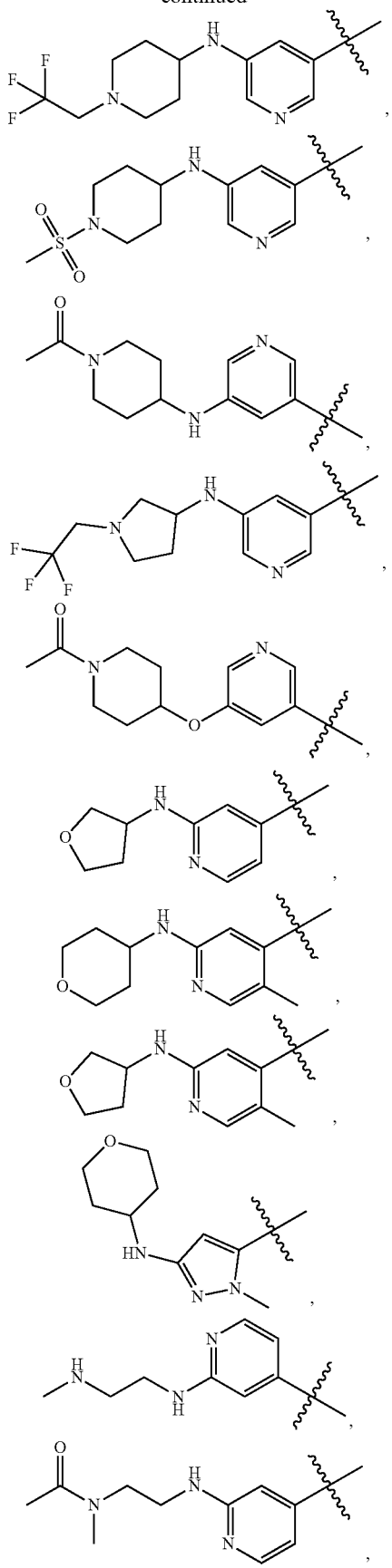
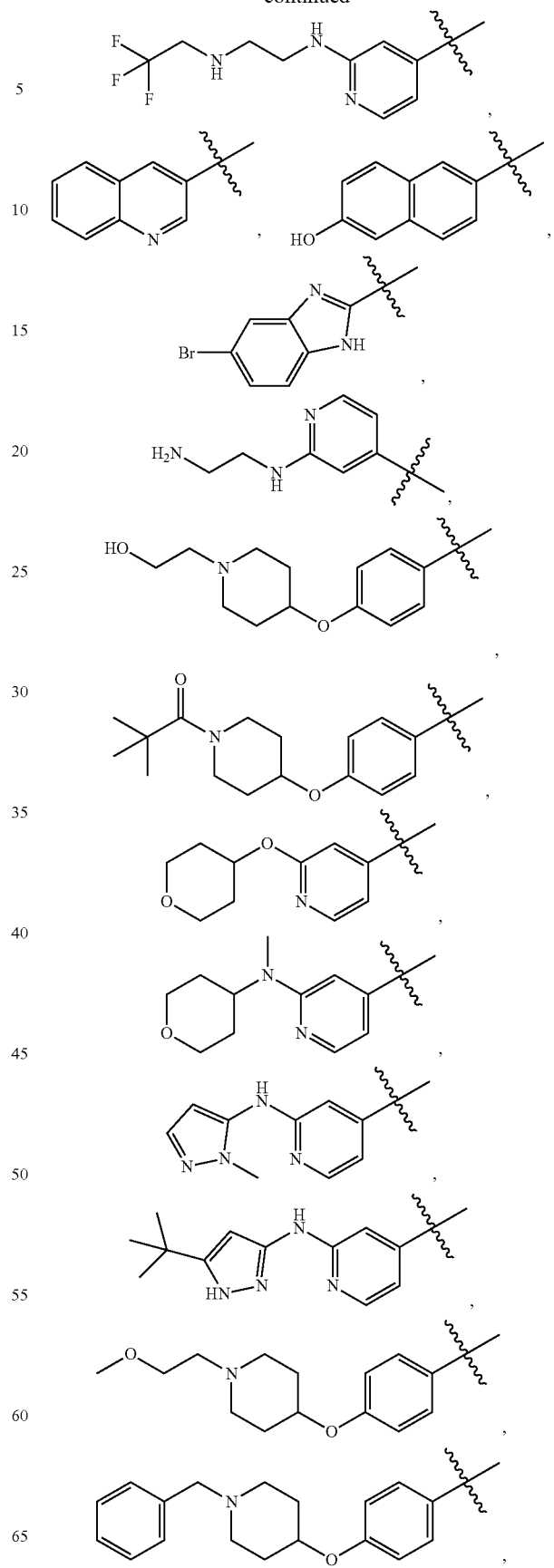

267
-continued
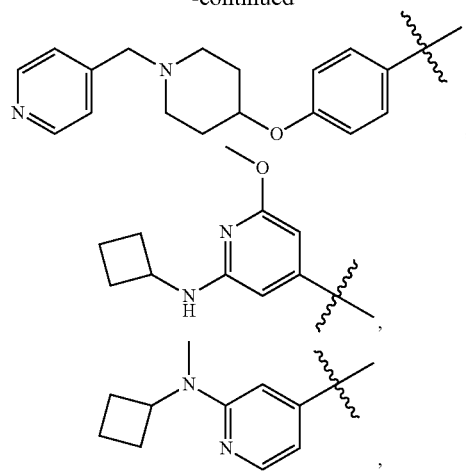
268
-continued
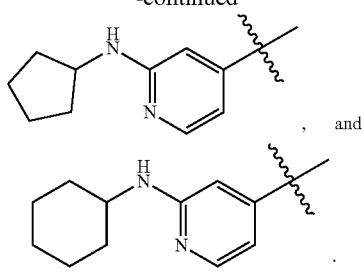
18. The method of claim 1, wherein the compound is selected from the group consisting of:
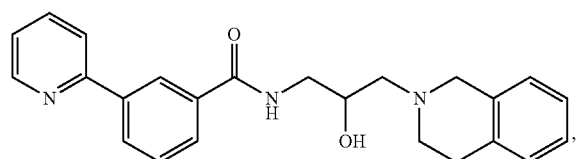
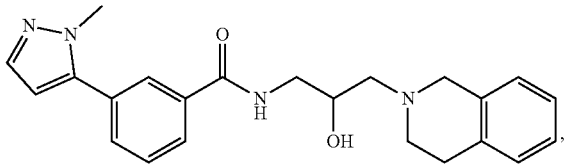
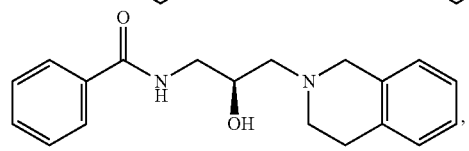
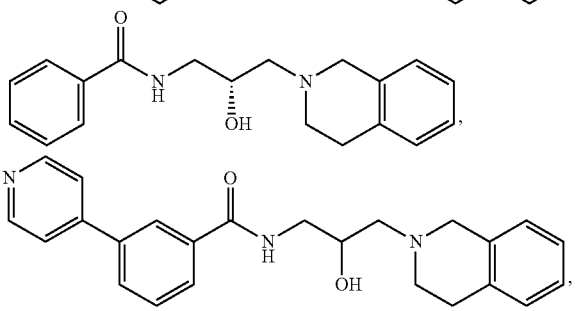
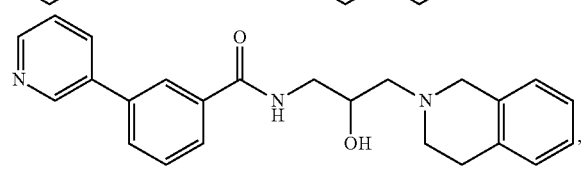
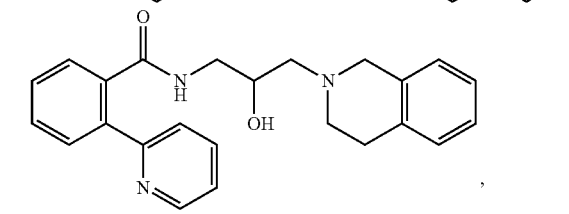
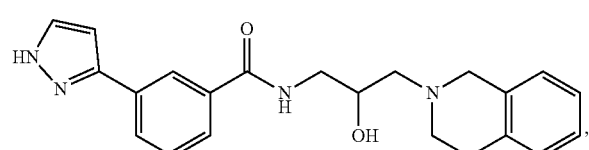
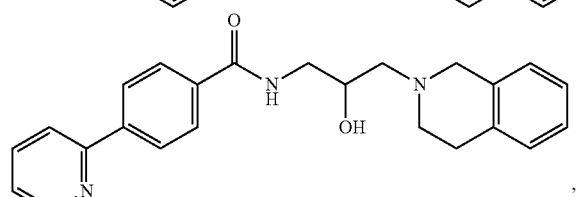
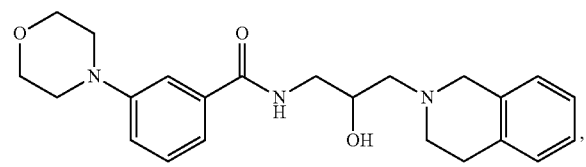
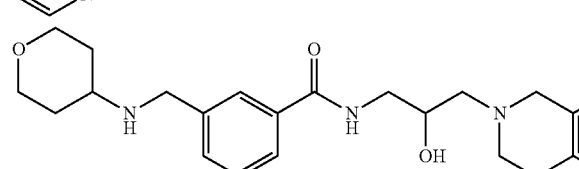
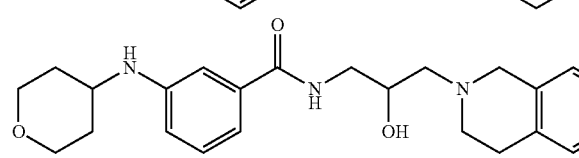
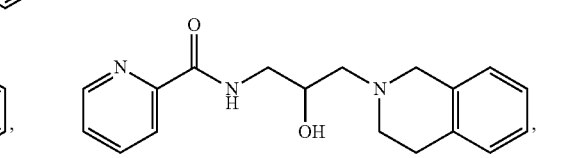

269
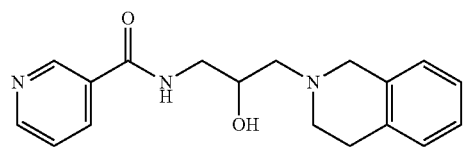
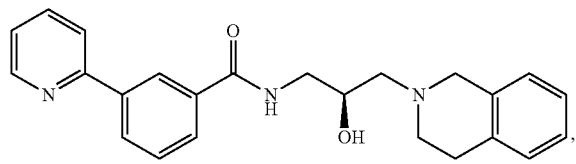
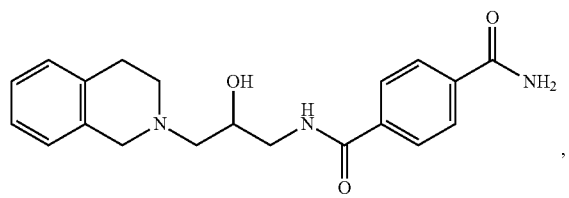
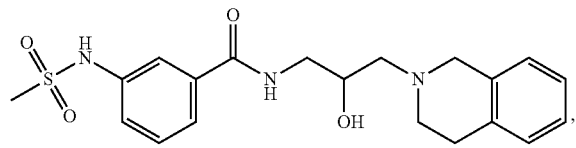
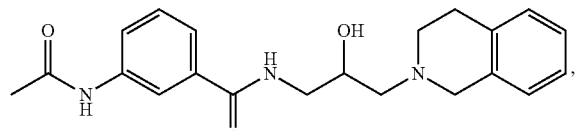
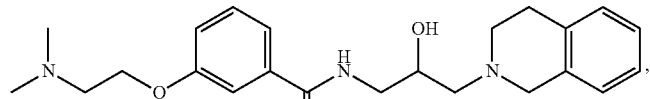
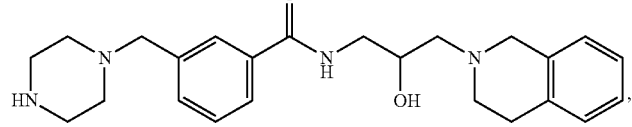
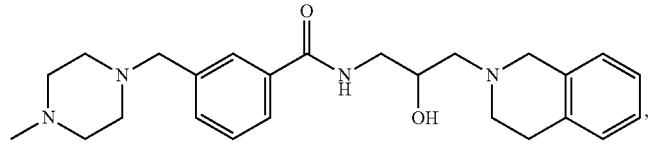
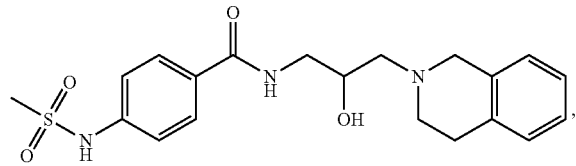
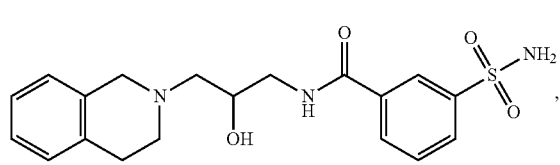
270
-continued
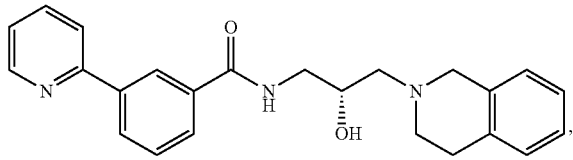
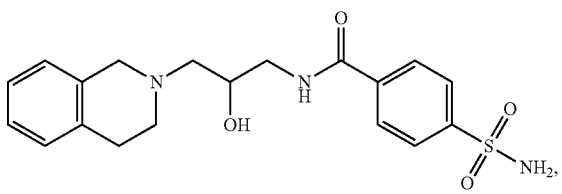
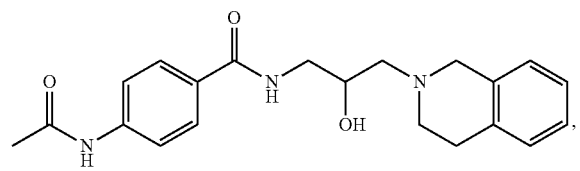
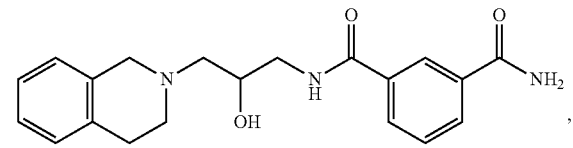
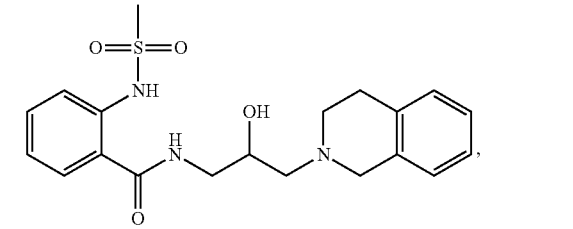
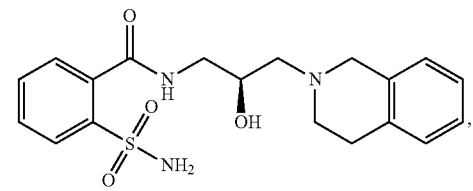

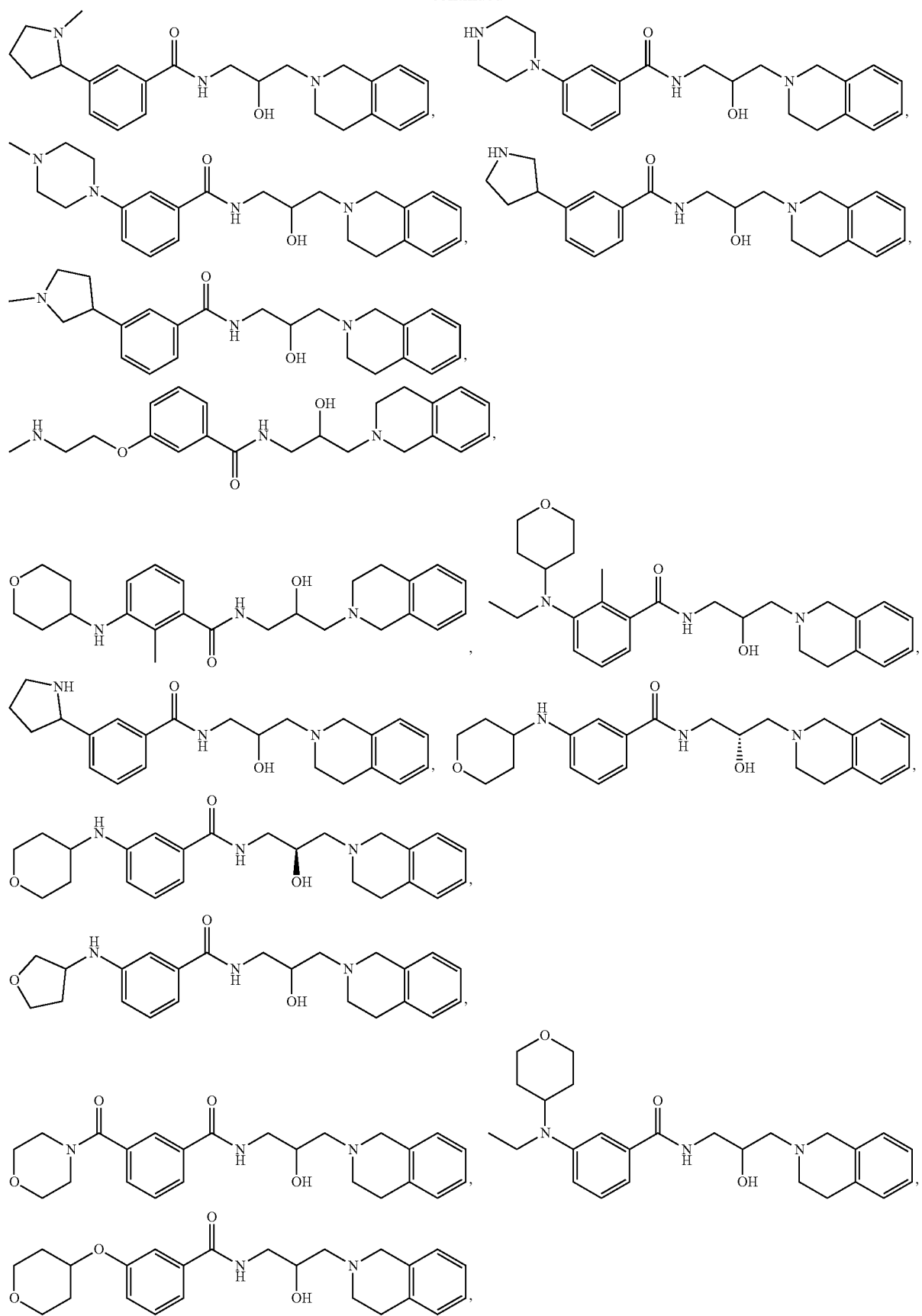

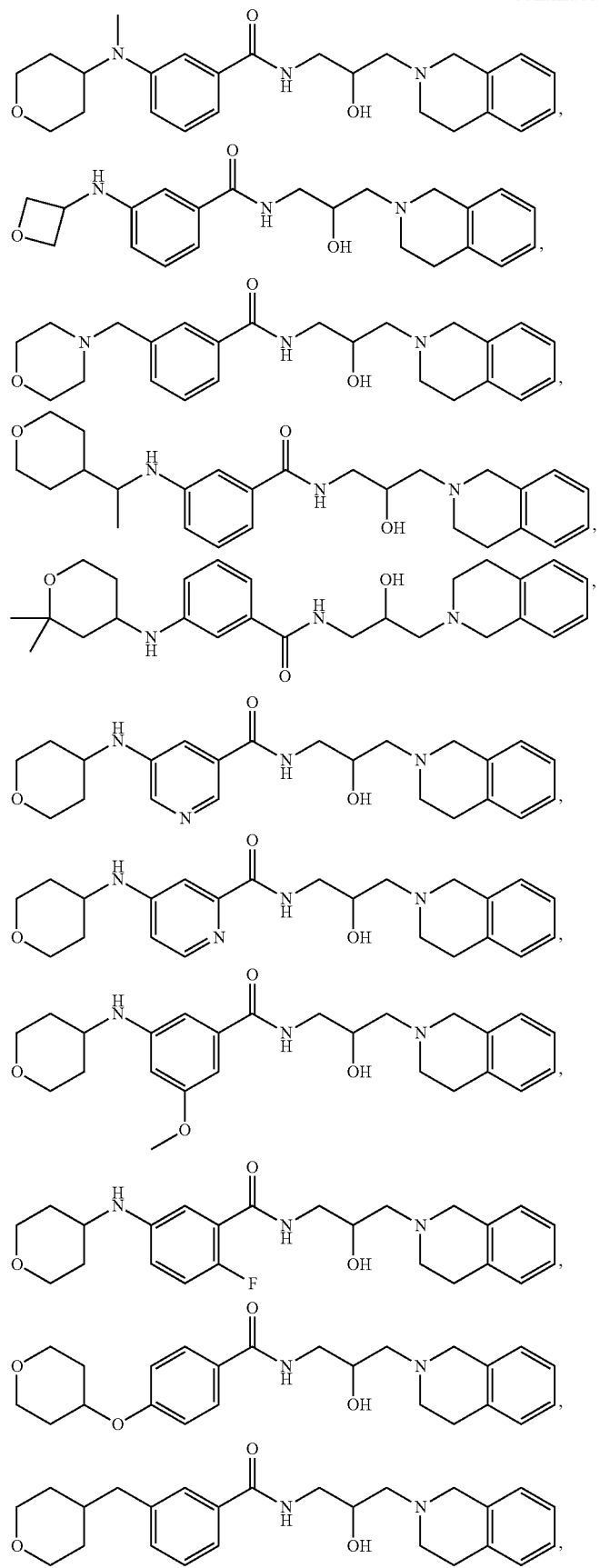

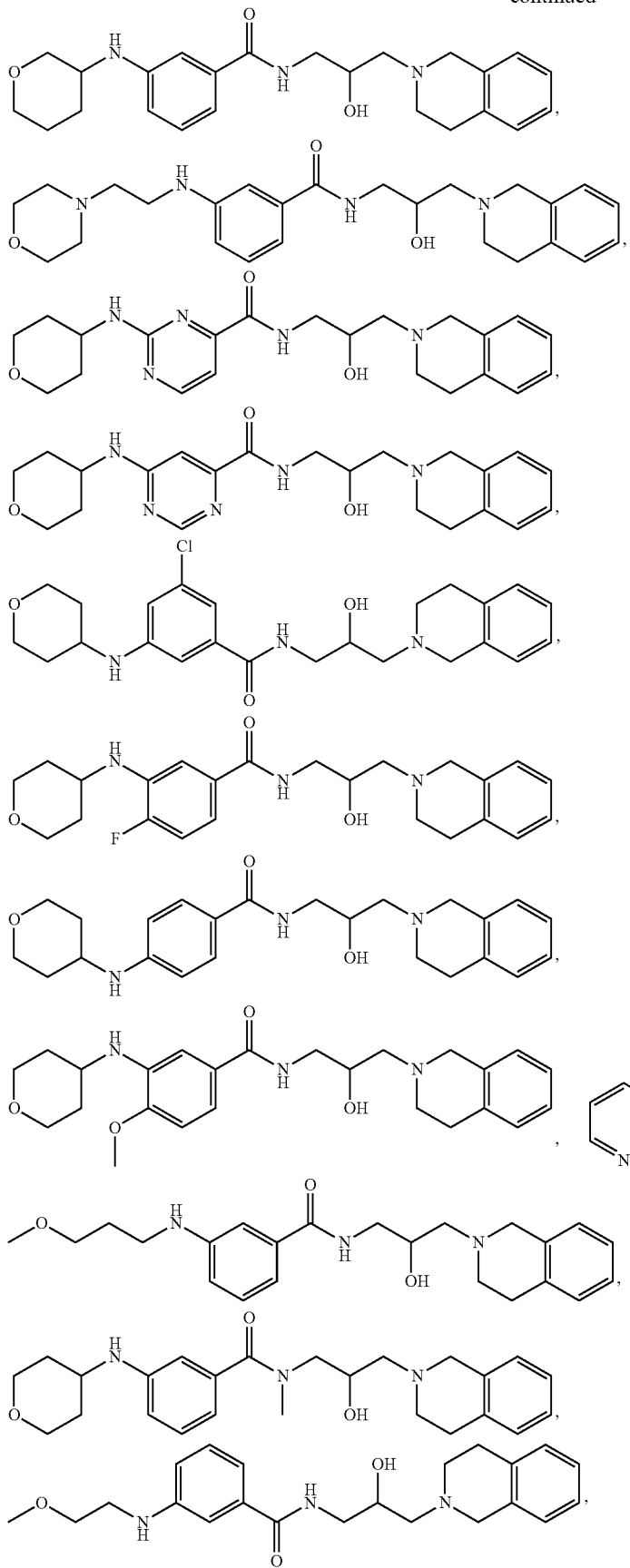

-continued
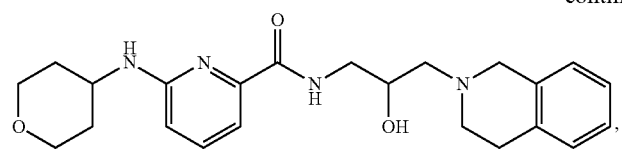
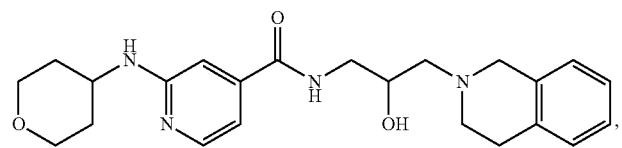
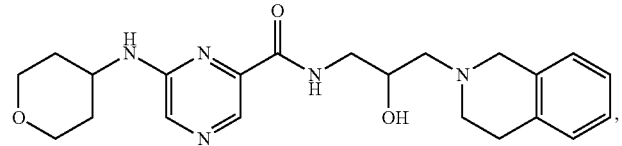
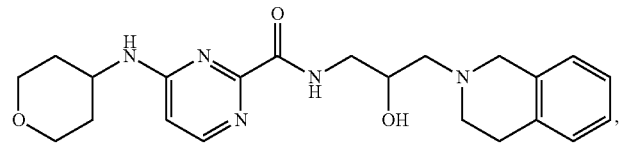
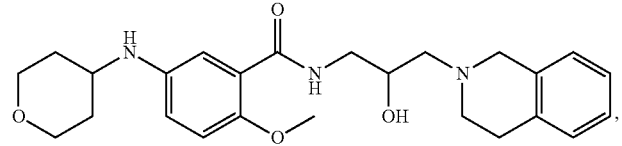
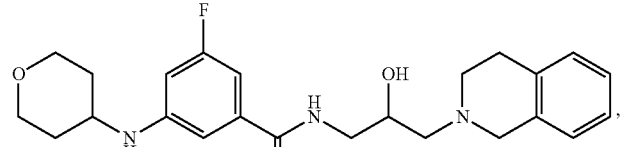
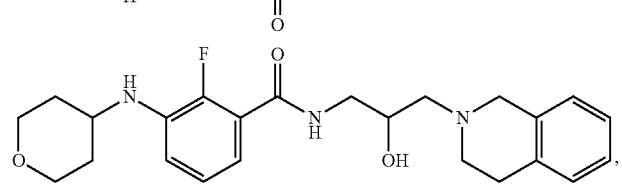
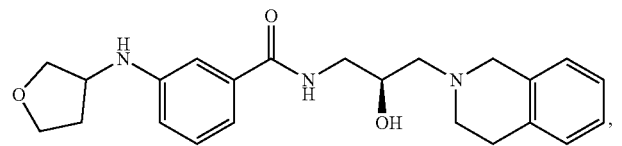
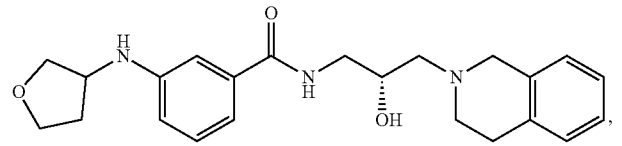
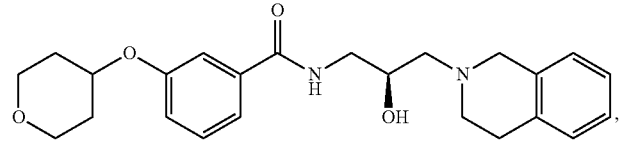
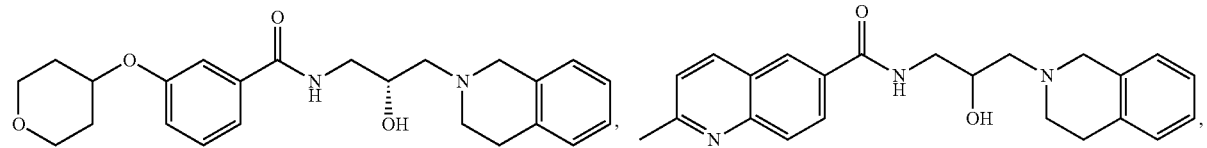

-continued
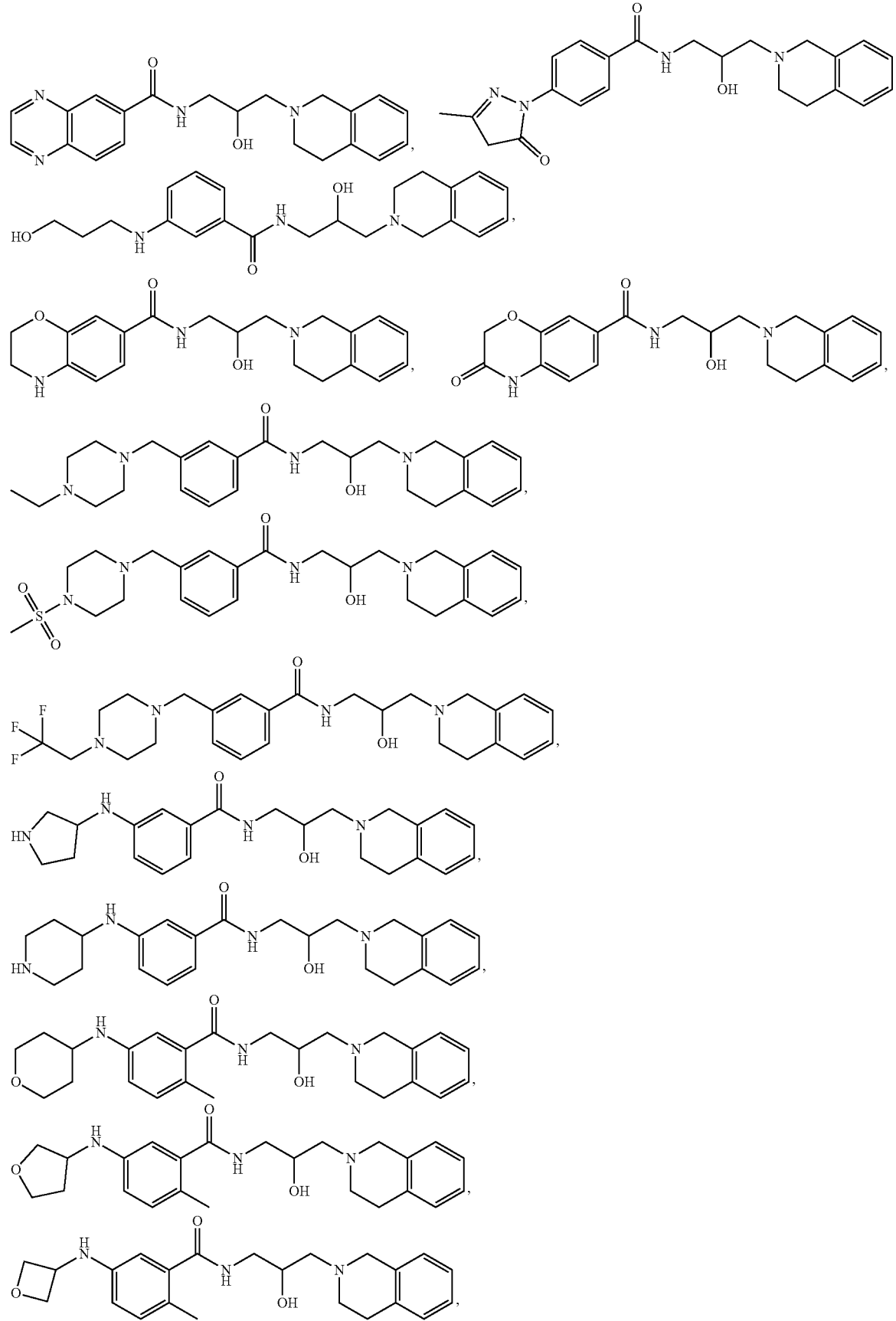

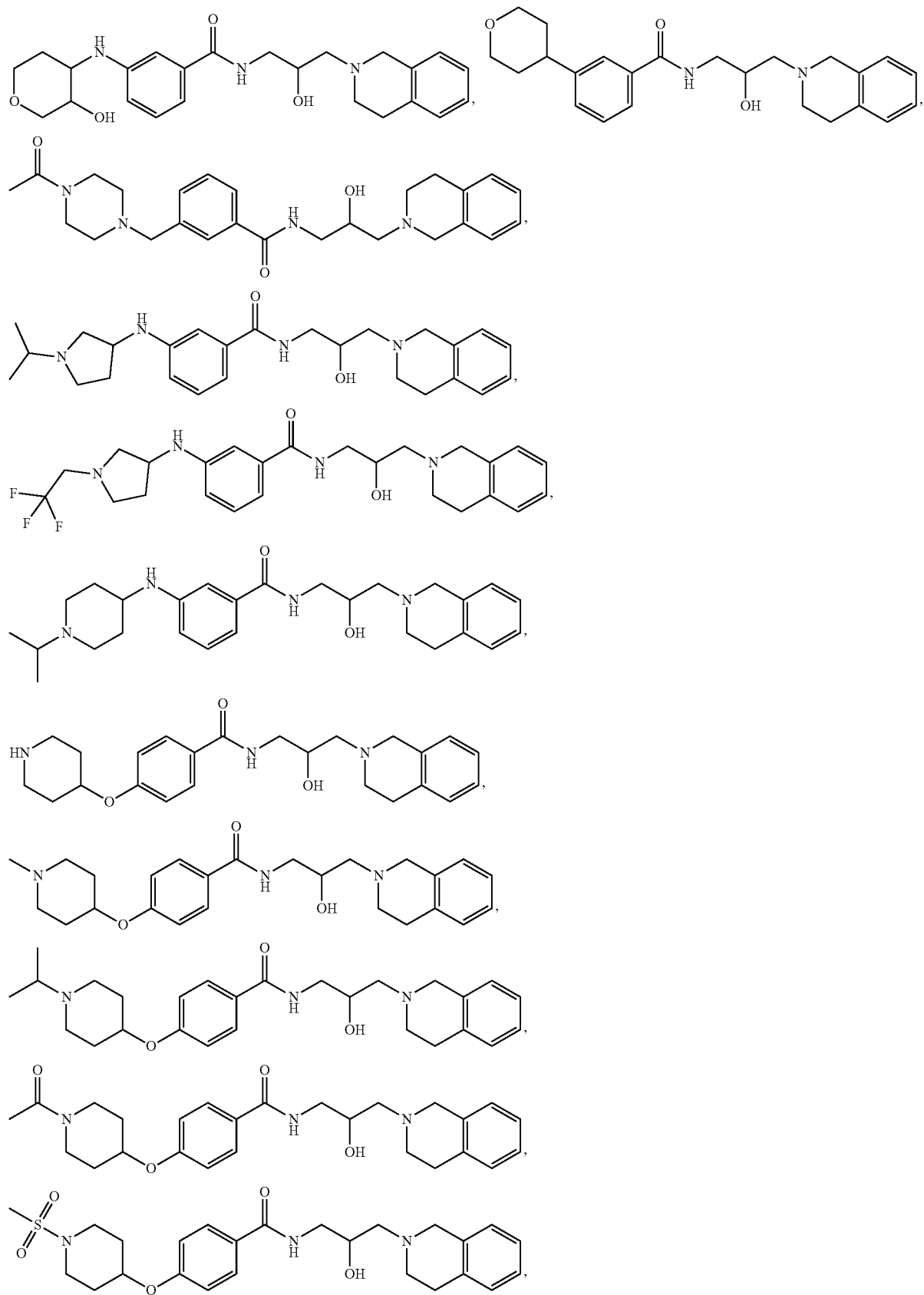

-continued
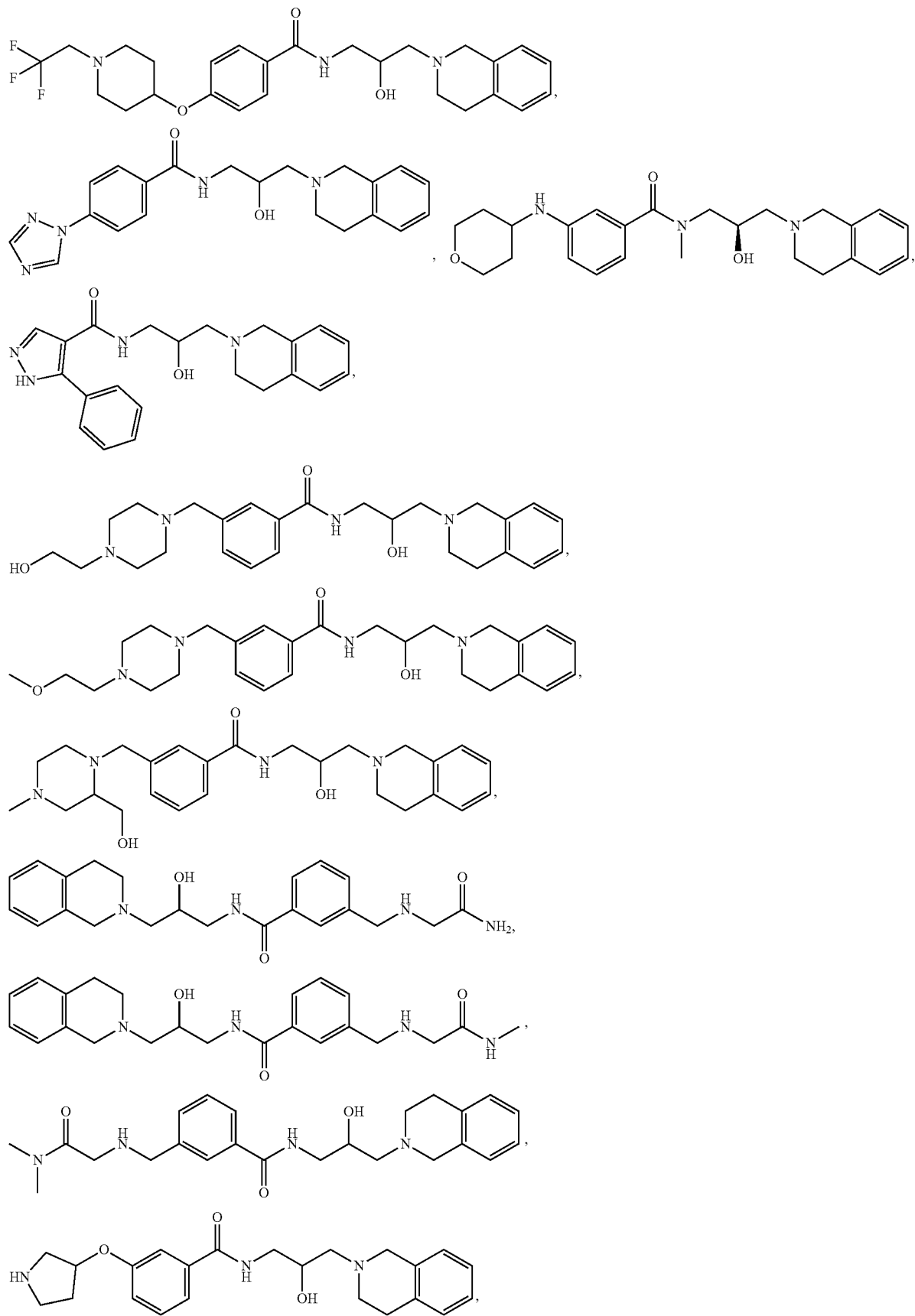

-continued
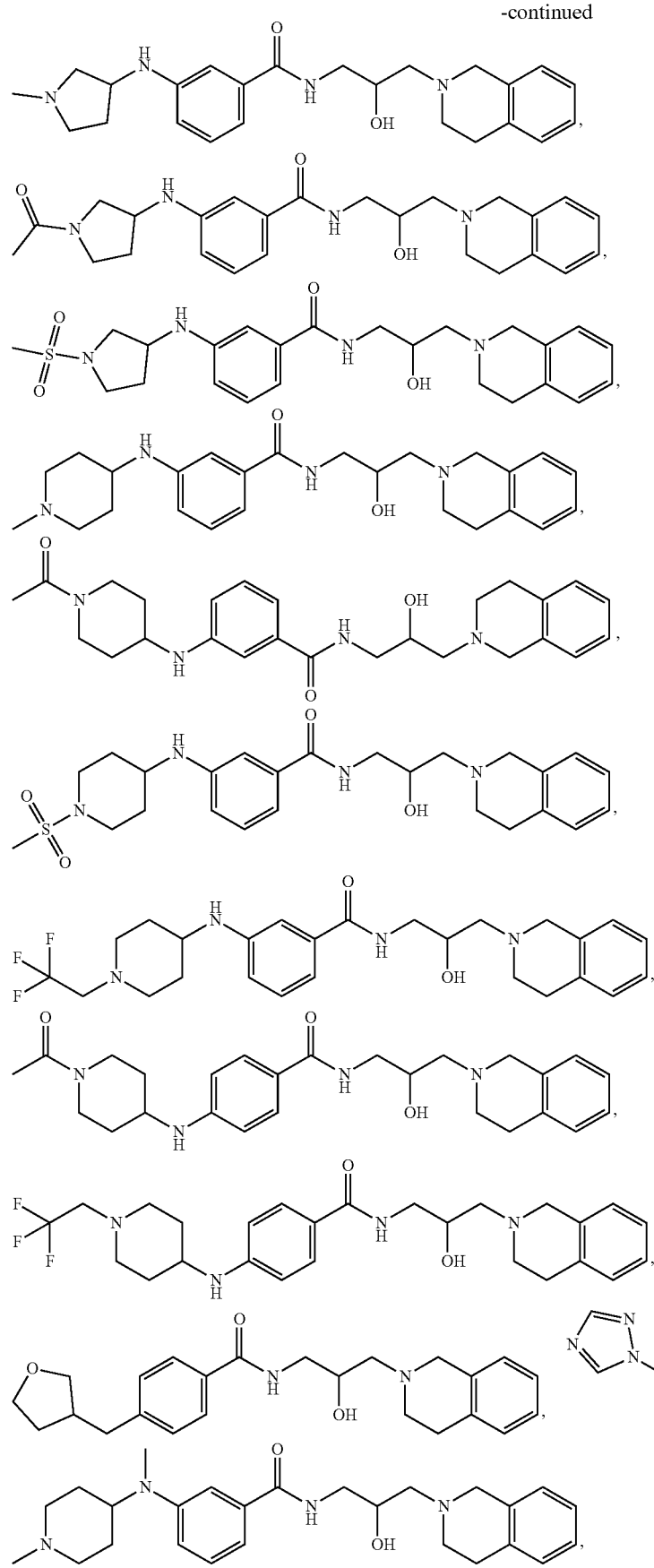

-continued
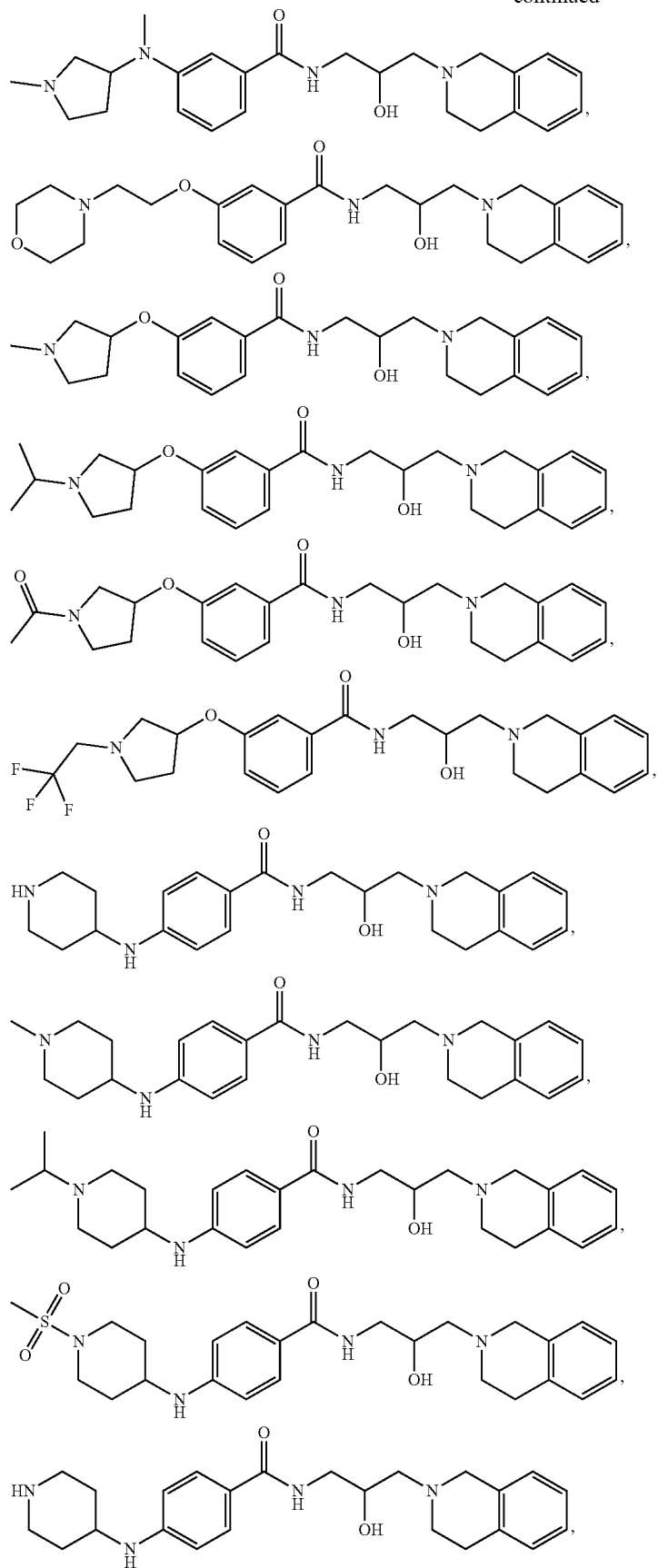

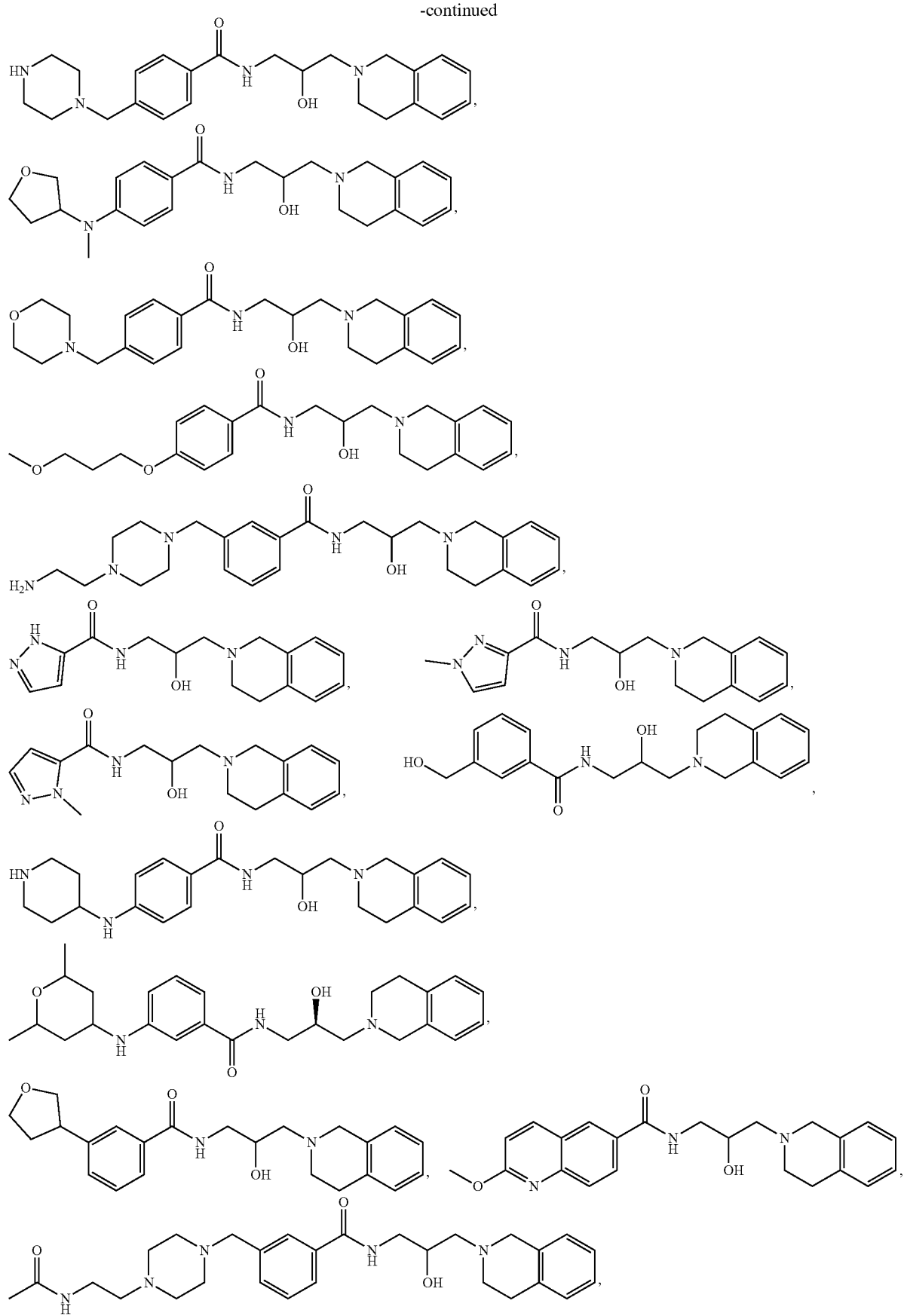

-continued
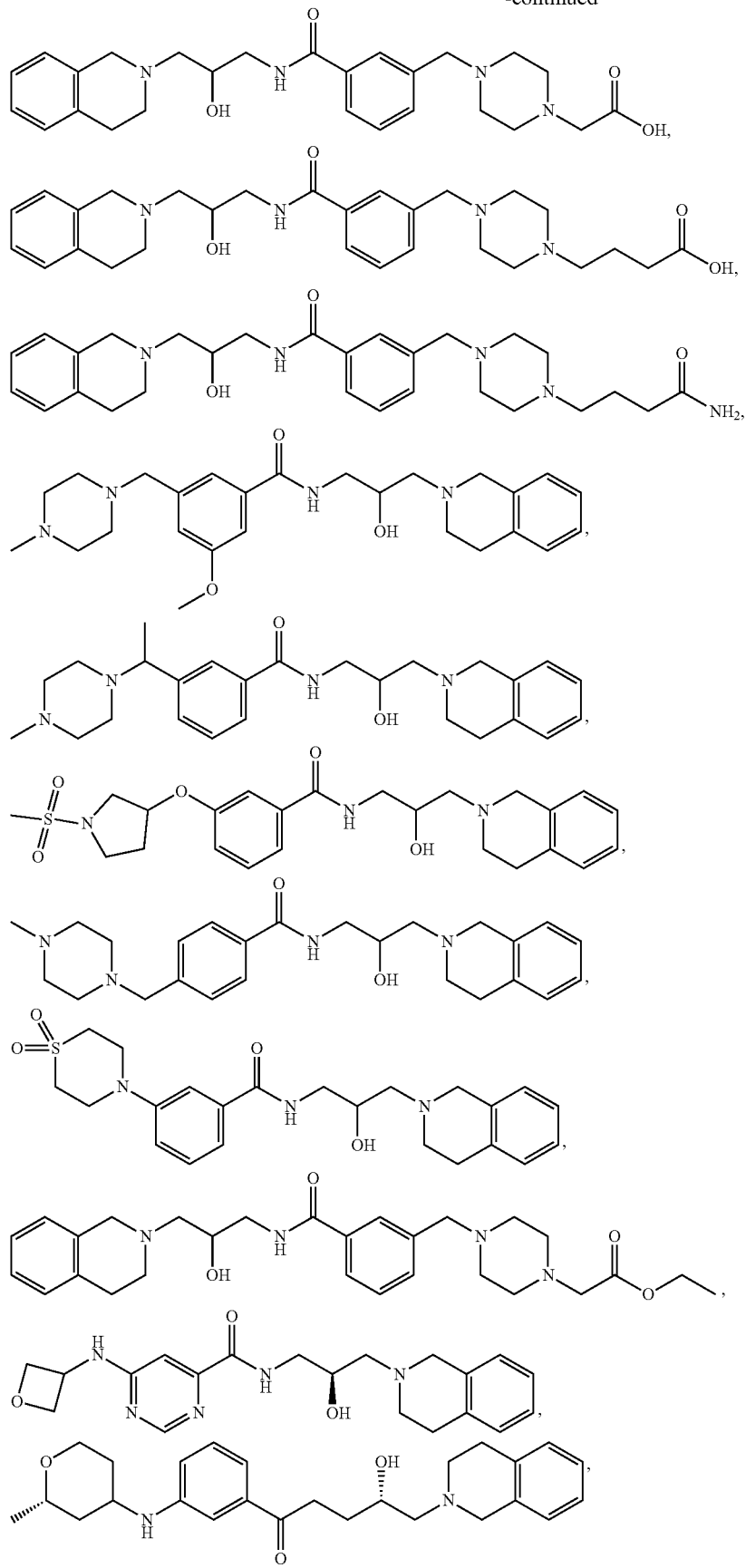

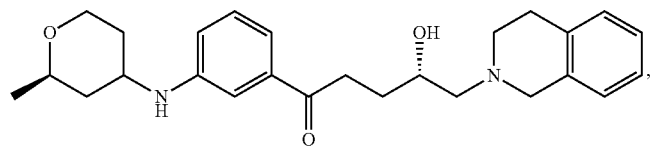
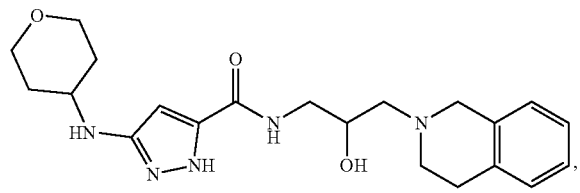
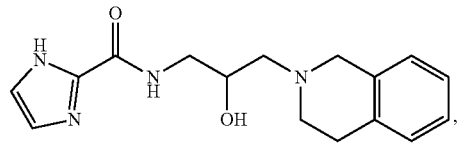
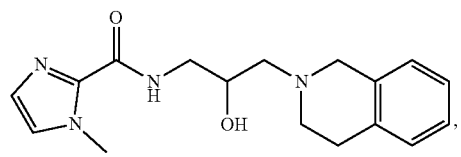
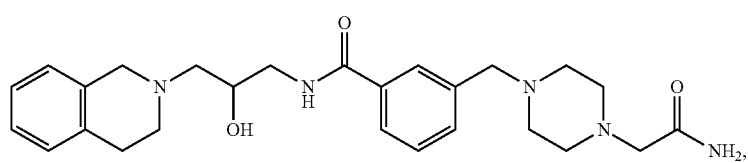
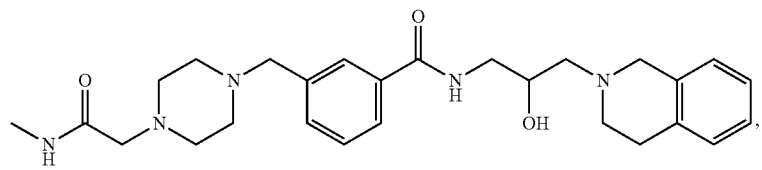
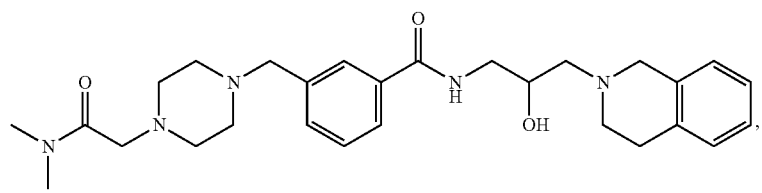
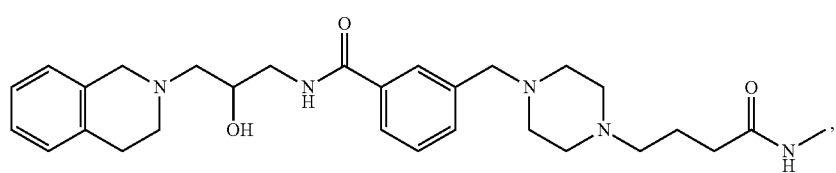
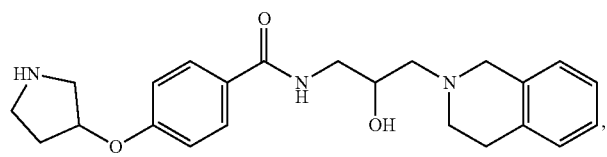
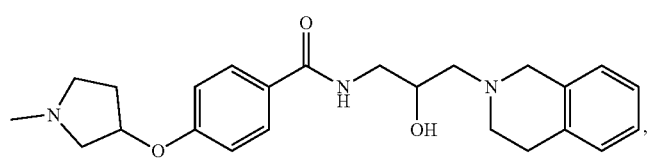
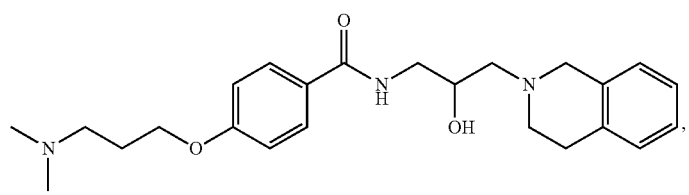

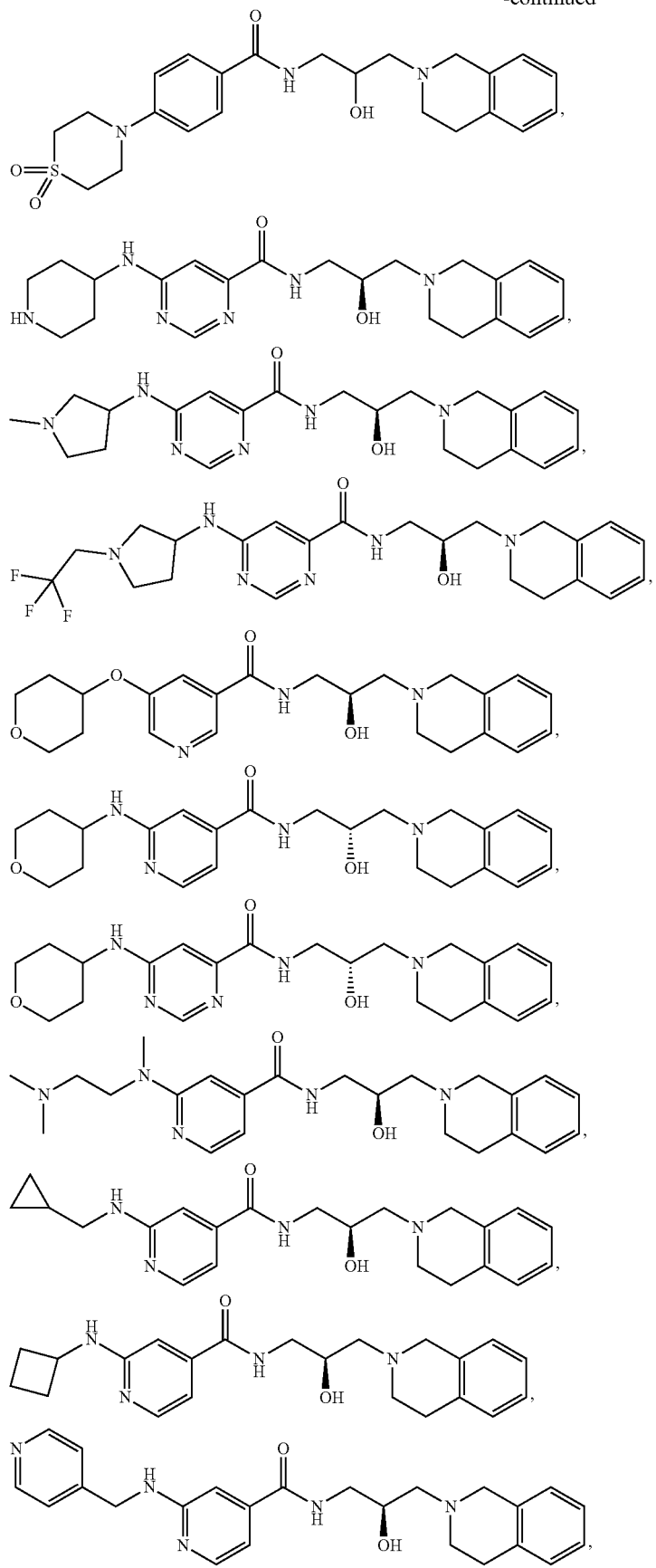

-continued
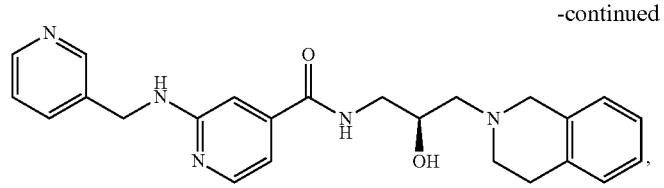,
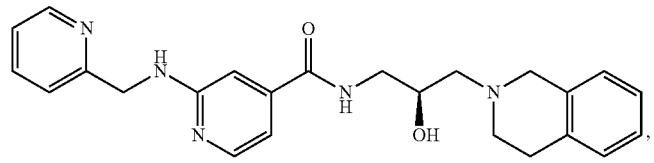,
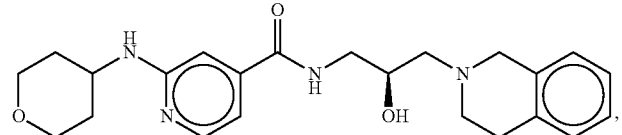,
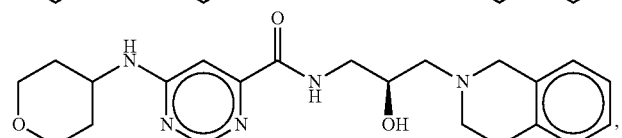,
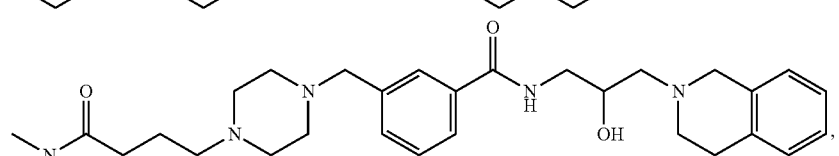,
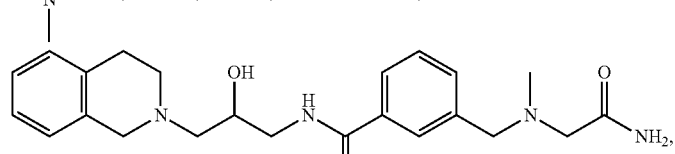,
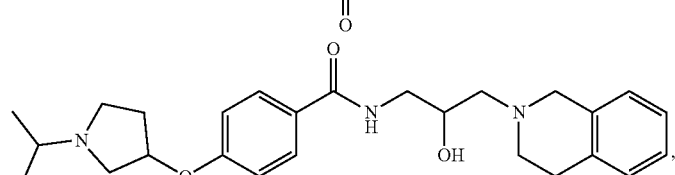,
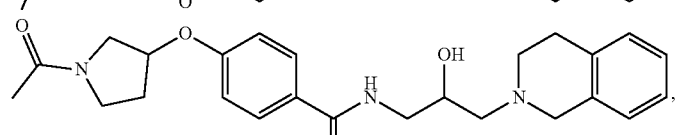,
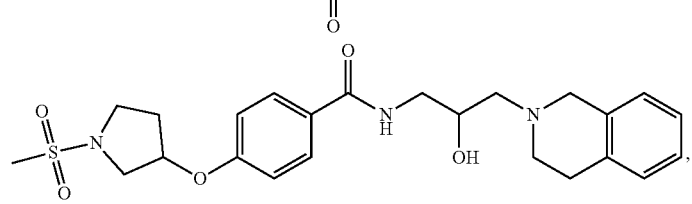,
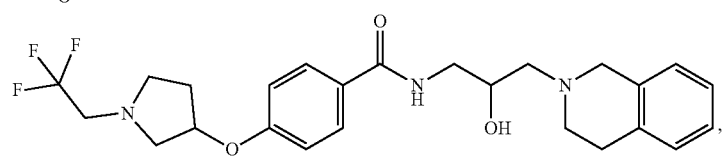,
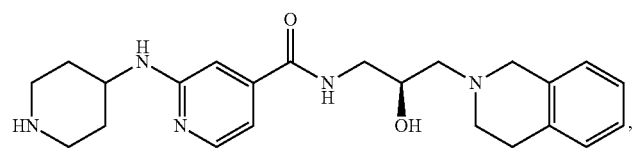,

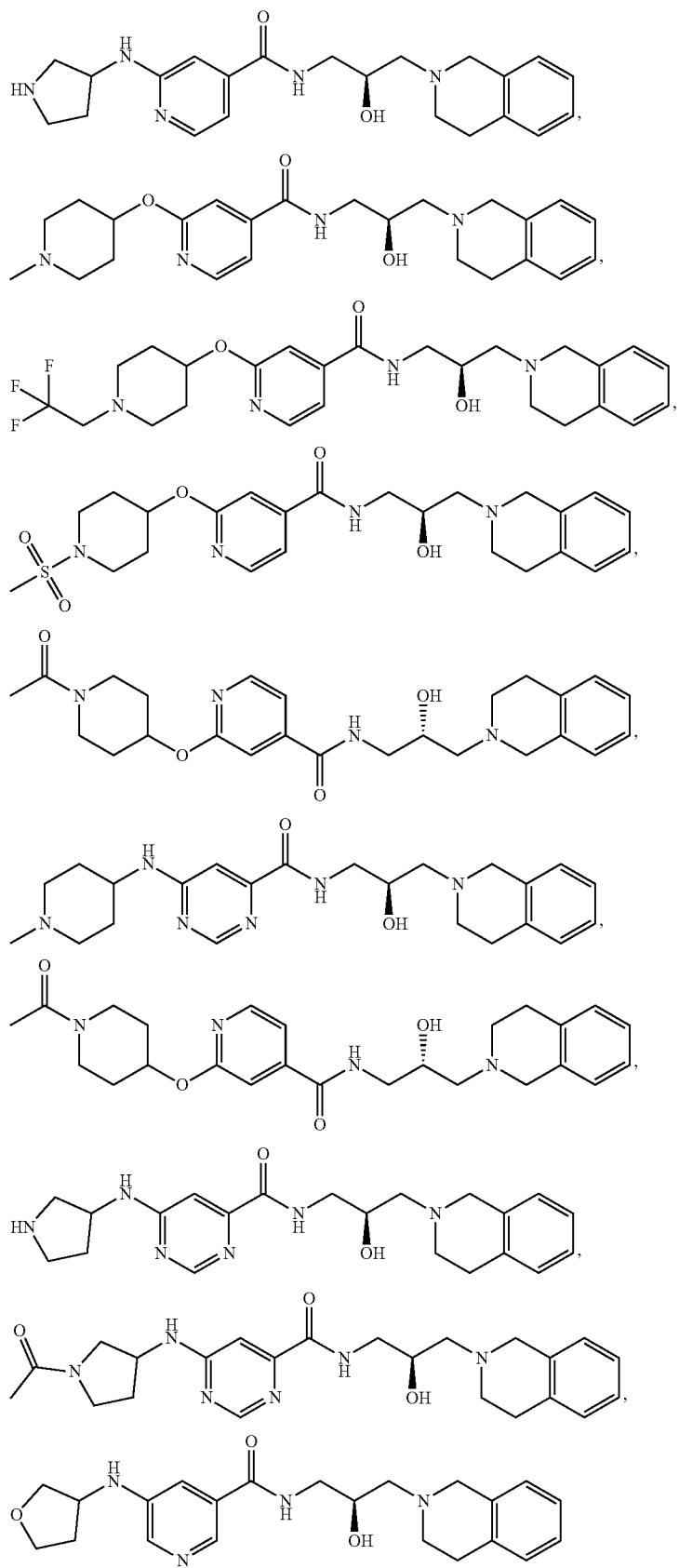

-continued
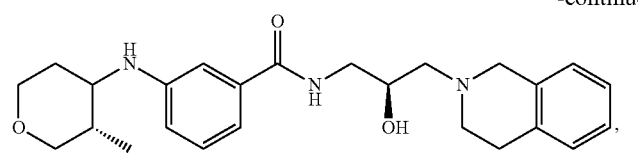
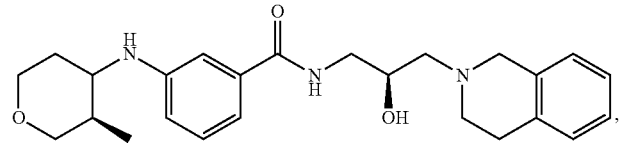
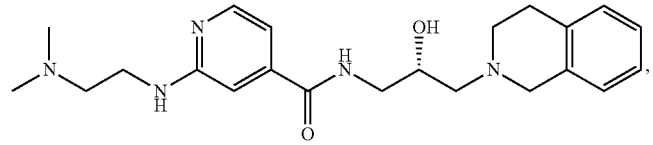
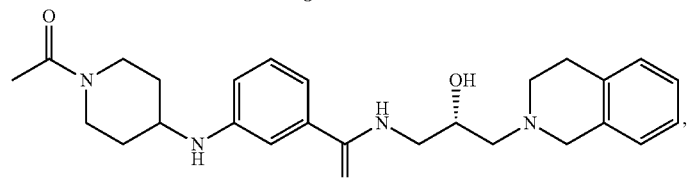
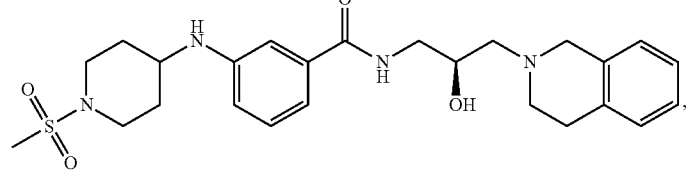
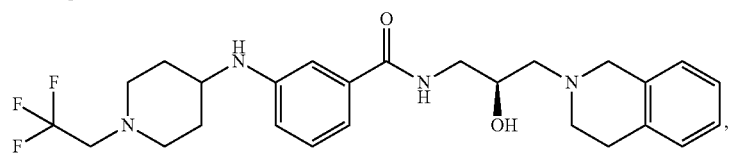
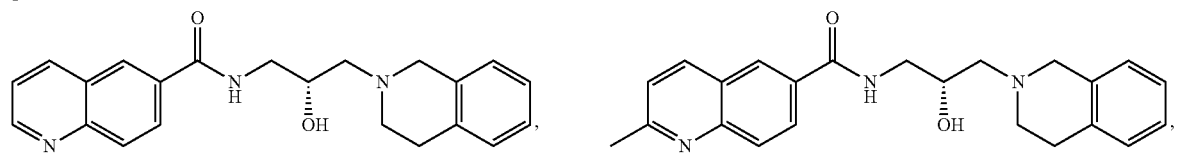
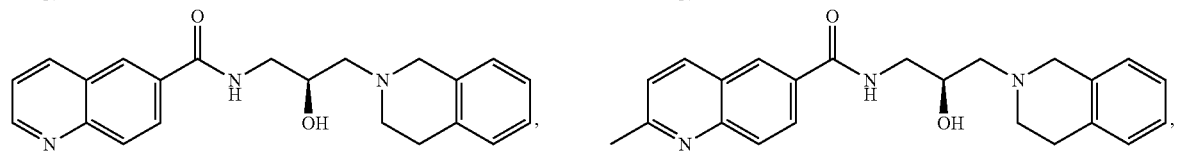
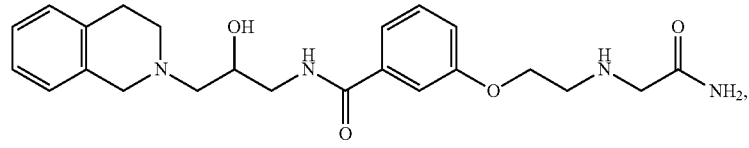
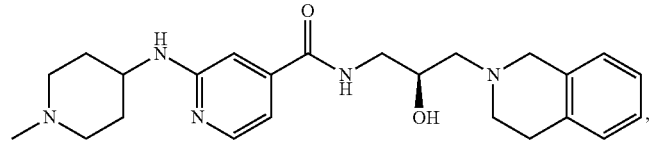
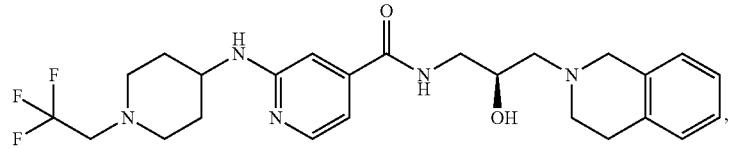

-continued
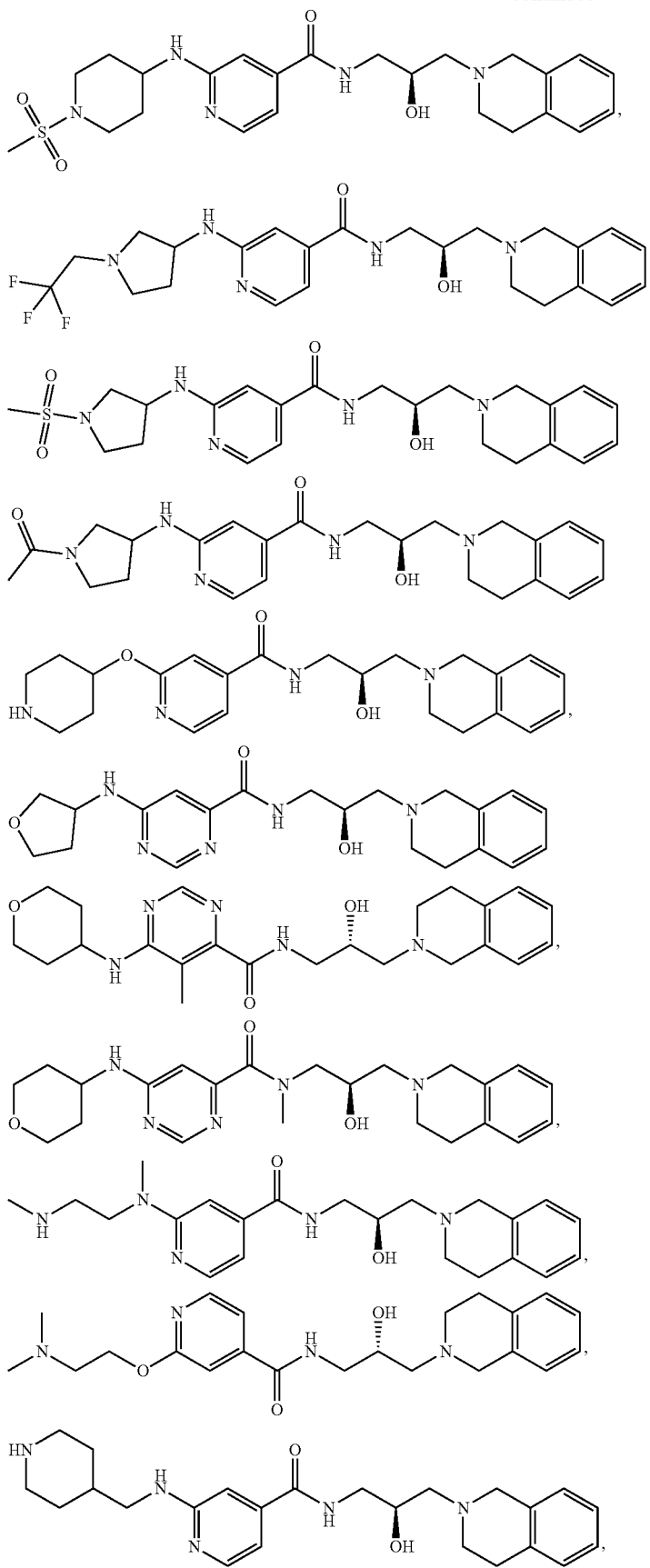

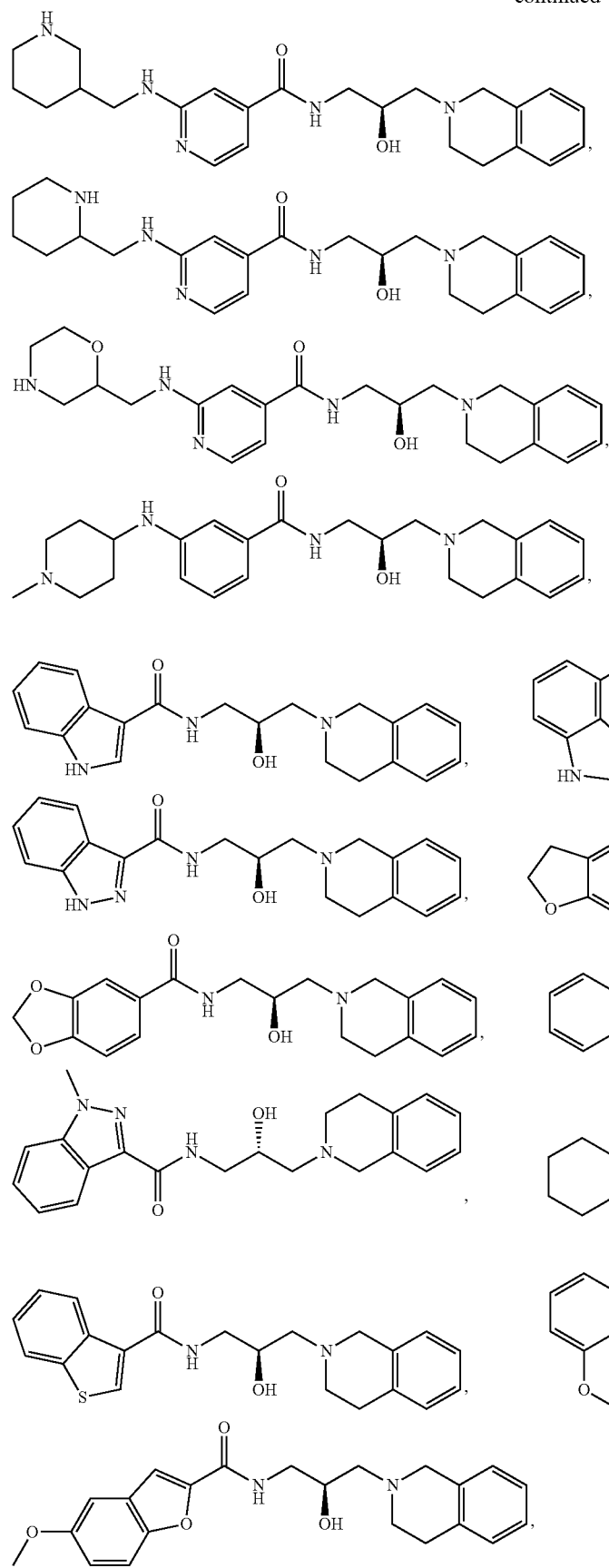

-continued
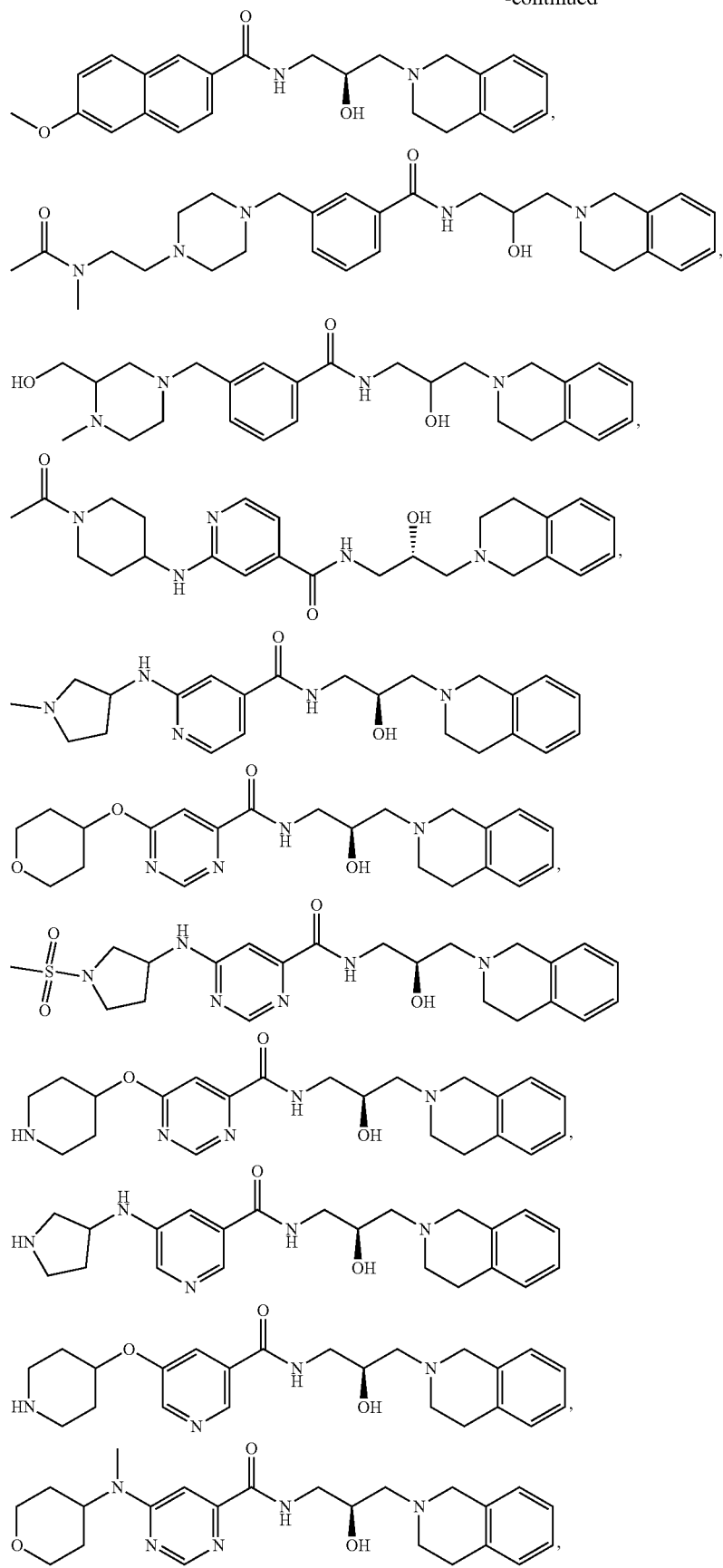

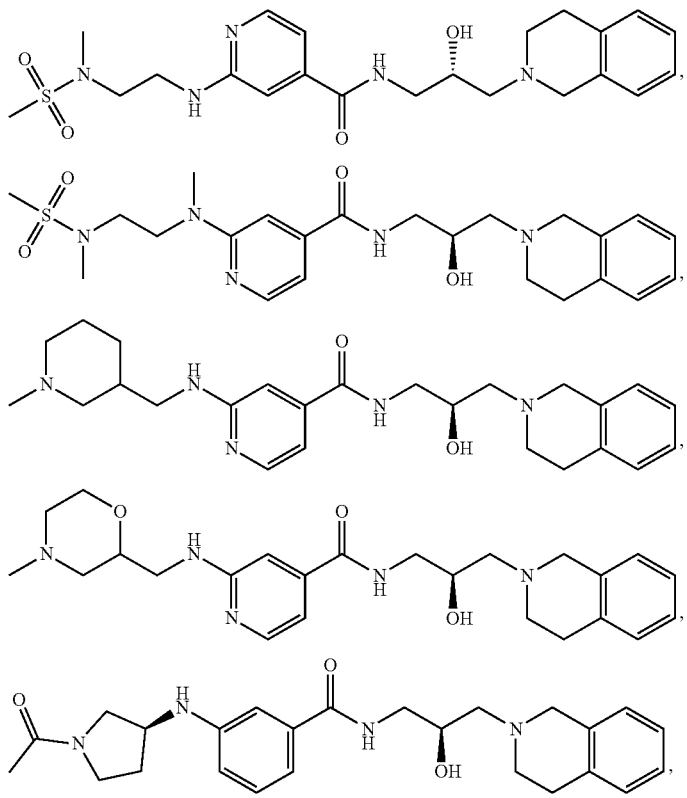
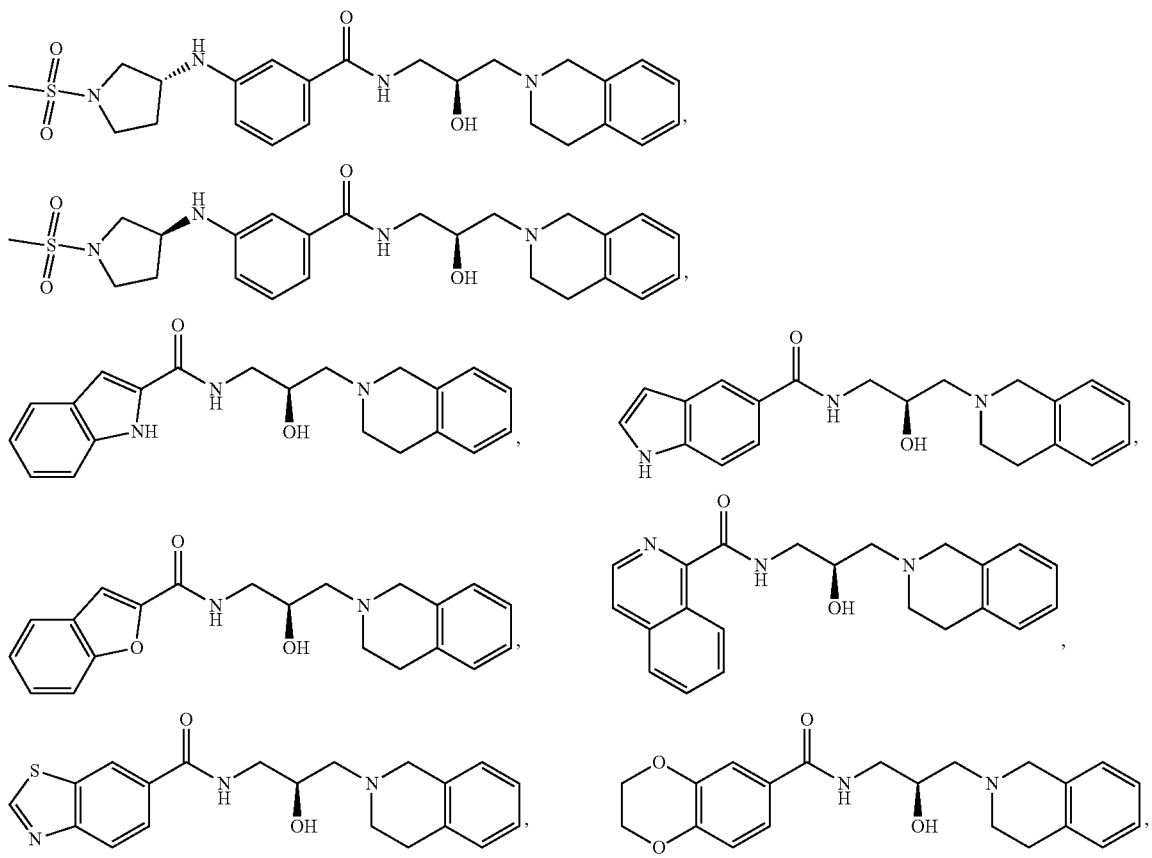

311                                    312
-continued
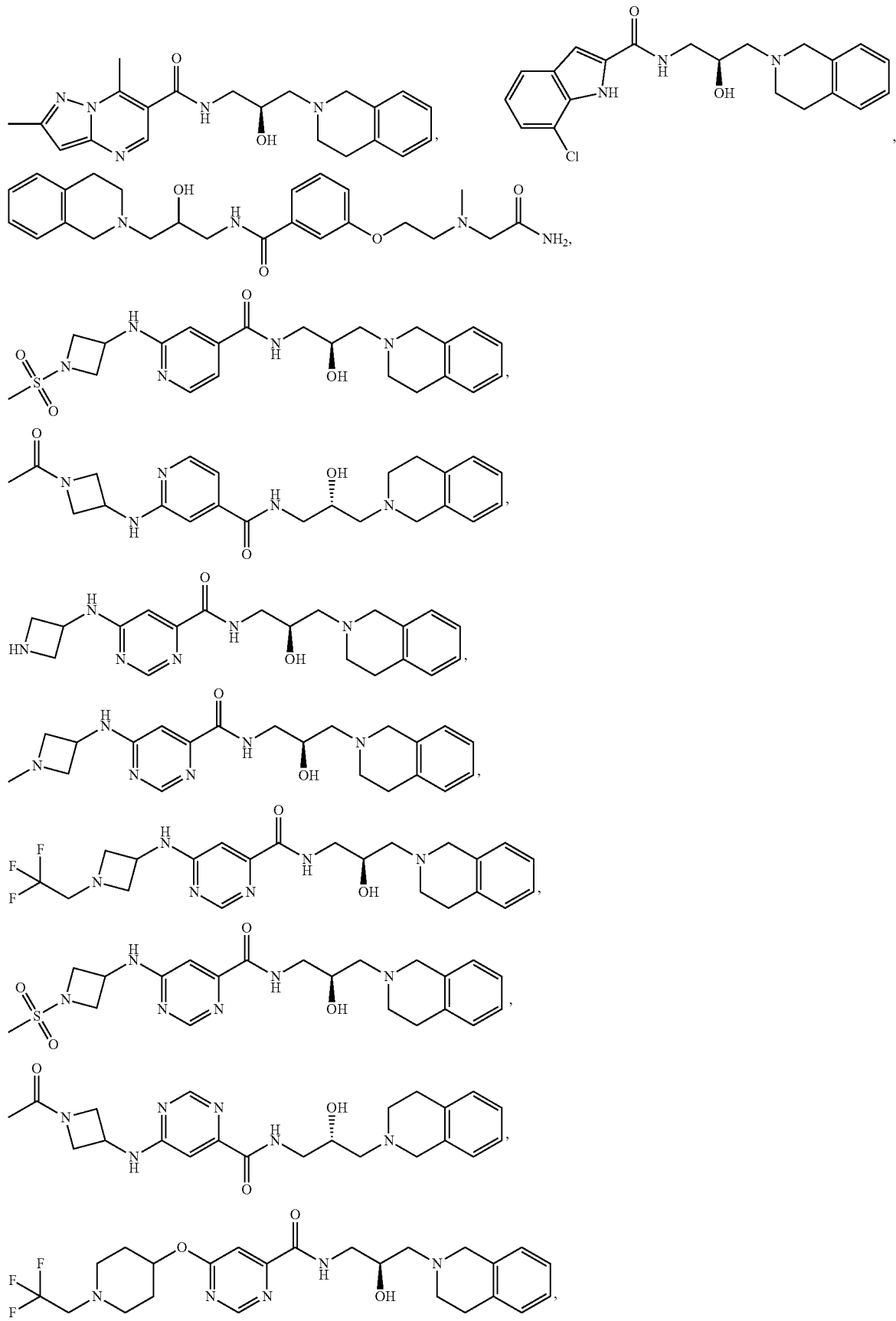

-continued
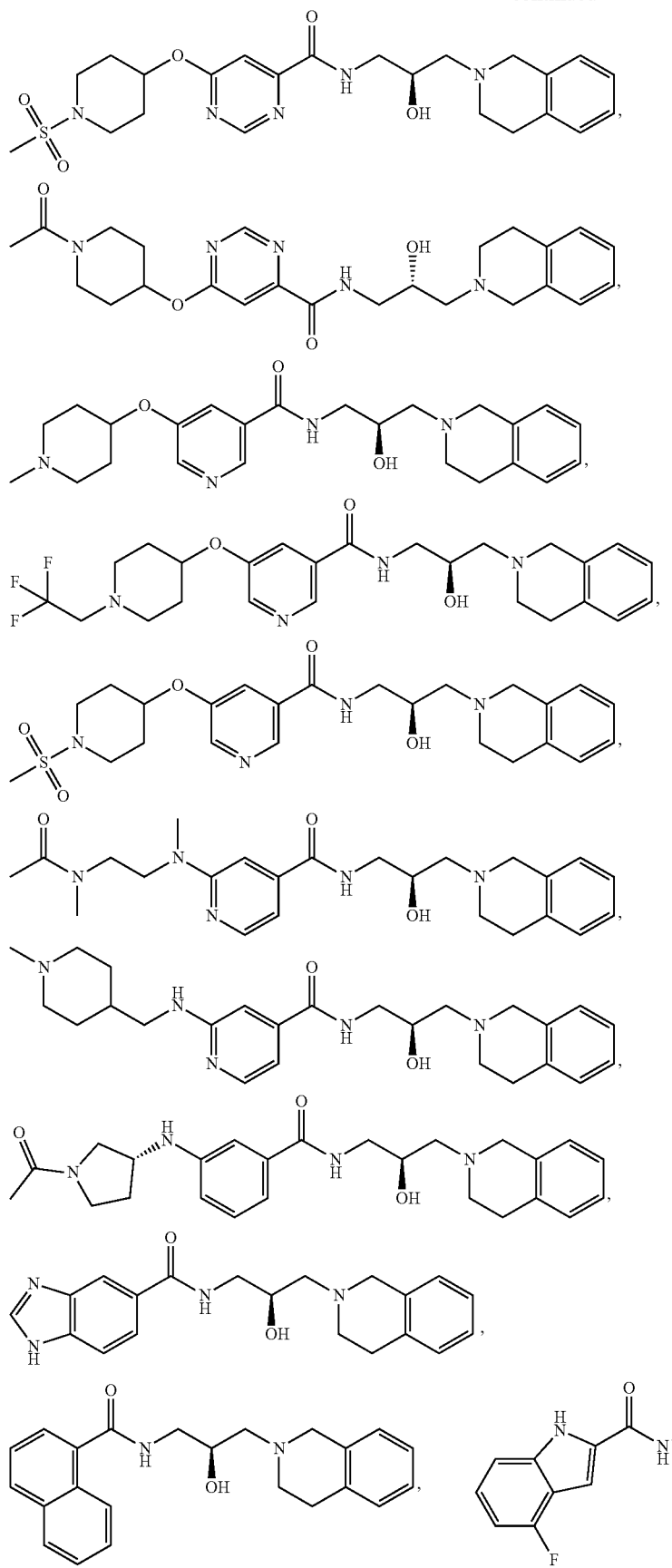

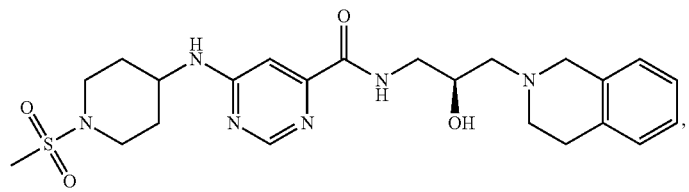
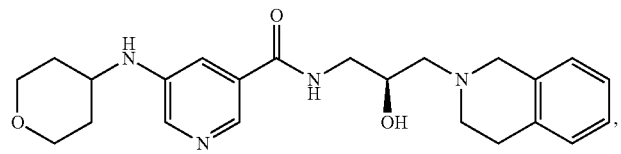
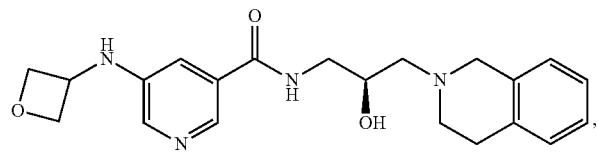
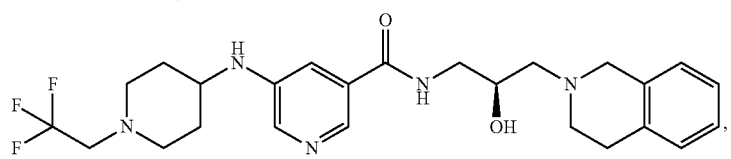
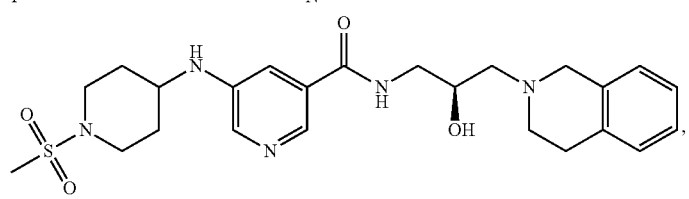
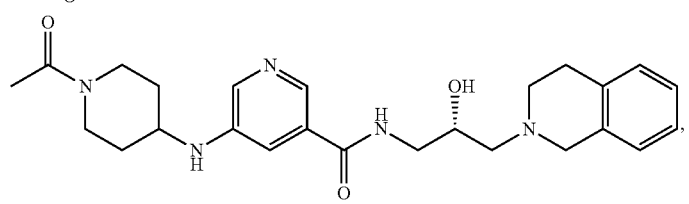
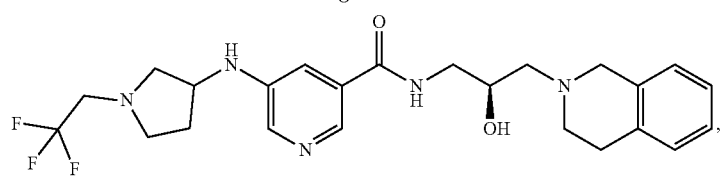
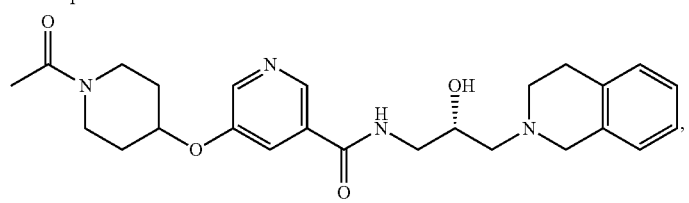
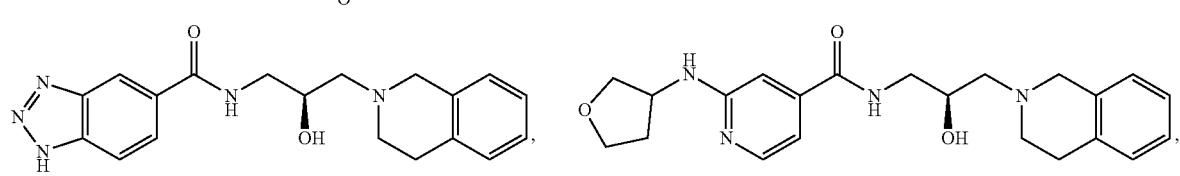
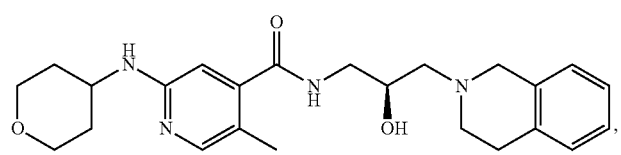

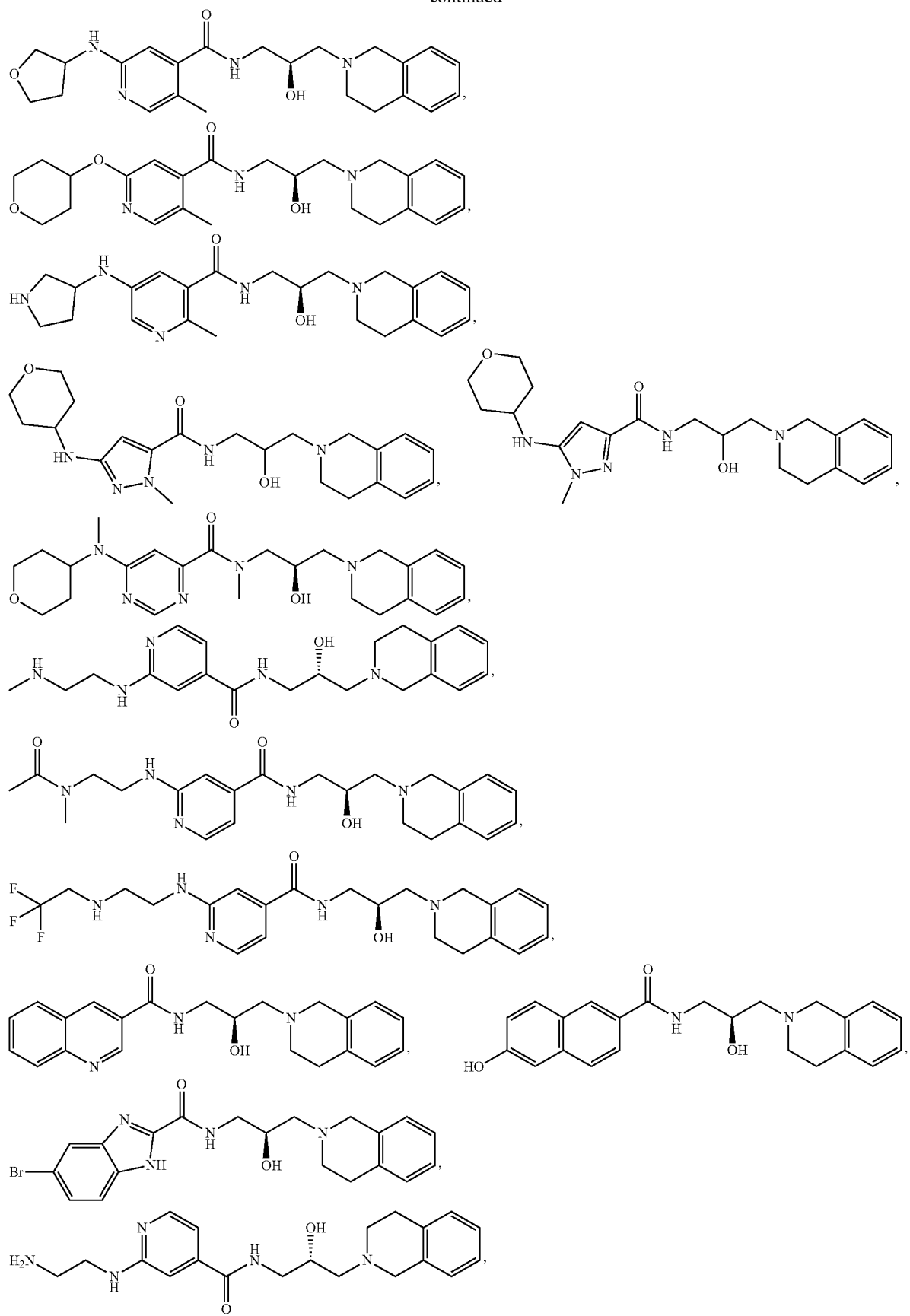

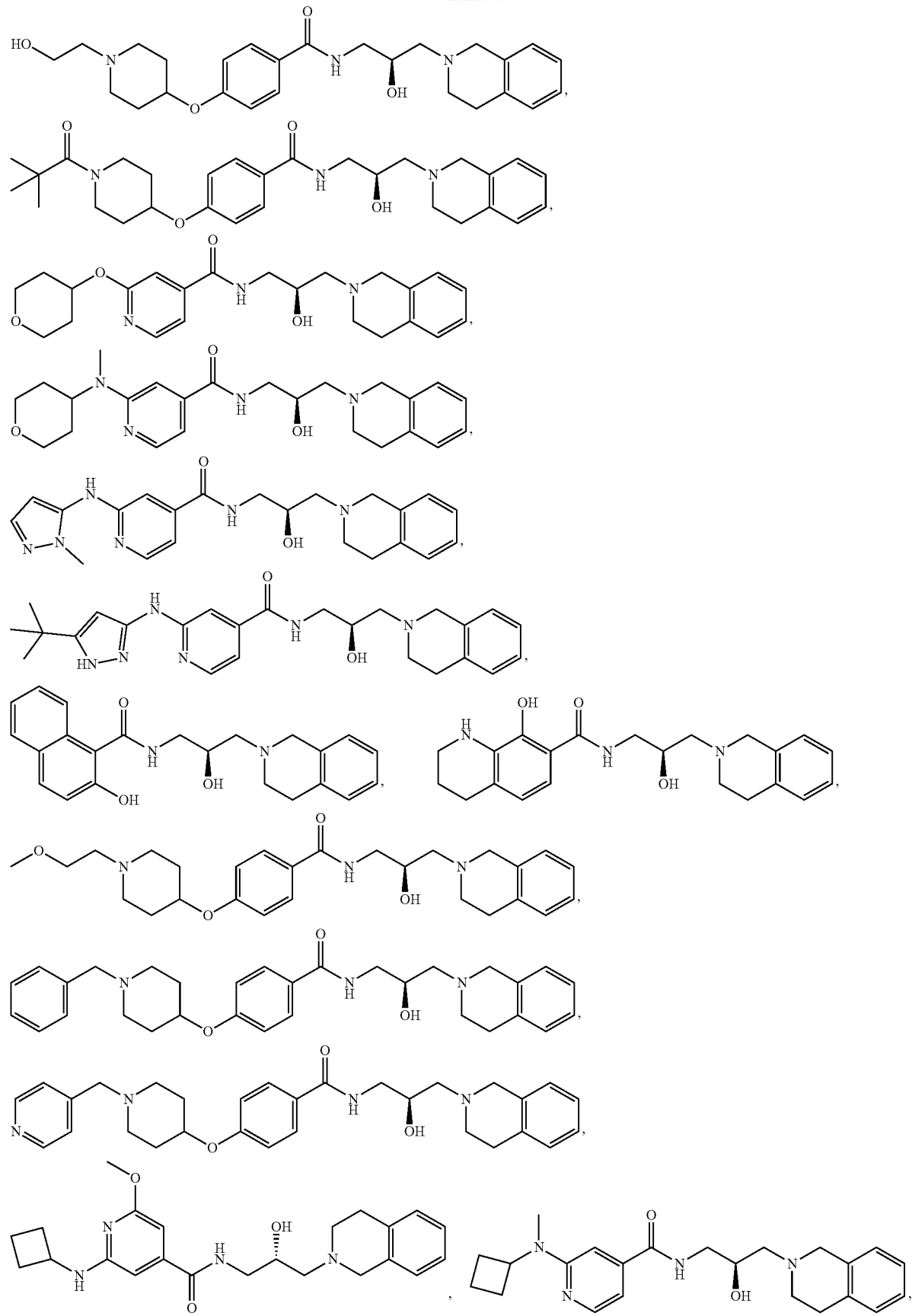

-continued
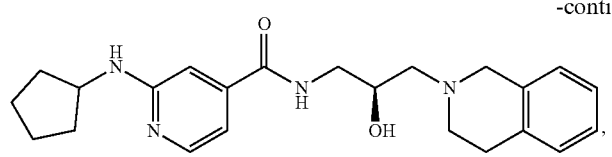
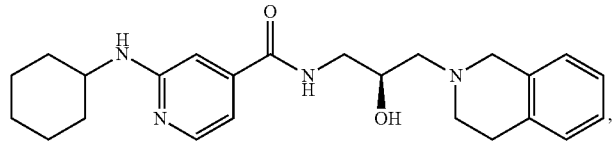
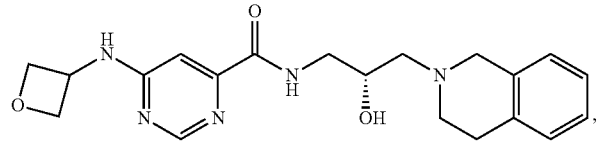
and pharmaceutically acceptable salts thereof.
19. A method of treating a disease comprising administering to a subject in need thereof a therapeutically effective amount of a compound selected from the group consisting of:
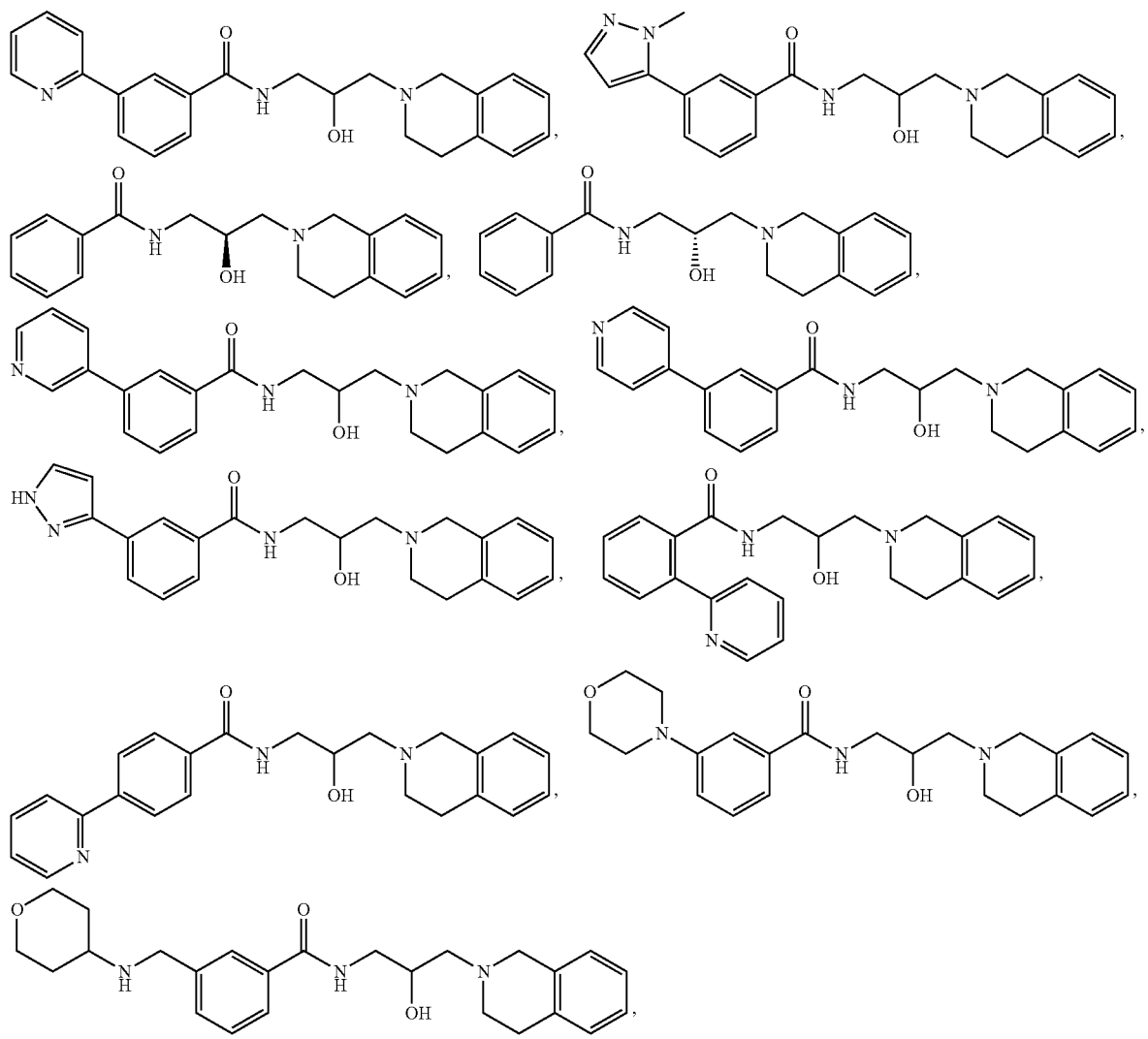

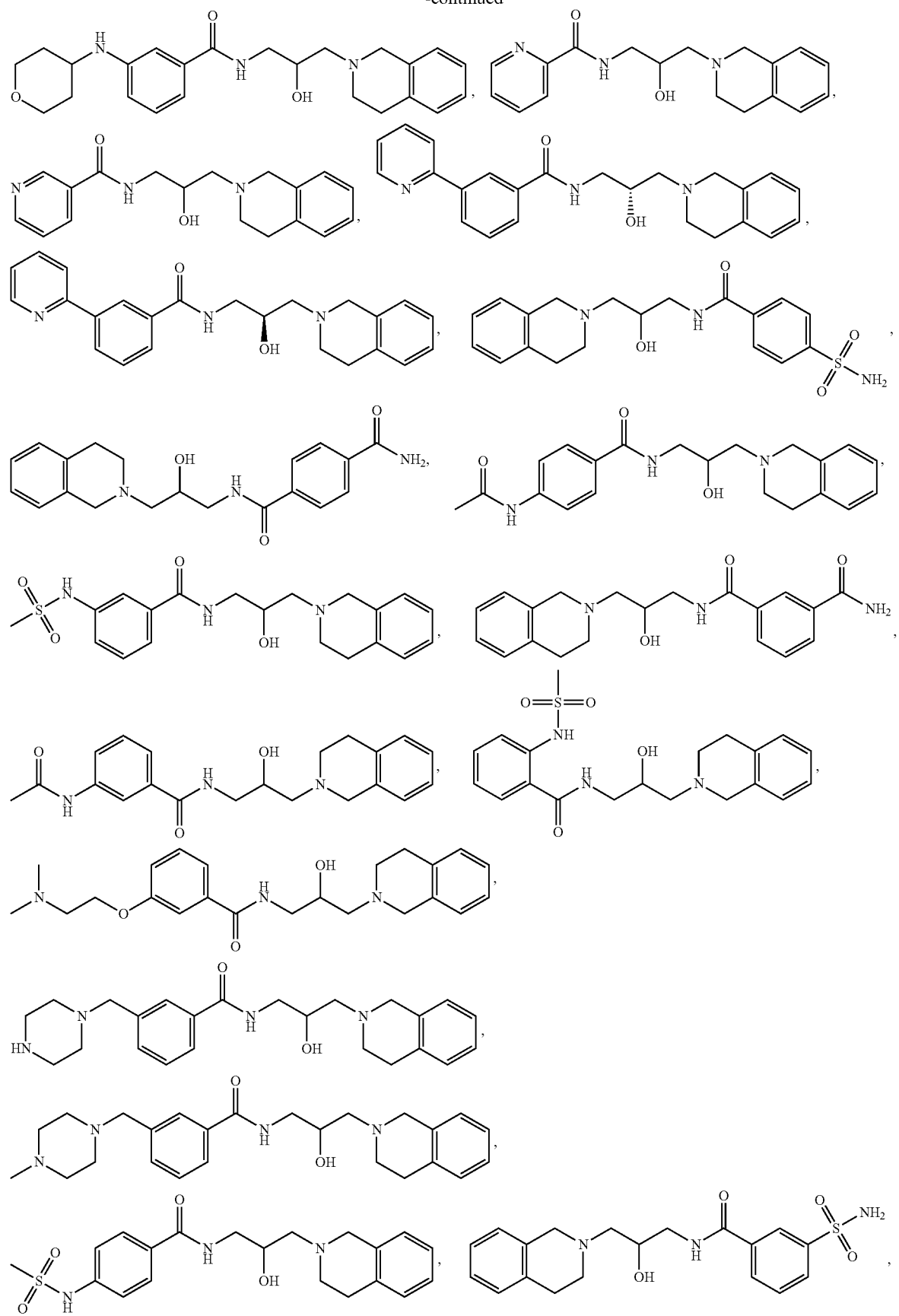

325
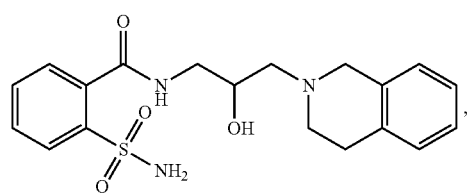
326
-continued
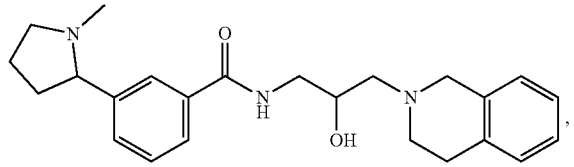
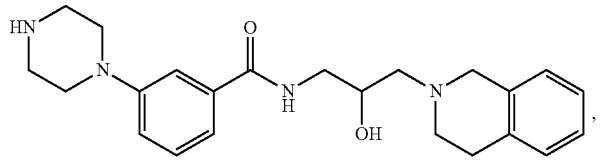
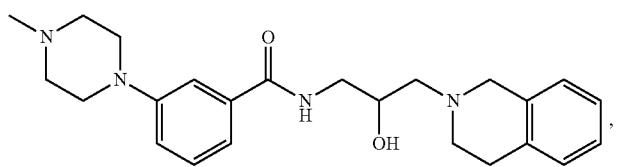
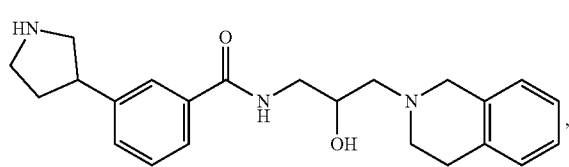
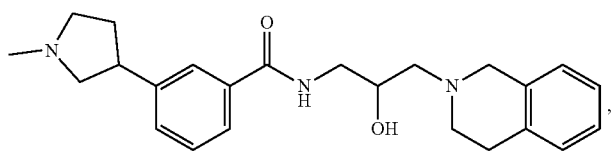
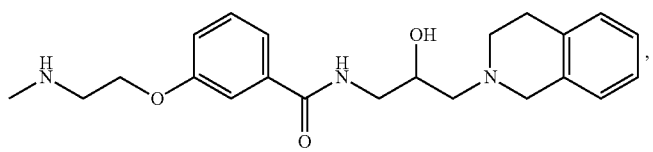
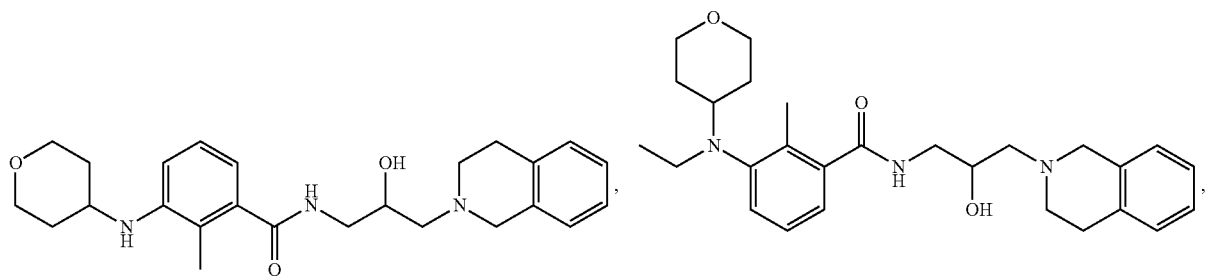
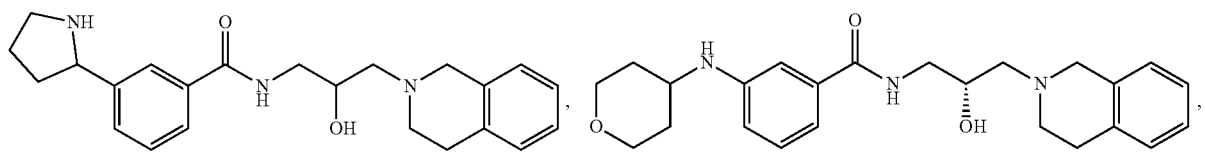
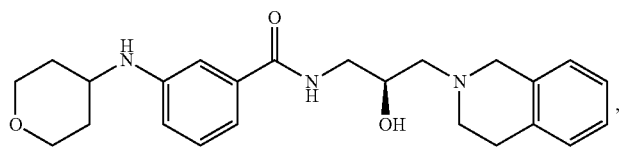
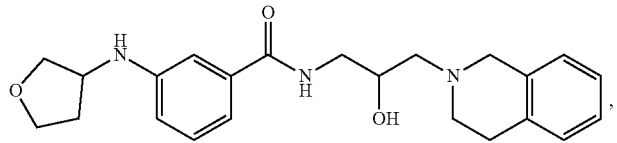

327
328
-continued
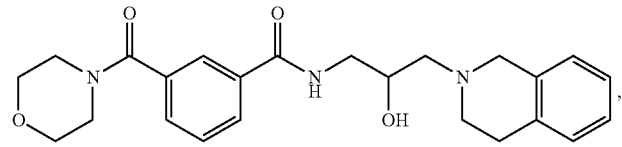
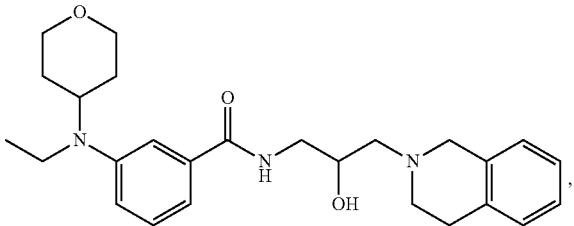
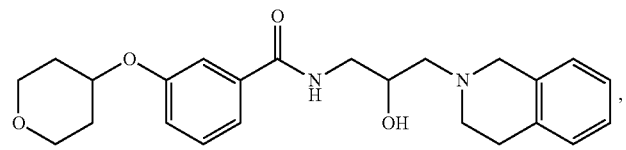
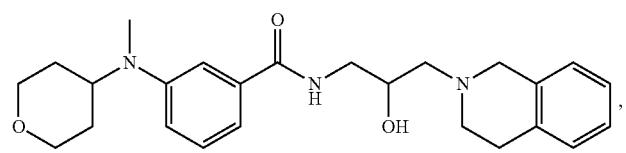
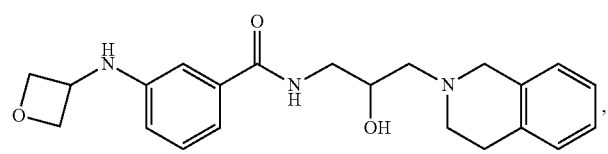
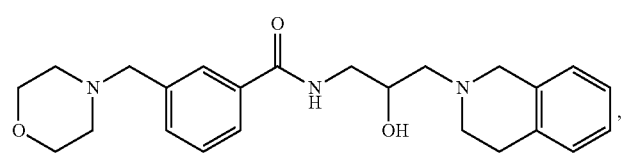
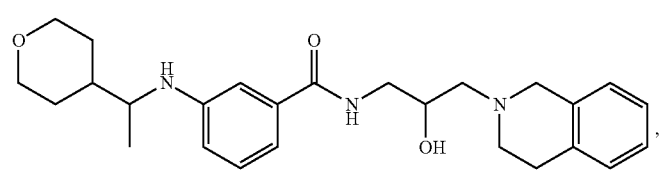
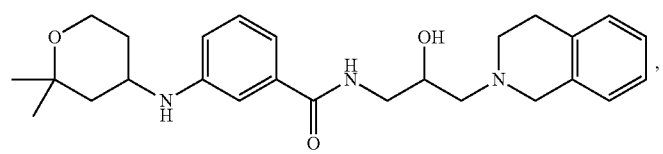
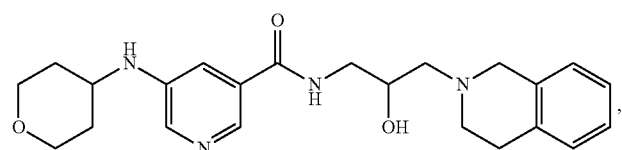
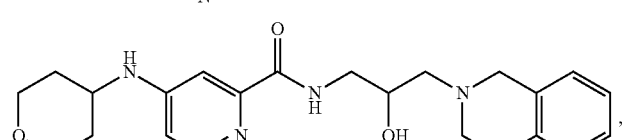
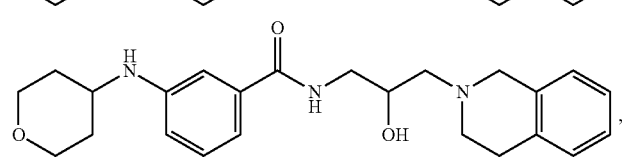

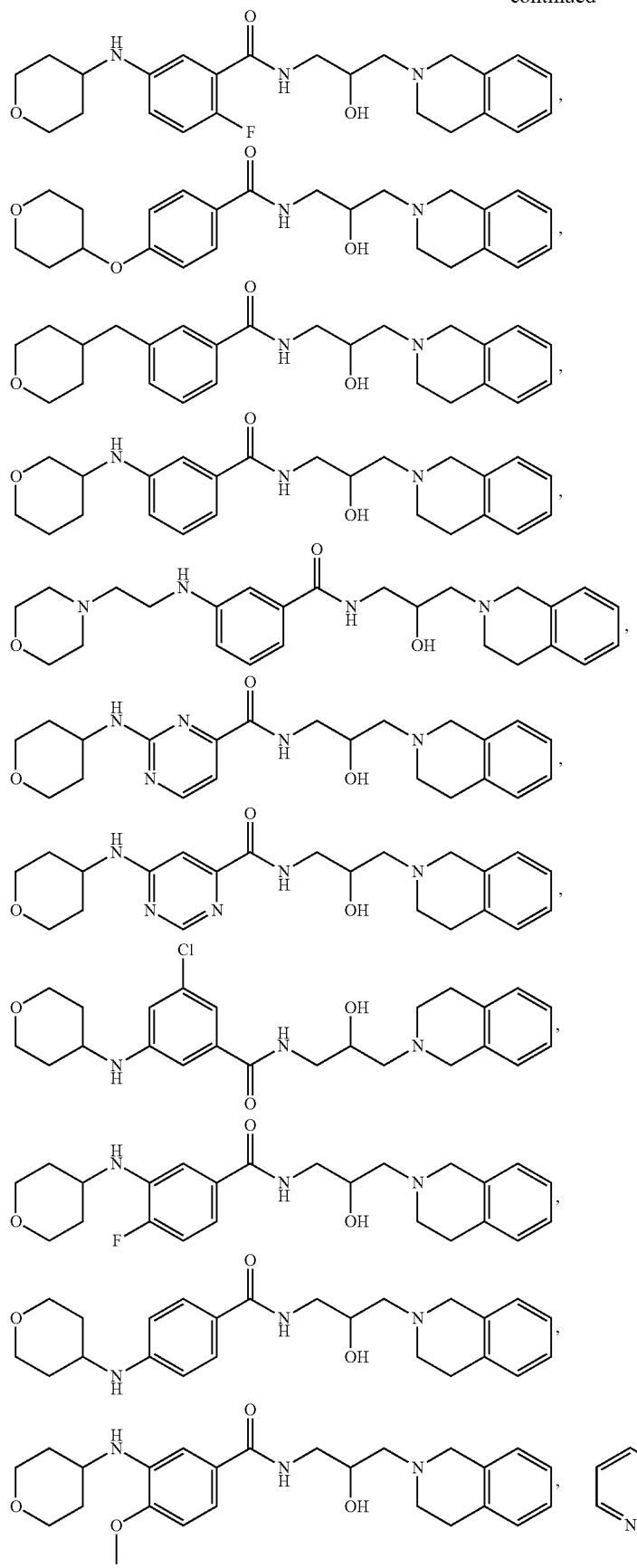

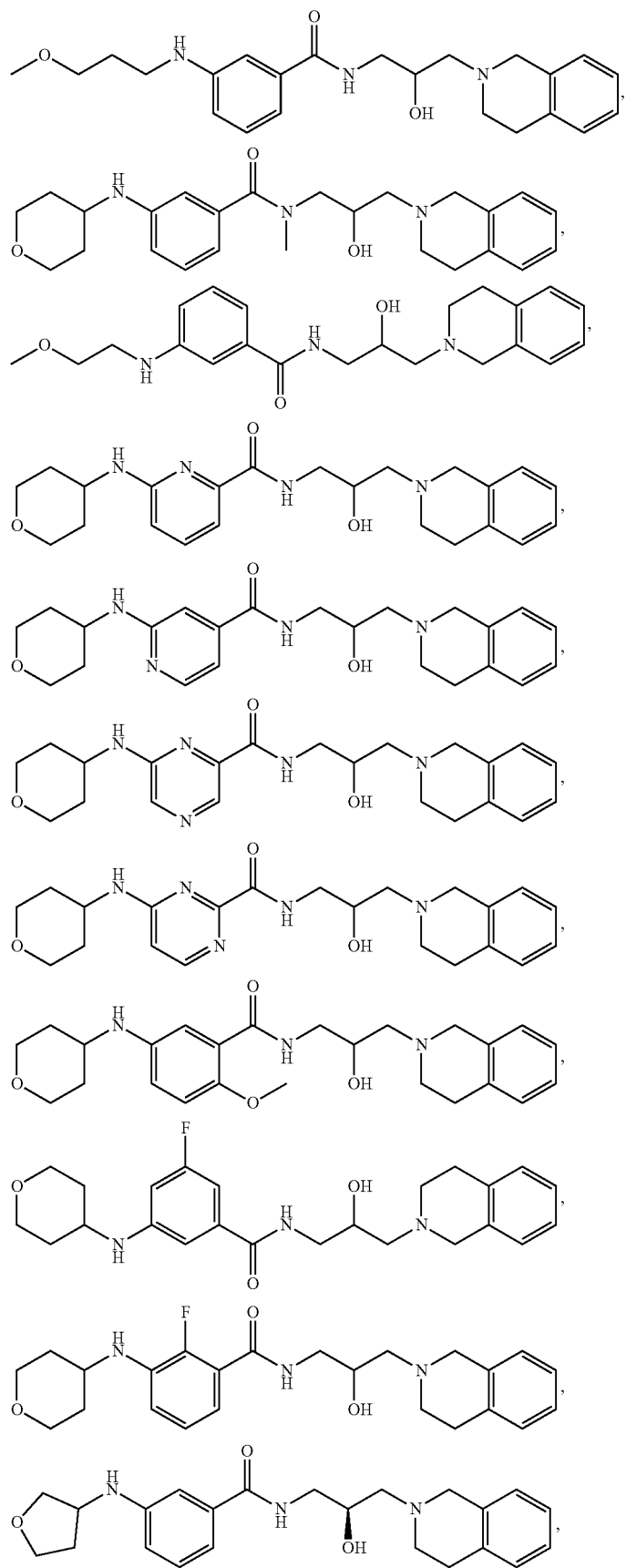

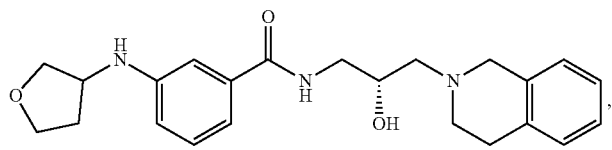
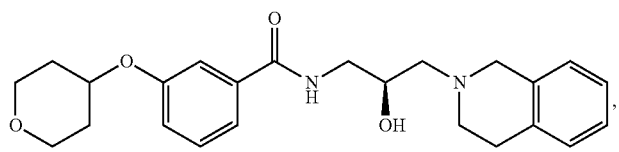
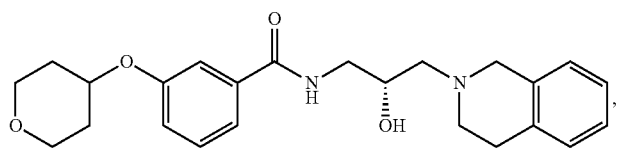
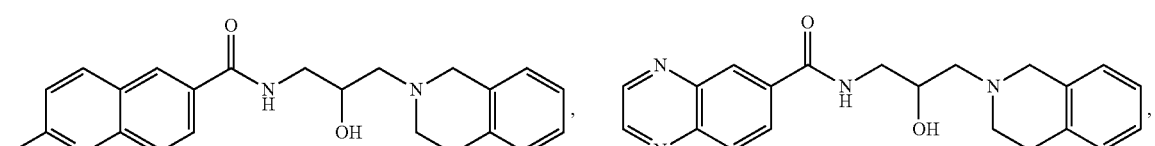
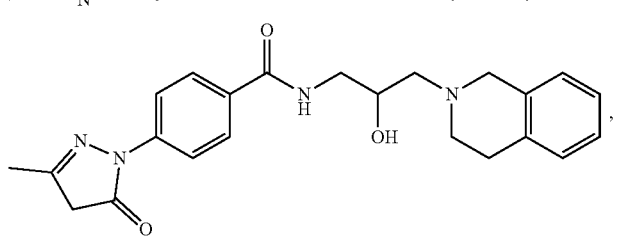
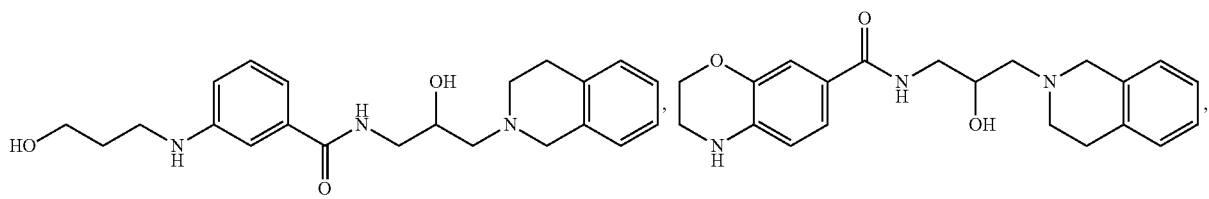
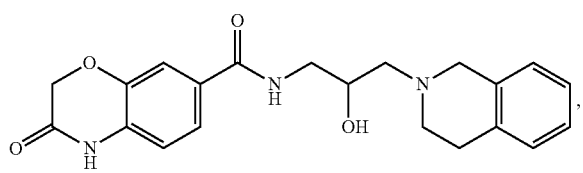
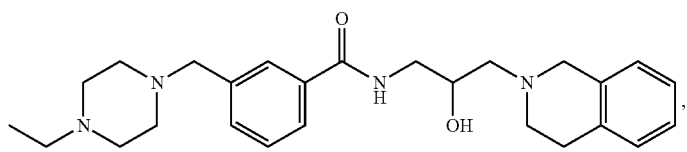
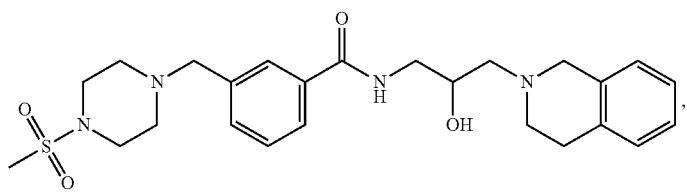
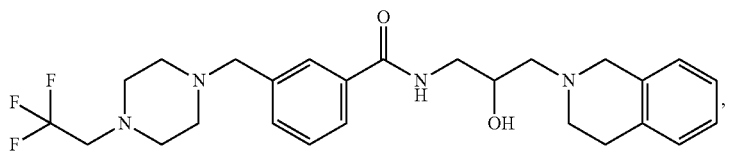

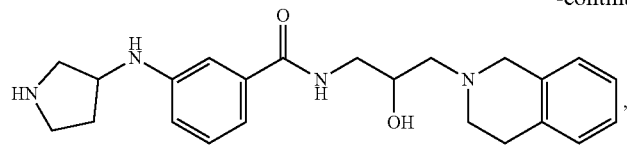
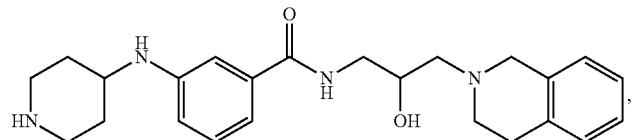
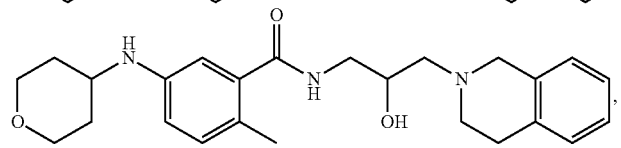
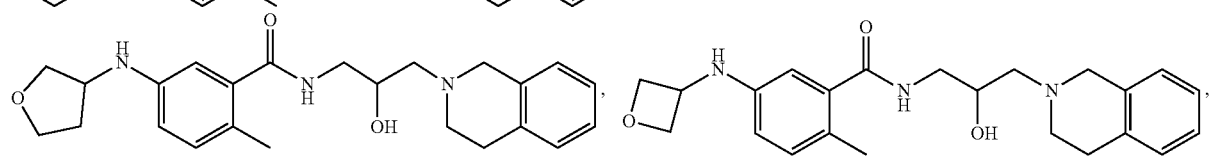
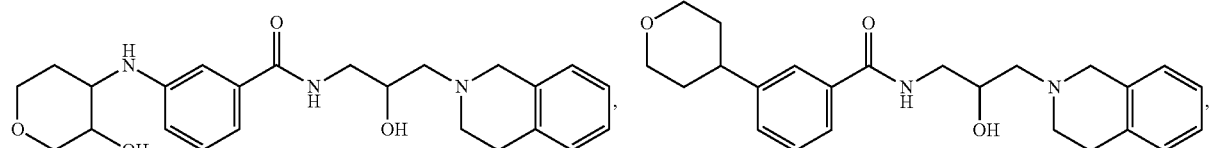
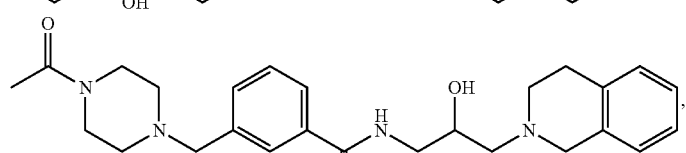
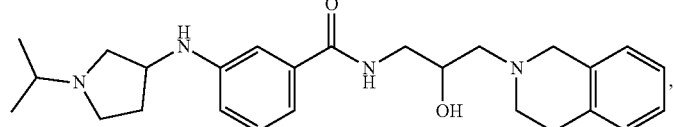
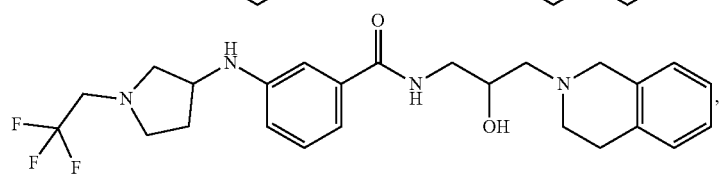
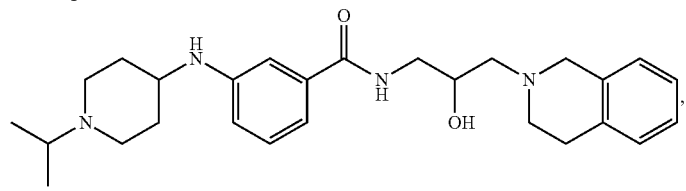
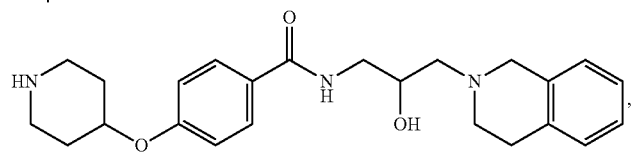
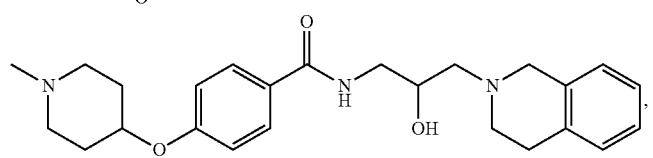

-continued
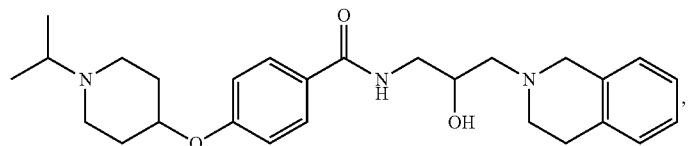
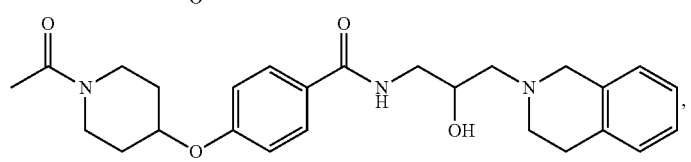
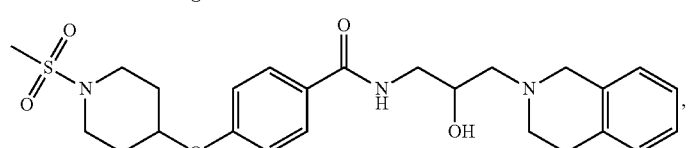
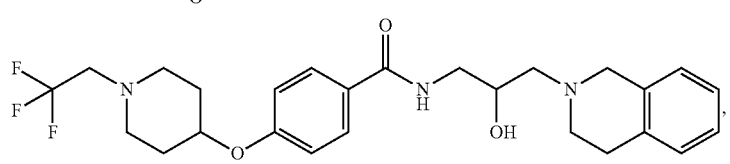
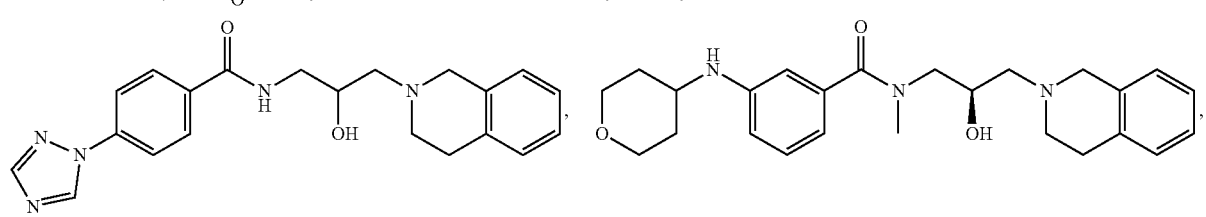
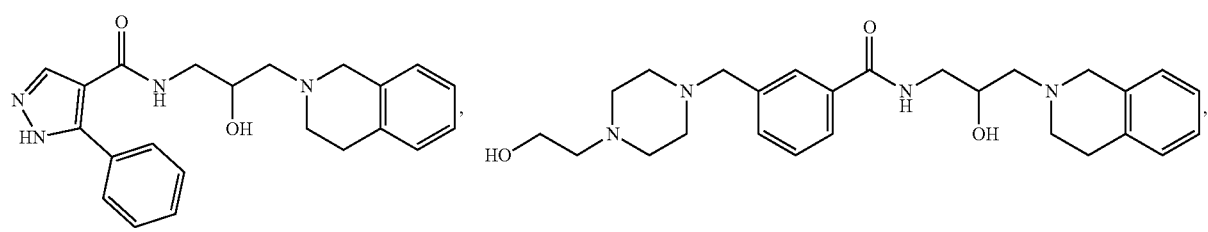
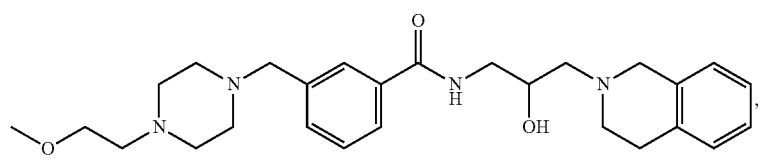
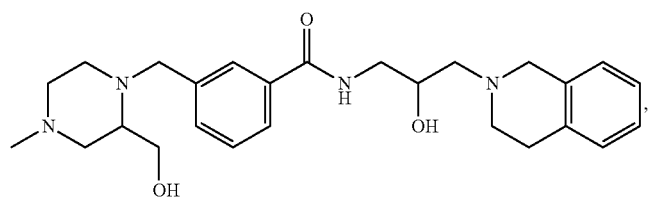
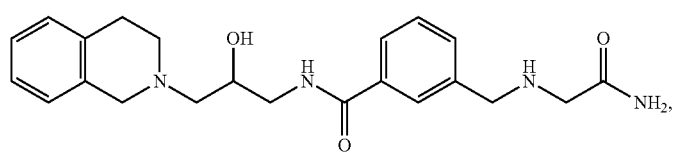
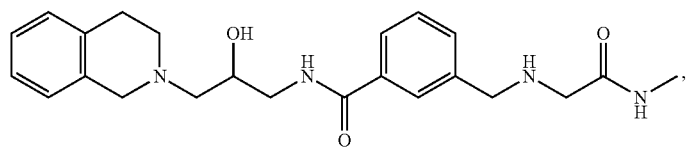

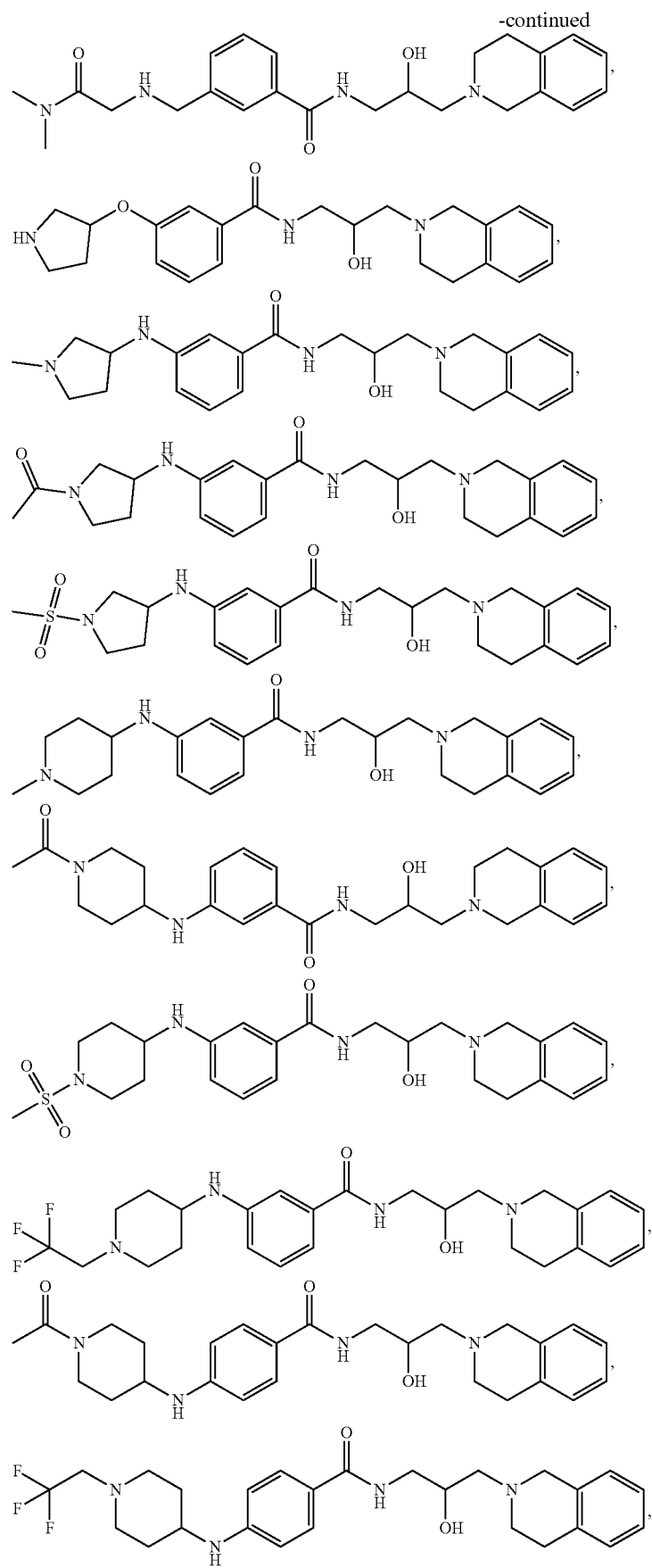

341 342
-continued
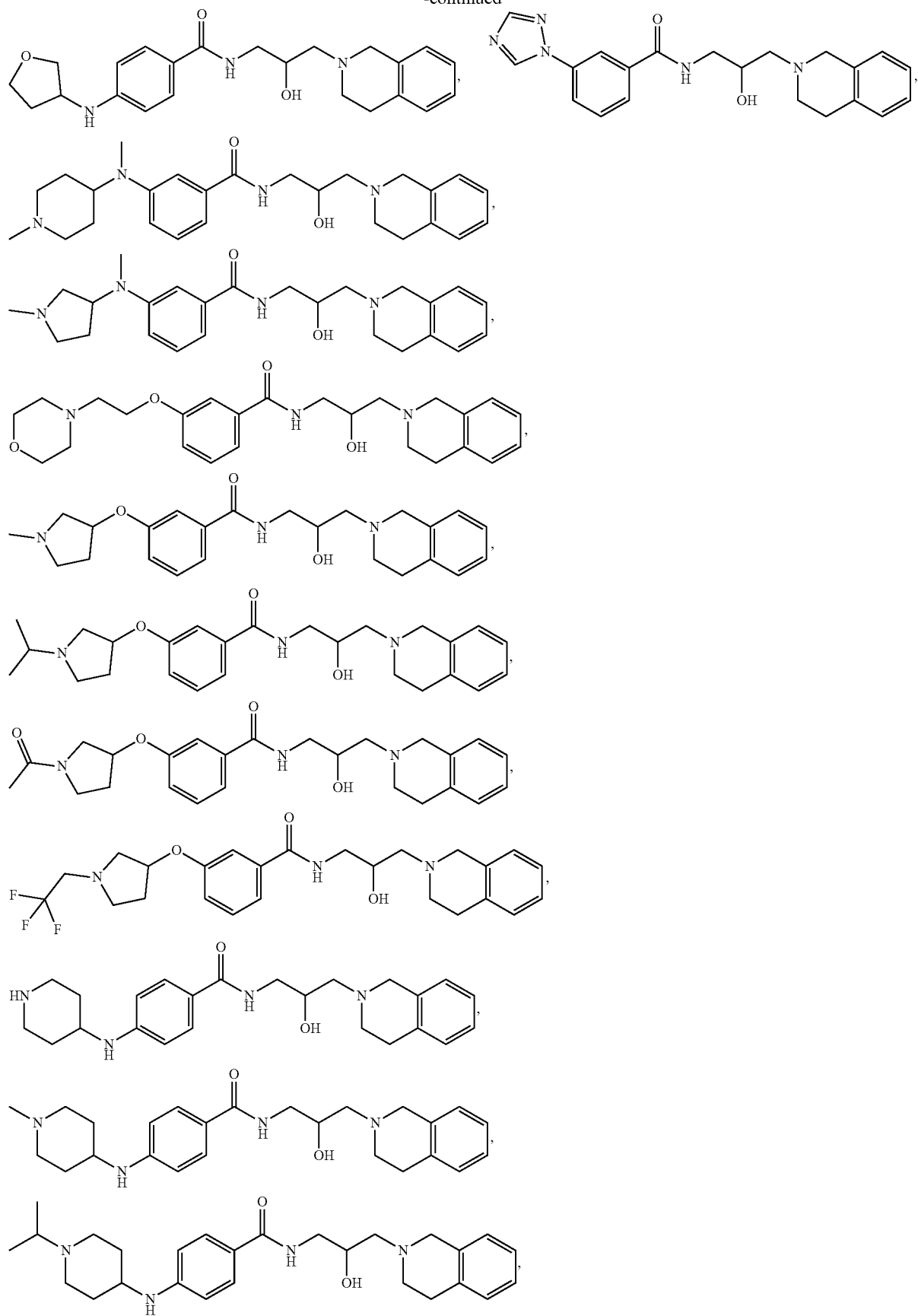

-continued
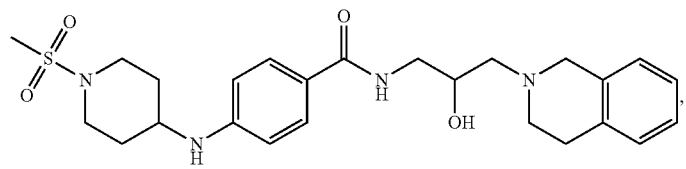
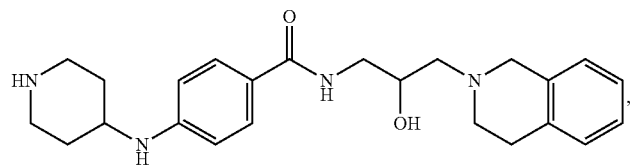
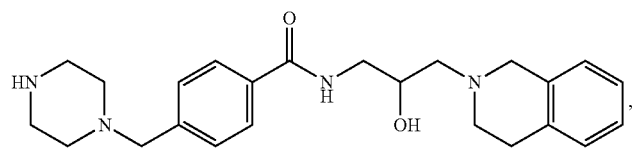
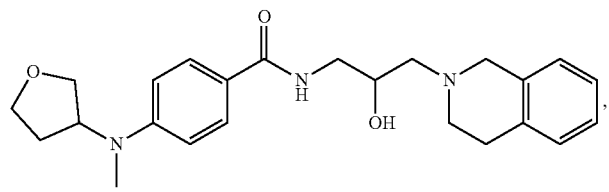
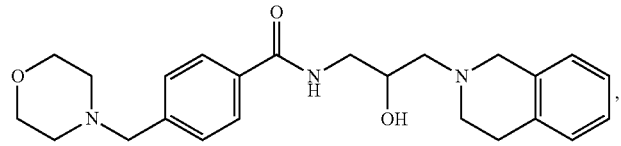
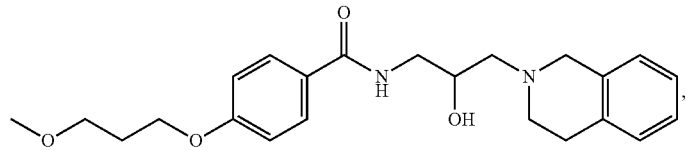
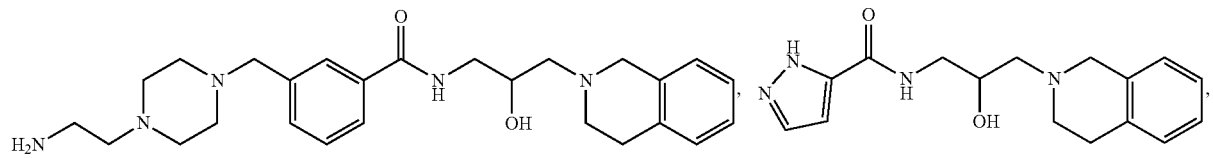
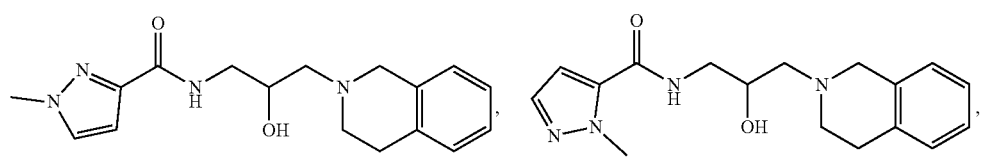
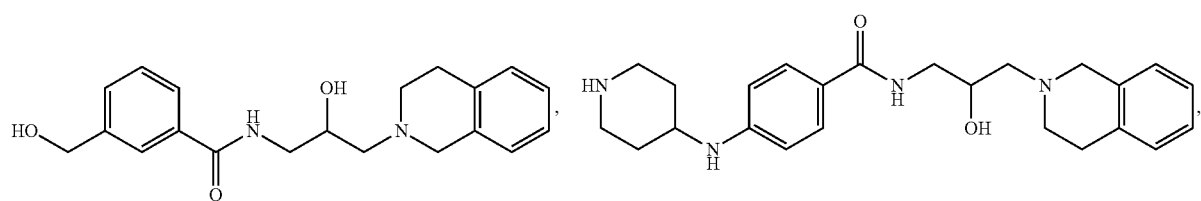
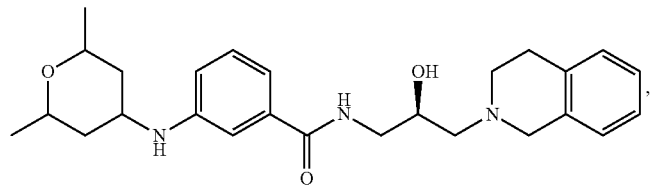

-continued
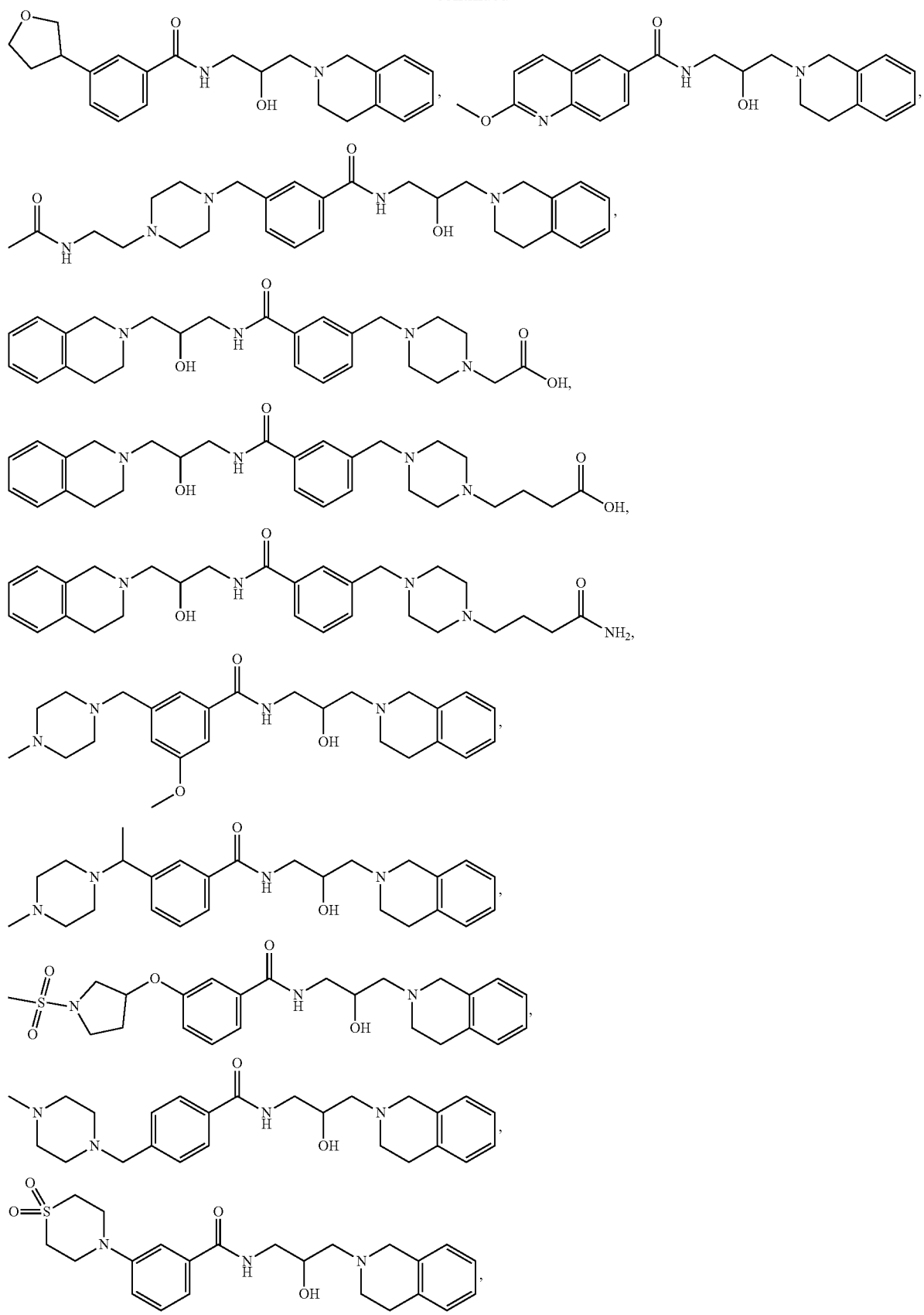

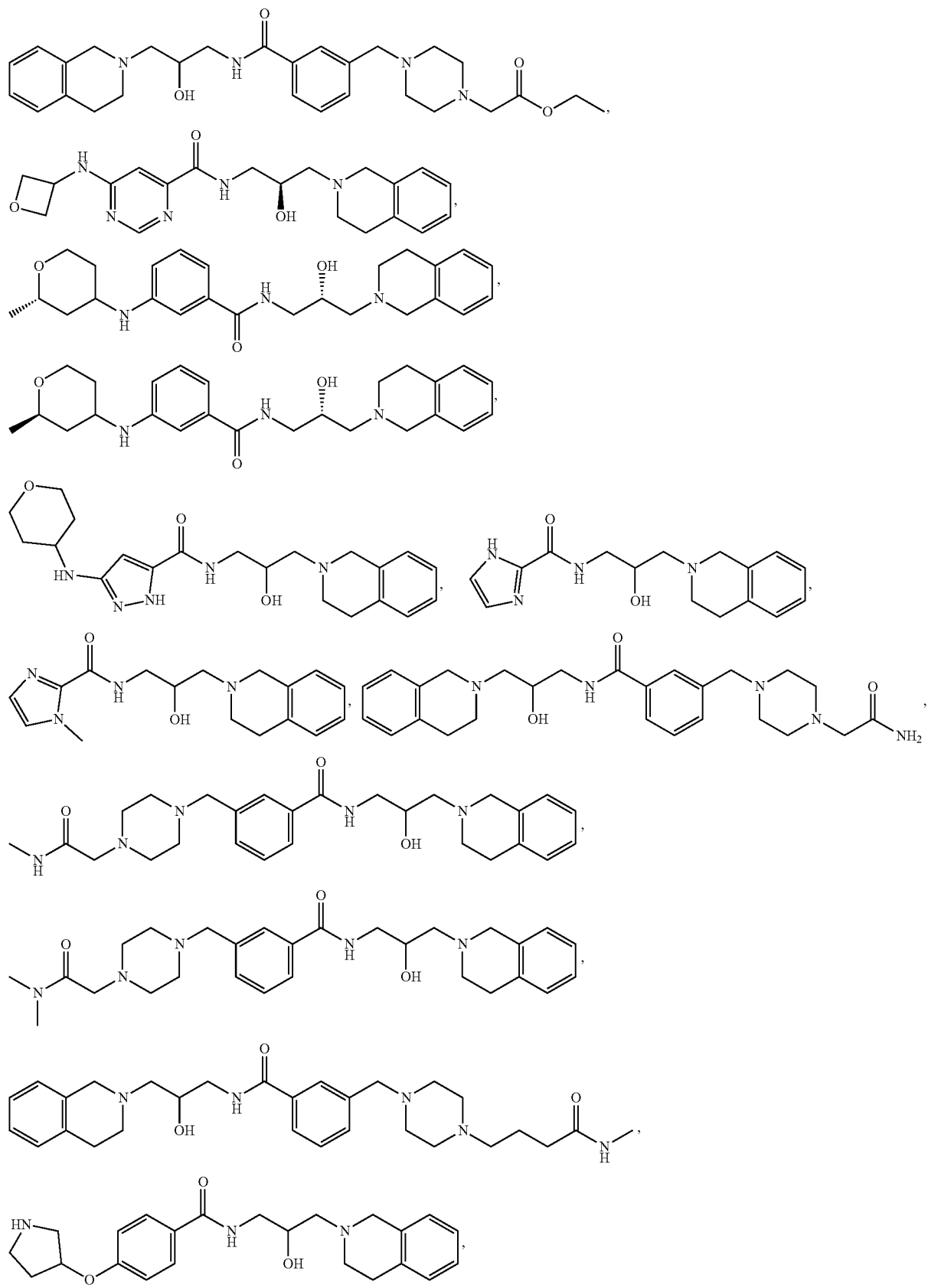

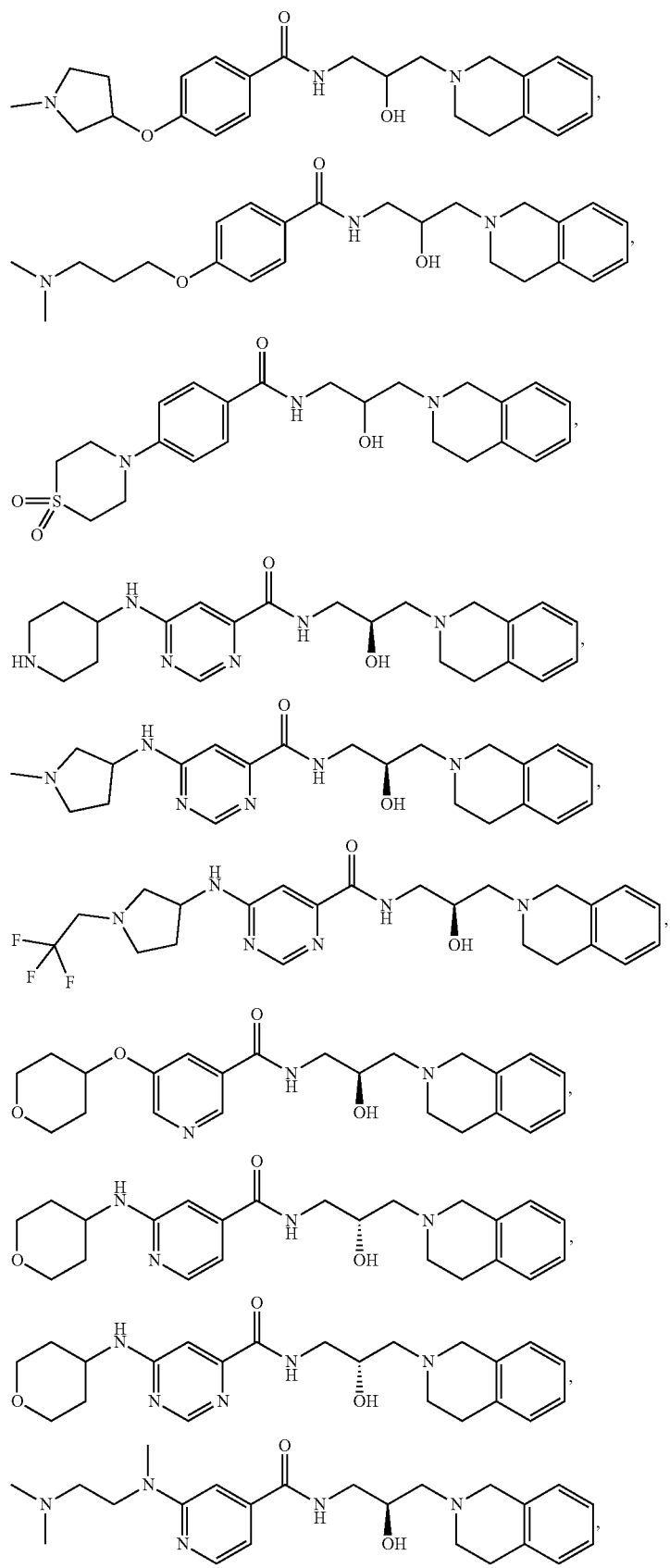

-continued
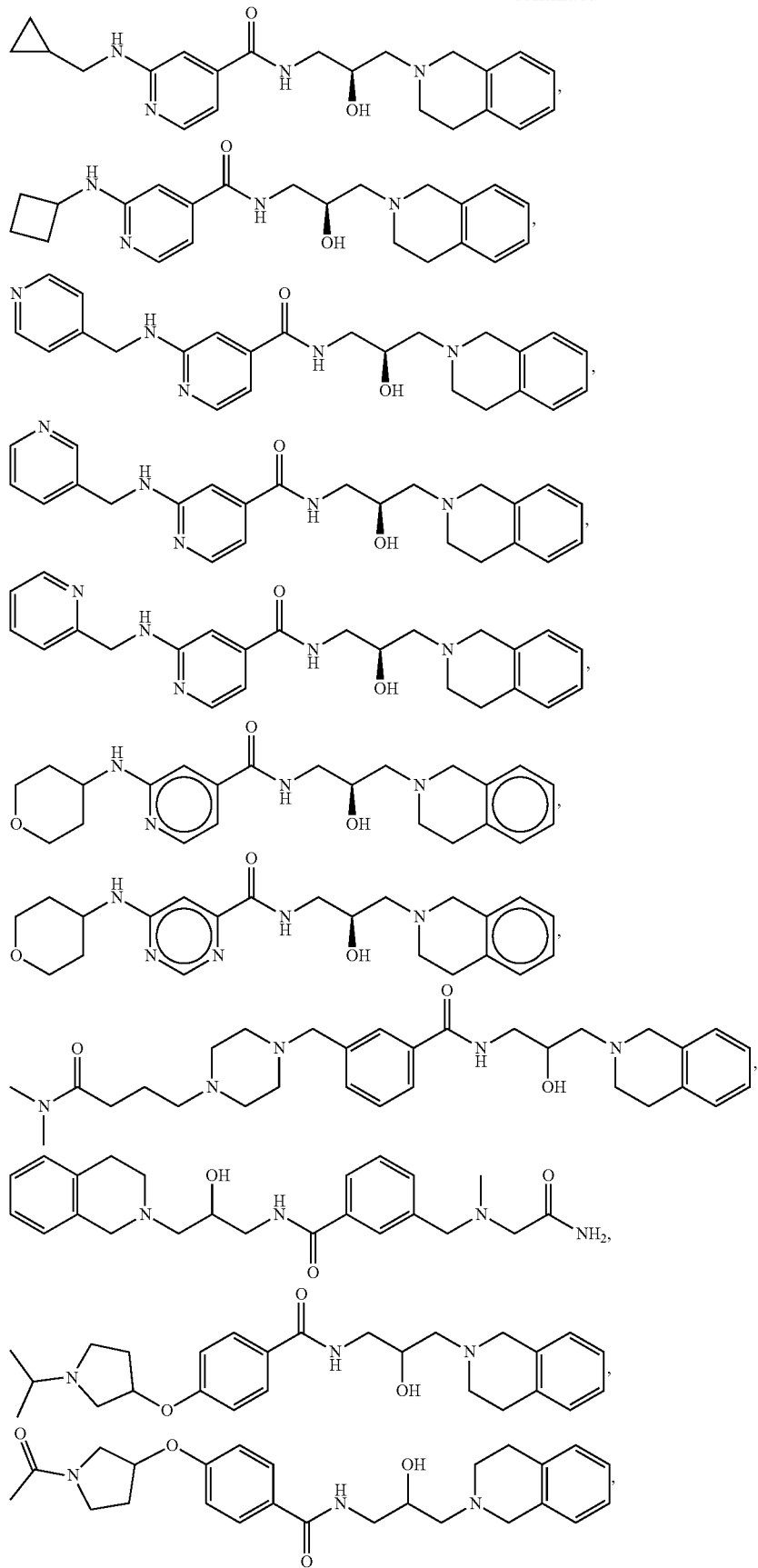

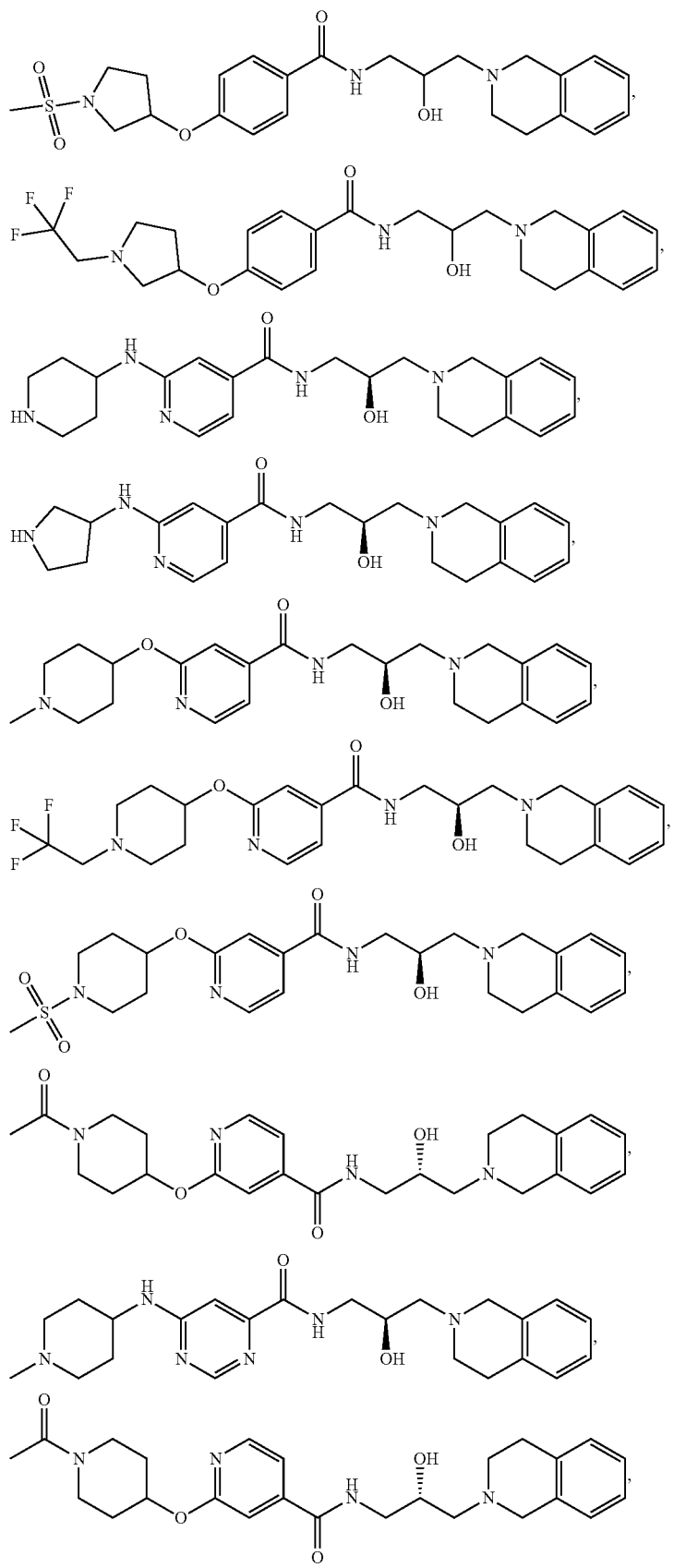

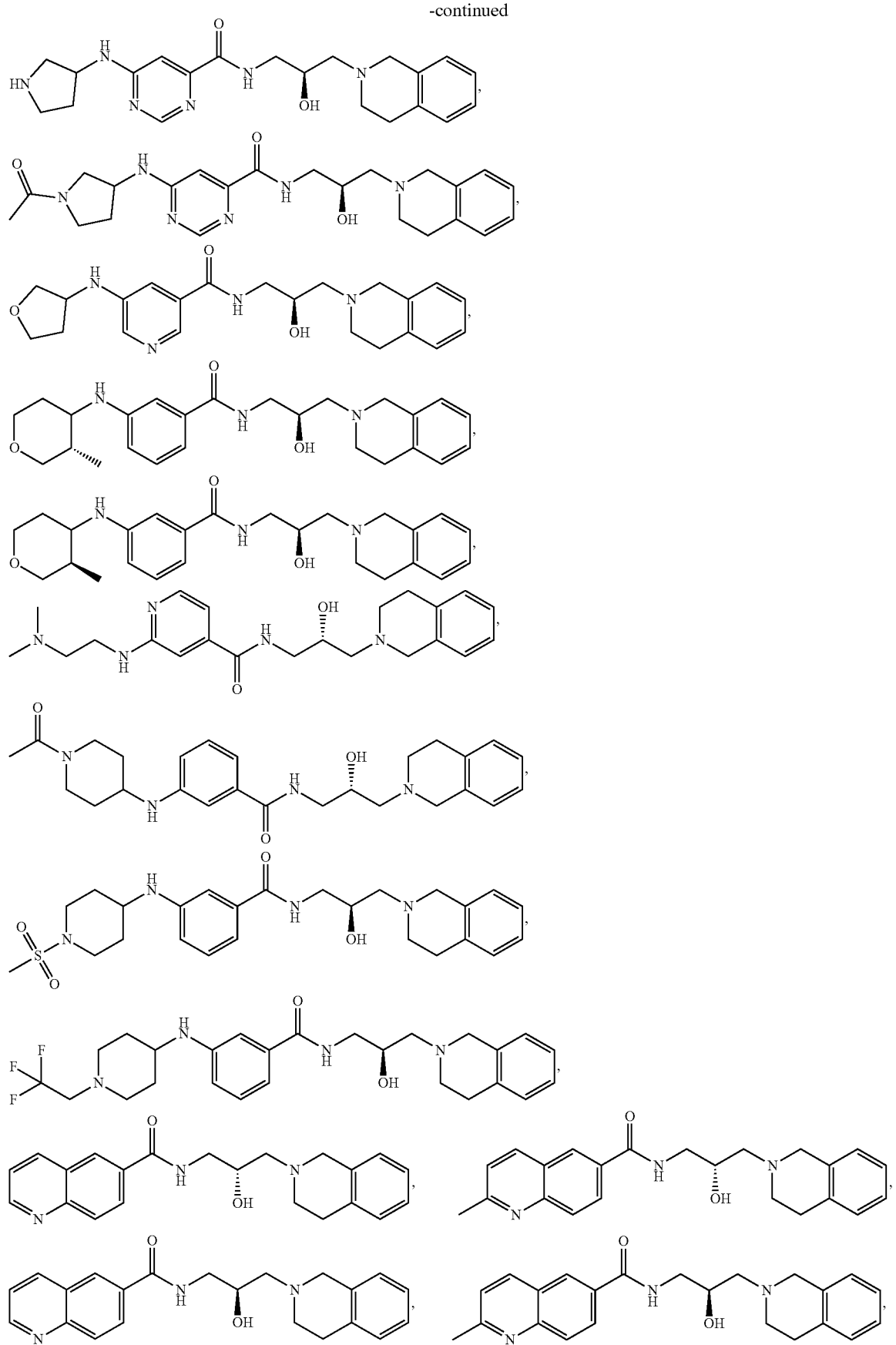

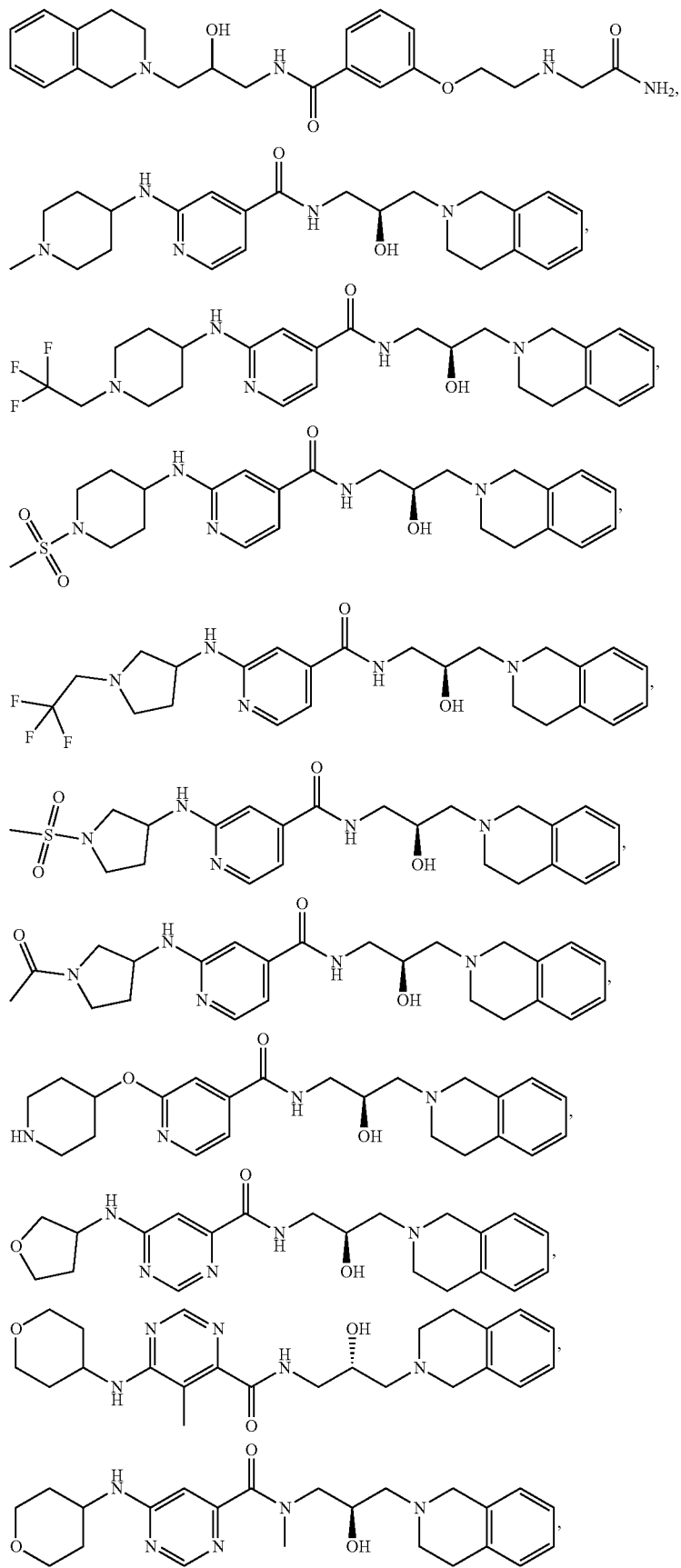

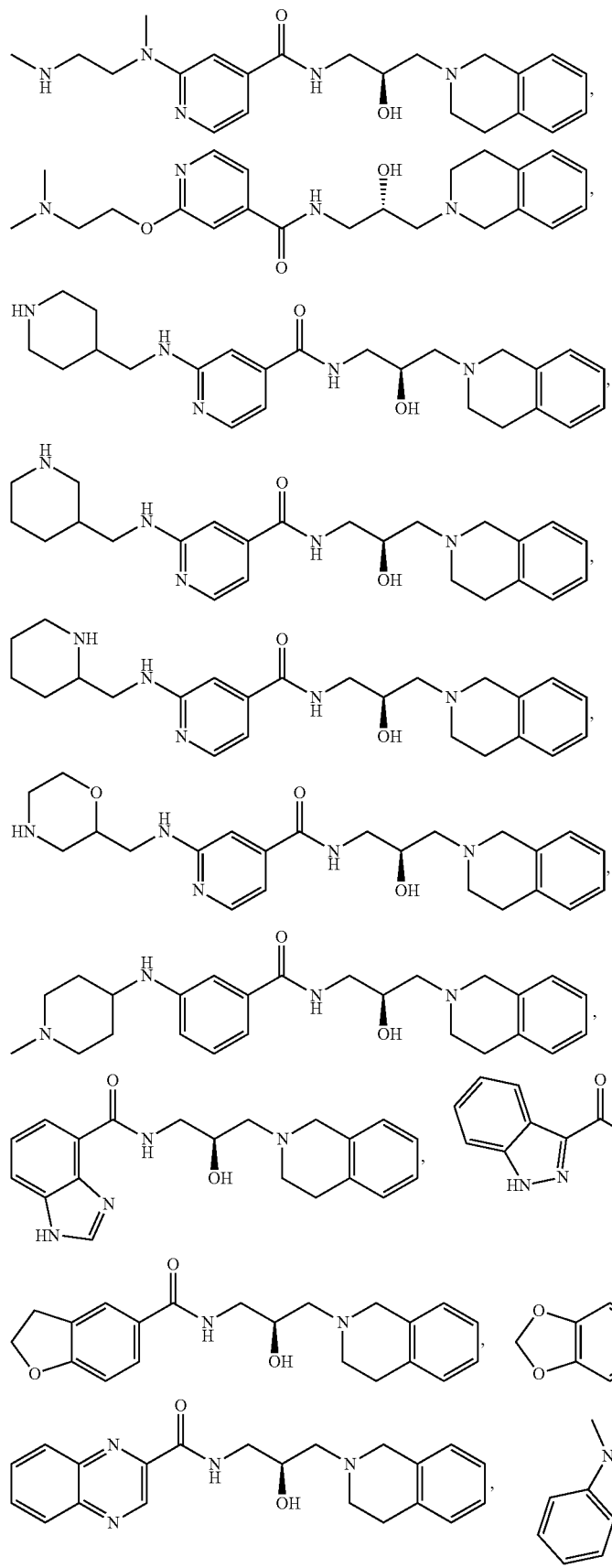

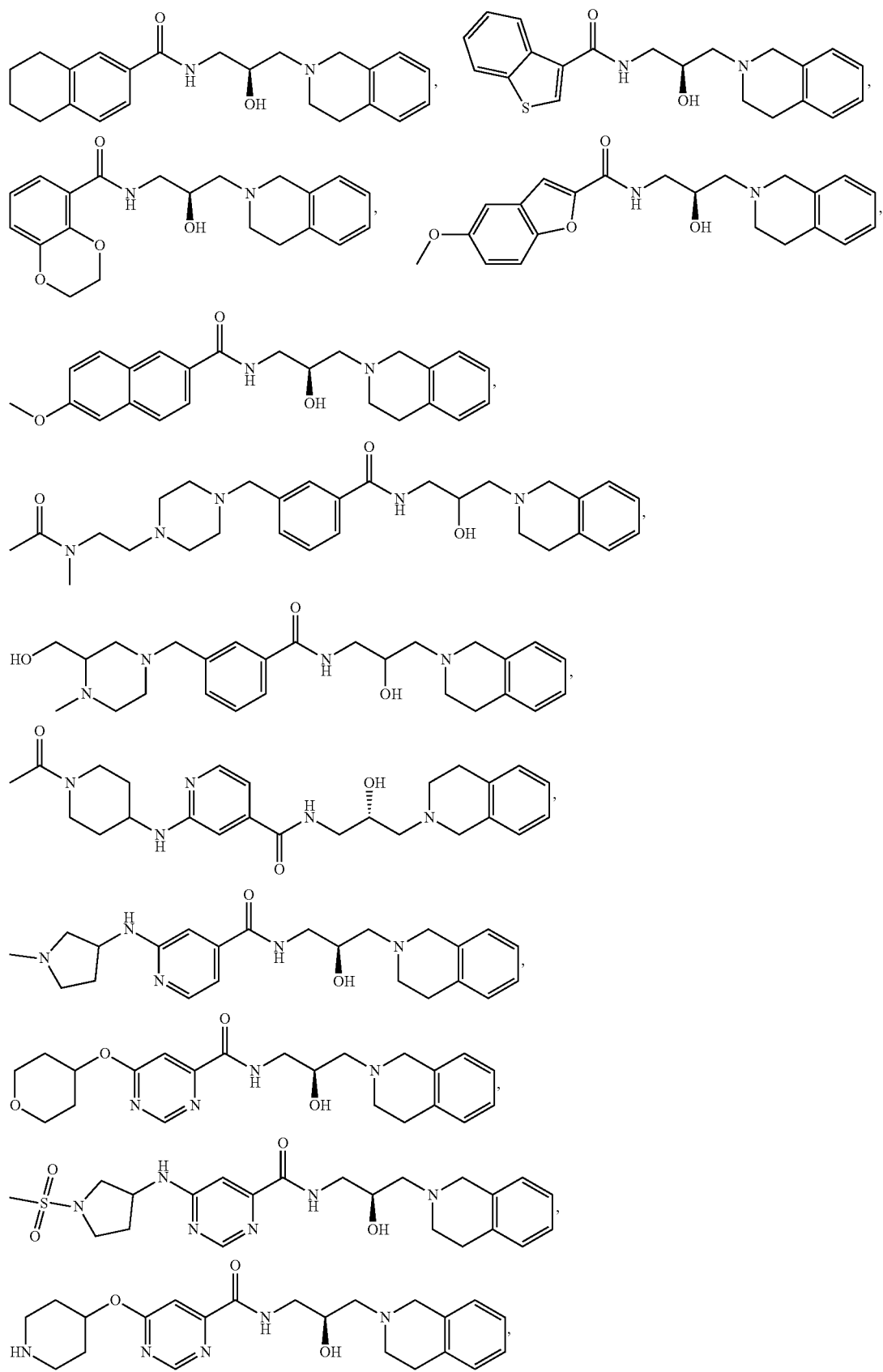

-continued
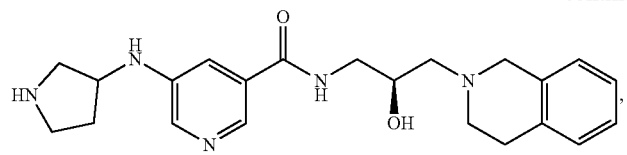
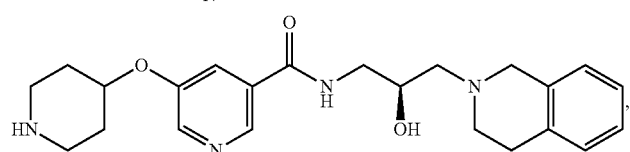
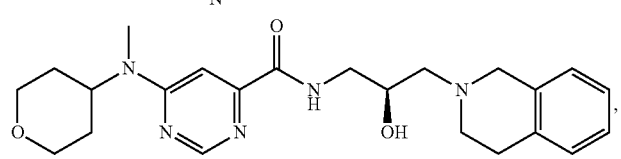
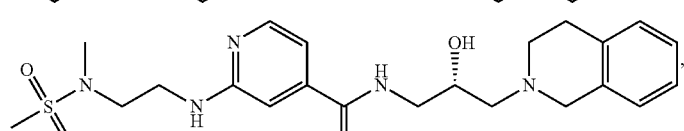
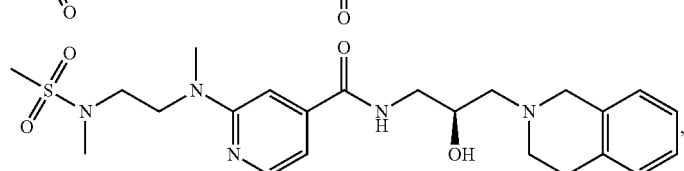
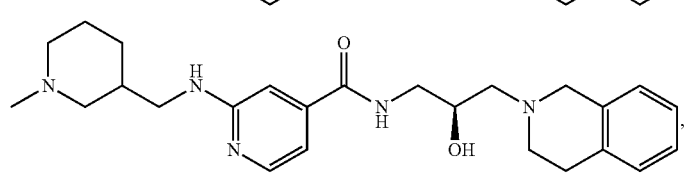
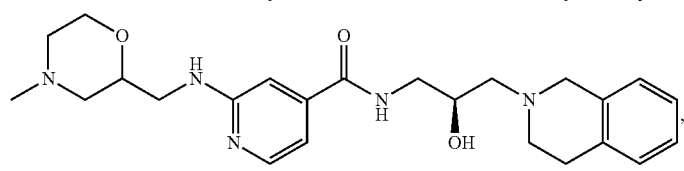
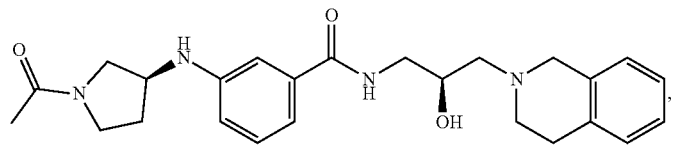
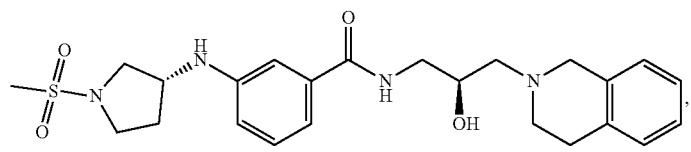
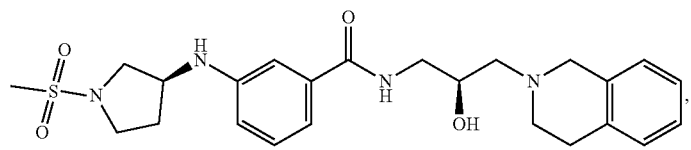
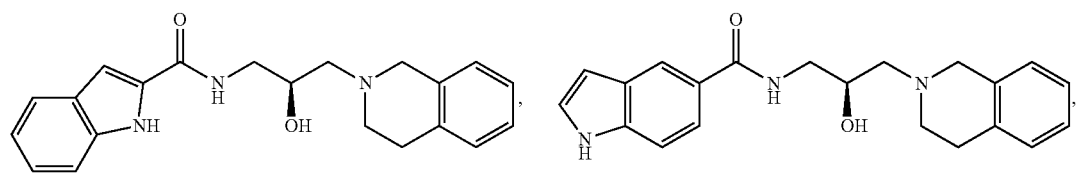

365
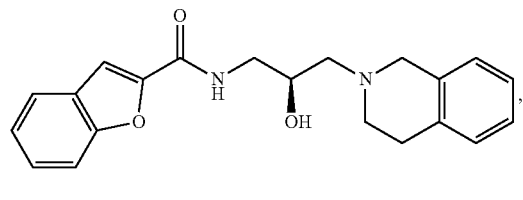
366
-continued
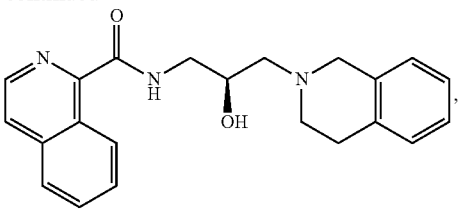
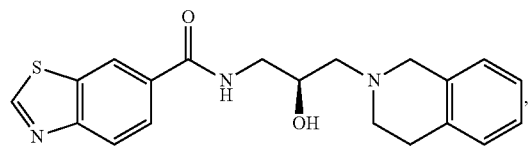
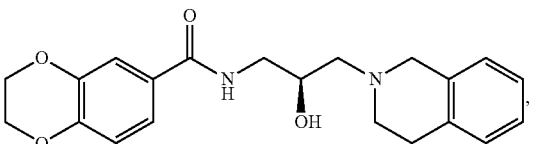
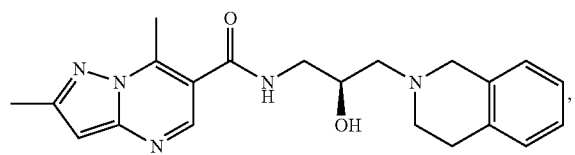
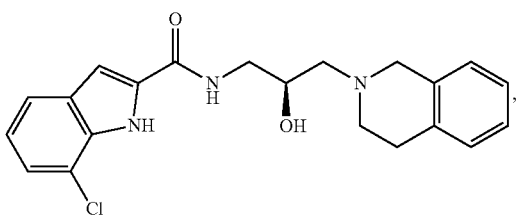
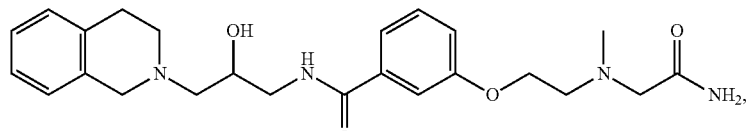
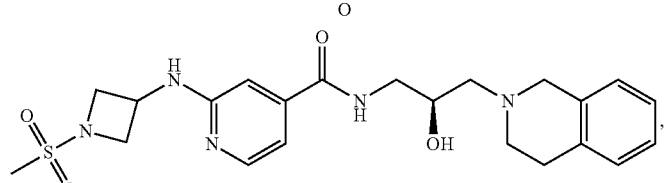
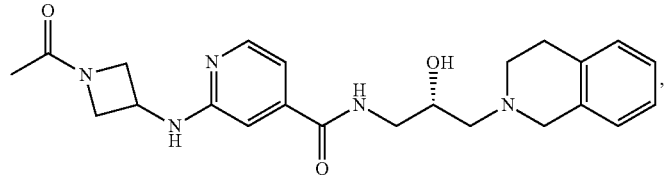
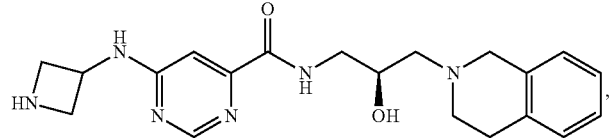
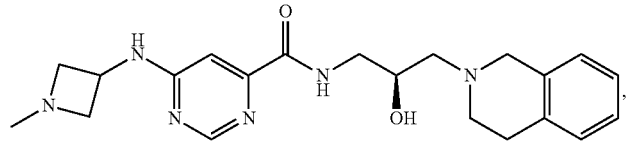
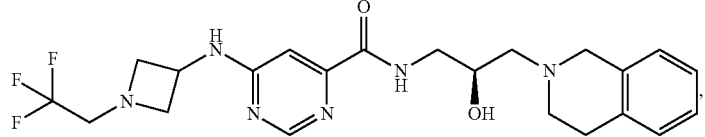
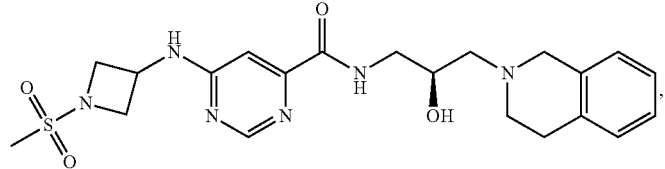

-continued
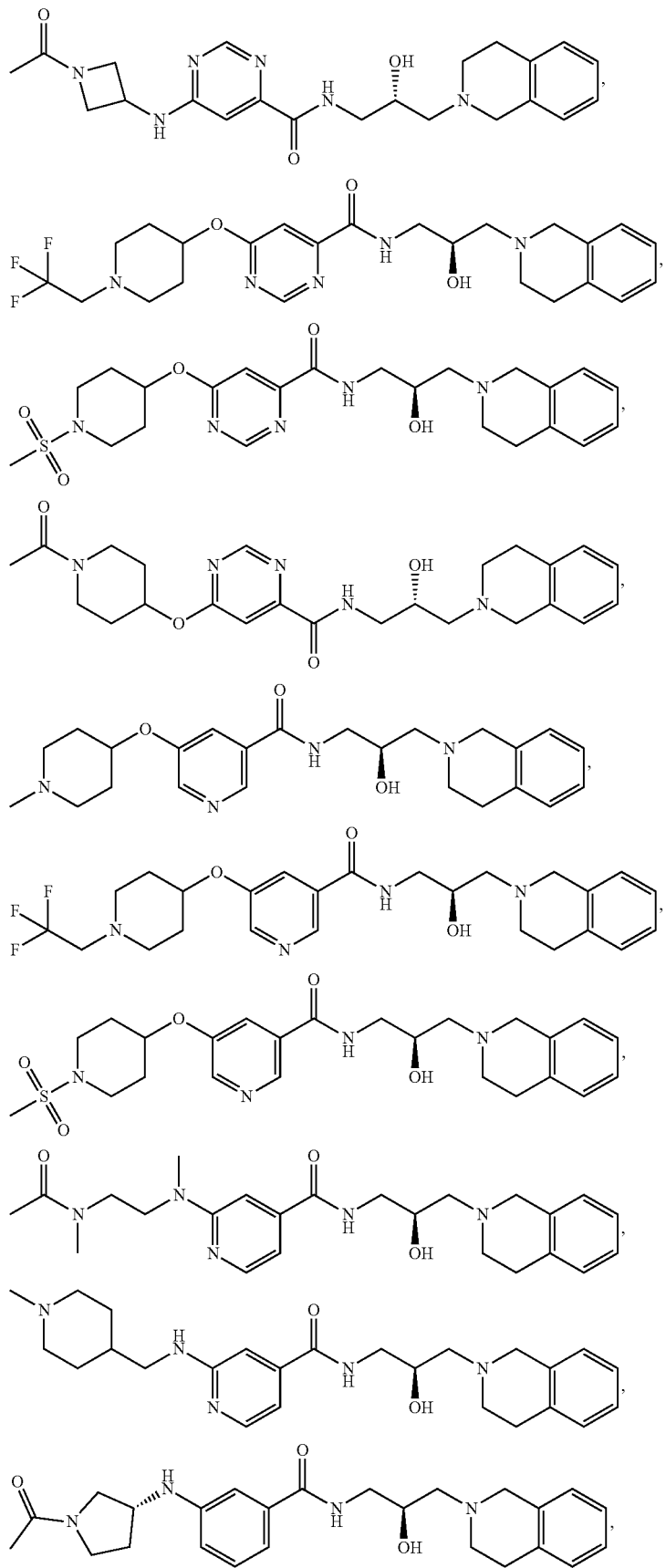

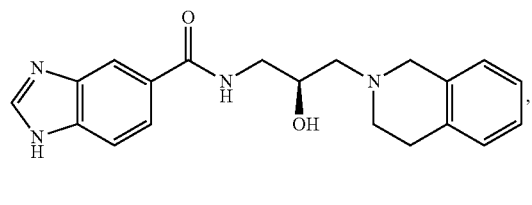
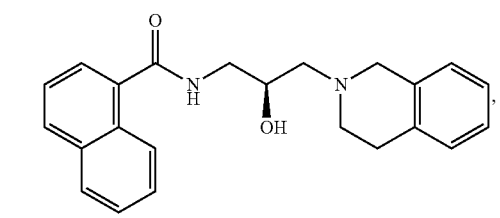
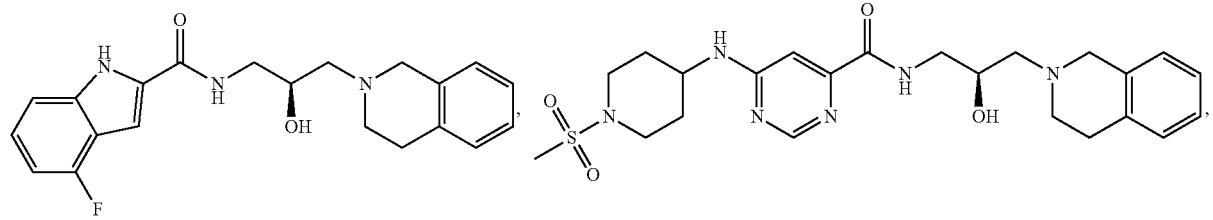
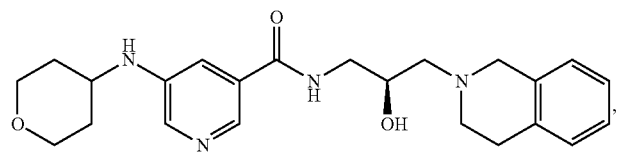
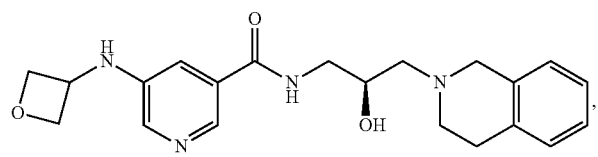
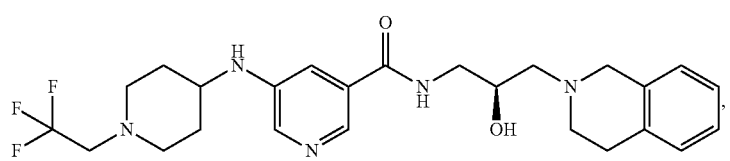
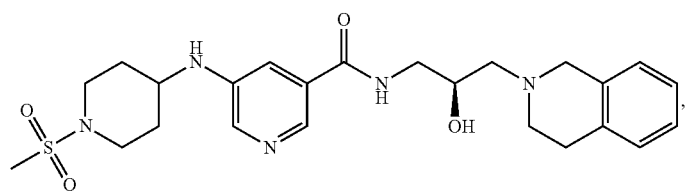
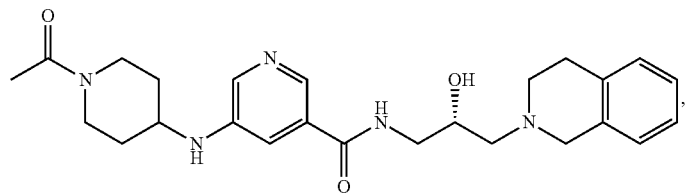
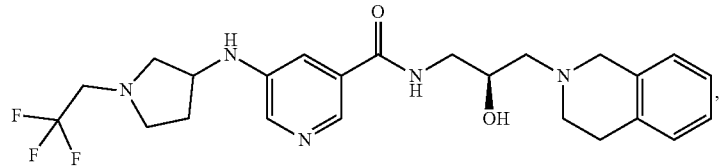
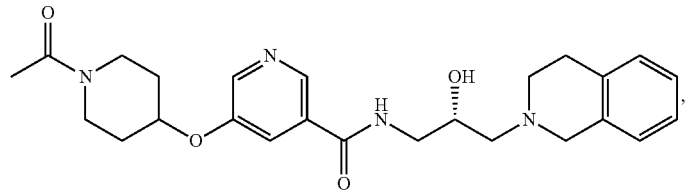

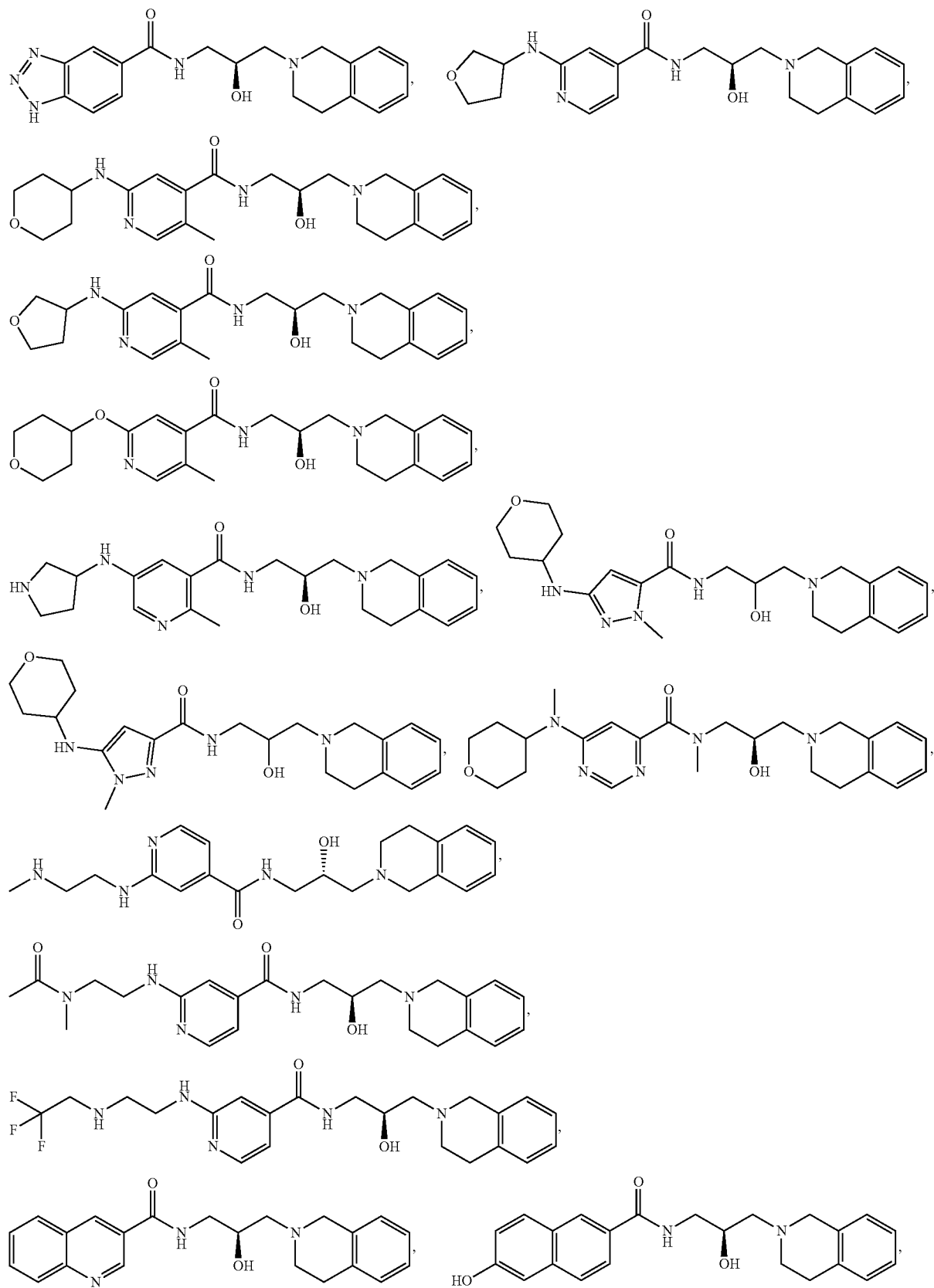

-continued
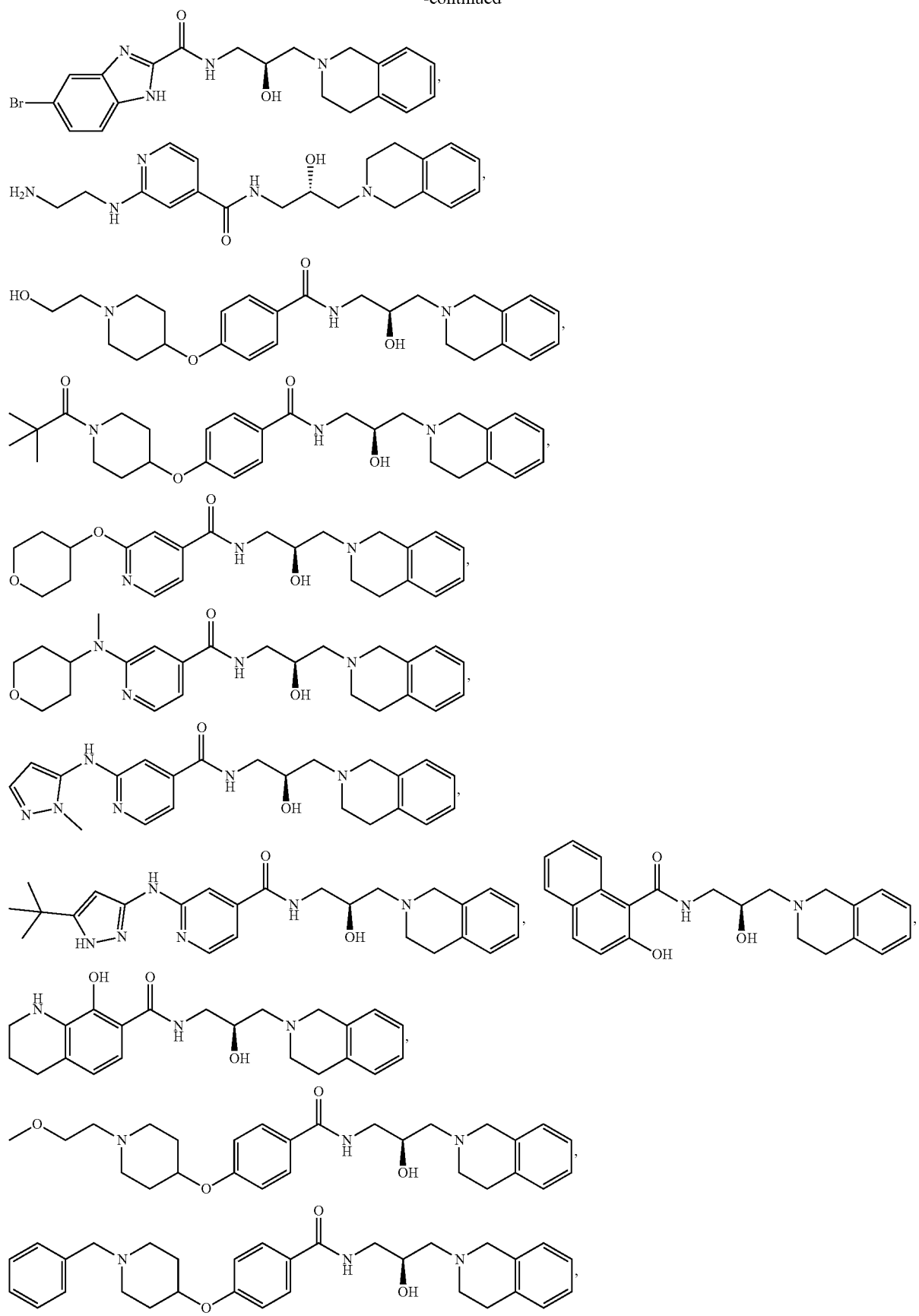

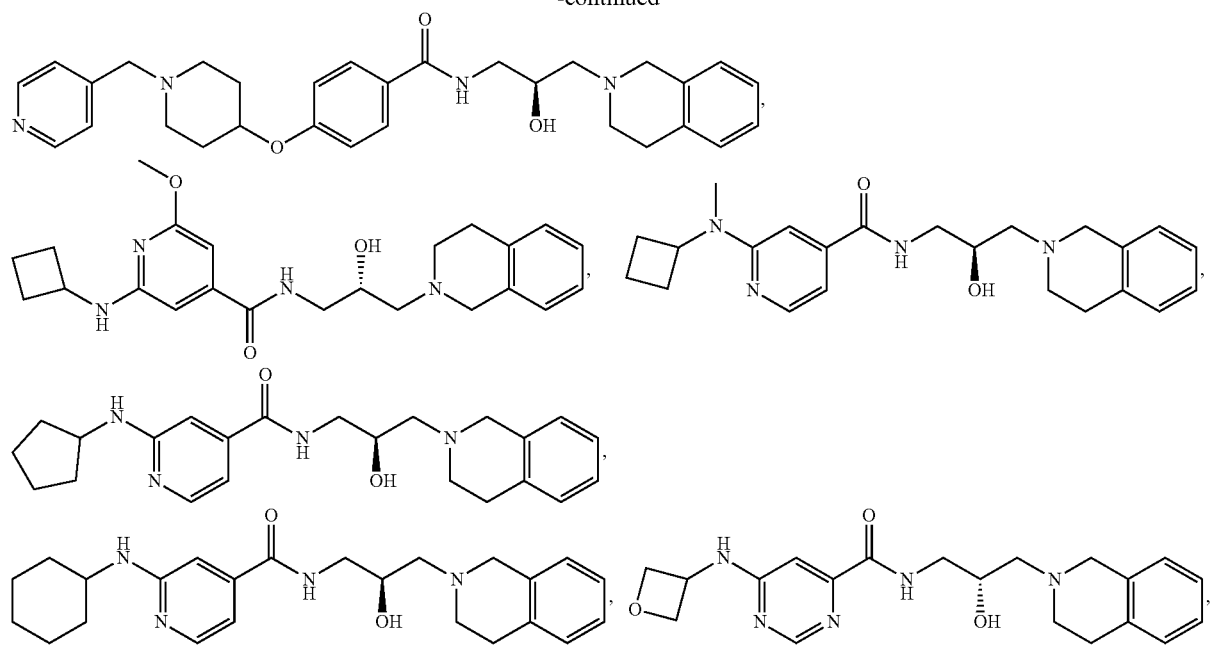

and pharmaceutically acceptable salts thereof;

wherein the disease is breast cancer, esophageal cancer, bladder cancer, lymphoma, medulloblastoma, rectum adenocarcinoma, colon adenocarcinoma, gastric cancer, liver cancer, adenoid cystic carcinoma, lung adenocarcinoma, head and neck squamous cell carcinoma, brain cancer, hepatocellular carcinoma, renal cell carcinoma, oligodendroglioma, ovarian clear cell carcinoma, ovarian serous cystadenocarcinoma, hematopoietic cancer, lung cancer, prostate cancer, melanoma, or pancreatic cancer.

* * * * *